(12) United States Patent
Scott

(10) Patent No.: US 9,534,228 B2
(45) Date of Patent: Jan. 3, 2017

(54) METHODS FOR MODULATING CELL PROLIFERATION IN THE SEED COAT AND/OR INTEGUMENT

(75) Inventor: Roderick Scott, Bath (GB)

(73) Assignee: The University of Bath, Bath (GB)

( * ) Notice: Subject to any disclaimer, the term of this patent is extended or adjusted under 35 U.S.C. 154(b) by 369 days.

(21) Appl. No.: 13/114,656

(22) Filed: May 24, 2011

(65) Prior Publication Data
US 2012/0159671 A1 Jun. 21, 2012

Related U.S. Application Data

(63) Continuation of application No. 10/591,418, filed as application No. PCT/GB2005/000857 on Mar. 7, 2005, now abandoned.

(30) Foreign Application Priority Data

| Mar. 5, 2004 | (GB) | 0405093.6 |
| Mar. 19, 2004 | (GB) | 0406275.8 |
| Mar. 25, 2004 | (GB) | 0406729.4 |

(51) Int. Cl.
C12N 15/82 (2006.01)
A01H 5/10 (2006.01)
C07K 14/415 (2006.01)

(52) U.S. Cl.
CPC ............ *C12N 15/8261* (2013.01); *A01H 5/10* (2013.01); *C07K 14/415* (2013.01); *C12N 15/823* (2013.01); *C12N 15/8234* (2013.01)

(58) Field of Classification Search
None
See application file for complete search history.

(56) References Cited

U.S. PATENT DOCUMENTS

| 6,222,097 B1 | 4/2001 | McBride et al. |
| 6,559,357 B1 | 5/2003 | Fischer et al. |
| 7,612,253 B2 | 11/2009 | Harada et al. |

FOREIGN PATENT DOCUMENTS

| WO | 01/35725 | 5/2001 |
| WO | 02/15675 | 2/2002 |
| WO | 03/013227 | 2/2003 |

OTHER PUBLICATIONS

Tiwari et al. The roles of auxin response factor domains in auxin-responsive transcription. The Plant Cell, vol. 15, 533-543, Feb. 2003.*
Jones et al. Down-regulation of DR12, an auxin-response-factor homolog, in the tomato results in a pleiotropic phenotype including dark green and blotchy ripening fruit. Plant J. Nov. 2002;32(4):603-13.*
Alonso et al. T-DNA mutagenesis in Arabidopsis. Methods Mol Biol. 2003;236:177-87.*
Herskowitz. Functional Inactivation of Genes by Dominant Negative Mutations. 1987. Nature, vol. 329, pp. 219-222.*
Wang et al. Expression of a Dominate Negative Heat Shock Factor-1 Construct Inhibits Aneuploidy in Prostrate Carcinoma Cells. The Journal of Biological Chemistry, 2004, vol. 279, No. 31, pp. 32651-32659.*
Accession No. BT000784 "*Arabidopsis thalia* clone RAFL07-10-G12 (R10939) auxin response factor (At5g62000) mRNA, complete cds." (Oct. 24, 2002).
Adams et al., "Parent-of-origin effects on seed development in *Arabidopsis thaliana* require DNA methylation," Development, 127, pp. 2493-2502, 2000.
Alexander et al., "Experimental Ecological Genetics in Plantago: X. The Effects of Maternal Temperature on Seed and Seedling Characters in P. Lanceolata," The Journal of Ecology, vol. 73, No. 1, pp. 271-282, 1985.
Alonso et al., "Genome-Wide Insertional Mutagenesis of *Arabidopsis thaliana*," Science, vol. 301, pp. 653-657, with 2 page Erratum, 2003.
Alonso-Blanco et al., "Natural allelic variation at seed size loci in relation to other life history traits of *Arabidopsis thaliana*," Proc. Natl. Acad. Sci. USA, vol. 96, pp. 4710-4717, 1999.
Austin, "Physiological limitations to cereal yields and ways of reducing them by breeding," Opportunities for increasing crop yields, Pitman Advanced Publishing Program, 1980.
Baker et al., "Interactions Among Genes Regulating Ovule Development in *Arabidopsis thaliana*," Genetics, 145, pp. 1109-1124, 1997.
Beeckman et al., "Histological Study of Seed Coat Development in *Arabidopsis thaliana*," J. Plant. Res., 113, pp. 139-148, 2000.
Bouman, "Integument initiation and testa development in some Cruciferae," Bot. J. Linn. Soc., 70, pp. 213-229, 1975.
Bouman, "The Ovule," Embryology of Angiosperms, Springer-Verlag, pp. 123-157, 1984.
Brown et al., "Splice Site Selection in Plant PRE-mRNA Splicing," Annu. Rev. Plant Physiol. Plant Mol. Biol., 49, pp. 77-95, 1998.
Cheng et al., "The *Miniature 1* Seed Locus of Maize Encodes a Cell Wall Invertase Required for Normal Development of Endosperm and Maternal Cells in the Pedicel," the Plant Cell, vol. 8, pp. 971-983, 1996.
Clough et al., "Floral dip: a simplified method for Agrobacterium-mediated transformation of *Arabidopsis thaliana*," The Plant Journal 16(6), pp. 735-743, 1998.

(Continued)

*Primary Examiner* — Cynthia Collins
(74) *Attorney, Agent, or Firm* — Hunton & Williams LLP

(57) ABSTRACT

This invention relates to methods for altering cell proliferation in a plant by modulating the expression of an endogenous plant gene whose expression product affects cell proliferation. These methods can be used to modify plant characteristics, such as seed size. In particular, the invention provides methods for modifying cell proliferation in the integuments and/or seed coats of a plant by inhibiting expression of endogenous gene encoding Auxin response factor 2 (ARF2/MNT) or an orthologue thereof, such that the number of cells in the integuments and/or seed coat is increased, resulting in increased seed size. The plant or plant propagating material can be transformed, e.g., with a nucleic acid construct, to increase or decrease the expression of endogenous genes or the orthologues thereof that affect cell proliferation. The invention also relates to modified plants and reproducible plant material produced by the methods, and nucleic acid constructs for use in such methods.

16 Claims, 51 Drawing Sheets

(56) References Cited

OTHER PUBLICATIONS

Debeaujon et al., "The *Transparent TESTA12* Gene of Arabidopsis Encodes a Multidrug Secondary Transporter-like Protein Required for Flavonoid Sequestration in Vacuoles of the Seed Coat Endothelium," The Plant Cell, vol. 13, pp. 853-871, 2001.

Devic et al., "The *BANYULS* gene encodes a DFR-like protein and is a marker of early seed coat development," The Plant Journal, 19(4), pp. 387-398, 1999.

Duvick et al., "Post-Green Revolution Trends in Yield Potential of Temperate Maize in the North-Central United States," Crop Sci., 39, pp. 1622-1630, 1999.

Ferreira et al., "Developmental Expression of the Arabidopsis Cyclin Gene *cyc1At*," the Plant Cell, vol. 6, pp. 1763-1774, 1994.

Garcia et al., "Arabidopsis *haiku* Mutants Reveal New Controls of Seed Size by Endosperm," Plant Physiology, vol. 131, pp. 1661-1670, 2003.

Goto et al., "Function and regulation of the *Arabidopsis* floral homeotic gene *Pistillata*," Genes & Development, 8, pp. 1548-1560, 1994.

Guilfoyle and Hagen (Sep. 2001) "Auxin response factors." Journal of Plant Growth Regulation 20(3): 281-291.

Hagen et al., "Auxin-responsive gene expression: genes, promoters and regulatory factors," Plant Molecular Biology, 49, pp. 373-385, 2002.

Hu et al., "The Arabidopsis Auxin-Inducible Gene *ARGOS* Controls Lateral Organ Size," The Plant Cell, vol. 15, pp. 1951-1961, 2003.

International Preliminary Report on Patentability of the International Searching Authority mailed Sep. 5, 2006 for PCT/GB2005/000857.

International Search Report of the International Searching Authority Report (PCT/ISA/210) mailed Feb. 21, 2006 for PCT/GB2005/000857.

Jack et al., "The Homeotic Gene *APETAL3* of Arabidopsis thaliana Encodes a MADS Box and Is Expressed in Petals and Stamens," Cell, vol. 68, pp. 683-697, 1992.

Jefferson et al., "GUS Fusions: β-glucuronidase as a sensitive and versatile gene fusion marker in higher plants," Embo Journal, vol. 6, No. 13, pp. 3901-3907, 1987.

Jones et al., "Kernel Sink Capacity in Maize: Genotypic and Maternal Regulation," Crop Physiology and Metabolism, Crop Sci., 36, pp. 301-306, 1996.

Klucher et al., "The *Aintegumenta* Gene of Arabidopsis Required for Ovule and Female Gametophyte Development is Related to the Floral Homeotic Gene *APETALA2*," Yhe Plant Cell, vol. 8, pp. 137-153, 1996.

Krannitz et al., "The effect of genetically based differences in seed size on seedling survival in Arabidopsis thaliana (Brassicaceae)," American Journal of Botany, 78(3), pp. 446-450, 1991.

Leyser, "Molecular Genetics of Auxin Signaling," Annu. Rev. Plant Biol. 53:377-98, 2002.

Liscum et al., "Genetics of AUC/IAA and ARF action in plant growth and development," Plant Molecular Biology, 49, pp. 387-400, 2002.

Lopez-Dee et al., "OsMADS13, A Novel Rice Mads-Box Gene Expressed During Ovule Development," Developmental Genetics, 25:237-244, 1999.

Manga et al., "Effect of seed size on developmental traits and ability to tolerate drought in pearl millet," Journal of Arid Environments, 29: 169-172, 1995.

Marshall, "Effect of Seed Size on Seedling Success in Three Species of Sesbana (Fabaceae)," Amer. J. Bot., 73(4), pp. 457-464, 1986.

Nesi et al., "The Arabidopsis *TT2* Gene Encodes an R2R3 MYB Domain Protein That Acts as a Key Determinant for Proanthocyanidin Accumulation in Developing Seed," The Plant Cell, vol. 13, pp. 2099-2114, 2001.

Nesi et al., "The *Transparent TESTA16* Locus Encodes the Arabidopsis Bsister Mads Domain Protein and Is Required for Proper Development and Pigmentation of the Seed Coat," The Plant Cell, vol. 14, pp. 2463-2479, 2002.

Nesi et al., "The *TT8* Gene Encodes a Basic Helix-Loop-Helix Domain Protein Required for Expression of *DFR* and *BAN* Genes in Arabidopsis Siliques," The Plant Cell, vol. 12, pp. 1863-1878, 2000.

Nicholas et al., "GeneDoc: Analysis and Visualization of Genetic Variation." 1997. EMBNEW. News 4:14.

Patrick et al., "Post-sieve Element Transport of Sucrose in Development Seeds," Aust. J. Plant Physiol., 22, pp. 681-702, 1995.

Paul et al., "Sink regulation of photosynthesis," Journal of Experimental Botany, vol. 52, No. 360, pp. 1383-1400, 2001.

Robinson-Beers et al., "Ovule Development in Wild-Type Arabidopsis and Two Female-Sterile Mutants," The Plant Cell, vol. 4, pp. 1237-1249, 1992.

Sagasser et al., "*A. thaliana* Transparent TESTA 1 is involved in seed coat development and defines the WIP subfamily of plant zinc finger proteins," Genes & Development, 16, pp. 138-149, 2002.

Sato et al., "Auxin response factor family in rice," Genes Genet. Syst., 76, pp. 373-380, 2001.

Schaal, "Reproductive Capacity and Seed Size in Lupinus texensis," American Journal of Botany, vol. 67, No. 5, pp. 703-709, 1980.

Scott et al., "Parent-of-Origin effects on seed development in *Arabidopsis thaliana*," Development 125, 3329-3341, 1998.

Soni et al., "A Family of Cyclin D Homologs from Plant Differentially Controlled by Growth Regulators and Containing the Conserved Retinoblastoma Protein and Interaction Motif," the Plant Cell, vol. 7, pp. 85-103, 1995.

Stals et al., "When plant cells decide to divide," Trends in Plant Science, vol. 6, No. 8, pp. 359-364, 2001.

Takei et al., "Identification of Genes Encoding Adenylate Isopentenyltransferase, a Cytokinin Biosynthesis Enzyme, in *Arabidopsis thaliana*," The Journal of Biological Chemistry, vol. 276, No. 28, pp. 26405-26410, 2001.

Till et al., "Large-Scale Discovery of Induced Point Mutations With High-Troughput Tilling," Genome Research, 13, pp. 524-530, 2003.

Tiwari et al., "The Roles of Auxin Response Factor Domains in Auxin-Responsive Transcription," The Plant Cell, vol. 15, pp. 533-543, 2003.

Ulmasov et al., "Activation and repression of transcription by auxin-response factors," Proc. Natl. Acad. Sci. USA, vol. 96, pp. 5844-5849, 1999.

Ulmasov et al., "Dimerization and DNA binding of auxin response factors," The Plant Journal, 19(3), pp. 309-319, 1999.

Villaneuva et al., "Inner No Outer regulates abaxial-adaxial patterning in *Arabidopsis ovules*," Genes & Development, 13, pp. 3160-3169, 1999.

Vinkenogg et al., "Hypomethylation Promotes Autonomous Endosperm Development and Rescues Postfertilization Lethality in *fie* Mutants," The Plant Cell, vol. 12, pp. 2271-2282, 2000.

Wan et al., "Early stages of seed development in *Brassica napus*: a seed coat-specific cysteine proteinase associated with programmed cell death of the inner integument," The Plant Journal, 31(1), pp. 1-10, 2002.

Weber et al., "Controlling seed development and seed size in *Vicia faba*: a role for seed coat-associated invertases and carbohydrate state," The Plant Journal, 10 (5), pp. 823-834, 1996.

Weschke et al., "The role of intertases and hexose transporters in controlling sugar ratios in maternal and filial tissues of barley caryopses during early development," The Plant Journal, 33, pp. 395-411, 2003.

Winn, "Effects of Seed Size and Microsite on Seedling Emergence of *Prunella vulgaris* in Four Habitats," Journal of Ecology, 73, pp. 831-840, 1985.

Written Opinion of the International Searching Authority mailed Feb. 21, 2006 for PCT/GB2005/000857.

Yamada et al., "Expression pattern of Inner No Outer homologue in *Nymphaea* (water lily family, Nymphaeaceae)," Dev Genes Evol, 213, pp. 510-513, 2003.

\* cited by examiner

Figure 1
1A mnt-1 vs wild-type seeds
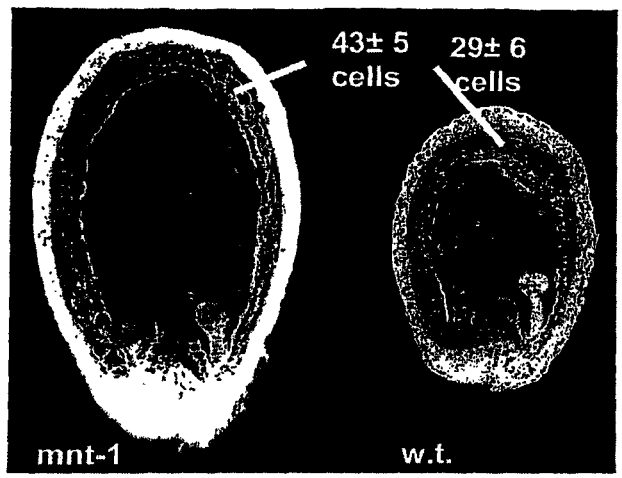
1B Seed weight vs no. seeds per pod in mnt-1
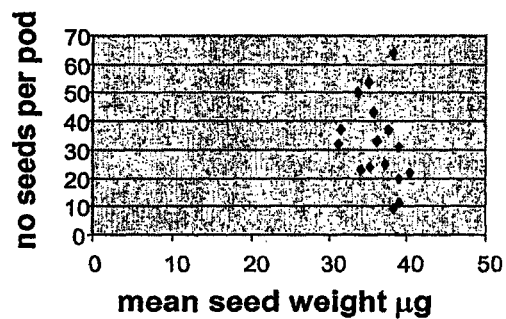
1C Maternal effect of mnt-1 mutation
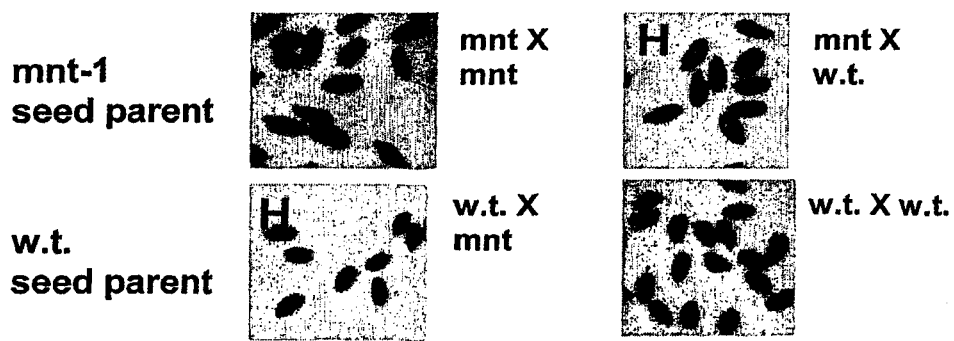

Figure 2B-D

Figure 3
Chalazal endosperm
w.t. 7DAP
mnt-1 7DAP
2x X 6x 5 DAP
Bars = 50 μm

Figure 4
4A Endosperm-led growth
 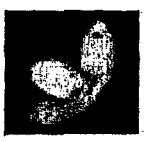 
big cavity — normal — small
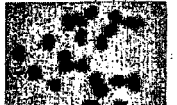 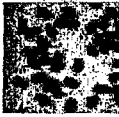 
4B Integument-led growth
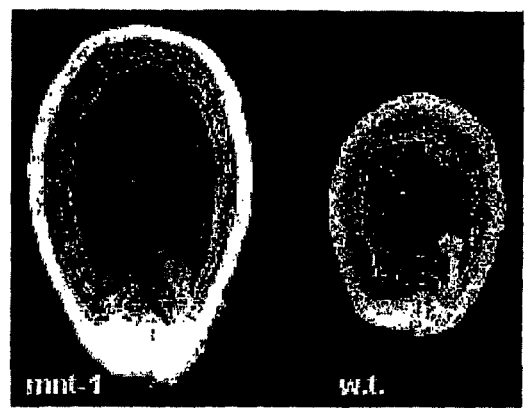
 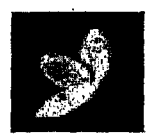
big cavity — normal
 
4C 'Big bag' hypothesis: seed and embyro size set by size of the seed cavity
1. Division in endosperm (maternal and paternal control)
2. Division in integuments/ seed coat (maternal control)

Allelism of mnt-1 and Salk insertion line 108995

```
MNT            *           20          *           40          *           60
ATGGCGAGTTCGGAGGTTTCAATGAAAGGTAATCGTGGAGGAGATAACTTCTCCTCCTCT
ATGGCGAGTTCGGAGGTTTCAATGAAAGGTAATCGTGGAGGAGATAACTTCTCCTCCTCT
mnt-1
               *           80          *          100          *          120
GGTTTTAGTGACCCTAAGGAGACTAGAAATGTCTCCGTCGCCGGCGAGGGGCAAAAAAGT
GGTTTTAGTGACCCTAAGGAGACTAGAAATGTCTCCGTCGCCGGCGAGGGGCAAAAAAGT

*          140          *          160          *          180
AATTCTACCCGATCCGCTGCGGCTGAGCGTGCTTTGGACCCTGAGGCTGCTCTTTACAGA
AATTCTACCCGATCCGCTGCGGCTGAGCGTGCTTTGGACCCTGAGGCTGCTCTTTACAGA

*          200          *          220          *          240
GAGCTATGGCACGCTTGTGCTGGTCCGCTTGTGACGGTTCCTAGACAAGACGACCGAGTC
GAGCTATGGCACGCTTGTGCTGGTCCCCTTGTGACGGTTCCTAGACAAGACGACCGAGTC

*          260          *          280          *          300
TTCTATTTTCCTCAAGGACACATCGAGCAGGTGGAGGCTTCGACGAACCAGGCGGCAGAA
TTCTATTTTCCTCAAGGACACATCGAGCAGGTGGAGGCTTCGACGAACCAGGCGGCAGAA

*          320          *          340          *          360
CAACAGATGCCTCTCTATGATCTTCCGTCAAAGCTTCTCTGTCGAGTTATTAATGTAGAT
CAACAGATGCCTCTCTATGATCTTCCGTCAAAGCTTCTCTGTCGAGTTATTAATGTAGAT

*          380          *          400          *          420
TTAAAGGCACAGGCAGATACAGATGAAGTTTATGCGCAGATTACTCTTCTTCCTGAGGCT
TTAAAG----AGGCAGATACAGATGAAGTTTATGCGCAGATTACTCTTCTTCCTGAGGCT

*          440          *          460          *          480
AATCAAGACGAGAATGCAATTGAGAAAGAAGCGCCTCTTCCTCCACCTCCGAGGTTCCAG
AATCAAGACGAGAATGCAATTGAGAAAGAAGCGCCTCTTCCTCCACCTCCGAGGTTCCAG

*          500          *          520          *          540
GTGCATTCGTTCTGCAAAACCTTGACTGCATCCGACACAAGTACACATGGTGGATTTTCT
GTGCATTCGTTCTGCAAAACCTTGACTGCATCCGACACAAGTACACATGGTGGATTTTCT
```

Figure 6

```
           *         560         *         580         *         600
GTTCTTAGGCGACATGCGGATGAATGTCTCCCACCTCTGGATATGTCTCGACAGCCTCCC
GTTCTTAGGCGACATGCGGATGAATGTCTCCCACCTCTGGATATGTCTCGACAGCCTCCC

*         620         *         640         *         660
ACTCAAGAGTTAGTTGCAAAGGATTTGCATGCAAATGAGTGGCGATTCAGACATATATTC
ACTCAAGAGTTAGTTGCAAAGGATTTGCATGCAAATGAGTGGCGATTCAGACATATATTC

*         680         *         700         *         720
CGGGGTCAACCACGGAGGCATTTGCTACAGAGTGGGTGGAGTGTGTTTGTTAGCTCCAAA
CGGGGTCAACCACGGAGGCATTTGCTACAGAGTGGGTGGAGTGTGTTTGTTAGCTCCAAA

AGGCTAGTTGCAGGCGATGCGTTTATATTTCTAAGGGGCGAGAATGGAGAATTAAGAGTT
AGGCTAGTTGCAGGCGATGCGTTTATATTTCTAAGGGGCGAGAATGGAGAATTAAGAGTT

*         800         *         820         *         840
GGTGTAAGGCGTGCGATGCGACAACAAGGAAACGTGCCGTCTTCTGTTATATCTAGCCAT
GGTGTAAGGCGTGCGATGCGACAACAAGGAAACGTGCCGTCTTCTGTTATATCTAGCCAT

*         860         *         880         *         900
AGCATGCATCTTGGAGTACTGGCCACCGCATGGCATGCCATTTCAACAGGGACTATGTTT
AGCATGCATCTTGGAGTACTGGCCACCGCATGGCATGCCATTTCAACAGGGACTATGTTT

*         920         *         940         *         960
ACAGTCTACTACAAACCCAGGACGAGCCCATCTGAGTTTATTGTTCCGTTCGATCAGTAT
ACAGTCTACTACAAACCCAGGACGAGCCCATCTGAGTTTATTGTTCCGTTCGATCAGTAT

*         980         *        1000         *        1020
ATGGAGTCTGTTAAGAATAACTACTCTATTGGCATGAGATTCAAAATGAGATTTGAAGGC
ATGGAGTCTGTTAAGAATAACTACTCTATTGGCATGAGATTCAAAATGAGATTTGAAGGC

*        1040         *        1060         *        1080
GAAGAGGCTCCTGAGCAGAGGTTTACTGGCACAATCGTTGGGATTGAAGAGTCTGATCCT
GAAGAGGCTCCTGAGCAGAGGTTTACTGGCACAATCGTTGGGATTGAAGAGTCTGATCCT

*        1100         *        1120         *        1140
ACTAGGTGGCCAAAATCAAAGTGGAGATCCCTCAAGGTGAGATGGGATGAGACTTCTAGT
ACTAGGTGGCCAAAATCAAAGTGGAGATCCCTCAAGGTGAGATGGGATGAGACTTCTAGT
```

Figure 6 (continued)

```
          *        1160         *        1180         *        1200
ATTCCTCGACCTGATAGAGTATCTCCGTGGAAAGTAGAGCCAGCTCTTGCTCCTCCTGCT
ATTCCTCGACCTGATAGAGTATCTCCGTGGAAAGTAGAGCCAGCTCTTGCTCCTCCTGCT

*        1220         *        1240         *        1260
TTGAGTCCTGTTCCAATGCCTAGGCCTAAGAGGCCCAGATCAAATATAGCACCTTCATCT
TTGAGTCCTGTTCCAATGCCTAGGCCTAAGAGGCCCAGATCAAATATAGCACCTTCATCT

*        1280         *        1300         *        1320
CCTGACTCTTCGATGCTTACCAGAGAAGGTACAACTAAGGCAAACATGGACCCTTTACCA
CCTGACTCTTCGATGCTTACCAGAGAAGGTACAACTAAGGCAAACATGGACCCTTTACCA

*        1340         *        1360         *        1380
GCAAGCGGACTTTCAAGGGTCTTGCAAGCTCAAGAATACTCGACCTTGAGGACGAAACAT
GCAAGCGGACTTTCAAGGGTCTTGCAAGCTCAAGAATACTCGACCTTGAGGACGAAACAT

*        1400         *        1420         *        1440
ACTGAGAGTGTAGAGTGTGATGCTCCTGAGAATTCTGTTGTCTGGCAATCTTCAGCGGAT
ACTGAGAGTGTAGAGTGTGATGCTCCTGAGAATTCTGTTGTCTGGCAATCTTCAGCGGAT

*        1460         *        1480         *        1500
GATGATAAGGTTGACGTGGTTTCGGGTTCTAGAAGATATGGATCTGAGAACTGGATGTCC
GATGATAAGGTTGACGTGGTTTCGGGTTCTAGAAGATATGGATCTGAGAACTGGATGTCC

*        1520         *        1540         *        1560
TCAGCCAGGCATGAACCTACTTACACAGATTTGCTCTCCGGCTTTGGGACTAACATAGAT
TCAGCCAGGCATGAACCTACTTACACAGATTTGCTCTCCGGCTTTGGGACTAACATAGAT

*        1580         *        1600         *        1620
CCATCCCATGGTCAGCGGATACCTTTTTATGACCATTCATCATCACCTTCTATGCCTGCA
CCATCCCATGGTCAGCGGATACCTTTTTATGACCATTCATCATCACCTTCTATGCCTGCA

*        1640         *        1660         *        1680
AAGAGAATCTTGAGTGATTCAGAAGGCAAGTTCGATTATCTTGCTAACCAGTGGCAGATG
AAGAGAATCTTGAGTGATTCAGAAGGCAAGTTCGATTATCTTGCTAACCAGTGGCAGATG

*        1700         *        1720         *        1740
ATACACTCTGGTCTCTCCCTGAAGTTACATGAATCTCCTAAGGTACCTGCAGCAACTGAT
ATACACTCTGGTCTCTCCCTGAAGTTACATGAATCTCCTAAGGTACCTGCAGCAACTGAT
```

Figure 6 (continued)

```
           *         1760         *         1780         *         1800
GCGTCTCTCCAAGGGCGATGCAATGTTAAATACAGCGAATATCCTGTTCTTAATGGTCTA
GCGTCTCTCCAAGGGCGATGCAATGTTAAATACAGCGAATATCCTGTTCTTAATGGTCTA

*         1820         *         1840         *         1860
TCGACTGAGAATGCTGGTGGTAACTGGCCAATACGTCCACGTGCTTTGAATTATTATGAG
TCGACTGAGAATGCTGGTGGTAACTGGCCAATACGTCCACGTGCTTTGAATTATTATGAG

*         1880         *         1900         *         1920
GAAGTGGTCAATGCTCAAGCGCAAGCTCAGGCTAGGGAGCAAGTAACAAAACAACCCTTC
GAAGTGGTCAATGCTCAAGCGCAAGCTCAGGCTAGGGAGCAAGTAACAAAACAACCCTTC

*         1940         *         1960         *         1980
ACGATACAAGAGGAGACAGCAAAGTCAAGAGAAGGGAACTGCAGGCTCTTTGGCATTCCT
ACGATACAAGAGGAGACAGCAAAGTCAAGAGAAGGGAACTGCAGGCTCTTTGGCATTCCT

*         2000         *         2020         *         2040
CTGACCAACAACATGAATGGGACAGACTCAACCATGTCTCAGAGAAACAACTTGAATGAT
CTGACCAACAACATGAATGGGACAGACTCAACCATGTCTCAGAGAAACAACTTGAATGAT

*         2060         *         2080         *         2100
GCTGCGGGGCTTACACAGATAGCATCACCAAAGGTTCAGGACCTTTCAGATCAGTCAAAA
GCTGCGGGGCTTACACAGATAGCATCACCAAAGGTTCAGGACCTTTCAGATCAGTCAAAA

*         2120         *         2140         *         2160
GGGTCAAAATCAACAAACGATCATCGTGAACAGGGAAGACCATTCCAGACTAATAATCCT
GGGTCAAAATCAACAAACGATCATCGTGAACAGGGAAGACCATTCCAGACTAATAATCCT

*         2180         *         2200         *         2220
CATCCGAAGGATGCTCAAACGAAAACCAACTCAAGTAGGAGTTGCACAAAGGTTCACAAG
CATCCGAAGGATGCTCAAACGAAAACCAACTCAAGTAGGAGTTGCACAAAGGTTCACAAG

*         2240         *         2260         *         2280
CAGGGAATTGCACTTGGCCGTTCAGTGGATCTTTCAAAGTTCCAAAACTATGAGGAGTTA
CAGGGAATTGCACTTGGCCGTTCAGTGGATCTTTCAAAGTTCCAAAACTATGAGGAGTTA

*         2300         *         2320         *         2340
GTCGCTGAGCTGGACAGGCTGTTTGAGTTCAATGGAGAGTTGATGGCTCCTAAGAAAGAT
GTCGCTGAGCTGGACAGGCTGTTTGAGTTCAATGGAGAGTTGATGGCTCCTAAGAAAGAT
```

Figure 6 (continued)

```
                *         2360          *         2380          *         2400
TGGTTGATAGTTTACACAGATGAAGAGAATGATATGATGCTTGTTGGTGACGATCCTTGG
TGGTTGATAGTTTACACAGATGAAGAGAATGATATGATGCTTGTTGGTGACGATCCTTGG

*         2420          *         2440          *         2460
CAGGAGTTTTGTTGCATGGTTCGCAAAATCTTCATATACACGAAAGAGGAAGTGAGGAAG
CAGGAGTTTTGTTGCATGGTTCGCAAAATCTTCATATACACGAAAGAGGAAGTGAGGAAG

*         2480          *         2500          *         2520
ATGAACCCGGGGACTTTAAGCTGTAGGAGCGAGGAAGAAGCAGTTGTTGGCGAACGATCA
ATGAACCCGGGGACTTTAAGCTGTAGGAGCGAGGAAGAAGCAGTTGTTGGCGAAGGATCA

*         2540          *         2560          *         2580
GATGCAAAGGACGCCAAGTCTGCATCAAATCCTTCATTGTCCAGCGCTGGGAACTCTTAA
GATGCAAAGGACGCCAAGTCTGCATCAAATCCTTCATTGTCCAGCGCTGGGAACTCTTAA
```

Figure 6 (continued)

```
MNT        *         20        *         40        *         60
MASSEVSMKGNRGGDNFSSSGFSDPKETRNVSVAGEGQKSNSTRSAAAERALDPEAALYR
MASSEVSMKGNRGGDNFSSSGFSDPKETRNVSVAGEGQKSNSTRSAAAERALDPEAALYR
mnt-1

*         80        *        100        *        120
ELWHACAGPLVTVPRQDDRVFYFPQGHIEQVEASTNQAAEQQMPLYDLPSKLLCRVINVD
ELWHACAGPLVTVPRQDDRVFYFPQGHIEQVEASTNQAAEQQMPLYDLPSKLLCRVINVD

*        140        *        160        *        180
LKAEADTDEVYAQITLLPEANQDENAIEKEAPLPPPPRFQVHSFCKTLTASDISTHGGES
LKRQIQMKFMRRLFFLRLIKTRMQLRKKRLPLHLRGSRGIRSAKP---------------

*        200        *        220        *        240
VLRRHADECLPPLDMSRQPPTQELVAKDLHANEWRFRHIFRGQPRRHLIQSGWSVFVSSK
-----------------------------------------------------------

*        260        *        280        *        300
RLVAGDAFIFLRGENGELRVGVRRAMRQQGNVPSSVISSHSMHLGVLATAWHAISIGIMF
-----------------------------------------------------------

*        320        *        340        *        360
TVYYKPRTSPSEFIVPFDQYMESVKNNYSIGMRFKMRFEGEEAPEQRFTGTTVGIERSDP
-----------------------------------------------------------

*        380        *        400        *        420
TRWPKSKWRSLKVRWDETSSIPRPDRVSPWKVEPALAPPALSPVPMPRPKRPRSNIAPSS
-----------------------------------------------------------

*        440        *        460        *        480
PDSSMLTREGTTKANMDPLPASGLSRVLQGQEYSTLRTKHIESVECDAPENSVVWQSSAD
-----------------------------------------------------------

*        500        *        520        *        540
DDKVDVVSGSRRYGSENWMSSARHEPTYTDLLSGFGTNIDPSHGQRIPFYDHSSSPSMPA
-----------------------------------------------------------

*        560        *        580        *        600
KRTLSDSEGKFDYLANQWQMTHSGLSLKLHESPKVPAATDASLQGRCNVKYSEYPVLNGL
-----------------------------------------------------------
```

Figure 7

```
        *         620          *         640          *         660
STENAGGNWPIRPRALNYYEEVVNAQAQAQAREQVTLQPFTIQEEIAKSREGNCRLFGIP

*         680          *         700          *         720
LTNNMNGTDSTMSQRNNLNDAAGLIQIASPKVQDLSDQSKGSKSTNDHREQGRPFQTNNP

*         740          *         760          *         780
HPKDAQTKTNSSRSCTKVHKQGIALGRSVDLSKFQNYEELVAELDRLFEFNGELMAPKKD

*         800          *         820          *         840
WLLVYTDEENDMMLVGDDPWQEFCCMVRKIFIYTKEEVRKMNPGILSCRSEEEAVVGEGS

*
DAKDAKSASNPSLSSAGNS
```

Figure 7 (continued)

MNT
```
         *        20         *         40        *        60
ATGGCGAGTTCGGAGGTTTTCATGAAAGGTAATCGTGGA---GGAGATAACTTCTCCTCC
ATGGCGAGTTCGGAGGTTTTCATGAAAGGAAATCGTGGACAGGAGAAAACTTCTCCTCC
```
BnARF2
```
         *        80         *        100        *       120
TCTGGTTTTAGTGACCCTAAGGAGACTAGAAATGTCTCCGTCGCCGGCGAGGGGCAAAAA
GCTGGTTAGAGTGACCC------GAC-------C-----GTCGCCGGCGAGGCGCAAAA

*       140         *        160        *       180
AGTAATCTACCCGATCGCTGCGGCTGAGCGTGTTTGGACCCTGAGGCTGCTCTTTAC
ACTCAGTCTACCCGATCTGTGCTGCAGAGCGGGTTTTGACCCCGAAGCTGCTCTCTAC

*       200         *        220        *       240
AGAGAGCTATGGCACGCTTGTGCTGGTCCTCTTGTGACGGTTCCTAGACAAGACGACCGA
CGTGAGCTGTGGCACGCTTGTGCTGGTCCTCTGGTGACAGTCCTCGACAAGATGACCGA

*       260         *        280        *       300
GTCTTCTATTTTCCTCAAGGCACACATCGAGCAGGTGGAGGCTTCGACGAACCAGGCCGCA
GTCTTCTACTTCCCTCAGGGGCACATCGAGCAGGTGGAAGCATCGACAAATCAGCTGCA

*       320         *        340        *       360
GAACAACAGATGCCTCTCTATGATCTTCCCTCAAAGCTTCTTGTCGAGTTATTAATGTA
GAACAGCAGATGCCTCTCTATGATCTTCCTTCGAAGATCCTTTGTCGTGTCATTAATGTT

*       380         *        400        *       420
GATTTAAAGGCAGAGGCAGATACAGATGAAGTTTATGCGCAGATTACTCTTCTTCCTGAG
GATTTAAAGGCAGAGGCAGACACCGACGAAGTTTATGCGCAGATTACTCTTCTTCCCGAG

*       440         *        460        *       480
GCTAATCAAGACGAGAATCCAATTGAGAAAGAAGCGCCTCTTCCTCCACCTCCGAGGTTC
CTGTCAAGACGAGAATTCAATAGAGAAAGAGGCGCCTCCTCCTCCGCCCCCAGGTTC

*       500         *        520        *       540
CAGGTGCATTCGTTCTGCAAAACCTTGACTGCATCCGACACAAGTACACATGGTGGATTT
CAAGTGCACTCCTTCTGCAAAACCTTGACTGCATCGGACACAAGTACACATGGTGGATTT
```

Figure 8

```
                    *         560         *         580         *         600
        TCTGTTCTTAGGCGACATGCGGATGAATGTCTCCCACCTCTGGATATGTCTCGACAGCCT
        TCTGTCCTTAGGCGGCATGCGGATGAATGTCTCCCACCTCTGGATATGTCCCGTCAACCT

*         620         *         640         *         660
        CCCACTCAAGAGTTAGTTGCAAAGGATTTGCATGCAAATGAGTGGCGATTCAGACATATA
        CCTACTCAGGAGTTAGTTGCAAAAGATCTGCATGCAAGCGAGTGGCGTTTCCGACATATT

*         680         *         700         *         720
        TTCCGGGGTCAACCACGGAGGCATTTGCTACAGAGTGGGTGGAGTGTGTTTGTTAGCTCC
        TTCCCAGGTCAACCACAAAGGCATTTGCTTCAGAGTGGATGGACGTGTTTGTTAGCTCC

*         740         *         760         *         780
        AAAAGGCTAGTTGCAGGCGATGCGTTTATATTTCTAAGGGGCGAGAATGGAGAATTAAGA
        AAGAGGCTGGTCGCAGGCGATGCTTTTATATTTCTAACGGGCGAGAATGGAGAATTACGT

*         800         *         820         *         840
        GTTGGTGTAAGGCGTGCGATGCGACAACAAGGAAACGTGCCGTCTTCTGTTATATCTAGC
        GTCGGTGTAAGGCGTGCAATGCGGCAGCAAGGAAATGTGCCATCCTCTGTTATATCAAGC

*         860         *         880         *         900
        CATAGCATGCATCTTGGAGTACTGGCCACGGCATGGCATGCCATTTCAACAGGGACTATG
        CAGAGCATGCATCTCGGAGTATTGGCCACTGCCTGGCAGGCTATTTCAACTGCAACCATG

*         920         *         940         *         960
        TTTACAGTCTACTACAAACCCAGGACCACCCCATCTGAGTTTATTGTTCCGTTCGATCAG
        TTTACAGTCTACTATAAACCGAGGACTAGTCCTTCAGAGTTTATTGTTCCGTTTGATCAG

*         980         *        1000         *        1020
        TATATGGAGTCTGTTAAGAATAACTACTCTATTGGCATGAGATTCAAAATGAGATTTGAA
        TATACGGAGTCCGTCAAGATTAACTACTCCATGGCATGAGATTTAAAATGAGATTTGAA

*        1040         *        1060         *        1080
        GGCGAAGAGGCTCCTGAGCAGAGGTTTACTGGCACAATCGTTGGGATTGAAGAGTCTGAT
        GGCGAAGAGGCTCCCGAGCAGAGGTTTACTGGCACAATCGTTGGGATTGAAGACTCTGAC

*        1100         *        1120         *        1140
        CCTACTAGGTGGCCAAAATCAAAGTGGAGATCCCTCAAGGTGAGATGGGATGAGACTTCT
        CCCACGAGGTGGGCAAAATCAAAATGGAGATCCCTCAAGGTACGGTGGGATGAGACCACT
```

Figure 8 (continued)

```
                *          1160           *         1180          *         1200
         AGTATTCCTCGACCTGATAGAGTATCTCCGTGGAAAGTAGAGCCAGCTCTTGCTCCTCCT
         AGTATTCCTCGCCCTGATAGAGTATCCCCGTGGAACATAGAGCCAGCTCTTTCTCCTCCT

*          1220           *         1240          *         1260
         GCTTTGAGTCCTGTTCCAATGCCTAGGCCTAAGAGGCCCAGATCAAATATAGCACCTTCA
         GCTTTGAGCCCTGTACCAATGCCTAGGCCTAAGAGGCCCAGATCTAATCTAGCTTCTTCA

*          1280           *         1300          *         1320
         TCTCCTGACTCTTCGATGCTTACCAGAGAAGGTACAACTAAGGCAAACATGGACCCTTTA
         ACTCCGGACTCTTCCATGCCCATAAGGGAAGCCTCATCTAAGGCAAACATGGACCCTTTA

*          1340           *         1360          *         1380
         CCAGCAAGAGGACTTTCAAGGGTCTTGCAAGGTCAAGAATACTCGACCTTGAGGACGAAA
         CCGGCAAGTGGACTATCAAGGGTCTTGCAAGGTCAAGAATACCCGACCTTGAGAACGAAA

*          1400           *         1420          *         1440
         CATACTGAGAGTGTAGAGTGTGATGCTCCTGAGAATTCTGTTGTCTGGCAATCTTCAGCC
         CATGTTGAGAGTGTAGAATGGGATGCTCCTGAAAATTCGGTTGTCTGGCAATCCTCAACT

*          1460           *         1480          *         1500
         GATGATGATAAGGTTGACGTGGTTTCGGGTTCTAGAAGATATGGATCTAGAACTGGATG
         GATGATGACAAGGTTGATGTGATTTCAGCTTCTAGGAGATATG------AGAACTGGATA

*          1520           *         1540          *         1560
         TCCTCAGCCAGGCATGAACCTACTTACACAGATTTGCTGTCCGGCTTTGGGACTAACATA
         TCCTCAGGTAGGCATGGACCTACTTCCACGGATTTGCTTTCTGGCTTTGGGACAAACATA

*          1580           *         1600          *         1620
         GATCCATCCCATGGTCAAGGGATACCTTTTTATGACCATT---CATCATCACCTTCTATG
         GAACCACCTCACGGTCATCAGATACCTTTTTATGACCGTTATCATCACCACCTTCTGTG

*          1640           *         1660          *         1680
         GCTGCAAGAGAATCTTGAGTGATTCAGAAGGCAAGTTCGATTATCTTGCTAACCAGTGG
         GCTGCAAGGAAAATCCTCAGCGACCAGGATGGCAAGTTTGAATATCTTGCTAACCAGTGG

*          1700           *         1720          *         1740
         CAGATGATACACTCTGGTCTTTCCCTGAAGTTACATGAATCTCCTAAGGTACCTGCAGCA
         ---ATGATGCACTCAGGCCTTTCCCTGAAGTTACATGAATCTCCTAAAGTCCCTGCCGCA
```

Figure 8 (continued)

```
              *         1760          *         1780          *         1800
ACTGATGCG TCT TCCAAGGG C AT GCAATGT AA TAC GCGAATAT CT  T TT  T
T CTGATGC  TCT TTCCAAGGG TA GCAAT C  AA TAC GCGAATAT GCTT  C TCGT

*         1820          *         1840          *         1860
GGT  T T CGACTGAGAATGCTG GTGG T AACTGGCCAATACGTCCACGTGCT T G AATTAT
G AGT GA CGACTGAGAATGCTG  TGG C AACTGGCCAATACGTCCACGTGCT  T A AATTAT

*         1880          *         1900          *         1920
T TGA GAAG TGGT CAATGC TCAAGC  AA GCTCAGGCTAG G GAGCA  GT ACAAAAC A
T TTGA AGAAG  GGT------TCA ------GCTCAGGCTAG  GAGCA TGT GACAAAACGT

*         1940          *         1960          *         1980
CC  TTC A--CG TACAAGAGGAG CAGCAAAG T CAAGAGA GGGAACTGCAGGCT  TTTG
CC- T C CT CG- TACAAGAGGAG G CAGCAAAG C CAAGAGA C GGGAACTGCAGGCT T TTTG

*         2000          *         2020          *         2040
GCATTCCTCTC  C AACAAC TGAATGGGACAGA T CAAC  A TGTCTCAGAGAAACAA  T
GCATTCCTCTG GT G AACAAC G TGAATGGGACAGA T A CAAC T T TGTCTCAGAGAAACAA TT

*         2060          *         2080          *         2100
GAATGA T GCTGCGGGGCT TAC A CAGAT GCATCACCAAAGGTTCAGGA  C TTTC  GATC
GAATGA C CTGCGGGGC C TAC G CAGATG GCATCACCAAAGGTTCAGGAT CTTTC T GA C

*         2120          *         2140          *         2160
AGTC  AAAGGGTCAAAATC A ACAAA GATCATCGTGA C CA G GGA GACCATTCC  GA  TA
AGTC C AAAGGGTCAAAATC G ACAAA T GATCATCGTGA GCA A GGA C GACCATTCC C G GTTA

*         2180          *         2200          *         2220
A TAA T CC T CATCCGAA GGA TG C TCAAAC G AAAAC C AACTCA  GTAGGAG T TGCAC  AAGG
G TAA  CC  CATCCGAA  GA C G TTCAAAC G AAAAC  AACTCAT GTAGGAG C TGCAC C AAGG

*         2240          *         2260          *         2280
TTCA  AAGCAGGG A ATTGCACTTGGCCG T CAGTGGATCT T TCAAACTTCCA  AACTATG
TTCA G AAGCAGGG G ATTGCACTTGGCCG  TCAGTGGATCT C TCAAACTTCCA G AACTATG

*         2300          *         2320          *         2340
AGGAGTT  GT C G CTGA GC TGGA C AGGCTGTTTGAGTTCAATGGAGAGTTGATGGCTCCTA
AGGAGTT  GGT T A CTGA A T TGGA T AGGCTGTTTGAGTTCAATGGAGAGTTGATGGCTCCTA
```

Figure 8 (continued)

```
         *         2360         *         2380         *         2400
AGAAAGATTGGTTGATAGTTTACACAGATGAAGAGAATGATATGATGCTTGTTGGTGACG
AGAAAGATTGGCTGATAGTTTACACAGATGATGAGAATGATATGATGCTTGTTGGAGACG

*         2420         *         2440         *         2460
ATCCTTGGCAGGAGTTTTGTTGCATGGTTCGAAAAATCTTCATATACACGAAAGAGGAAG
ATCCTTGGCAGGAGTTTTGTTGCATGGTTCGTAAAATCTTCATATACACGAAAGAGGAGG

*         2480         *         2500         *         2520
TGAGGAAGATGAACCCGGGCACTTTAAGCTGTAGGACCGAGGAAGAAGCAGTTGTTGGGG
TAGGAAGATGAACCCGGGAACTTTATGCTGTAGGAACGAGGAAGAACCAGTTGTTGGGG

*         2540         *         2560         *         2580
AAGGATCAGATGCAAAGGACGCAAAGTCTGCATCAAATCCTTCATTGTCCAGCGCTGGGA
AAGGATCAGATGCAAAGGACGCGAAGTCTGCATCAAATCCTTCATTGTCCAGCGCGGGAA

ACTCTTAA
ACTCTTAA
```

Figure 8 (continued)

```
              *          20          *          40          *
MNTwt  : MASSEVSMKGNRG-GDNFSSSGFSDPKETRNVSVAGEGQKSNSTRSAAAERALDP
BnARF2 : MASSEVSMKGNRGRGFNFSSAGYSDP------TVAGEAQKTQSNRSVAAERVVDP
OsARF2 : ------------------------------------------------------GDP

60          *          80          *         100          *
MNTwt  : EAALYRELWHACAGPLVTVPRQDDRVFYFPQGHIEQVEASTNQAAEQQMPLYDLP
BnARF2 : EAALYRELWHACAGPLVTVPRQDDRVFYFPQGHIEQVEASTNQAAEQQMPLYDLP
OsARF2 : ---LYDELWHACAGPLVTVPRVGDIVFYFPQGHIEQVEASMNQVADSQMRLYDLP

120         *         140         *         160
MNTwt  : SKLLCRVINVDLKAEADTDEVYAQITLLPEANQDENATEKEAPLPPP--PRFQVH
BnARF2 : SKILCRVINVDLKAEADTDEVYAQITLLPEPVQDENSIEKEAPPPPP--PRFQVH
OsARF2 : SKLLCRVINVELKAEQDTDEVYAQVMLMPEPEQNEMAVEKTTPTSGPVQARPPVR

*         180         *         200         *         220
MNTwt  : SFCKTLTASDTSTHGGFSVLRRHADECLPPLDMSRQPPTQELVAKDLHANEWRFR
BnARF2 : SFCKTLTASDTSTHGGFSVLRRHADECLPPLDMSRQPPTQELVAKDLHASEWRFR
OsARF2 : SFCKTLTASDTSTHGGFSVLRRHADECLPPLDMTQSPPTQELVAKDLHSMDWRFR

*         240         *         260         *
MNTwt  : HIFRGQPRRHLLQSGWSVFVSSKRLVAGDAFIFLRGENCELRVGVRRAMRQQGNV
BnARF2 : HIFRGQPRRHLLQSGWSVFVSSKRLVAGDAFIFLRGENCELRVGVRRAMRQQGNV
OsARF2 : HIFRGQPRRHLLQSGWSVFVSSKRLVAGDAFIFLRGENCELRVGVRRAMRQLSNV

280         *         300         *         320         *
MNTwt  : PSSVISSHSMHLGVLATAWHAISTGTMFTVYYKPRTSPSEFIVPFDQYMESVKNN
BnARF2 : PSSVISSHSMHLGVLATAWHAISTGTMFTVYYKPRTSPSEFIVPFDQYTESVKIN
OsARF2 : PSSVISSQSMHLGVLATAWHAINTKSMFTVYYKPRTSPSEFIIPMDQYMESVKNN

340         *         360         *         380
MNTwt  : YSIGMRFKMRFEGEEAPEQRFTGTIVGIEESDPTRWPKSKWRSLKVRWDETSSIP
BnARF2 : YSIGMRFKMRFEGEEAPEQRFTGTIVGIEDSDPTRWAKSKWRSLKVRWDETTSIP
OsARF2 : YSVGMRFRMRFEGEEAPEQRFTGTIIGSENLDEV-WPESSWRSLKVRWDEFSTIP

*         400         *         420         *         440
MNTwt  : RPDRVSPWKVEPALAPPALSPVPMPRPKRPRSNIAPSSPDSSMLTREGTTKANMD
BnARF2 : RPDRVSPWKIEPALSPPALSPVPMPRPKRPRSNLASSTPDSSMRIREGSSKANMD
OsARF2 : RPDRVSPWKIEPASSPP-VNPLPLSRVKRPRPNAPPASPESPILTKEAATKVDTD
```

Figure 9

```
                        *       460         *         480         *
MNTwt   : PLPA--SGLSRVLQGQEYSTLRTKHTESVECDAPENS-VVWQSSADDDKVDVVSG
BnARF2  : PLPA--SGLSRVLQGQEYPTLRTKHMESVECDAPENS-VVWQSSTDDDKVDVISA
OsARF2  : PAQAQRSQNSTVLQGQEQMTLRSNLTESNDSDVTAHKPMMWSPSPNAAKAHPLTF

500         *         520         *         540         *
MNTwt   : SRRYGSENWMSSARHEPTYTDLLSGFGTNIDPSHGQRIPFYDH-SSSPSMPA-KR
BnARF2  : SRRY--ENWISSGRHGPTCTDLLSGFGTNIEPPHGHQIPFYDRLSSPPSVAA-RK
OsARF2  : QQRPPMDNWMQLCRRETDFKDVRSG-SQSFGDSPGFFMQNFDE--APNRLTSFKN

560         *         580         *         600
MNTwt   : ILSDSEGKFDYLANQWQMIHSGLSLKLHESPKVPAATDASLQGRCNVKYSEYPVL
BnARF2  : ILSDQDGKFEYLANQW-MMHSGLSLKLHESPKVPAASDASFQGIGNPNYGEYALP
OsARF2  : QFQDQ-GSARHFSDPYYYV-----------SPQPSLTVESSTQMHTDSK---ELHFW

*        620         *         640         *         660
MNTwt   : NGLSTENAGGNWPIRPRALNYYEEVVNAQAQAQAR-EQ---VTKQPFTIQE-ETAK
BnARF2  : RAVTTENAAGNWPIRPRALNYFEEAVHAQ-----AR-EH---VTKRPAVVQE-EAAK
OsARF2  : NGQST--VYGNSRDRPQNFRFEQNSSWLNQSFARPEQPRVIRPHASIAPVELEK

*        680         *         700         *
MNTwt   : SREGNCRLFGIPL-TNNM---NGTDSTMSQRNN--LNDAAGLTQIASPKVQDLSDQ
BnARF2  : PRDGNCRLFGIPL-VNNV---NGTDTTLSQRNN--LNDPAGETQMASPKVQDLSDQ
OsARF2  : TEGSGFKIFGFKVDTTNAPNNHLSSPMAATHEPMLQTPSSLNQLQPVQTDCIPEV

720         *         740         *         760         *
MNTwt   : SKGSKSTNDHREQGRPFQTNNPHPKDAQTKTN---SSRSCTKVHKQGIALGRSVDL
BnARF2  : SKGSKSTNDHREQGRPFPVSKPHPKDVQTKTN---SQRSCTKVQKQGIALGRSVDL
OsARF2  : SVSTAGTATENEKSG--QQAQQSSKDVQSKTQVASTRSCTKVHKQGVALGRSVDL

780         *         800         *         820
MNTwt   : SKFQNYEELVAELDRLFEFNGELMAPKKDWLIVYTDEENDMMLVGDDPWQEFCCM
BnARF2  : SKFQNYEELVTELDRLFEFNGELMAPKKDWLIVYTDDENDMMLVGDDPWQEFCCM
OsARF2  : SKFSNYDELKAELDKMFEFDGELVSSNKNWQIVYTDNEGDMMLVGDDPWEEFCSI

*        840         *         860         *
MNTwt   : VRKIFIYTKEEVRKMNPGTLSCRSEEEAVVGEGSDAKDAKSASNPSLSSAGNS
BnARF2  : VRKIFIYTKEEVEKMNPGTLCCRNEEEPVVGEGSDAKDAKSASNPSLSSAGNS
OsARF2  : VRKIYIYTKEEVQKMNSKSNAPRKD---------DSSENEKGHLPMPNKSDN-
```

Figure 9 (continued)

Vectors used for cloning

10A BJ60

Figure 11
Cloning strategy, Example 3
Example 3a(i)
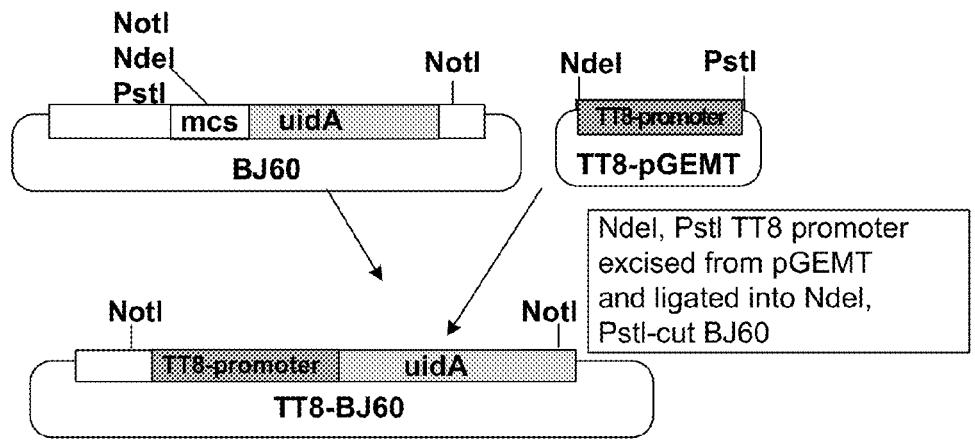
Example 3a(ii)
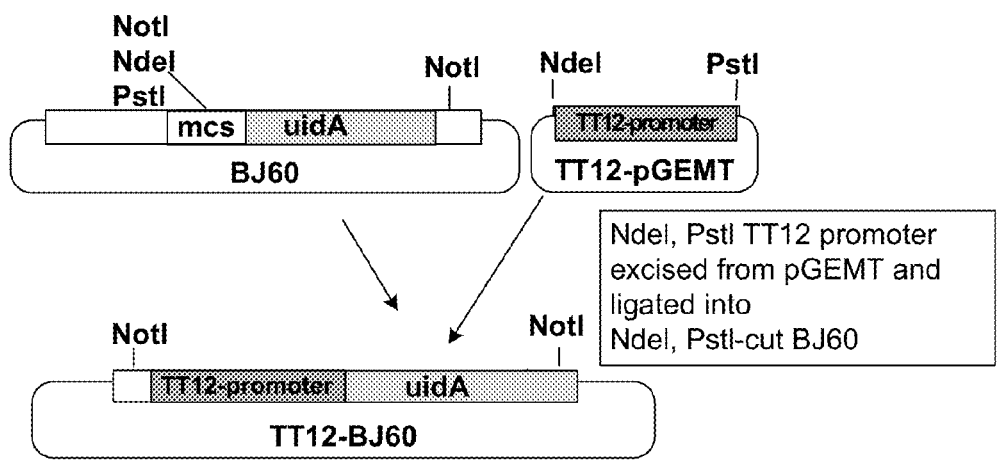
Figure 11A Example 3b(i)
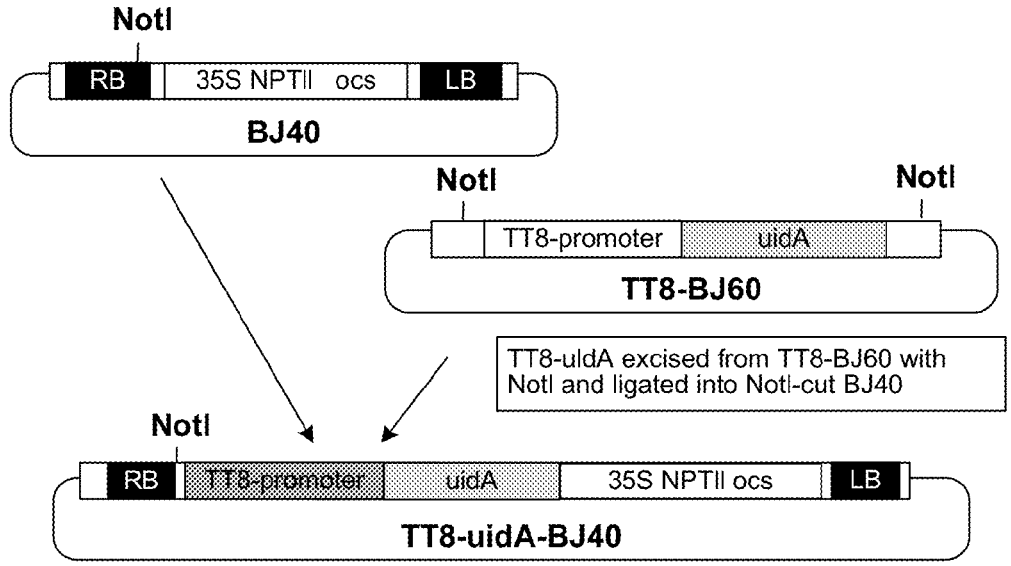
Example 3b(ii)
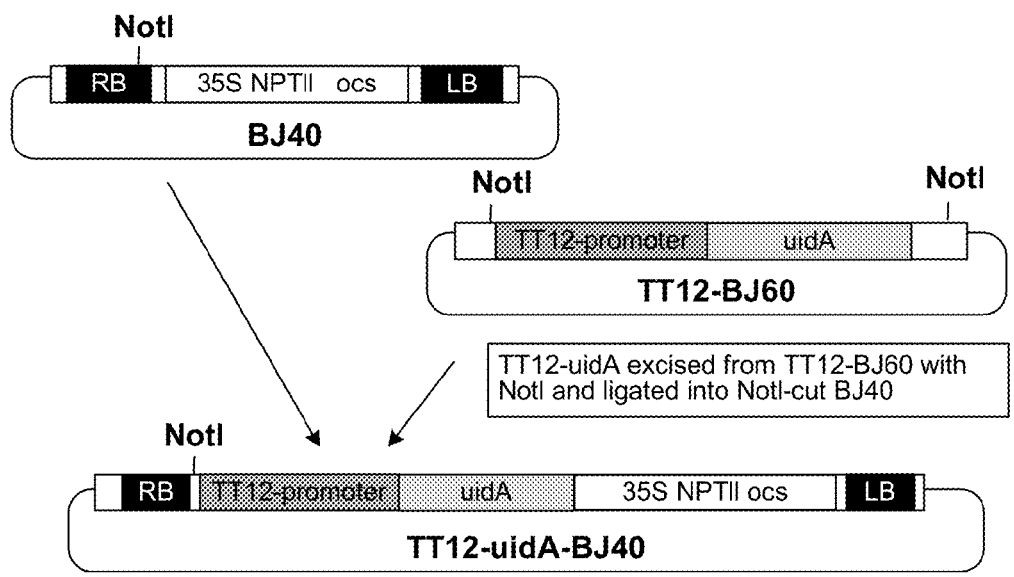
Figure 11-2
Figure 11B

TT12::uidA

Cloning strategy, Example 4

Plants transformed with the *35S::MNT* RNAi vector
Example 4

Cloning strategy, Example 5

Figure 15
Cloning strategy, Example 6
Example 6a(i)
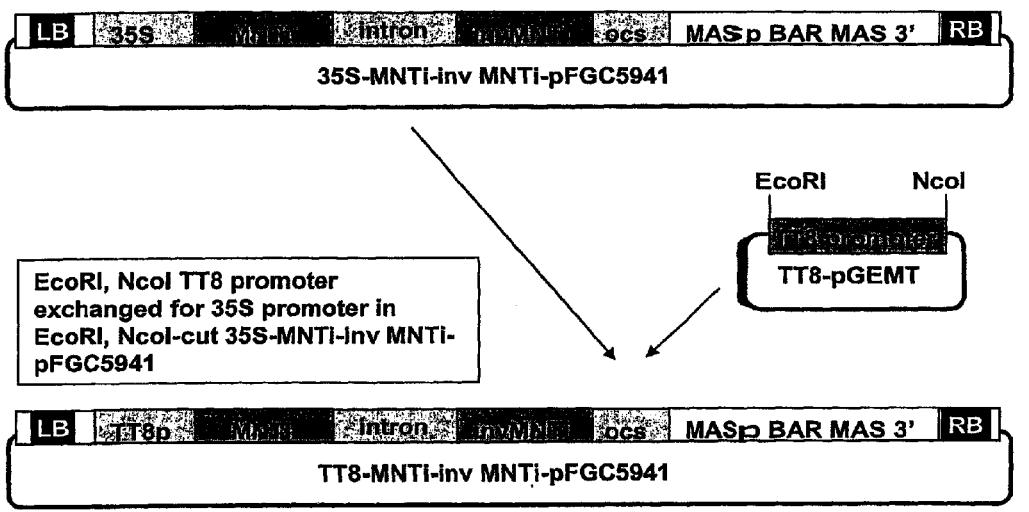
Example 6a(ii)
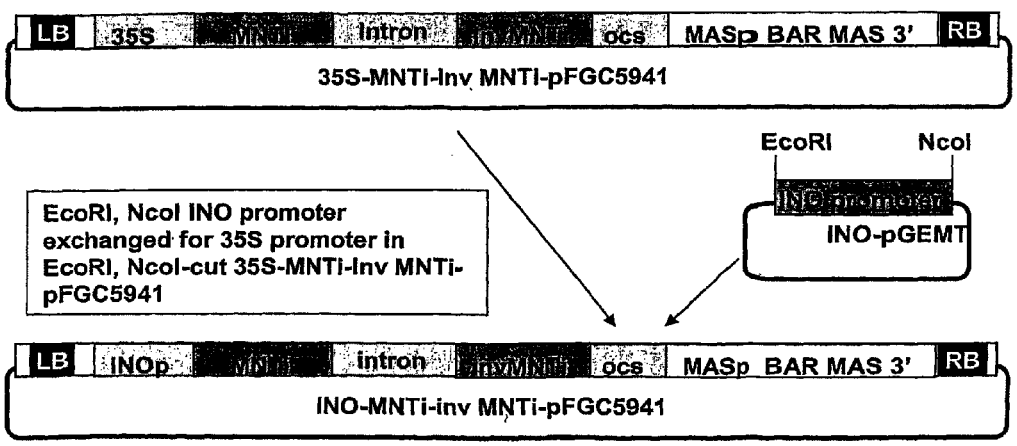

Figure 16
Cloning strategy, Example 7
Example 7a(i)
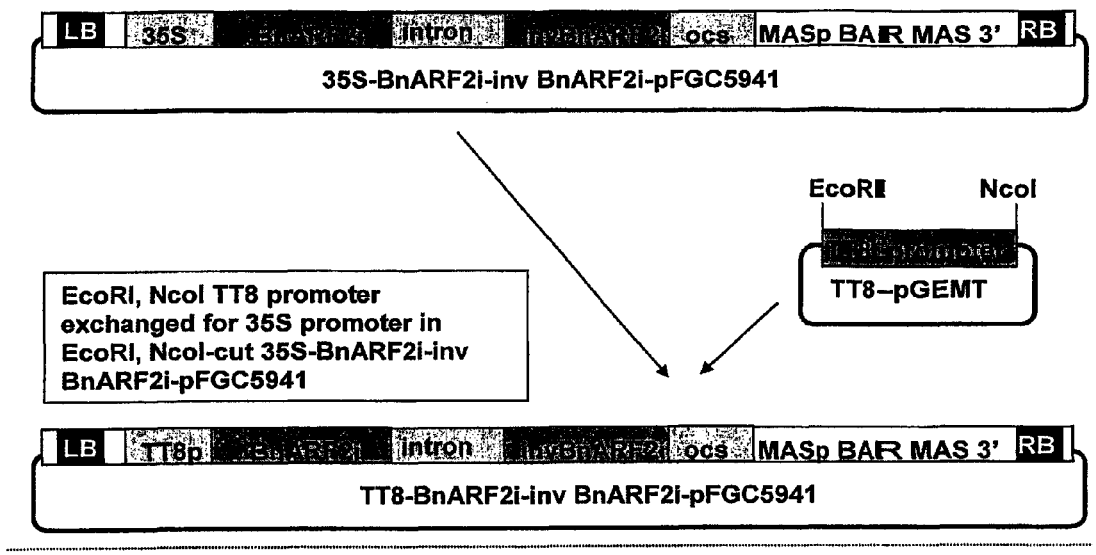
Example 7a(ii)
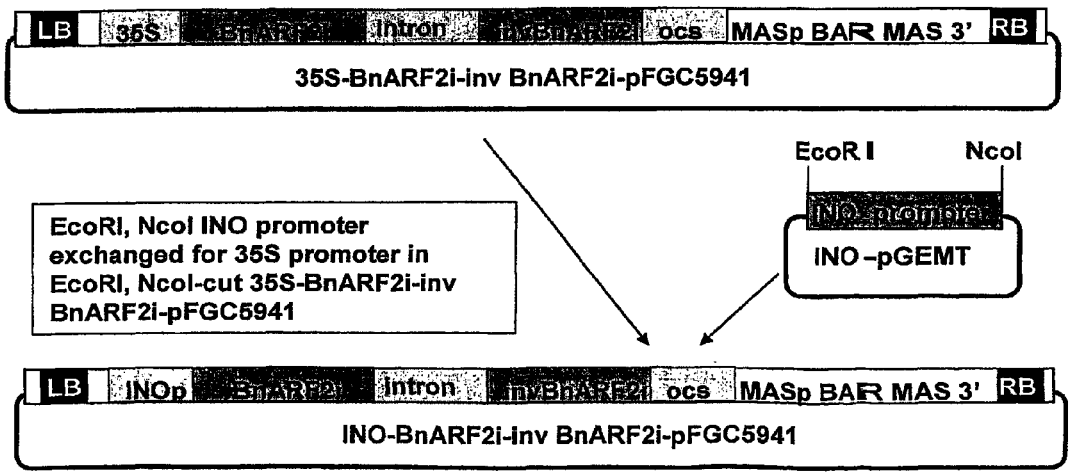

Figure 17A
Cloning strategy, Example 8, 9
Example 8a
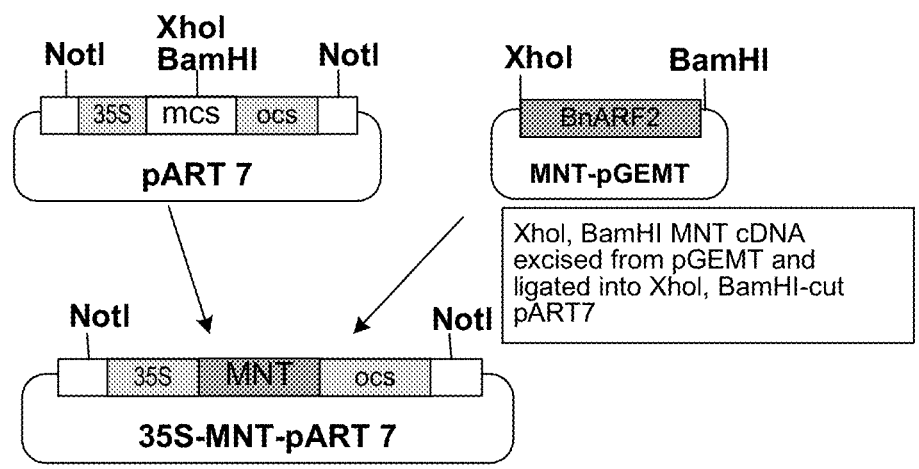
Example 9a
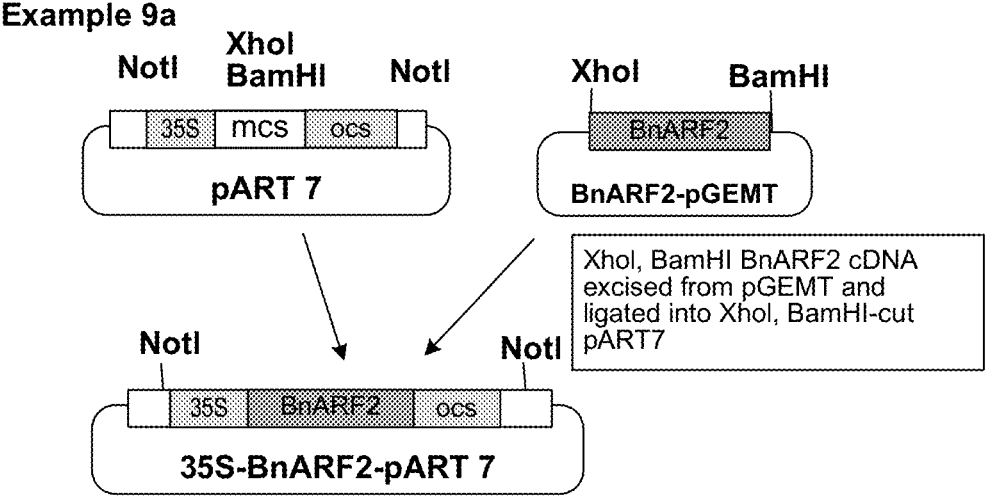
Figure 17A

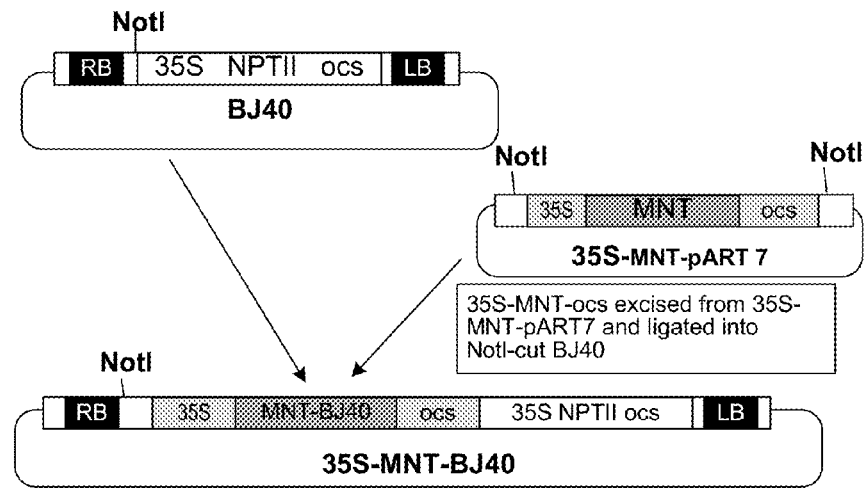
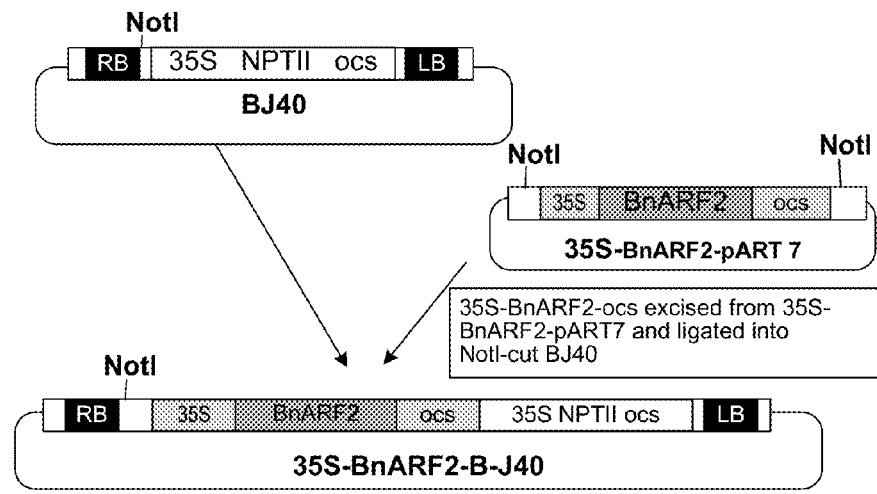
Figure 17A (continued)

Figure 17B
Analysis of wild-type plants transformed with the *35S::MNT* vector
Example 8
*35S::MNT*
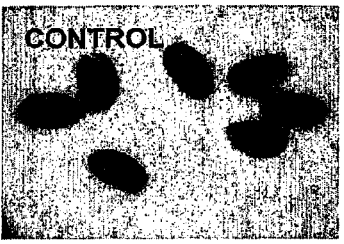
wild-type Col-3
mean wt 15.0 µg
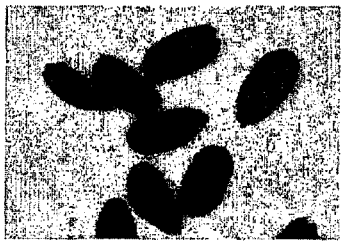
*35S::MNT* line 1
mean wt 23.1 µg
*35S::MNT* line 2
mean wt 28.7 µg
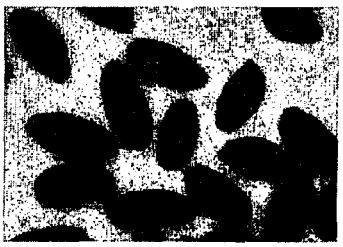
*35S::MNT* line 3
mean wt 24.6 µg
Semiquantitative RT-PCR
w.t.    35S::MNT line 1    line 2    line 3
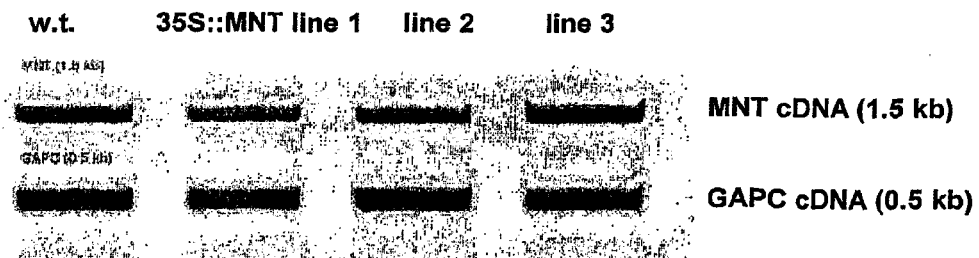
MNT cDNA (1.5 kb)
GAPC cDNA (0.5 kb)

Figure 18
Cloning strategy, Example 10
Example 10a(i)
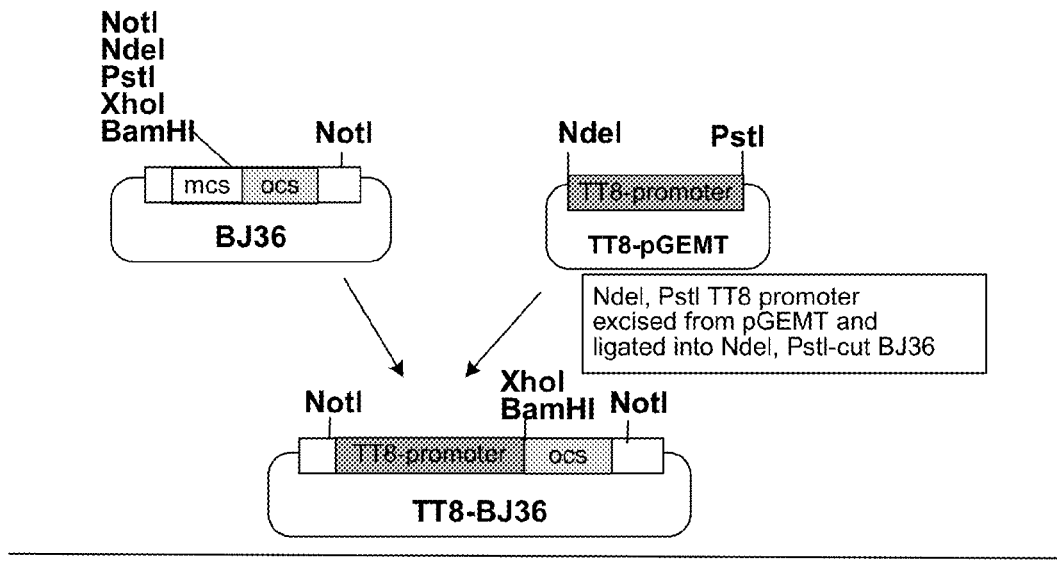
Example 10a(ii)
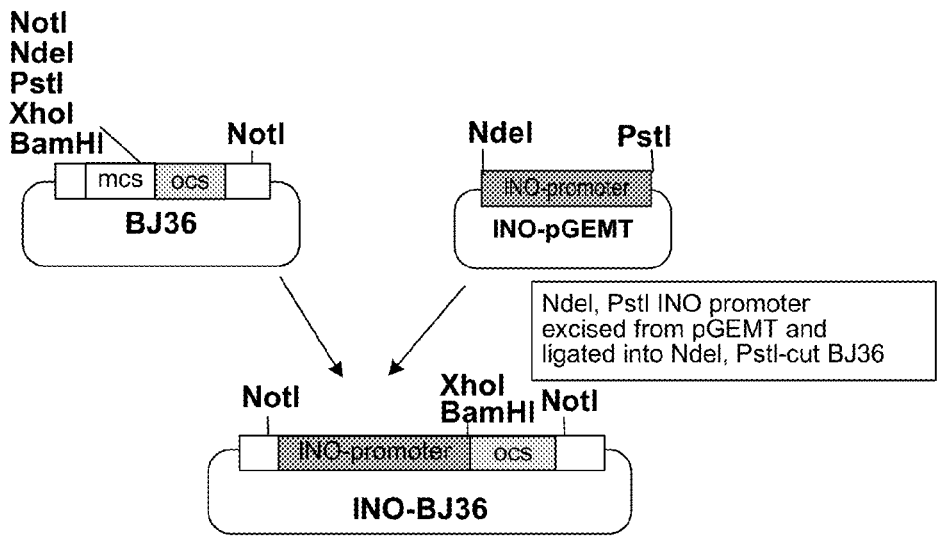
Figure 18

Example 10b(i)
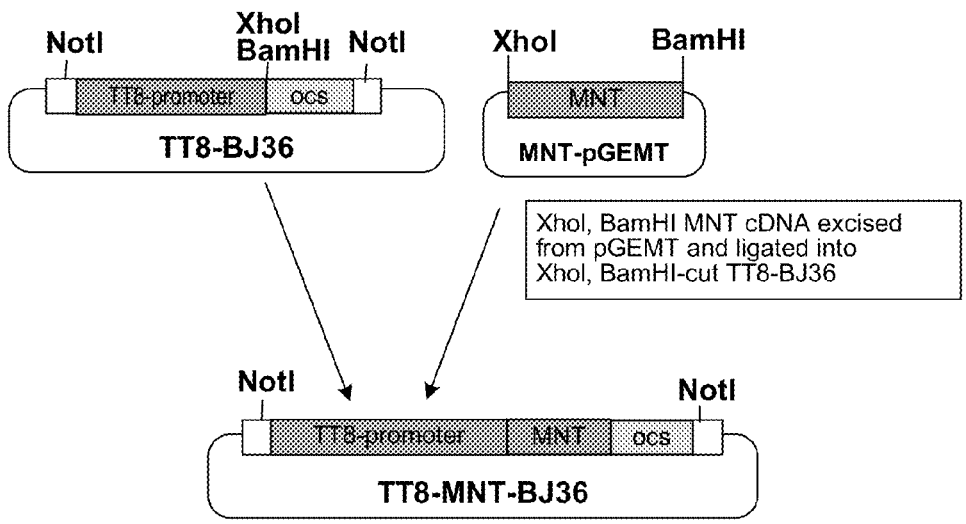
Example 10b(ii)
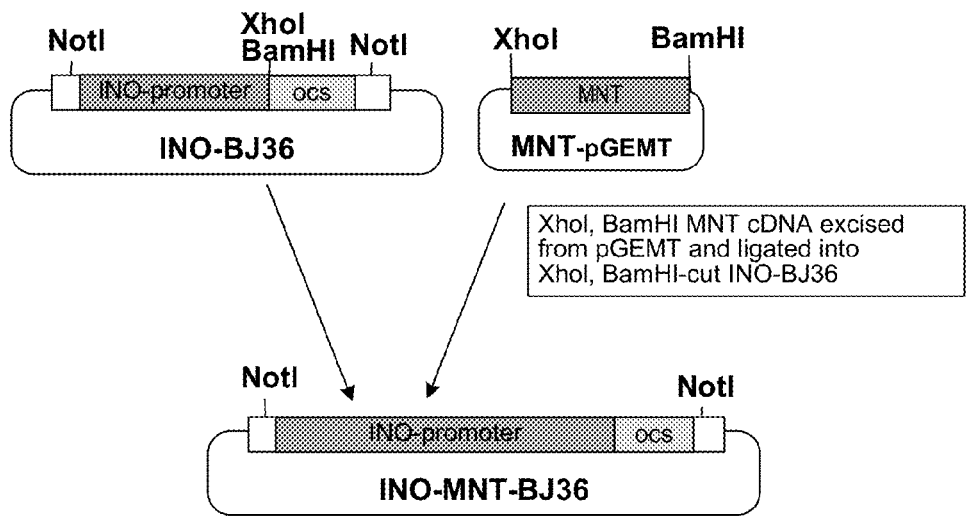
Figure 18 (continued)

Example 10c(i)
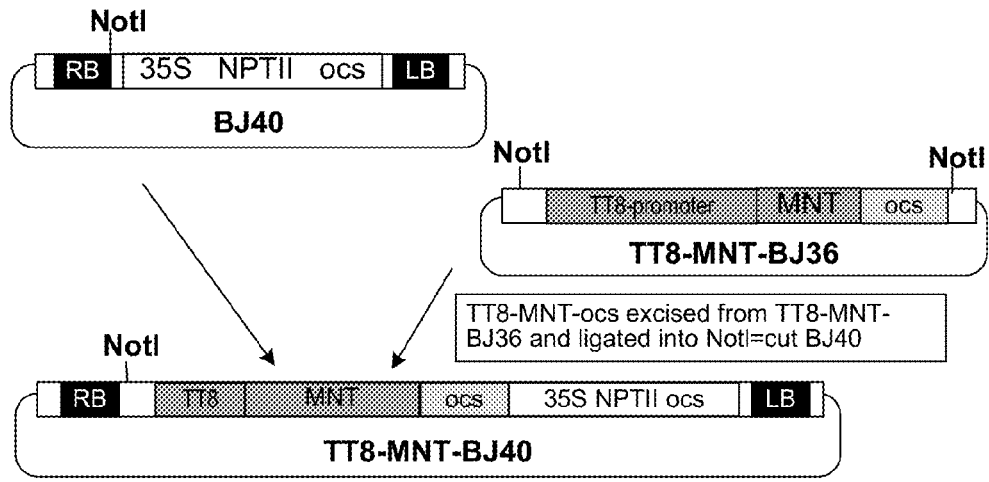
Example 10c(ii)
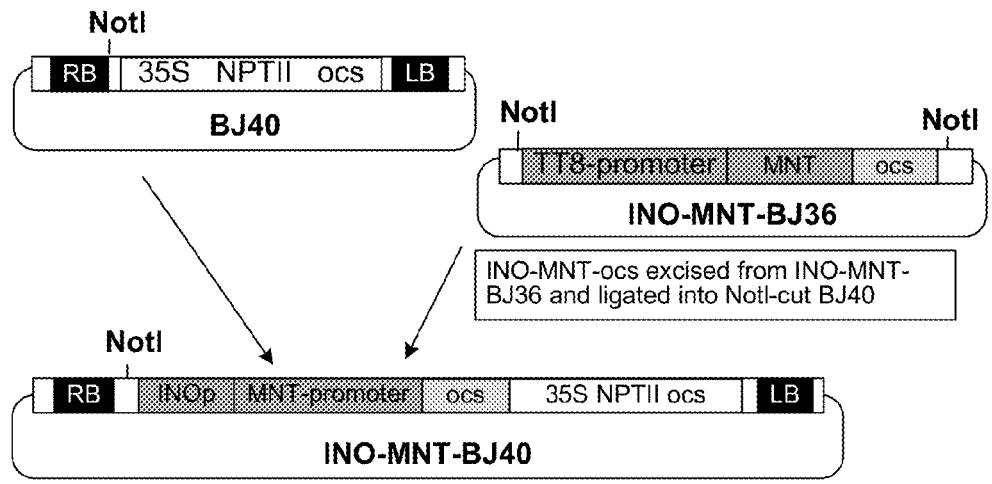
Figure 18 (continued)

Figure 19
Cloning strategy, Example 11
Example 11a(i)
NotI
NdeI
MluI
XhoI
BamHI
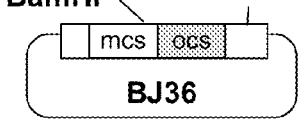
BJ36
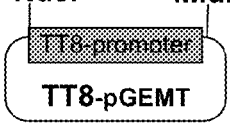
TT8-pGEMT
Ndel, MluI TT8 promoter excised from pGEMT and ligated into Ndel, MluI-cut BJ36
TT8-(Ndel MluI)-BJ36
Example 11a(ii)
NotI
NdeI
MluI
XhoI
BamHI
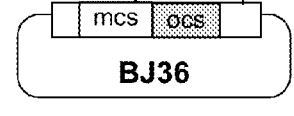
BJ36
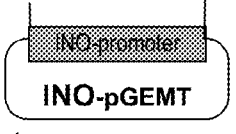
INO-pGEMT
Ndel, MluI INO promoter-excised from pGEMT and ligated into Ndel, MluI-cut BJ36
INO (Ndel MluI)-BJ36
Figure 19

Example 11b(i)
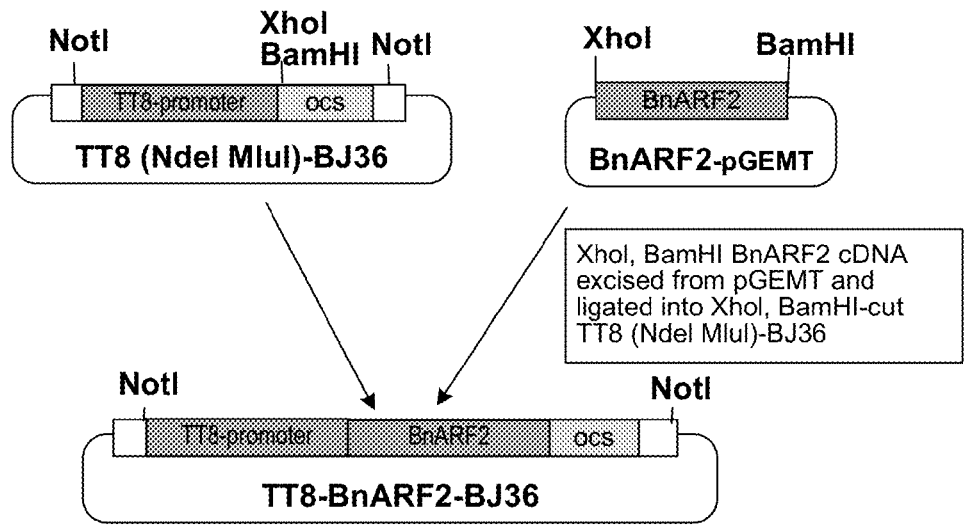
Example 11b(ii)
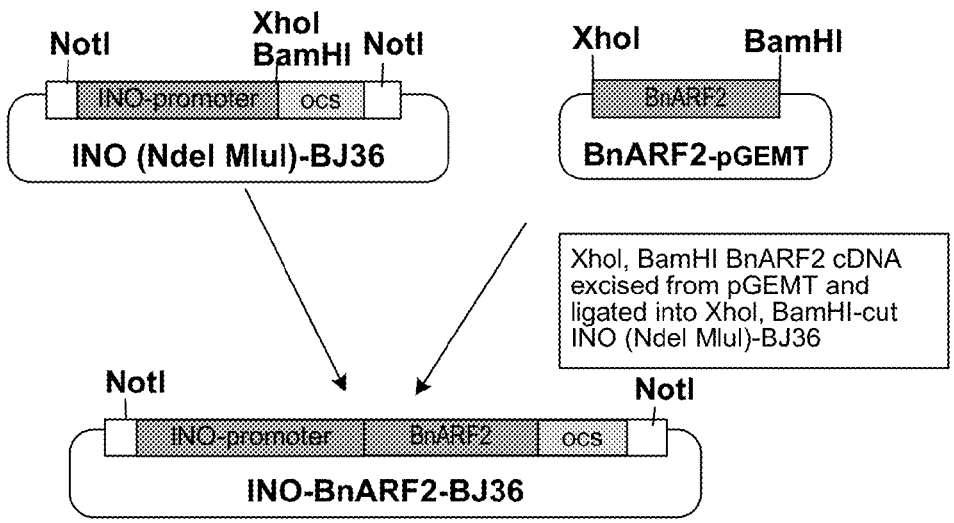
Figure 19 (continued)

Example 11c(i)
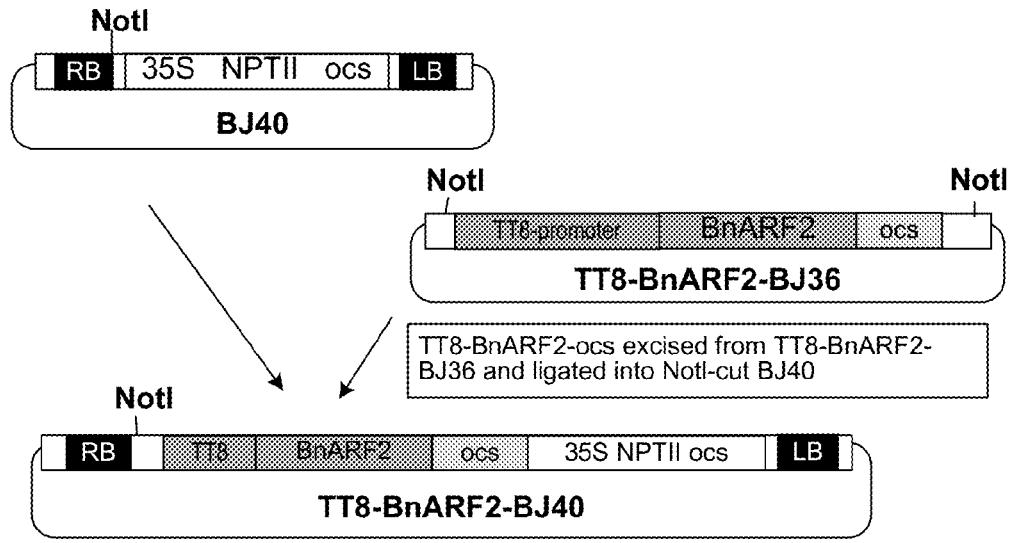
Example 11c(ii)
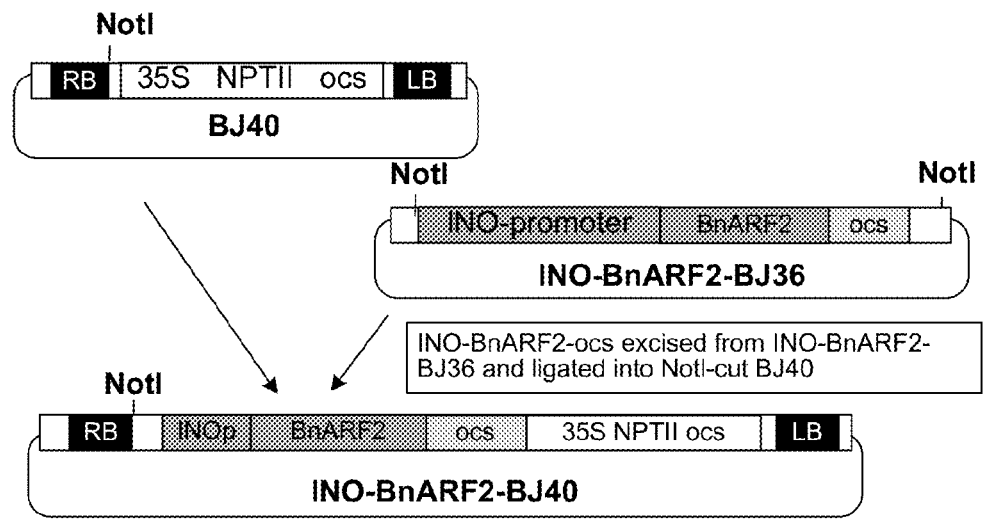
Figure 19 (continued)

Figure 20
Cloning strategy, Examples 12, 13
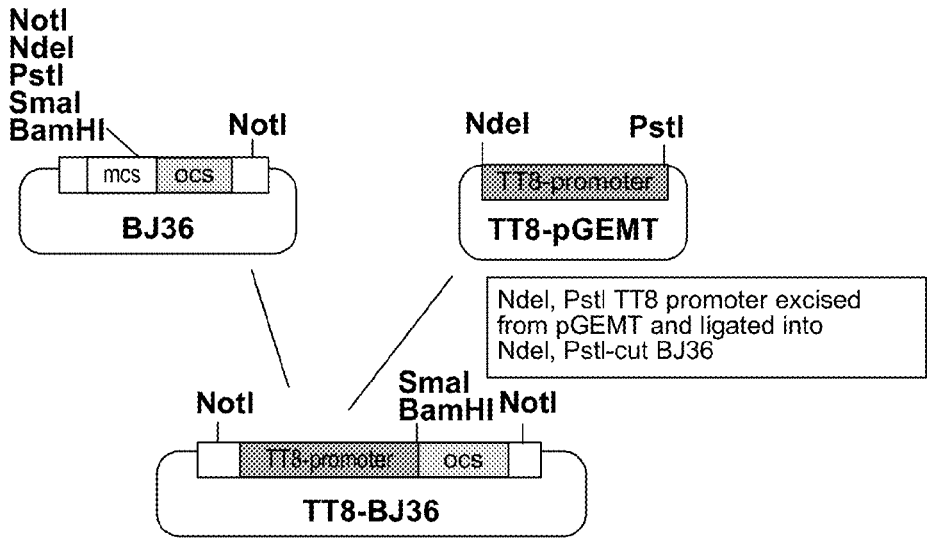
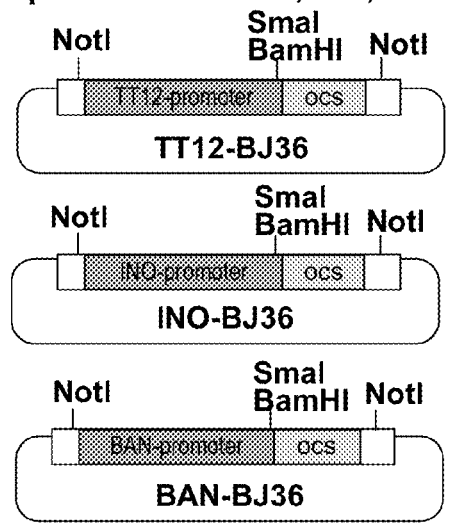
Figure 20

Examples 12b, 13b

Repeat process with IPT1, ANT, CYCB1;1 cDNAs and
TT12, INO, BAN promoters

TT8-IPT1-BJ40          INO-CYCD3;1-BJ40
TT8-ANT-BJ40           INO-IPT1-BJ40
TT8-CYCB1;1-BJ40       INO-ANT-BJ40
TT12-CYCD3;1-BJ40      INO-CYCB1;1-BJ40
TT12-IPT1-BJ40         BAN-CYCD3;1-BJ40
TT12-ANT-BJ40          BAN-IPT1-BJ40
TT12-CYCB1;1-BJ40      BAN-ANT-BJ40
                       BAN-CYCB1;1-BJ40

Figure 21A
Expression cassettes to increase seed size
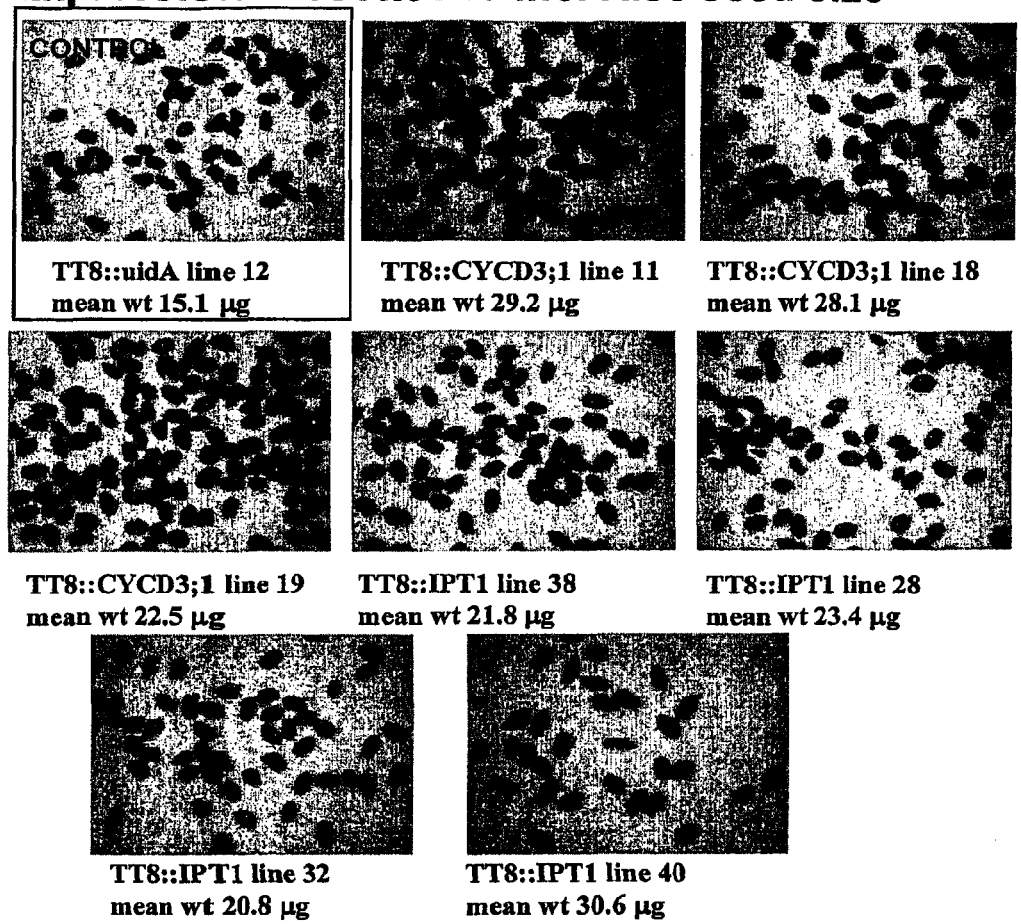
TT8::uidA line 12
mean wt 15.1 µg
TT8::CYCD3;1 line 11
mean wt 29.2 µg
TT8::CYCD3;1 line 18
mean wt 28.1 µg
TT8::CYCD3;1 line 19
mean wt 22.5 µg
TT8::IPT1 line 38
mean wt 21.8 µg
TT8::IPT1 line 28
mean wt 23.4 µg
TT8::IPT1 line 32
mean wt 20.8 µg
TT8::IPT1 line 40
mean wt 30.6 µg
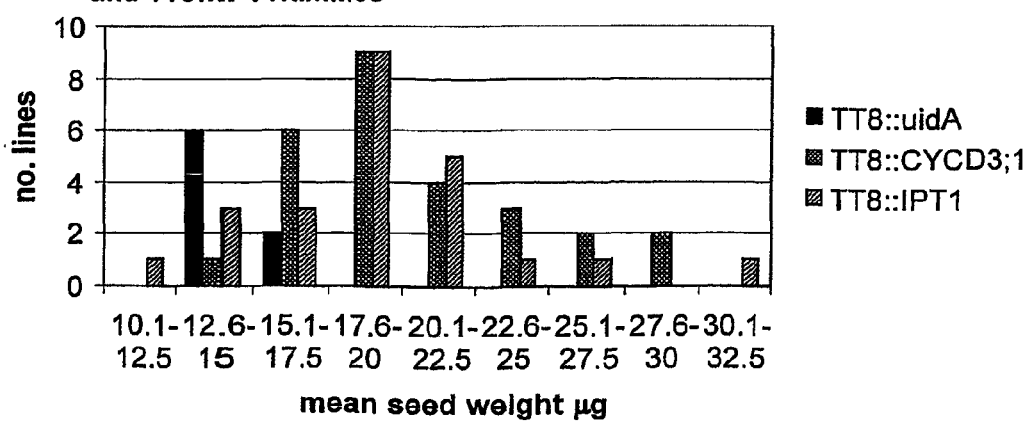
Distribution of seed weights in TT8::uidA (control), TT8::CYCD3;1, and TT8::IPT1 families

Figure 21B
Expression cassettes to increase seed size
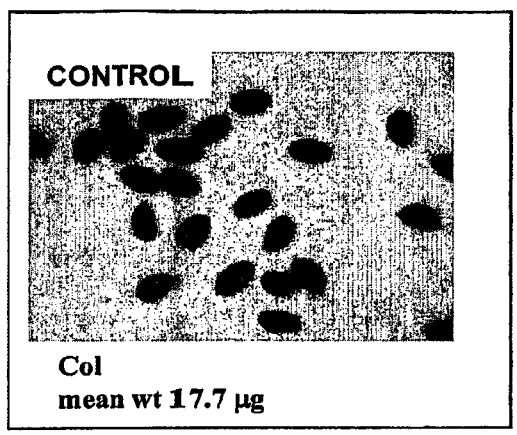
Col
mean wt 17.7 µg
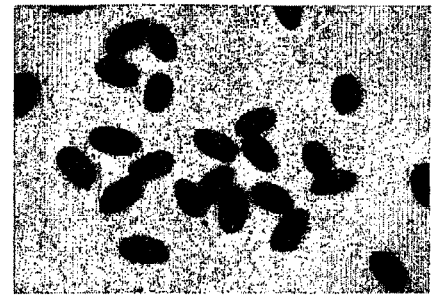
BAN::CYCD3;1 line 1
mean wt 23.9 µg
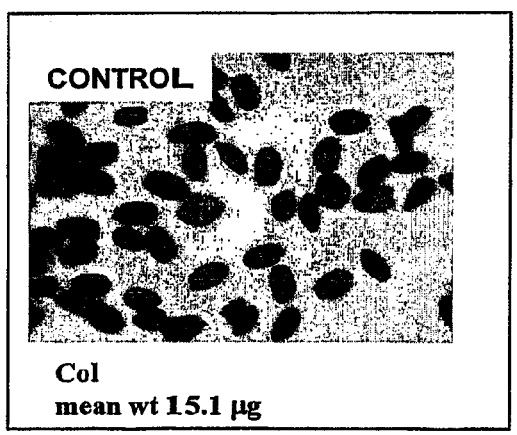
Col
mean wt 15.1 µg
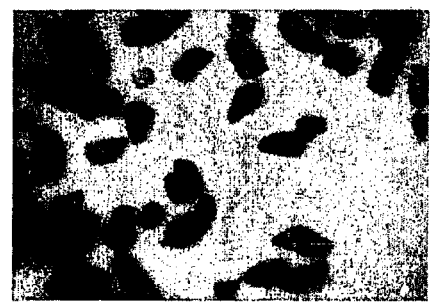
INO::IPT1 line 9
mean wt 23.1 µg Cloning strategy, Example 14

Figure 23
Cloning strategy, Example 15
Example 15a
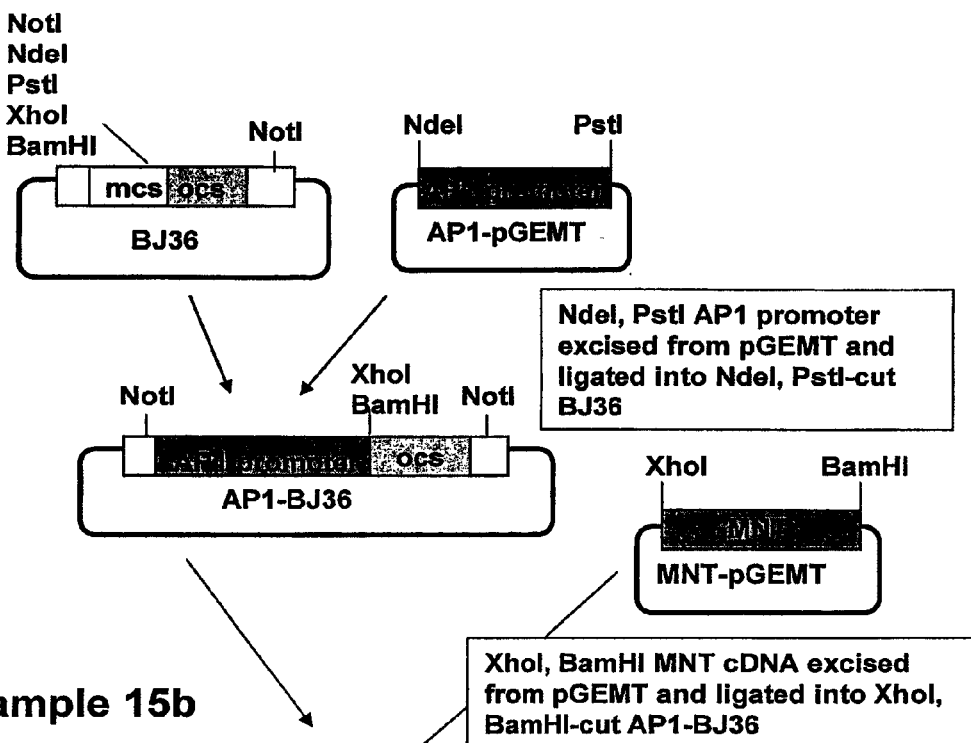
Example 15b
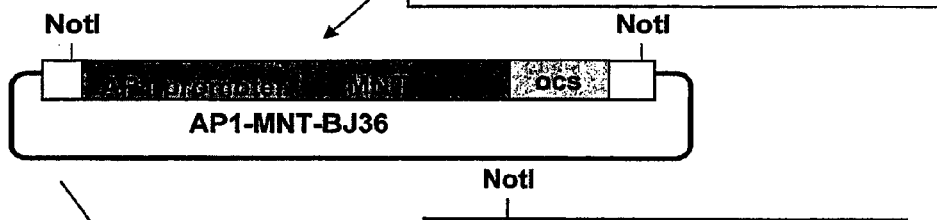
Example 15c
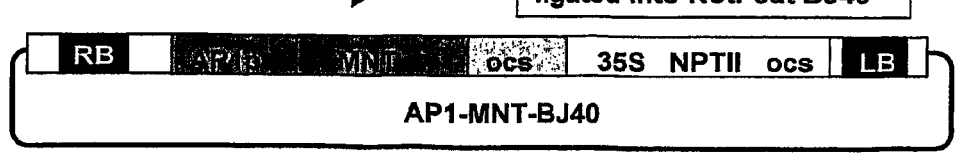

Figure 24
24A Wild-type vs *mnt-1* plants
w.t.
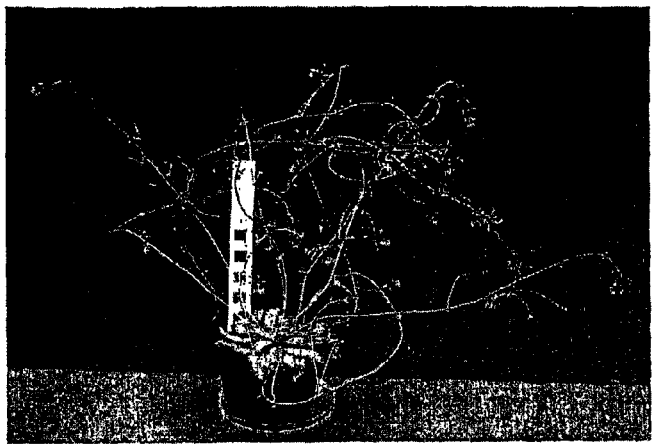
*mnt-1*
24B Wild-type vs *mnt-1* stems, transverse sections
w.t.
*mnt-1*
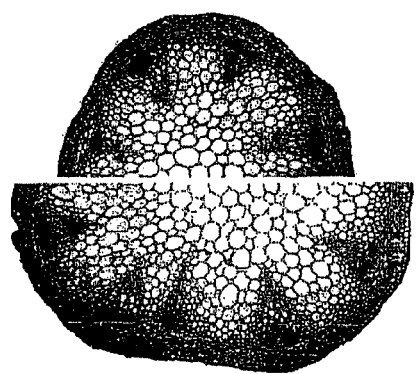
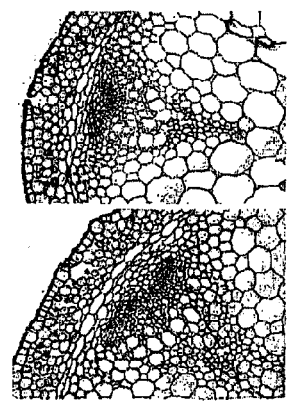

Cloning strategy, Example 18

METHODS FOR MODULATING CELL PROLIFERATION IN THE SEED COAT AND/OR INTEGUMENT

CROSS-REFERENCE TO RELATED APPLICATIONS

This application is a Continuation Application of U.S. patent application Ser. No. 10/591,418, filed Jul. 10, 2007, which is a National Stage application of International Patent Application No. PCT/GB2005/000857, filed Mar. 7, 2005, which claims the benefit of priority to United Kingdom Patent Application No. GB 0405093.6, filed Mar. 5, 2004, United Kingdom Patent Application No. GB 0406275.8, filed Mar. 19, 2004, and United Kingdom Patent Application No. GB 0406729.4, filed Mar. 25, 2004, the disclosures of each of which are herein incorporated by reference in their entireties.

FIELD OF THE INVENTION

The present invention relates particularly, though not exclusively, to methods for modifying characteristics such as seed size in plants, especially flowering plants, and to plants and reproducible plant material produced by the methods. The invention also relates to nucleic acid constructs for use in such methods, as well as to modified plants and reproducible plant material per se.

BACKGROUND OF THE INVENTION

The seeds industry can be split into two high-value, commercial sectors: seeds for field crops such as corn, oil seeds, sugar beet and cereals, and vegetable and flower seed. The scientific improvement of crop plants has gone through a succession of innovations leading to the development of hybrid varieties for many crops and, most recently, to the introduction of genetically enhanced crops. The worldwide commercial seeds market is valued at around $30 billion (International Seed Federation).

1. Importance of Seed Size

Yield in crop plants where seed is the harvested product is usually defined as weight of seed harvested per unit area (Duvick, 1992). Consequently, individual seed weight is regarded as a major determinant of yield. Increasing seed size is desirable because it may increase total yield (Reynolds et al., 2001). There is also evidence that seed size (weight) is positively correlated with a number of components of 'seed quality' such as the percentage of germination (Schaal, 1980; Alexander and Wulff, 1985; Guberac et al, 1998); time to emergence (Winn, 1985; Wulff, 1986); durability (survival under adverse growing conditions) (Krannitz et al, 1991; Manga and Yadav, 1995); and growth rate (Marshall, 1986). Seed quality is an important factor in the cost of production of commercial seed lots since these must be tested before sale. Consequently, increasing total seed weight, even without increases in total seed yield, may have economic benefits through improvements in seed quality. Conversely, decreasing seed size may also be desirable in some circumstances, for example by facilitating water uptake required for germination (Harper et al., 1970), or in plants grown for their fruit.

Modification of seed size is also likely to improve yield through increasing the 'sink strength' of the seed (i.e. its capacity to demand nutrients from the seed parent), or increasing the period in which the seed is acting as a strong sink. It is well established that the demands of sink organs such as seeds have significant control over the rate of photosynthesis and the movement of photoassimilates from source to sink tissues (Patrick and Offler, 1995; Paul and Foyer, 2001). In wheat, the seed parent can supply more nutrients than developing seeds are able to demand for the first 15-20 days after pollination (Austin, 1980). Therefore modifications that enable seeds to draw nutrients earlier in development, for example by speeding up seed growth, will allow seeds to capture resources that would otherwise be wasted. An 'improved source-sink balance permitting higher sink demand during grainfilling' has also been proposed as a method for increasing yield in wheat (Reynolds et al., 2001).

2. Composition of Seeds

Mature seeds of flowering plants consist of three components: the seed coat, which is of exclusively maternal origin; and the two fertilization products, embryo and endosperm, which have maternal and paternal genetic contributions. Seeds develop from fertilized ovules. Ovule development has been described for many species (Bouman, 1984), including *Arabidopsis thaliana* (Robinson-Beers et al., 1992; Schneitz et al., 1995). The main structures of the mature ovule are: the embryo sac, which contains the female reproductive cells (egg and central cell); the nucellus, which surrounds the embryo sac at least partially; and the inner and outer integuments, which envelop the embryo sac and nucellus. After fertilization the embryo and nutritive endosperm develop inside the embryo sac while the integuments differentiate into the seed coat, which expands to accommodate the growing endosperm and embryo.

Most monocotyledonous plants, e.g. cereals including maize, wheat, rice, and barley (see Esau, 1965), produce albuminous seeds—that is, at maturity they contain a small embryo and a relatively massive endosperm. Most dicotyledonous plants, e.g. *Brassica napus*, (oil seed rape, canola), soybean, peanut, *Phaseolus vulgaris* (e.g. kidney bean, white bean, black bean) *Vicia faba* (broad bean), *Pisum sativum* (green pea), *Cicer arietinum* (chick pea), and *Lens culinaris* (lentil), produce exalbuminous seeds—that is, the mature seeds lack an endosperm. In such seeds the embryo is large and generally fills most of the volume of the seed, and accounts for almost the entire weight of the seed. In exalbuminous seeds the endosperm is ephemeral in nature and reaches maturity when the embryo is small and highly immature (usually heart/torpedo stage). Commonly embryo development depends on the presence of the endosperm, which is generally accepted to act as a source of nutrition for the embryo.

3. Control of Seed Size

Seed size control can be viewed from the perspective of (1) 'development'—the extent of cell division and expansion in one or more seed components (e.g. Reddy and Daynard, 1983; Swank et al, 1987; Scott et al., 1998; Garcia et al., 2003) or (2) 'metabolism'—metabolic activity and transport of nutrients within the seed and between the seed and seed parent (e.g. Weber et al., 1996, 1997). Development and metabolism are interdependent: for example, invertase activity (involved in hexose transport) at the boundary of maternal tissues and endosperm or embryo sac is required for endosperm proliferation in maize (Cheng et al., 1996), and high invertase activity is correlated with increased cell numbers in broad bean seed coat (Weber et al., 1996), legume embryos (Weber et al., 1997), and barley endosperm (Weschke et al., 2003). Our present investigations focus on the developmental aspects of seed size control, although it can be assumed that changes to cell division/expansion in the seed will also be correlated with changes in metabolic activity and nutrient flow.

3a. Endosperm-LED Seed Growth

Several studies show a correlation between endosperm growth and final seed size, for example in maize (Lin, 1984; Jones et al., 1996), and even in the dicot *Arabidopsis thaliana*, which has an ephemeral endosperm (Scott et al., 1998; Garcia et al., 2003). Work in our laboratory has shown that overproliferation of the endosperm leads to large seeds with large embryos, while inhibition of endosperm proliferation produces small seeds with small embryos. We have manipulated endosperm proliferation and seed size using a variety of methods, including modifications to the ratio of paternally to maternally inherited chromosomes in the endosperm, cytosine methylation status of the parents contributing to the seed, and use of the fis3/fie mutation (Scott et al., 1998; Adams et al., 2000; Vinkenoog et al., 2000). In these experiments we considered the resultant changes to seed growth to be 'endosperm-led', and effects on the embryo and the seed coat to be indirect. Some of our experiments specifically ruled out a direct effect on seed coat growth because the seed parent was wild-type and only the fertilization products were directly modified: for example, in the case of wild-type diploid seed parents crossed with tetraploid pollen parents, which produce large seeds (Scott et al., 1998), or wild-type seed parents crossed with pollen parents hypomethylated by a DNA METHYLTRANS-FERASE 1 antisense construct, which produce small seeds (Adams et al., 2000). Similarly, Garcia et al. (2003) described the haiku mutants of *Arabidopsis thaliana*, which produce small seeds due to early arrest of endosperm proliferation. The authors also noted a failure of cell elongation after fertilization in the integuments of haiku mutants, and concluded this was an indirect effect of limited endosperm growth.

3b Role of Integuments/Seed Coat in Establishing Seed Size

Alonso-Blanco et al. (1999) investigated seed size in wild-type plants of two *Arabidopsis thaliana* accessions, Cvi and Ler: seeds of the former weigh 80% more than seeds of the latter and are 20% longer. In both accessions, the authors found that 'seed coat and endosperm growth preceded embryo growth, determining the overall final length of the embryo and the seed'. They did find that the outer layer of the mature seed coat has more cells in Cvi than Ler, but did not investigate or comment on whether these extra cells were formed before or after fertilization. Moreover, the authors' inspection of mature unfertilized ovules showed that ovules in Ler were slightly longer than in Cvi, and therefore the authors concluded that 'ovule size differences could not account for the final Ler/Cvi seed size variation'. Their overall major conclusion was that 'the larger size of Cvi seeds compared with Ler is mainly because of the faster and prolonged growth of the integuments and the endosperm' (i.e. after fertilization); they did not address the question of whether this growth was led by the integuments or the endosperm. The authors suggested that the final cell number and size in the seed coat 'may be determined during ovule development', but significantly, there was no suggestion that a larger number of integument cells before fertilization was responsible for a larger final seed size.

Garcia et al. (2005) examined crosses between *Arabidopsis* mutant or transgenic plants that produce small seeds because of the inhibition of either endosperm growth or integument/seed coat growth. These authors proposed a model in which seed size is determined by a reciprocal interaction between endosperm growth and elongation of integument/seed coat cells. They also reported that genotypes with fewer cells in the integument compensate by increasing cell elongation. The authors concluded, 'The final cell number in the integument [seed coat] is balanced by cell elongation and does not influence the size of the seed.'

Jofuku et al. (2005) and Ohto et al. (2005) reported that mutations in the APETALA2 (AP2) gene increase seed size; Jofuku et al. (2005) also found that suppression of AP2 activity through antisense or sense cosuppression had the same effect. ap2 mutant seeds have seed coat abnormalities including large and irregular outer integument cells, lack of mucilage, and hypersensitivity to bleach; and the increase in seed size was found to be a mainly (Jofuku et al., 2005) or wholly (Ohto et al., 2005) maternal effect. However, neither paper investigated any possible correlation between (1) seed size and (2) cell number or any other aspect of integument/seed coat morphology in ap2 mutants or transgenics.

Weber et al. (1996) compared growth of the seed coat in large- and small-seeded genotypes of *Vicia faba* (broad bean). They found that large-seeded genotypes contained more cells in the seed coat at 9 days after pollination, but cell numbers in the two genotypes were similar at 4 days after pollination. Therefore the number of cells in the integuments before fertilization could not be a factor in final seed size.

4. Relevant Patent Publications (i) Fischer and Mizukami (2003), 'Methods for Altering Organ Mass in Plants', US Patent Application 20030159180

Mutations in the AINTEGUMENTA (ANT) gene of *Arabidopsis thaliana* prevent formation of the integuments (Klucher et al., 1996; Baker et al., 1997). Mizukami and Fischer (2000) describe the phenotype of *Arabidopsis thaliana* plants over-expressing the wild-type ANT gene under the control of the constitutive 35S promoter. Ectopic ANT expression increases the size of many plant organs including seeds, as well as causing male sterility through failure of anther dehiscence. Most of the transgenic plants are also female sterile 'because of abnormally extended proliferation of the chalazal nucellar cells'. However weak overexpressers could generate seeds after hand-pollination with wild-type pollen. 'The enlarged 35S::ANT fruit included T2 seeds that were larger than normal (not shown in the application), because of enlarged embryos.' The size of unpollinated ovules, and the number or size of cells in the integuments/seed coat, were not investigated or discussed. The large seed size of 35S::ANT seeds was attributed only to size of the nucellus and embryo. US patent application no. 20030159180 describes uses of a modified ANT polypeptide for altering the size of plant organs including seeds. It was reported that the transgenic plants had varying degrees of fertility that were not correlated with organ size. There was no investigation of the effect of expressing the modified ANT polypeptide on integument or seed coat growth.

(ii) Jofuku and Okamuro (2001), 'Methods for Improving Seeds', U.S. Pat. No. 6,329,567

Mutations in the APETALA2 (AP2) gene increase seed size (Okamuro and Jofuku, 1997). The mutations have a maternal effect on seed size but the only phenotype described for the integument/seed coat in apt mutants is that the cells of the outer layer of the seed coat are enlarged with an irregular shape, along with some other morphological abnormalities (Jofuku et al., 1994). U.S. Pat. No. 6,329,567 describes methods of modulating seed mass using AP2 transgenes, but this patent does not assess any effect of the transgenes on the integuments or seed coat.

(iii) Lepiniec et al. (2003), 'Regulating Nucleic Acid for Expressing a Polynucleotide of Interest Specifically in the Endothelium of a Plant Seed and Uses Thereof', WO 03/012106 A2

The BANYULS (BAN) gene is expressed exclusively in the inner layer of the inner integument (this layer is also called the endothelium) in early seed development (pre-globular stage) (Devic et al., 1999). International patent application WO 03/012106 A2 describes use of the BAN promoter to drive expression of various genes specifically in the testa (the seed coat layer derived from the inner integument). The authors propose uses such as modifying the tannin or fibre composition, or the hormonal equilibrium, but no relevant expression cassettes were reported or described. Modification of seed size is also proposed but only in the context of reducing or ablating seeds in fruit crops. A BAN promoter::BARNASE construct was shown to ablate the endothelium.

(iv) Zinselmeier et al. (2000), 'Regulated Expression of Genes in Plant Seeds', WO00/63401

This patent application relates to expression of genes such as ipt that 'affect metabolically effective levels of cytokinins in plant seeds, as well as in the maternal tissue from which such seeds arise, including developing ears, female inflorescences, ovaries, female florets, aleurone, pedicel, and pedicel-forming regions', and to transgenic plants with enhanced levels of cytokinin that exhibit 'improved seed size, decreased tip kernel abortion, increased seed set during unfavorable environmental conditions, and stability of yield'. A nucellus promoter (nucellus is the maternal tissue surrounding the embryo sac and enclosed within the integuments) is among those suggested for driving expression cassettes, but integuments are not specifically mentioned in the patent application, nor were any maternal tissue-specific expression cassettes described. The disclosure of this patent application is particularly concerned with maize.

(v) Scott (2002), 'Modified Plants', WO/0109299

This patent application relates to methods for controlling endosperm size and development through use of an anti-sense DNA METHYLTRANSFERASE 1 gene that reduces cytosine methylation. As described in WO01/09299, and in Section 3a, above, modification to the cytosine methylation status of the seed or pollen parent alters seed size by altering the rate and extent of endosperm proliferation. Therefore the disclosure of this patent application relates exclusively to 'endosperm-led' seed growth.

In summary, documents in the prior art do not include an understanding that altering the size of integuments specifically through increasing the number of cells before fertilization could affect seed size after fertilization. A small number of published papers and patent applications touch on a possible relationship between seed coat size and seed size but do not make a link between (1) integument growth pre-fertilization and (2) final seed size.

5. Integument-LED Seed Growth

We were surprised therefore to discover in our laboratory a mutant, termed the mnt-1 mutant, that produces enlarged seeds through a primary effect on the integuments. Specifically, we observed that the seed cavity (i.e. the space within the post-fertilization embryo sac) is longer than normal giving the embryo more space to grow as a result of an increase in cell number in the integument. This was particularly surprising in view of the earlier research mentioned in section 3a above which indicated that changes in seed growth were 'endosperm-led'. It was also surprising in view of the work of Alonso-Blanco et al (1999) mentioned in section 3b above which did not suggest that an increase in number of integuments cells led to an increase in seed size; and also in view of the work of Weber et al 1999 who found similar numbers of cells in the seed coat in small and large-seeded genotypes of broad bean soon after fertilization; and also in view of the work of Garcia et al. (2005) who claimed that 'The final cell number in the integument [seed coat] is balanced by cell elongation and does not influence the size of the seed'; and also in view of the work of Jofuku et al. (2005) and Ohto et al. (2005) who found a maternal effect of the ap2 mutation on seed size but did not report a correlation between cell number in the integuments or in the seed coat and final seed size.

6. Increased Stem Diameter in mnt-1 Mutants

Increased stem diameter is also desirable in agriculture, as it may lead to an increase in plant biomass, which may in turn increase yield (Reynolds et al., 2001). Increased stem diameter and biomass are also desirable in certain crops such as trees and vegetables. Thicker stems are also desirable because this trait increases resistance to lodging, a serious problem that reduces yields in crops including cereals (Zuber et al., 1999), soybean (Board, 2001), and oilseed rape (Miliuviene et al., 2004). A further aspect of the mnt-1 mutant phenotype is increased diameter of the stems.

DEFINITIONS

The following non-limiting definitions of terms used in this specification are given by way of explanation.

"Function" when used in relation to a gene embraces both the operation of that gene at a molecular level as well as the downstream effects of expression of the gene which may result in phenotypic changes.

"Nucleic acid sequence": refers to a single or double-stranded polymer of deoxyribonucleotide or ribonucleotide bases read from the 5' to the 3' end, including chromosomal DNA, plasmids, infectious polymers of DNA or RNA and DNA or RNA that performs a primarily structural role.

"Orthologues": refers to genes derived from a common ancestral gene and which are found in different species as a result of speciation. Genes found in different species are considered orthologues when their nucleotide sequences and/or their encoded protein sequences have a high percentage of sequence identity and/or similarity. Functions of orthologues are often highly conserved among species.

"Homologue": A gene (or protein) with a similar nucleotide (or amino acid) sequence to another gene (or protein) in the same or another species.

"Promoter": a region or sequence located upstream and/or downstream from the start of transcription involved in recognition and binding of RNA polymerase and other proteins to initiate transcription.

"Plant promoter" refers to a promoter capable of initiating transcription in plant cells.

"Operably linked" refers to a functional linkage between a promoter and a DNA sequence, wherein the promoter sequence initiates and mediates transcription of the DNA sequence. Generally, "operably linked" means that the nucleic acid sequences being linked are contiguous, and, where necessary to join two protein coding regions, contiguous and in the same reading frame.

"Plant": includes whole plants, plant parts, and plant propagative material including: shoot vegetative organs and/or structures (e.g. leaves, stems and tubers), roots, flowers and floral organs (e.g. bracts, sepals, petals, stamens, carpels, anthers), ovules (including egg and central cells), seed (including zygote, embryo, endosperm, and seed coat), fruit (e.g., the mature ovary), seedlings, plant tissue (e.g., vascular tissue, ground tissue), cells (e.g., guard cells, egg cells, trichomes and the like), and their progeny.

"Plant cell": includes cells obtained from or found in seeds, suspension cultures, embryos, meristematic regions, callus tissue, leaves, roots, shoots, gametophytes, sporophytes, pollen, and microspores as well as whole plants. The term "plant cells" also includes modified cells, such as protoplasts, obtained from the aforementioned tissues.

"Wild type" in the context of a plant or plant material which has been modified in some way refers to a comparable plant which has not been modified in that way and grown or produced under similar conditions. For a given plant it may be the genotype or phenotype that is found in nature or in standard laboratory stock. References in this specification to relative changes in characteristics of plants or plant material are relative to wildtype.

SUMMARY OF THE INVENTION

According to one aspect, the invention provides a method of modifying cell proliferation in a plant which comprises modulating the expression of a gene whose expression or transcription product is capable of directly or indirectly modulating cell proliferation in the plant or plant propagating material, whereby cell proliferation, within the integuments and/or seed coats of the plant, is modified. Cell proliferation in other parts of the plant may also be modified. For example, in the stem of the plant.

According to another aspect, the present invention provides a method of modifying cell proliferation in a plant which comprises the step of transforming a plant or plant propagating material with a nucleic acid molecule comprising at least one regulatory sequence, typically a promoter sequence, capable of directing expression within the integuments and/or seed coat of at least one nucleic acid sequence whose expression or transcription product is capable of directly or indirectly modulating cell proliferation, whereby, on expression of that sequence, cell proliferation is modified. Preferably, the overall size of the integuments/seed coat in the plant is modified. This may be useful where a product is produced in the integument/seed coat. In some embodiments, this will be achieved without affecting the growth or development of any part of the plant other than the seed.

In one embodiment, the function of a gene or gene product that promotes cell division is enhanced or the function of a gene or gene product that represses cell division is inhibited. Cell division in the integuments/seed coat may be increased resulting in a larger seed compared to wild type. This may be advantageous because increases in seed size can be achieved which are desirable as mentioned above. The seed may be at least 15%, or 25%, larger than wild type. More specifically, the seed may be at least 5%, 10%, 20%, 30%, 40%, 50%, 75%, 100%, 150%, or even 200% heavier than wild-type. The number of cells in the integuments/seed coat of the plant may be increased compared to wild type. The number of cells in the integuments/seed coat of the plant may be increased by at least 30%, or 50%, compared to wild type.

The diameter of the stem of the plant may be greater, for example at least 10% greater, than wild type. Preferably, the diameter of the stem of the plant is at least 20% greater than wild type. This may be advantageous as discussed above.

The sepal length of the plant may sufficiently greater than wild type to inhibit flower opening. For example, the sepal length may be at least 20%, or at least 50% greater than wild type.

Equally, the method allows the production of smaller seeds which can also be advantageous as mentioned above, and in another embodiment, the function of a gene or gene product that promotes cell division is inhibited or the function of a gene product that represses cell division is enhanced. Cell division in the integuments/seed coat may decreased resulting in a smaller seed compared to wild type. The seed may be at least 5% smaller than wild type, preferably 25% or more. The number of cells in the integuments/seed cost may be decreased compared to wild type. In particular the number of cells in the integuments/seed coat may be reduced by at least 30%, or 50%, compared to wild type.

The function of a gene that modulates cell proliferation may be enhanced compared to wildtype. Transcription of the gene is activated. Activation of transcription results in increased levels of mRNA and/or protein encoded by the gene. Typically, levels of mRNA may be increased by at least 20%. For example, the levels of mRNA may be increased by 50% or 75% or more.

A plant promoter may be operably linked to a coding region of the gene in the sense orientation. The function of the gene may be modulated by operably linking a plant promoter to a nucleic acid fragment from the gene to form a recombinant nucleic acid molecule such that an antisense strand of RNA will be transcribed.

The function of a gene may be modulated by introducing a nucleic acid fragment of the gene into an appropriate vector such that double-stranded RNA is transcribed where directed by an operably linked plant promoter. Decreased levels of mRNA and/or protein encoded by endogenous copies of the gene may be produced. Levels of mRNA and protein encoded by homologues of the gene may be reduced.

The function of the gene may be modulated by operably linking a plant promoter to a 'dominant negative' allele of the gene, which interferes with the function of the gene product.

The plant may be monocotyledonous, and is preferably a crop plant. For example, the plant may be *Tritcum* spp (wheat), *Oryza sativa* (rice), *Zea mays* (maize), *Hordeum* spp. (barley), *Secale cereale* (rye), *Sorghum bicolor* (*sorghum*), or *Pennisetum glaucum* (pearl millet). Alternatively the plant is dicotyledonous. For example, the plant is *Brassica napus* (oil seed rape, canola) or any other *Brassica* species used to produce oilseeds (e.g. *Brassica carinata*), *Glycine max* (soybean), *Arachis hypogaea* (peanut), *Helianthus annuus* (sunflower), *Phaseolus vulgaris* (e.g. kidney bean, white bean, black bean), *Vicia faba* (broad bean), *Pisum sativum* (green pea), *Cicer arietinum* (chick pea), *Lens culinaris* (lentil), or *Linum usitatissimum* (flax, linseed).

Integument and seed coat development is similar in all species examined in the family Brassicaceae (Bouman, 1975), to which *Arabidopsis thaliana* belongs. In *Brassica napus*, a crop plant closely related to *Arabidopsis thaliana*, the seed coat is also very similar in structure (Wan et al., 2002). Therefore modifications that affect growth and development of integuments/seed coat in *Arabidopsis thaliana* should be directly applicable to members of the Brassicaceae, including *Brassica napus*.

The mature seeds of monocots such as cereals have a distinct structure. However cereal ovules have fundamental similarities with ovules of *Arabidopsis thaliana* and other dicots, also consisting of integuments enclosing a nucellus and embryo sac.) In rice, for example, the inner integument encloses the ovule before fertilization, and its growth precedes that of the endosperm and embryo, as in *Arabidopsis thaliana* (Lopez-Dee et al., 1999). Therefore modification to growth of the integuments/seed coat may also be effective in altering overall seed growth in cereal crops. Specifically in rice a modification to growth of the inner integuments may be useful in modifying seed size.

It is notable that the INO gene, which in *Arabidopsis thaliana* is expressed in the outer integument and required for its growth (Villanueva et al., 1999), has been identified in *Nymphaea alba* (water lily), where it is also expressed in the integuments (Yamada et al., 2003). As the Nymphaeaceae are basal eudicots, which are ancestral to both dicots and monocots, this suggests that the sequence and expression patterns of at least some integument genes will be conserved even among distantly related groups of flowering plants.

The present invention is complementary to the invention disclosed in WO01/09299. Modifications to endosperm-led and integument-led seed growth could be combined for an even larger effect. In some situations integument-led seed growth alone may be preferable, as it only requires modification to the seed parent, while endosperm growth is determined both by maternal and paternal contributions.

Where the regulatory sequence is a promoter, the promoter sequence may be constitutive, directing gene expression in most or all cells of the plant. An example of a constitutive promoter that may be used in some embodiments of the invention is the 35S promoter, derived from the gene that encodes the 35S subunit of Cauliflower Mosaic Virus (CaMV) coat protein. Alternatively, the promoter sequence may be specific, directing expression exclusively or primarily in one organ, tissue, or cell type of the plant. A variety of plant promoters can be used in the invention to direct expression exclusively or primarily in the integuments or seed coat. Suitable plant promoters include those obtained from plants, plant viruses, and bacteria which comprise genes expressed in plant cells, such as *Agrobacterium* or *Rhizobium*. Some embodiments use promoters expressed in the pre-fertilization integuments. These include but are not restricted to the promoters of the following genes: INO (Villanueva et al., 1999; At1g23420, accession no. AF195047) and BEL1 (Reiser et al., 1995; At5g41410; accession no. NM_123506). Other embodiments use promoters expressed in the seed coat after fertilization. These include but are not restricted to the promoters of the following genes: BAN (Devic et al., 1999; At1g61720, accession no. AF092912), TT1 (Sagasser et al., 2002), TT2 (Nesi et al., 2001; At5g35550; accession no. NM_122946), TT8 (Nesi et al., 2000; At4g09820, accession no. AJ277509), TT12 (Debeaujon et al., 2001; At3g59030, accession no. AJ294464), and TT16 (Nesi et al., 2002; At5g23260; accession no. NM_203094). A flower-preferred promoter that may be used is the promoter of the LFY gene (Weigel et al., 1992; At5g61850, accession no. NM_125579), which can be used to obtain desired flower-specific effects such as reductions in flower opening. Where a promoter is to be introduced into a plant, a promoter-containing nucleotide sequence of up to 2000 bp would typically be used.

The use of other regulatory sequences than a promoter to direct expression within the integuments and/or seed coat is contemplated. An example is an intron directing tissue-specific expression (see e.g. Deyholos and Sieburth, 2000).

There are a number of genes known or suspected to be involved in modulating cell proliferation, either directly or indirectly. Some embodiments of the invention use genes involved in hormone response, biosynthesis, translocation, or other aspects of hormone action. These include but are not restricted to MNT (described above), IPT1 (Takei et al., 2001; At1g68460, accession no. AB062607), and ARGOS (Hu et al., 2003; At3g59900, accession no. AY305869). Other embodiments use core cell cycle genes (Vandepoele et al., 2002). These include but are not restricted to CYCD3;1 (formerly Cycδ3; Soni et al., 1995; Vandepoele et al., 2002; At4g34160, accession no. X83371) and CYCB1;1 (formerly Cyc1aAt; Ferreira et al., 1994; Vandepoele et al., 2002; At4g37490, accession no. NM_119913). Other embodiments use transcription factors involved in regulation of the extent or rate of cell proliferation. These include but are not restricted to ANT (Klucher et al., 1996; At4g37750, accession no. NM_119937).

An expression cassette may be used either to enhance or inhibit the function of a gene that modulates cell proliferation.

One method of enhancing function is to activate transcription of the gene, resulting in increased levels of mRNA and protein encoded by the gene. This is achieved by linking a plant promoter to the coding region of the gene (either with or without introns) in the sense orientation.

Partial or complete inhibition of gene function in order to achieve desirable characteristics in plants such as fertility may be achieved or "engineered" in several ways. One method, which uses 'antisense technology', is to link a plant promoter to a nucleic acid segment from the desired gene such that the antisense strand of RNA will be transcribed (see e.g. Branen et al., 2003; Choi et al., 2003). Another method, which uses 'RNAi technology', is to link a plant promoter to a nucleic acid segment from the desired gene and place the resulting recombinant nucleic acid into an appropriate vector such that double-stranded RNA is transcribed (Wang and Waterhouse, 2001). Both of these techniques may result in decreased levels of mRNA and protein encoded by the endogenous copies of the gene. For example, levels of mRNA may be reduced by at least 20%, preferably by at least 50% so as to achieve usefully large seeds without compromising fertility compared to wildtype. A nucleic acid fragment for antisense or RNAi technology may also be designed to decrease levels of mRNA and protein encoded by homologues or orthologues of the gene. A third method of inhibiting gene function is to link a plant promoter to a 'dominant negative' allele of the gene, which interferes negatively with the function of the gene product (see e.g. Hemerly et al., 1995; Nahm et al., 2003). In the case of inhibition of genes (e.g., by antisense, or the use of RNAi technology) it will be recognized that the inserted polynucleotide sequence need not be identical, but may be only "substantially identical" to a sequence of the gene from which it was derived. Inhibition of gene function may be achieved by reduction of expression of the gene through a feedback loop acting on that expression.

Alternatively, the nucleic acid sequence is a mutant form of an auxin response factor encoding gene, or a construct that inhibits expression or function of an auxin response factor. The auxin response factor gene may be MNT in the case of *Arabidopsis thaliana* or its orthologues in other species. For example, in the case of *Brassica napus* the gene may be BnARF2 as used in Example 2 below. In the case of rice the gene may be OsARF2. The mnt-1 mutant phenotype shows that the wild-type function of the MNT gene is to repress cell division in the integuments. Therefore inhibition of endogenous MNT expression or function may result in larger integuments and a larger seed. Alternatively, enhancement of MNT expression or function may result in a smaller seed. In some situations, overexpressing the MNT gene may, in fact, result in a larger seed size possibly due to a feedback loop on the expression of the MNT gene.

In some embodiments of the invention, cell division in the integuments/seed coat will be increased, resulting in a larger seed compared to wild type. This may be achieved by enhancing function of a gene or gene product that promotes cell division, or inhibiting function of a gene or gene product that represses cell division. In other embodiments, cell division in the integuments/seed coat will be decreased, resulting in a smaller seed. This may be achieved by enhancing function of a gene or gene product that represses cell division, or inhibiting function of a gene or gene product that promotes cell division. In these embodiments the gene or gene product may be MNT or an orthologue of MNT; alternatively it may be another gene or gene product that affects cell division.

A plant may be further modified to maintain desirable characteristics may have been otherwise lost as a result of the transformation step. For example, the desirable characteristic may be fertility.

The plant may be engineered or bred further to maintain or introduce desirable characteristics. For example, the plant may be bred so that it is heterozygous for the modulated gene which directly or indirectly modifies cell proliferation. In particular, we have found that plants heterozygous for the mnt mutation have normal flowers and normal fertility, but that their seeds that are consistently significantly heavier than wild-type (typically about 10-20%), though not as heavy as seeds from mnt homozygous mutants. In other words, if MNT function is reduced by about 50% rather than abolished completely, the plants produce desirable heavier seeds without compromising fertility. For example, plants may be engineered as described above in order to reduce mRNA/protein levels for the cell proliferation gene.

For example, in further embodiments of the invention, MNT function is restored to petals and stamens of an mnt mutant such that seeds have the enlarged mnt-1 mutant phenotype but fertility is not impaired. This may be achieved by operably linking the promoter of a gene that directs expression in petals and stamens but not carpels (which contain the ovules), such as AP3 (Jack et al., 1992), to the wild-type MNT gene. In different species, different wild type genes may be supplied. In other embodiments, MNT function may be restored to sepals and petals of an mnt mutant such that seeds have the enlarged mnt-1 mutant phenotype but fertility is not impaired. This may be achieved by operably linking the promoter of a gene that directs expression in sepals and petals but not carpels, such as AP1 (Mandel et al., 1992), to the wild-type MNT gene. In different species, different wild-type genes may be supplied.

According to another aspect of the invention there is provided a plant which includes a nucleic acid molecule comprising at least one regulatory sequence capable of directing expression within the integuments and/or seed coat of at least one nucleic acid sequence whose expression or transcription product is capable of directly or indirectly modulating cell proliferation, whereby, on expression of that sequence, cell proliferation is modified. The plant may have been obtained by a method in accordance with the invention and will have the resulting features in terms of genetic structures and phenotype as described above.

According to a further aspect of the invention there is provided reproducible or propagatable plant material including a nucleic acid molecule comprising at least one regulatory sequence capable of directing expression within integuments and/or seed coat and at least one nucleic acid sequence whose expression or transcription product is capable of directly or indirectly modulating cell proliferation, whereby on expression of that nucleic acid sequence cell proliferation is modified.

According to another aspect of the invention, there is provided a method of modifying cell proliferation in a plant which comprises the step of modulating the response of the plant to an auxin whereby the overall cell number of the integuments/seed coat of the plant is modified. The response to an auxin may be modified by altering the expression of an auxin response factor. Preferably, the auxin response factor is ARF2. The function of a gene encoding the auxin response factor may be modulated so as to affect the function of the factor. In the case of *Arabidopsis thaliana*, the gene may be MNT. In the case of *Brassica napus* the gene may be BnARF2. In the case of rice the gene may be OsARF2. Orthologues of these genes may be used in other species.

Most preferably, the function of an endogenous auxin response factor encoding gene is modulated for example by RNAi technology as described above. Most preferably, the function of that gene in the integuments/seed coat is affected.

In a further aspect of the invention, there is provided a method of modifying the function of a gene that directly or indirectly modulates cell proliferation, such as MNT, in a plant such that the seeds are enlarged but characteristics such as flower opening and/or fertility, preferably both flower opening and fertility, are not impaired. The seeds may be at least 10% or 20% larger than wild type. This may be achieved by breeding a plant that is heterozygous for a mutation in the gene such as MNT or an orthologue of that gene in other species. In another embodiment the plant has a partial loss-of-function mutation in a gene the function of which affects cell proliferation, such as MNT or an orthologue in other species. In another embodiment, the level of the RNA of that gene and protein is reduced in a wild-type plant by 30%, 40%, 50%, or 60%, for example by operably linking a promoter, such as the constitutive 35S promoter, to a nucleic acid fragment from the gene to form a recombinant nucleic acid molecule such that an antisense strand of RNA will be transcribed; or to nucleic acid fragments of the gene in an appropriate vector such that double-stranded RNA is transcribed.

According to a further aspect, the present invention provides a method of modifying cell proliferation in a plant which comprises the step of transforming a plant or plant propagating material with a nucleic acid molecule comprising at least one regulatory sequence, typically a promoter sequence, capable of directing expression within the stem of at least one nucleic acid sequence whose expression or transcription product is capable of directly or indirectly modulating cell proliferation, whereby, on expression of that sequence, cell proliferation is modified. Preferably, the overall size of the stems in the plant is modified. The stem may be at least 10%, 20%, 30%, or 40% greater in diameter than wild-type. In one embodiment of the invention, MNT function, or that of an orthologue, is at least partially inhibited in the stem, for example by operably linking a promoter such as the constitutive 35S promoter to a nucleic acid fragment from the MNT gene or MNT orthologue to form a recombinant nucleic acid molecule such that an antisense strand of RNA will be transcribed; or to nucleic acid fragments of the MNT gene or MNT orthologue in an appropriate vector such that double-stranded RNA is transcribed.

In another embodiment of the invention, the function of a gene that directly or indirectly modulates cell proliferation such as MNT or an orthologue thereof is restored to flowers of an mnt mutant such that stems have the enlarged mnt-1 mutant phenotype but fertility is not impaired. This may be achieved for example by operably linking the promoter of a gene that directs expression in flowers but not stems, such as LEAFY (LFY) (Weigel et al., 1992; At5g61850, accession no. NM_125579), to the wild-type MNT gene. In different species, different wild type genes may be supplied.

BRIEF DESCRIPTION OF THE DRAWINGS

Embodiments in accordance with the invention will now be described, by way of example only, with reference to the accompanying drawings FIGS. 1 to 25 in which:

FIG. 1A Top: Confocal micrographs of seeds with globular stage embryos from mnt-1 (left) and wild-type (right) seed parents; Bottom: Mature seeds and embryos from mnt-1 mutants and wild-type plants, photographed at the same scale;

FIG. 1B is a scatter plot of number of seeds in each pod produced by mnt-1 mutants vs mean seed weight in that pod, following controlled pollinations;

FIG. 1C shows seeds from manually pollinated mnt-1 and wild-type plants, and reciprocal crosses between them, photographed at the same scale;

FIG. 3 shows micrographs of the chalazal endosperm in developing seeds of *Arabidopsis thaliana*, all at the same scale. The mnt-1 seed is an example of integument-led growth while the 2x×6x seed provides an example of endosperm-led growth;

FIG. 4A shows micrographs of *Arabidopsis thaliana* seeds illustrating endosperm-led seed growth illustrated by interploidy crosses in the C24 accession of *Arabidopsis thaliana* (see also Scott et al., 1998);

FIG. 4B shows micrographs illustrating integument-led seed growth illustrated by the mnt-1 mutant in the Columbia accession of *Arabidopsis thaliana*;

FIG. 4C is a micrograph of a seed illustrating the 'big bag' hypothesis;

FIG. 6 is an alignment of wild-type MNT cDNA (SEQ ID NO:55) and mutant mnt-1 (SEQ ID NO:5) cDNA from translational start to stop;

FIG. 7 is an alignment of wild-type MNT predicted protein (SEQ ID NO:3) and mutant mnt-1 predicted protein (SEQ ID NO:6);

FIG. 8 is an alignment of *Arabidopsis thaliana* MNT cDNA (SEQ ID NO:55) with its orthologue in *Brassica napus*, BnARF2 (SEQ ID NO:9);

FIG. 9 is an alignment of *Arabidopsis thaliana* MNT predicted protein (SEQ ID NO:3) with its orthologues in *Brassica napus* (oilseed rape) (BnARF2) (SEQ ID NO:10) and *Oryza sativa* (rice) (OsARF2) (SEQ ID NO:61);

FIGS. 11A-B illustrates a cloning strategy for constructing reporter vectors (Example 3). In this and following figures, FIG. 11A (Example 3a(i)) and FIG. 11B (Example 3b(i)), only restriction sites significant to the strategy are shown on the diagrams;

FIG. 15 illustrates a cloning strategy for constructing RNAi vectors to decrease MNT expression primarily in the integuments/seed coat (Example 6);

FIG. 16 illustrates a cloning strategy for constructing RNAi vectors to decrease BnARF2 expression primarily in the integuments/seed coat (Example 7);

FIG. 17A illustrates a cloning strategy for constructing vectors for constitutive expression of MNT (Example 8) or BnARF2 (Example 9);

FIG. 17B is a series of photographs illustrating seed sizes and weights from independently transformed lines containing the 35S::MNT expression cassette compared with a wild-type control. Seeds were photographed at the same scale;

FIG. 18 illustrates a cloning strategy for constructing vectors for expression of MNT in the integuments/seed coat (Example 10);

FIG. 19 illustrates a cloning strategy for constructing vectors for expression of BnARF2 in the integuments/seed coat (Example 11);

FIG. 21A is a series of photographs illustrating seed sizes and weights from individual primary transformants containing expression cassettes designed to increase seed size (TT8::CYCD3;1 and TT8::IPT1) compared with controls (TT8::uidA). Data is taken from Table 2A. Seeds were photographed at the same scale;

FIG. 21B is a series of photographs illustrating seed sizes and weights from transformed plants containing expression cassettes designed to increase seed size compared with wild-type controls. Data is taken from Table 2B. Seeds were photographed at the same scale;

FIG. 23 illustrates a cloning strategy for constructing a vector for expression of MNT in sepals and petals (Example 15);

FIG. 24A shows a wild-type Col-3 (left) and mnt-1 (right) plant, illustrating the stem phenotype;

FIG. 24B shows transverse sections of the inflorescence stem between nodes 2 and 3 as counted from the base of a wildtype from a wild-type (top) and mnt-1 (bottom) plant. Each pair of images (low magnification, left; high magnification, right) was photographed at the same scale.

DESCRIPTION OF PREFERRED EMBODIMENTS

Figure 2A:
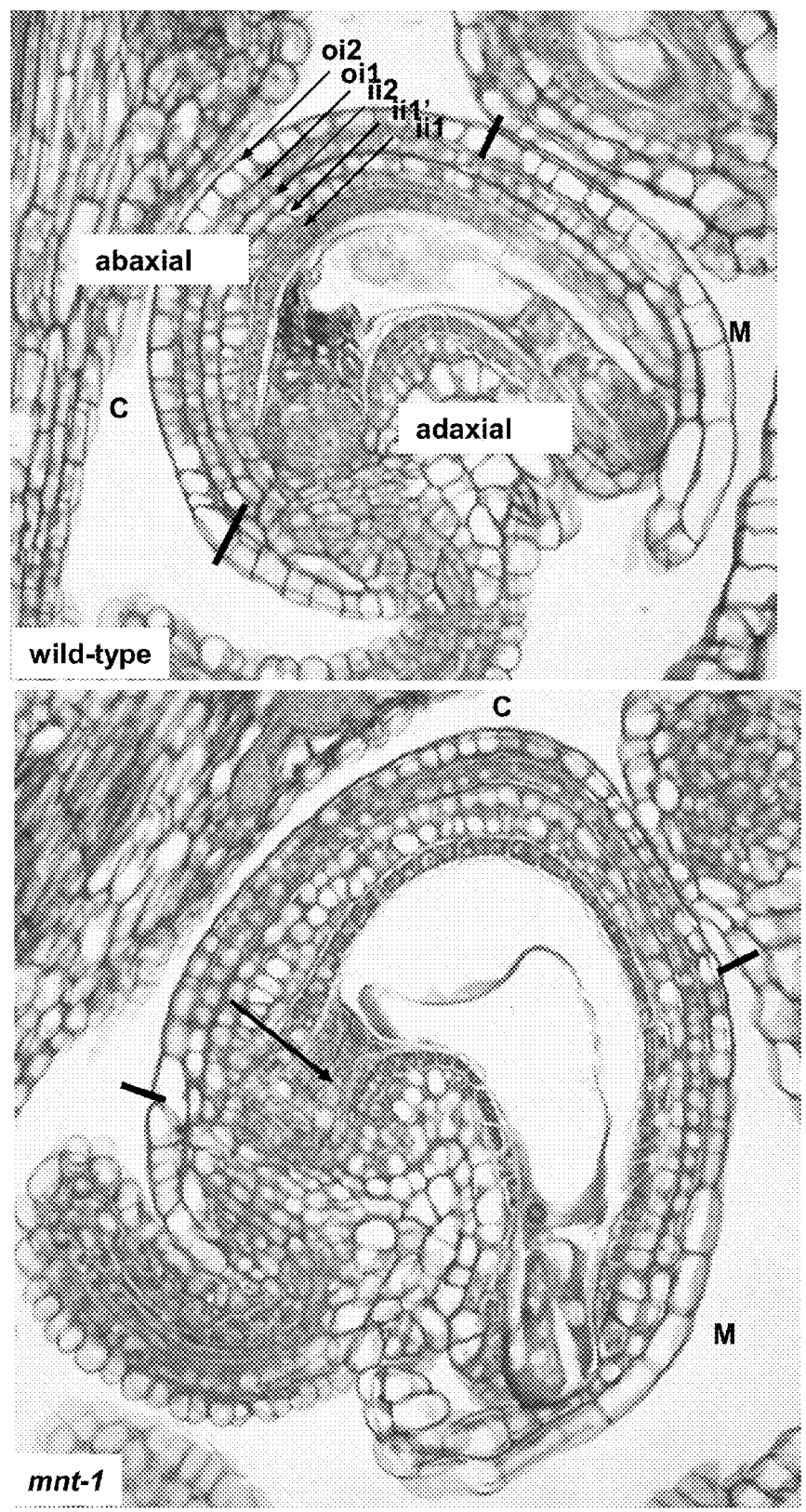
FIG. 2A shows light micrographs of mature unfertilized ovules, stage 3-VI (staging as in Schneitz et al., 1995), from wild-type (top) and mnt-1 (bottom) plants.
Figure 2B:
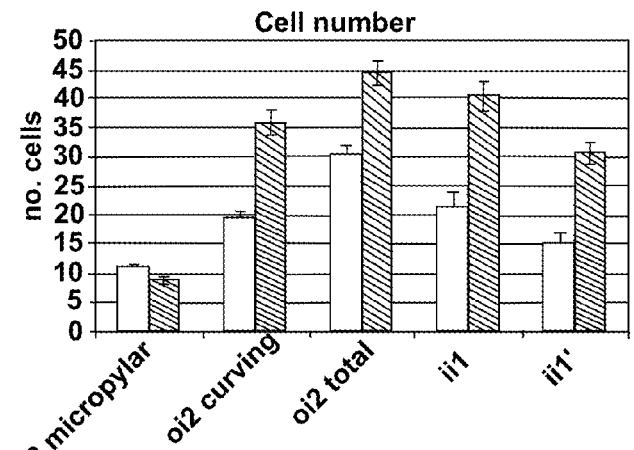
FIGS. 2B-D shows graphs showing number of cells (FIG. 2B), total length (FIG. 2C), and mean cell length for several integument layers in mnt-1 and wild-type stage 3-VI ovules (FIG. 2D). (The width is also shown for layer ii1').
Figure 2C:
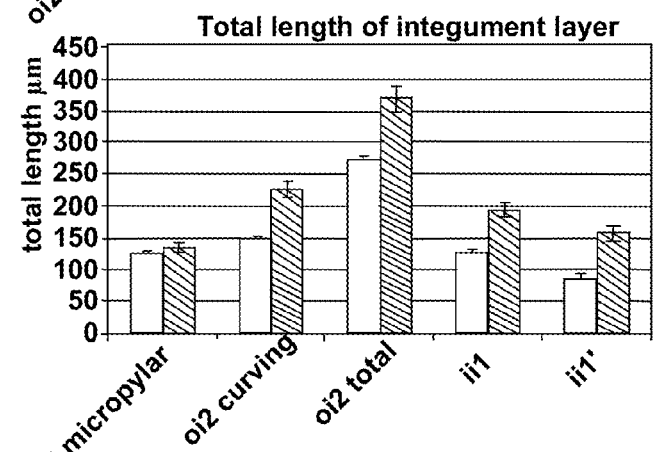
Figure 2D:
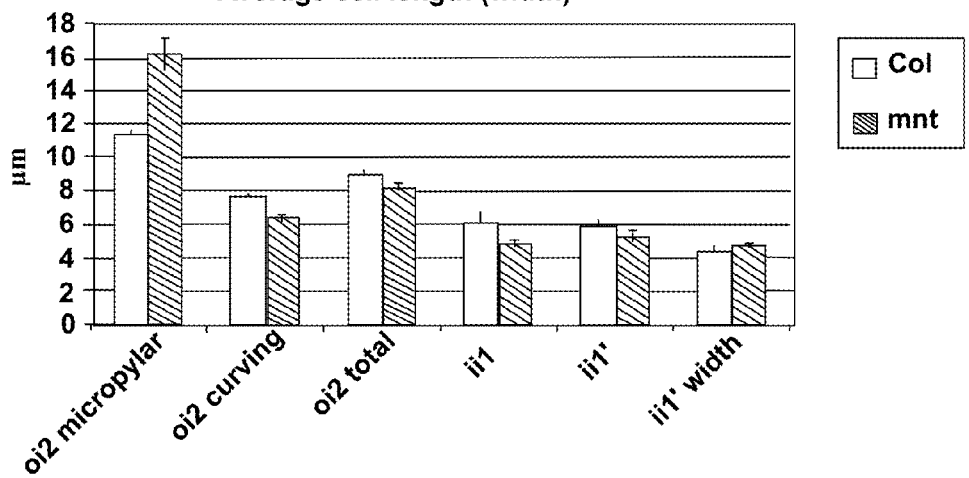

Methods and products in accordance with the present invention will now be described with reference to the following examples, which should not be construed as in any way limiting the invention.

The following vectors are used in the examples:
pGEMT (Promega, Southampton, UK)
BJ36, BJ40, BJ60 (gift of Bart Janssen, Horticultural & Food Research Institute of New Zealand)
pART7 (Gleave, 1992)
pFGC5941 (Cambia, Canberra, Australia; ChromDB)

Plant transformation protocols are based on Clough and Bent (1998) for *Arabidopsis thaliana* and Moloney et al. (1989) for *Brassica*.

Protein predictions and sequence alignments are carried out with GeneDoc software version 2.6.001 (Nicholas and Nicholas, 1997).

A. Identification of the mnt-1 Mutant

We identified the mutant, megaintegumenta-1 (mnt-1), in a screen for large seeds yielded by a population of EMS (ethyl methanesulfonate)-mutagenized *Arabidopsis thaliana* in the Col-3 accession. Mature seeds produced by a seed parent homozygous for the mnt-1 mutation are larger and more pointed than wild-type, with extra cells in the seed coat, and contain larger embryos (FIG. 1A). Specifically, FIG. 1A shows that mnt-1 mutants produce larger seeds with more cells in the seed coat (counts are for ii1, the outer layer of the inner integument).

Seeds collected from self-pollinated mnt-1 mutant plants are up to twice the weight of wild-type Col-3 seeds (Table 1A).

TABLE 1A

Seed weights in μg from mnt-1 and w.t. Col-3 crosses, self seed, all siliques left on plant

|  | mnt self | w.t. self |
|---|---|---|
|  | 27.1 (n = 60) | 14.4 (n = 178) |
|  | 27.9 (106) | 15.8 (75) |
|  | 29.7 (127) |  |
| Mean | 28.2 | 15.1 |
| Range | 27.1 to 29.7 | 14.4 to 15.8 |
| Standard error | 0.8 | 1.4 | n = number of seeds weighed from each plant

However, mnt-1 mutant plants are self-sterile until late in development due to floral abnormalities (see below), raising the possibility that the mutant produces large seeds because there are few seeds requiring maternal resources. Therefore we also conducted controlled pollinations in which only three siliques (seed pods) were allowed to set seed per plant, for both mnt-1 and wild-type (Table 1B).

TABLE 1B

Seed weights in μg from mnt-1 and w.t. Col-3 crosses, manual pollinations, 3 siliques per plant

|  | mnt X mnt | mnt X w.t. | w.t. X mnt | w.t. X w.t. |
|---|---|---|---|---|
|  | 31.1 (n = 32) | 30.4 (n = 36) | 30.5 (n= 20) | 30.6 (n = 34) |
|  | 37.7 (37) | 32.6 (22) | 28.2 (30) | 29.7 (34) |
|  | 31.4 (37) | 37.4 (43) | 28.2 (32) | 22.1 (49) |
|  | 39 (20) | 31.8 (17) | 27.1 (46) | 31.5 (31) |
|  | 33.7 (50) | 34.4 (33) | 26.5 (44) | 29.6 (28) |
|  | 40.5 (22) | 36 (50) | 28 (44) | 26.9 (53) |
|  | 38.3 (9) | 37.1 (49) | 30.3 (44) | 30.2 (61) |
|  | 39.1 (11) | 38 (24) |  | 31.7 (48) |
|  | 37.2 (25) |  |  | 21.2 (32) |
|  | 35.2 (24) |  |  |  |
|  | 35.7 (43) |  |  |  |
|  | 39 (31) |  |  |  |
|  | 38.3 (64) |  |  |  |
|  | 34 (23) |  |  |  |
|  | 36.1 (33) |  |  |  |
|  | 35.1 (54) |  |  |  |
| Mean | 36.3 | 34.7 | 28.4 | 28.7 |
| Range | 31.1 to 40.5 | 31.8 to 38.0 | 26.5 to 30.5 | 22.1 to 31.7 |
| Standard error | 0.7 | 1.0 | 0.6 | 1.3 | n = number of seeds in silique
ttest [mnt X mnt] vs [w.t. X w.t.]: $P < 0.000$, significant
ttest [mnt X mnt] vs [mnt X w.t.]: $P > 0.2$, not significant
ttest [w.t. X w.t.] vs [w.t. X mnt]: $P > 0.9$, not significant This treatment raised the mean weight of wild-type seeds by 90% and mnt-1 seeds by 29%, indicating that low seed number is a component of large seed size in mnt-1 mutants but that the mnt-1 mutation also has a significant effect. On average mnt-1 seeds weighed 26% more than wild-type when only three siliques per plant set seed; the difference in weights was significant at $P<0.000$. We also investigated whether occasional low seed set within individual mnt-1 siliques might raise seed weight; however a scatter plot (FIG. 1B) of mean seed weight of each pod vs number of seeds per pod following controlled pollinations in mnt-1 (data from Table 1B) shows no correlation.

We also compared the weight of seeds produced by mnt heterozygotes with the weight of seeds produced by wild-type plants (Table 1C). We generated the heterozygotes through crosses in both directions, i.e. [w.t.×mnt-1] (designated [wxm]) and [mnt-1×w.t.] (designated [mxw]). We found that the weights of seeds from w.t. and mnt-1 heterozygous plants were significantly different (t-test, $H_0$ w.t.=mnt-1 heterozygous, P=0.0002).

TABLE 1C

Seed weights in μg from w.t. Col-3 and mnt-1 heterozygous plants, self seed, all siliques left on plant

|  | w.t. | mnt heterozygous |
|---|---|---|
| Plant 1 | 17.1 (n = 35) | 19.4 (n = 44) [wXm] |
| Plant 2 | 16.5 (37) | 20.8 (60) |
| Plant 3 | 16.4 (49) | 19.3 (50) |
| Plant 4 | 16.2 (50) | 18.8 (50) |
| Plant 5 | 16.3 (45) | 19.5 (46) |
| Plant 6 | 16.2 (40) | 20.0 (62) |
| Plant 7 | 15.3 (52) | 19.3 (44) |
| Plant 8 | 16.6 (42) | 18.4 (59) |
| Plant 9 | 17.5 (54) | 18.7 (45) |
| Plant 10 | 17.9 (56) | 18.3 (57) |
| Plant 11 |  | 16.2 (64) [mXw] |
| Plant 12 |  | 17.7 (67) |
| Plant 13 |  | 20.0 (42) |
| Plant 14 |  | 17.3 (42) |
| Plant 15 |  | 18.3 (75) |
| Plant 16 |  | 17.1 (45) |

TABLE 1C-continued

Seed weights in μg from w.t. Col-3 and mnt-1 heterozygous plants, self seed, all siliques left on plant

|  | w.t. | mnt heterozygous |
|---|---|---|
| Plant 17 |  | 17.0 (67) |
| Plant 18 |  | 17.7 (49) |
| Plant 19 |  | 18.3 (54) |
| Plant 20 |  | 16.6 (40) |
| Mean | 16.6 (460) | 18.4 (1062) |
| Range | 15.3 to 17.9 | 16.2 to 20.8 |
| Standard error | 0.2 | 0.3 |

We also conducted two further experiments to compare the weights of seeds from (a) wild-type plants, (b) mnt-1 homozygotes, and (c) mnt-1 heterozygotes under conditions of restricted pollination. In the first experiment, six siliques on the primary shoot were pollinated and all other siliques on the primary shoot were removed; but all secondary shoots were allowed to set self-seed (Table 1D). In the second experiment, only six siliques on the primary shoot were pollinated and all other siliques on the plant were removed (Table 1E). In both experiments we carried out manual pollinations on six siliques per plant to enable young mnt-1 homozygous mutant plants to set seed.

TABLE 1D

Seed weights in μg from w.t. Col-3, mnt-1 homozygous, and mnt-1 heterozygous plants, 6 siliques pollinated on primary shoot, secondary shoots allowed to self-pollinate

|  | w.t. | mnt homozygous | mnt heterozygous |
|---|---|---|---|
| Plant 1 | 24.7 (n = 289) | 35.5 (178) | 31.0 (n = 237) [wXm] |
| Plant 2 | 24.6 (336) | 34.5 (217) | 28.7 (275) |
| Plant 3 | 24.4 (337) | 36.9 (224) | 29.8 (140) |
| Plant 4 | 23.9 (223) | 37.8 (227) | 30.7 (195) |
| Plant 5 | 25.8 (135) | 37.4 (149) | 29.3 (260) |
| Plant 6 |  |  | 29.2 (109) [mXw] |
| Plant 7 |  |  | 29.6 (307) |
| Plant 8 |  |  | 29.0 (198) |
| Plant 9 |  |  | 26.8 (346) |
| Plant 10 |  |  | 27.6 (341) |
| Mean seed weight | 24.7 (1320) | 36.4 (995) | 29.2 (2408) |
| Range | 23.9 to 25.8 | 34.5 to 37.8 | 26.8 to 31.0 |
| Standard error | 0.3 | 0.6 | 1.3 | n = number of seeds weighed from each plant
t-test: $H_0$ w.t. = mnt-1 homozygous, P < 0.0000, difference is significant
t-test: $H_0$ w.t. = mnt-1 heterozygous, P < 0.0000, difference is significant

TABLE 1E

Seed weights in μg from w.t. Col-3, mnt-1 homozygous, and mnt-1 heterozygous plants, 6 siliques pollinated on primary shoot, secondary shoots removed

|  | w.t. | mnt homozygous | mnt heterozygous |
|---|---|---|---|
| Plant 1 | 33.0 (n = 307) | 38.7 (n = 274) | 37.1 (n = 53) [wXm] |
| Plant 2 | 32.2 (222) | 37.5 (221) | 35.1 (300) |
| Plant 3 | 35.1 (74) | 41.1 (226) | 37.7 (347) |
| Plant 4 | 35.0 (252) | 41.0 (302) | 35.6 (110) |
| Plant 5 | 34.8 (230) | 38.5 (205) | 38.1 (195) |
| Plant 6 |  |  | 40.9 (193) [mXw] |
| Plant 7 |  |  | 37.8 (245) |
| Plant 8 |  |  | 36.7 (280) |
| Plant 9 |  |  | 38.1 (210) |
| Plant 10 |  |  | 39.9 (222) |
| Mean seed weight | 34.0 (1085) | 39.4 (1228) | 37.7 (2155) |

TABLE 1E-continued

Seed weights in μg from w.t. Col-3, mnt-1 homozygous, and mnt-1 heterozygous plants, 6 siliques pollinated on primary shoot, secondary shoots removed

|  | w.t. | mnt homozygous | mnt heterozygous |
|---|---|---|---|
| Range | 23.2 to 35.1 | 37.5 to 41.1 | 35.1 to 40.9 |
| Standard error | 0.6 | 0.7 | 1.8 | n = number of seeds weighed from each plant
t-test: $H_0$ w.t. = mnt-1 homozygous, P = 0.0004, difference is significant
t-test: $H_0$ w.t. = mnt-1 heterozygous, P = 0.0013, difference is significant mnt-1 homozygotes and mnt-1 heterozygotes produced heavier seeds than wild-type plants in both experiments, and the difference in weight was significant in all cases at $P<0.002$. When secondary shoots were allowed to set seed, seeds from mnt-1 homozygotes were on average 47% heavier than seeds from wild-type plants, and seeds from mnt-1 heterozygotes were on average 18% heavier than seeds from wild-type plants. When secondary shoots were removed, so that only six siliques set on each plant regardless of genotype, seeds from mnt-1 homozygotes weighed 16% more than wild-type, and seeds from mnt-1 heterozygotes weighed 11% more than wild-type.

The mnt-1 mutation has a maternal effect on seed size. That is, an mnt-1 homozygous mutant seed parent yields large seeds regardless of whether it is pollinated by an mnt-1 or wild-type plant, while a wild-type parent yields normal seeds even if pollinated by an mnt-1 plant (FIG. 1C). In FIG. 1C seeds produced by mnt-1 seed parents are shown on top and seeds from wild-type seed parents are below. H=fertilization products (embryo and endosperm) are heterozygous for the mnt-1 mutation. This shows that seed size in mnt-1 mutants depends on the genotype of the seed parent, not the fertilization products. This is also shown by the lack of a significant difference between seed weights from [mnt-1×mnt-1] and [mnt-1×w.t] seeds, and between [w.t.×w.t.] and [w.t.×mnt-1] seeds (Table 1B).

The primary difference between mnt-1 and wild-type seeds is that the mutant seeds contain more cells in the seed coat. Comparison of ovule development in mnt-1 and wild-type plants shows that mnt-1 ovules are of normal size and morphology until they are near maturity, at which time we observe that both the inner and outer integuments of mnt-1 ovules are significantly longer than in wild-type, primarily due to a significantly greater number of cells (FIG. 2). In relation to the results depicted in FIG. 2, in *Arabidopsis thaliana* and other members of the Brassicacea most cell division and expansion occurs in the integuments on the abaxial side of the ovule (marked on wild-type ovule in FIG. 2A). Similarly, the nucellus in rice is enveloped by the abaxial inner integument (Lopez-Dee et al., 1999). In *Arabidopsis*, ii1, ii1', and ii2 are the three cell layers of the inner integument and oi1 and oi2 are the two layers of the outer integument. The cells of layer ii1', which does not completely span the embryo sac, significantly expand in width after fertilization as part of seed growth (Beeckman et al., 2000). mnt-1 ovules have longer integuments with extra cells and in some cases an extra layer (arrow), as well as a larger seed cavity (FIG. 2A). C=the 'curving zone' of the abaxial outer integument (the region overlying ii1'; Beeckman et al., 2000), M=the 'micropylar zone', regions delimited with black bars (FIG. 2A). Measurements shown in FIG. 2B were taken for the abaxial integuments only. Layers ii1', ii1, and the curving zone of oi2 are longer in mnt-1 mutant ovules, almost exclusively due to greater cell number. Mean cell length is greater in the micropylar zone of mnt-1 ovules but smaller or not significantly different in the oi2 curving zone and the other integument layers measured. There is no difference in mean width between mnt-1 and wild-type cells of layer ii1'.

The peripheral endosperm in mnt-1 mutant seeds also generates more nuclei than in wild-type seeds. The mean number of peripheral endosperm nuclei in mnt-1 seeds at the heart stage is 1150, compared with 550 for a wild-type Col-3 seed at a comparable stage; see Scott et al. (1998) for a description of endosperm morphology and the counting method. However, we consider there are two crucial differences between mnt-1 mutant seeds and large seeds that show endosperm-led growth. First, the chalazal region of the endosperm, which becomes greatly enlarged in endosperm-led seeds (e.g. seeds from interploidy crosses generating paternal excess, crosses where the DNA of the seed parent is hypomethylated, or fis mutants), is of roughly normal size in mnt-1 mutants (although the pinched shape of the chalazal pole of mnt-1 seeds results in a longer and narrower chalazal endosperm) (FIG. 3). We measured the maximum cross-sectional area of the chalazal cyst plus nodules at 6 DAP, a stage at which differences are apparent between wild-type and paternalized endosperms (Scott et al., 1998). Mean areas were 2690 $\mu m^2$ (±s.e.m. 328) for wild-type seeds (n=4) and 2537 $\mu m^2$ (±416) for mnt-1 seeds (n=5), and there was no significant difference between the mutant and wild-type endosperms (t-test, $H_0$ w.t.=mnt-1, P=0.79). Second, the size difference between mnt-1 and wild-type seeds follows from differences existing before fertilization i.e. before the endosperm has been created. The overproliferation of peripheral endosperm may follow from the larger seed volume created by enlarged integuments/seed coat.

B. The 'Big Bag' Hypothesis

We observe that seeds with enlarged endosperms and seeds with large seed coats have a feature in common: the seed cavity (i.e. the space within the post-fertilization embryo sac) is larger than normal, giving the embryo more space to grow (FIG. 4A, 4B). Specifically, endosperm-led seed growth is illustrated by interploidy crosses in the C24 accession of *Arabidopsis thaliana* (see also Scott et al., 1998). As shown in FIG. 4A extra paternal genomes produce seeds with a large cavity (top left, 2x×6x cross), and ultimately large seeds with large embryos (2x×4x cross, bottom left). Conversely, extra maternal genomes generate seeds with small cavities (top right, 6x×2x cross), and ultimately small seeds with small embryos (4x×2x cross, bottom right). The control 2x×2x cross is shown in the middle.

In contrast in integument-led seed growth as illustrated in FIG. 4B the seeds also have a large seed cavity (top left) compared with wild-type (top right). Mature seeds and embryos are compared below.

This leads to our 'big bag' hypothesis, which states that seed and ultimately embryo size is set by the size of the seed cavity, which may be controlled by several factors including extent of endosperm proliferation and extent of integument/seed coat proliferation (FIG. 4C).

It is well established in the literature that after fertilization in *Arabidopsis thaliana* there is no further division in the seed coat, and growth occurs only by cell expansion (Léon-Kloosterziel et al., 1994; Beeckman et al., 2000; Windsor et al., 2000). Obviously seeds with large endosperms must also have large seed coats; however, in this case, the seed coat grows by cell expansion after fertilization. In seeds where large seed coat is considered the primary cause of seed enlargement (integument-led seed growth), the integument/seed coat contains extra cells, as observed in mnt-1 mutants.

C. Further Aspects of the mnt-1 Mutant Phenotype

The mnt-1 mutation affects floral morphology as well as seed size. Most flowers fail to open; this is associated with a deviation from the normal ratio of sepal to petal length, so that the petals are shorter than the sepals. Specifically, mnt mutant sepals are about 60% longer than wild-type. This deviation is mainly due to overgrowth of the sepals caused by extra cell division, although under some conditions the petals also fail to expand normally. This characteristic may be commercially useful in some crop species. A smaller increase in sepal length may be sufficient to prevent flower opening whilst allowing self-fertilization. Additionally, pollen is shed from the anthers on to the sides of the carpel rather than the stigma. This is associated with overgrowth of the gynoecium caused by extra cell division, although under some conditions the stamen filaments do not extend normally.

The floral phenotypes result in sterility of plants unless manual pollination is carried out (mnt-1 homozygotes are female fertile, and the pollen that completes development is also fertile). However the last few flowers produced by mnt-1 mutants appear wild-type and these are self-fertile.

Germination frequency of mnt-1 seeds is normal, and the seedlings are vigorous.

mnt-1 mutants have thick inflorescence stems compared with wild-type plants (FIG. 24). A comparison of primary inflorescence stems shows that mnt-1 stems have a 20% greater diameter than wild-type (mean diameters mnt-1, 1.59 mm±s.e.m. 0.04; w.t., 1.32 mm±0.06; n=6 for each). Transverse sections (FIG. 24B) show that cells are of normal size in mnt-1 mutant stems but many more cells are formed.

Figure 5:
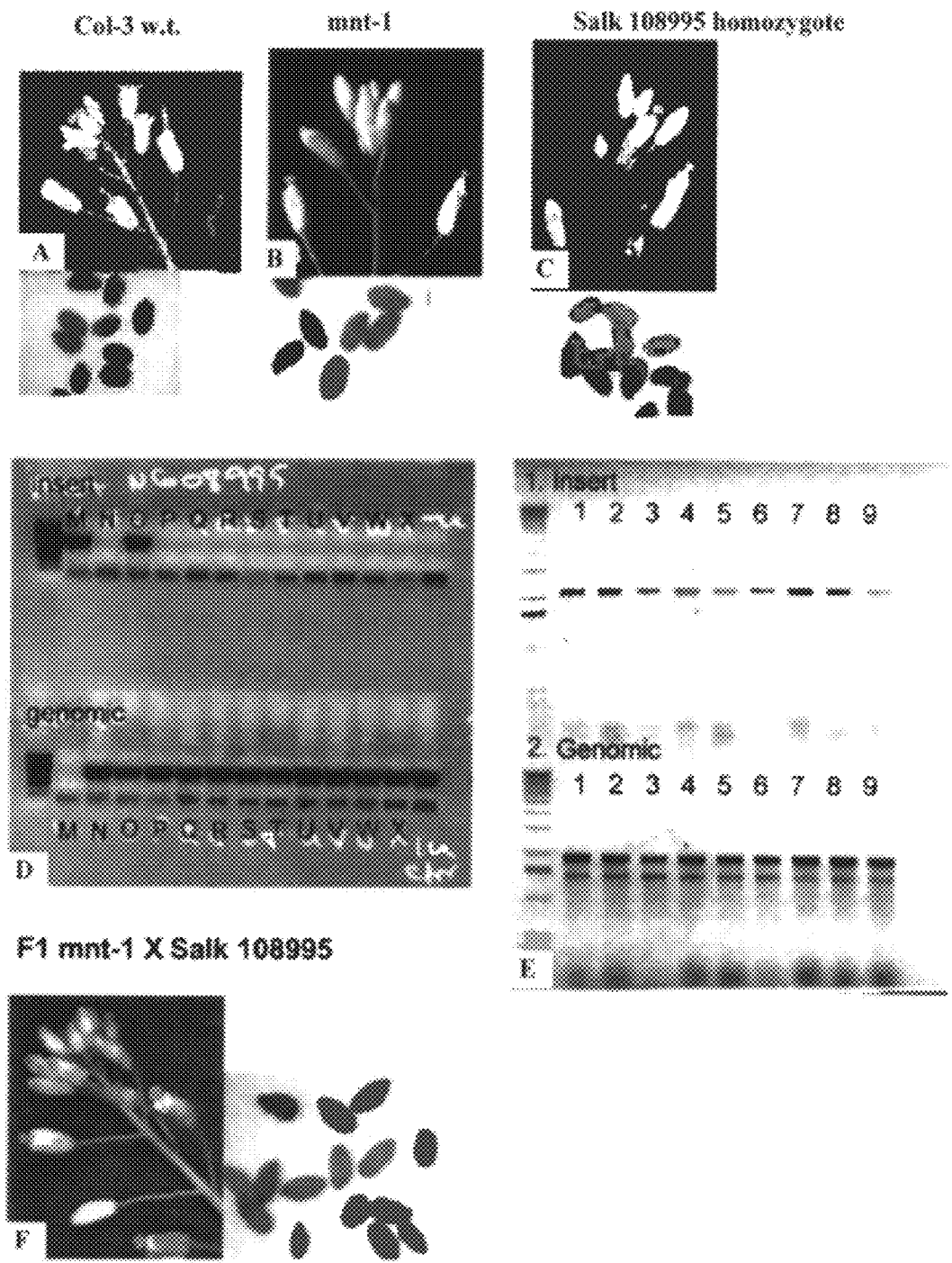
FIGS. 5A-C is a photograph illustrating a comparison of floral phenotype and seed size in wild-type Col-3 (5A), mnt-1 mutants (5B), and a Salk insertion mutant (Salk line 108995) homozygous for an insertion in the ARF2 gene (5C)
FIG. 5D is a photograph of a gel showing PCR-based scoring of segregants for the T-DNA insertion in Salk line 108995.
FIG. 5E is a photograph of a gel showing scoring of presence of the insertion (top) and presence of homozygotes (bottom) in F1 progeny of the cross between an mnt-1 homozygous mutant seed parent and the Salk 108995 homozygous pollen parent. All F1 progeny have a single copy of the insertion.
FIG. 5F is a photograph illustrating floral and seed phenotype in an F1 hybrid plant resulting from a cross between a homozygous mnt-1 mutant and a homozygous Salk insertion mutant (Salk line 108995)

D. Molecular Characterization of the Wild-Type MNT Gene and mnt-1 Mutant Allele i) Wild-Type MNT Sequence We mapped the MNT locus to a 60.9 kb region of chromosome 5 that was annotated by The *Arabidopsis* Information Resource (TAIR) to contain 17 genes. T-DNA insertion lines with insertions in these genes generated by The Salk Institute Genome Analysis Laboratory (SIGnAL) (Alonso et al., 2003) were obtained from the Nottingham *Arabidopsis* Stock Centre (NASC). Salk line no. 108995 (NASC stock no. N608995), with an insertion in the coding region of the AUXIN RESPONSE FACTOR 2 (ARF2) gene, included a plant homozygous for the insertion with a similar phenotype to mnt-1 mutants, including closed flowers and large seeds (FIG. 5A-C). Genotypic scoring of segregants from the Salk 108995 family, including one heterozygote and the homozygote, is shown in FIG. 5D. Specifically in FIG. 5D Top: Scoring for presence of an insertion in the ARF2 gene. Primers used were 5' TGG TTC ACG TAG TGG GCC ATC G 3' (SEQ ID NO:62), and 5' GAG TGG GTG GAG TGT TG 3' (SEQ ID NO:63). Lanes M and O show presence of the insertion. Bottom: Scoring for homozygous insertion mutants. Primers used were 5' GAG TGG GTG GAG TGT GTT TG 3' (SEQ ID NO:63) and 5' AGT TGG TTT TCG TTT GAG CAT 3' (SEQ ID NO:64). PCR conditions are set so that the gene will only amplify if there is no insertion: therefore PCR products will be amplified from DNA extracted from wild-type plants and also those hemizygous for the insertion, but not homozygous plants. Lane M shows no amplification, indicating this plant is homozygous for the insertion. An allelism test was conducted by crossing a seed parent homozygous for the mnt-1 mutation with the Salk 108995 homozygote as pollen parent.

F1 progeny were hemizygous for the insertion (FIG. 5E) and had the mnt-1 mutant phenotype (FIG. 5F), confirming that MNT is the ARF2 gene.

MNT/ARF2 will be referred to as MNT in the remainder of this document. The MNT gene=At5g62000, accession no. NM_125593. The genomic DNA for MNT, including the coding region plus 4371 bases of 5' and 525 bases of 3' flanking region, is shown in SEQ ID NO. 1. SEQ ID NO. 2 is the complete cDNA, and SEQ ID NO. 3, the predicted protein.

ARFs form part of the system for responding to auxin, a hormone known to be involved in many plant developmental processes including cell division and expansion (Stals and Inzé, 2001; Leyser, 2002). ARFs are transcription factors that in general are not induced by auxin themselves but which regulate expression of auxin-inducible genes, such as members of the Aux/IAA class (Liscum and Reed, 2002). ARFs have been shown to bind to Auxin Response Elements (AREs) containing the motif TGTCTC in the promoters of auxin-inducible genes (Ulmasov et al., 1999a). Twenty-two ARFs predicted to be functional have been annotated in the *Arabidopsis thaliana* genome (Hagen and Guilfoyle, 2002). ARFs contain two conserved domains—an N-terminal DNA binding domain and a C-terminal dimerization domain—and a variable middle region. An ARF may activate or repress transcription of its targets and this is thought to depend on the sequence of the middle region (Ulmasov et al., 1999b). Evidence so far suggests that ARF2 is likely to be a repressor (Tiwari et al., 2003).

ii) Mutant mnt-1 Sequence

We sequenced the coding region from genomic DNA of the mnt-1 allele plus 4371 bases of the 5' and 525 bases of the 3' flanking regions (this genomic sequence is shown in SEQ ID NO. 4). A single base change with respect to the wild-type Col-3 sequence, from G to A, was identified at position 665 from translational start, at the end of intron 3. This was predicted to affect splicing by changing the conserved 3' splice site (Brown and Simpson, 1998) from the consensus AG sequence to AA. We sequenced the first 837 bases of the mnt-1 cDNA from start of translation and confirmed that four bases are deleted from the beginning of exon 4. The mnt-1 cDNA from translational start to stop, consisting of the 837 directly sequenced bases plus the remainder of the cDNA coding region as predicted from the sequenced mnt-1 genomic DNA, is shown in SEQ ID NO. 5. Wild-type MNT and mutant mnt-1 cDNA sequences are aligned in FIG. 6.

The predicted mnt-1 protein (SEQ ID NO. 6) has a frameshift from amino acid position 123 and an early stop codon at position 167. Wild-type MNT and mutant mnt-1 predicted protein sequences are aligned in FIG. 7. The frameshift and early stop codon are both within the DNA binding domain and therefore the mnt-1 allele is likely to cause a complete loss of MNT function.

Example 1

Value of mnt Mutants in Understanding and Modifying Growth of Integuments/Seed Coat The mnt mutant seed phenotype demonstrates that there is a correlation between the size of integuments before fertilization and the size of the mature seed in *Arabidopsis thaliana* (FIGS. 1, 2). Due to the similarities in seed structure among even distantly related groups of flowering plants, this leads to the expectation that modification to integument/seed coat size in other species, and certainly in members of the Brassicaceae such as *Brassica napus*, will also result in changes to seed size.

Our knowledge of the mnt mutant phenotype and MNT gene sequence can be exploited in other species through TILLING ('Targeting induced local lesions in genomes'). In this reverse genetics technique, chemically mutagenized populations are screened for presence of a point mutation in a nucleic acid sequence of interest; this can be done as a high-throughput procedure and is applicable to many species (Till et al., 2003). For example, TILLING could be applied to the *Brassica napus* or rice orthologues of MNT in order to modify seed size in these crop species.

Our knowledge that mnt-1 heterozygotes are self-fertile and produce larger seeds than wild-type plants shows that a plant with reduced MNT function (as in a heterozygote for an MNT mutation or in a plant which has been genetically modified in some way to achieve the same effect as conventional breeding) will advantageously produce large seeds without a loss of fertility.

Example 2

Modifying Expression of MNT Orthologues in Other Species

Knowledge of the MNT sequence in *Arabidopsis thaliana* also allows us to search for orthologues in crop species as a necessary first step in targeted modification of the expression of the gene in these species.

By way of example, we amplified the putative *Brassica napus* orthologue (BnARF2) of MNT using primers (SEQ ID NO 7, 8) based on the MNT sequence and on publicly available *Brassica oleracea* sequence. The BnARF2 cDNA was amplified from total RNA isolated from seedlings of *Brassica napus* var. *Westar*. The BnARF2 cDNA from translational start to stop is shown in SEQ ID NO. 9 and is aligned with *Arabidopsis thaliana* MNT cDNA in FIG. 8. The BnARF2 predicted protein (SEQ ID NO. 10) has 85% identity to *Arabidopsis thaliana* MNT.

A family of ARFs has also been characterized in rice and one of these, OsARF2 (accession no. AB071293), is considered to be the orthologue of *Arabidopsis thaliana* ARF2 (Sato et al., 2001). FIG. 9 shows an alignment of the predicted protein sequences of MNT (*Arabidopsis thaliana* ARF2), BnARF2, and OsARF2.

Orthologues of MMT may be determined for other species using similar techniques.

Example 3

Construction, Transformation, and Analysis of Reporter Vectors to Show where Integument/Seed Coat Promoters are Expressed in *Arabidopsis thaliana*

This is to test which promoters are suitable for driving integument/seed coat-specific or -preferred expression of nucleic acids such as MNT antisense or RNAi constructs, or other genes modifying cell proliferation.

Figures 10, 10A:
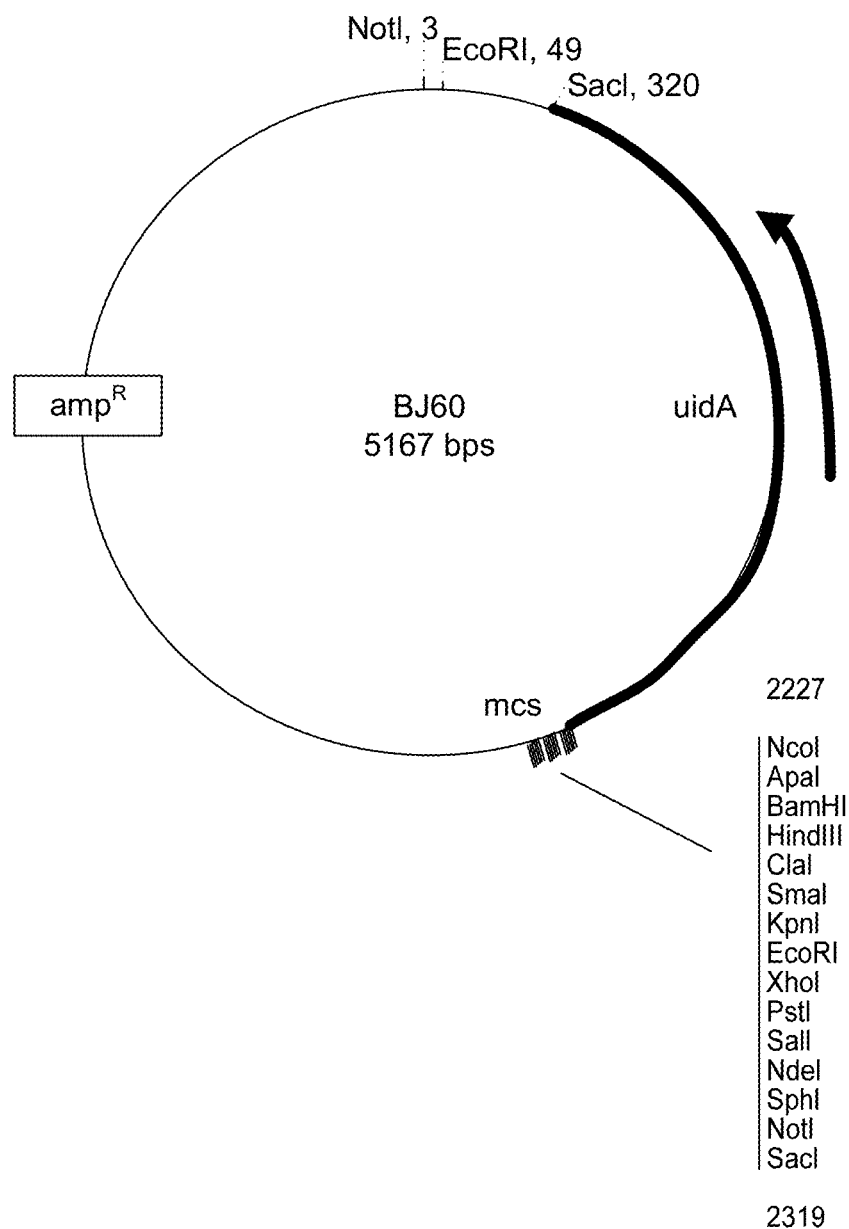
FIGS. 10A-E illustrates the BJ60 (FIG. 10A), BJ40 (FIG. 10B), pFGC5941 (FIG. 10C), pART7 (FIG. 10C), and BJ36 (FIG. 10D) vectors used for the cloning strategies described in the following examples.
Figure 10B:
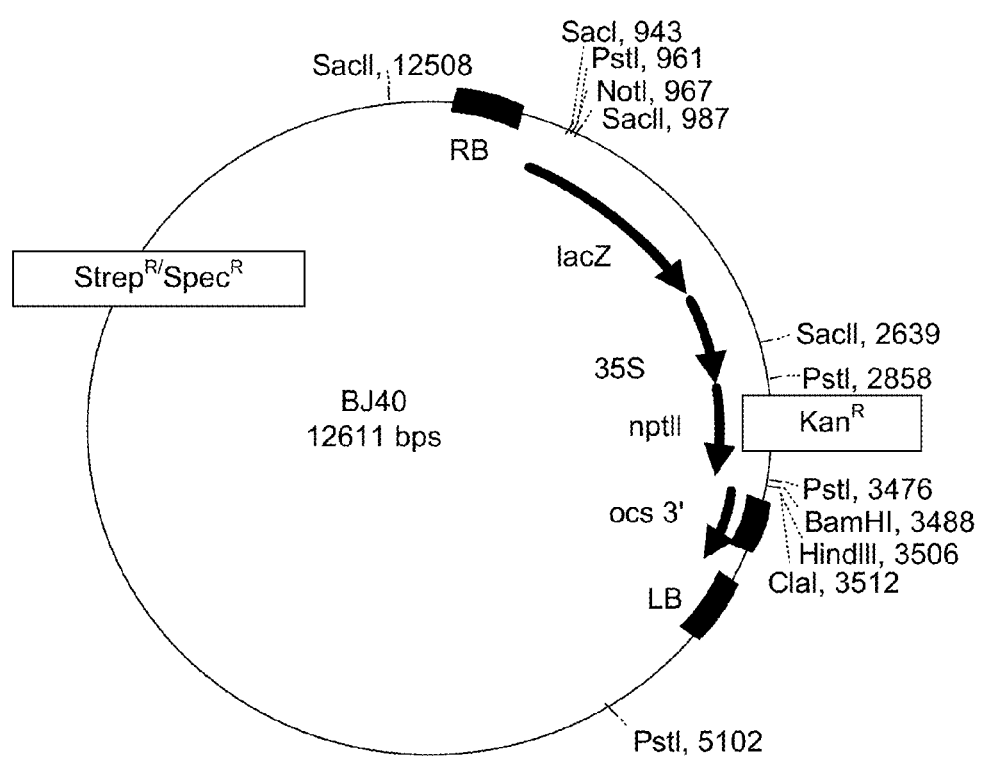
Figure 10C:
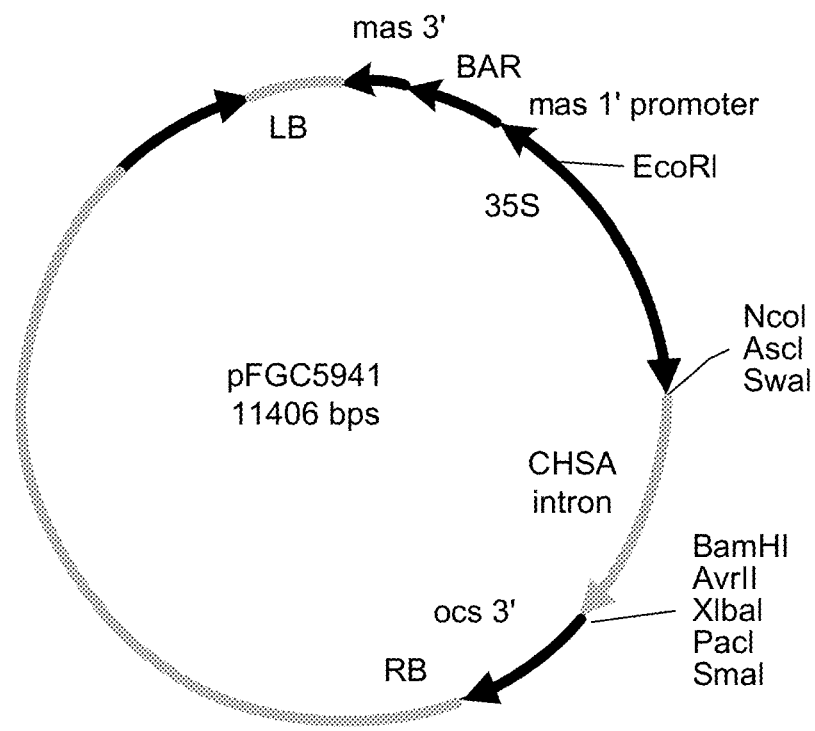
Figure 10D:
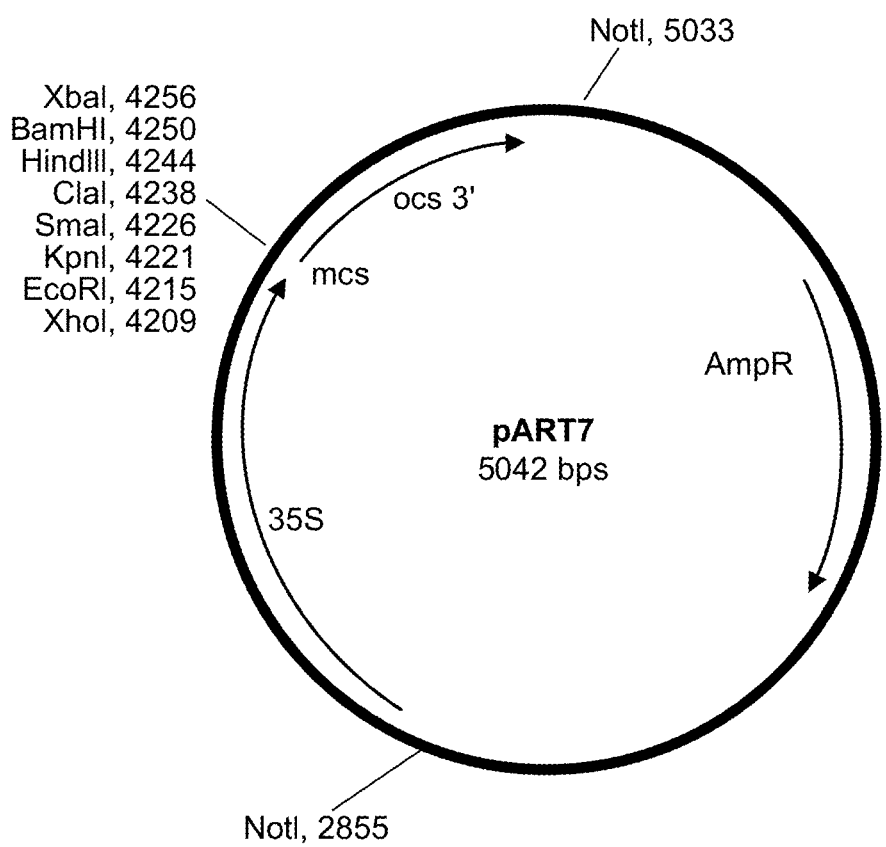
Figure 10E:
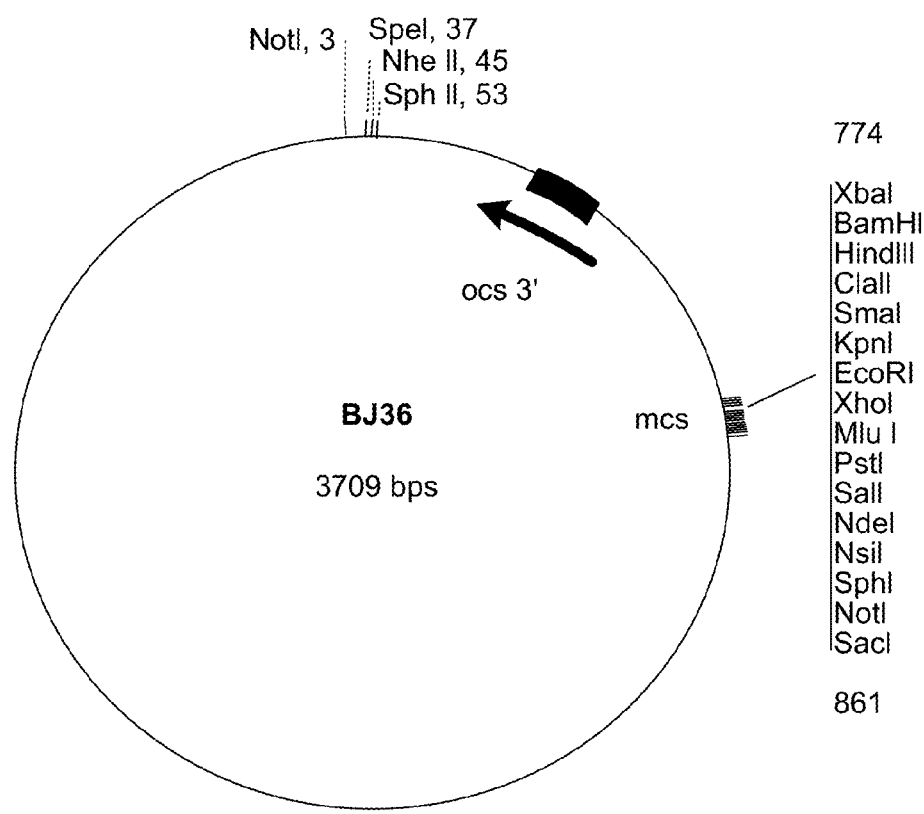

Diagrams of the BJ60, BJ40, pFGC5941, pART7, and BJ36 vectors used in the cloning strategies described in this and following examples are shown in FIG. 10.

The cloning strategy is shown in FIG. 11.

3a Construction of Reporter Vectors

3a(i) TT8

A reporter vector based on the promoter of the TT8 gene (Nesi et al., 2000; At4g09820, accession no. AJ277509) is constructed as described below. A 1.7 kb fragment including the TT8 promoter is amplified by the polymerase chain reaction (PCR) from *Arabidopsis thaliana* genomic DNA 5' to translational start of the TT8 gene using the primers TT8F and TT8R which introduce an NdeI and a PstI site at the 5' and 3' ends of the TT8 PCR fragment respectively.

```
                                    SEQ ID NO. 11
5' AAACATATGCCAACGGGATCATGGGATTAC 3' TT8F
      NdeI

SEQ ID NO. 12
5' AAACTGCAGCGTTCCCGGAGATACGAAAAC 3' TT8R
      PstI
```

The TT8 PCR fragment is A-tailed and ligated into pGEMT, then excised with NdeI and PstI and ligated into the NdeI and PstI sites of BJ60, 5' to the uidA reporter which includes a terminator signal, forming the vector TT8-BJ60.

3a(ii) TT12

A reporter vector based on the promoter of the TT12 gene (Debeaujon et al., 2000; At3g59030, accession no. AJ294464) is constructed as described below. A 1.7 kb fragment including the T772 promoter is amplified by PCR from *Arabidopsis thaliana* genomic DNA 5' to translational start of the TT12 gene using the primers TT12F and TT12R which introduce an NdeI and a PstI site at the 5' and 3' ends of the 7712 PCR fragment respectively.

```
                                    SEQ ID NO. 13
5' AAACATATGGGAATTCACAATCGGAAAGTC 3' TT12F
      NdeI

SEQ ID NO. 14
5' AAACTGCAGGGTCCGTTTATTAGTTCCTC 3' TT12R
      PstI
```

The TT12 PCR fragment is A-tailed and ligated into pGEMT, and then excised with NdeI and PstI and ligated into the NdeI and PstI sites of BJ60, 5' to the uidA reporter gene forming TT12-BJ60.

3b Construction of Binary Vectors and Transformation into *Arabidopsis thaliana*

Reporter cassettes are excised with NotI from the following vectors:

TT8-BJ60

TT12-BJ60 and ligated into the NotI sites of the binary vector BJ40, forming the following vectors for transformation:

TT8-uidA-BJ40

TT12-uidA-BJ40

The binary vectors are transformed into *Agrobacterium tumefaciens* and then into *Arabidopsis thaliana*.

3c Analysis of Expression Patterns

The uidA gene encodes β-glucuronidase (GUS), which is assayed using standard protocols (e.g. Jefferson, 1987). For FIG. 12 (below) the following assay was used. Seeds were dissected from siliques into GUS staining buffer (100 mM Tris-HCl pH 7.2, 50 mM NaCl, 0.1% Triton-X-100, 2 mM 5-bromo-4-chloro-3-indolyl-beta-D-glucoronic acid (X-Gluc), 2 mM $K_3Fe(CN)_6$, 2 mM $K_4Fe(CN)_6$) and incubated overnight at 37° C.

Figure 12:
FIG. 12 is a micrograph of a globular stage seed from a plant containing the TT12::uidA construct assayed for GUS expression; the inner layer of the inner integument is stained (arrow)

FIG. 12 shows a globular stage seed from a plant containing the TT12::uidA construct assayed for GUS expression; the inner layer of the inner integument is stained (arrow), indicating activity of the TT12 promoter fragment in that integument.

Example 4

Figure 13A:
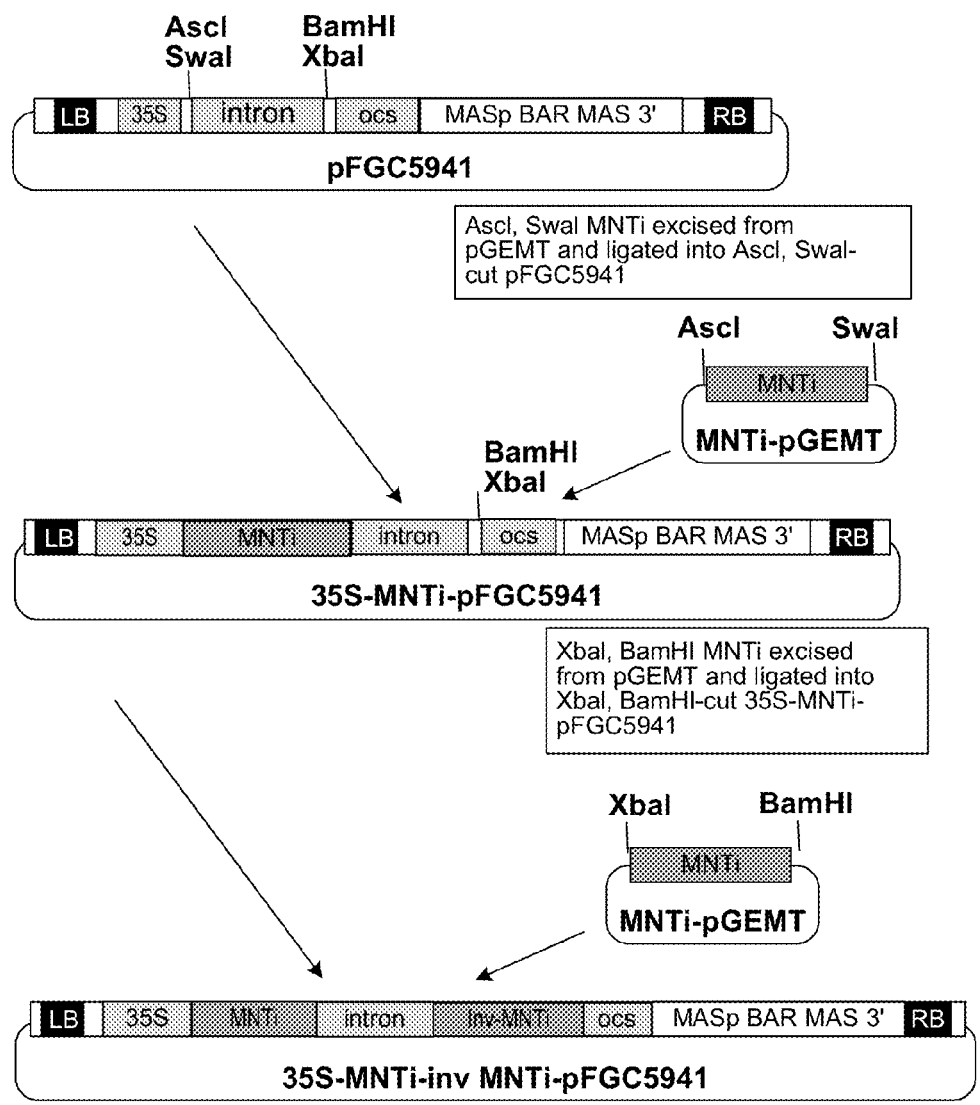
FIG. 13A illustrates a cloning strategy for constructing an RNAi vector to constitutively decrease MNT expression (Example 4)

Construction and Transformation of an RNAi Cassette that Decreases MNT Expression In *Arabidopsis thaliana*, Including Decreased Expression in the Integuments/Seed Coat The cloning strategy is shown in FIG. 13A.

4a Construction of RNAi Cassette

An RNAi vector based on the MNT gene (see above) is constructed as described below. A 0.57 kb fragment of the MNT cDNA ('MNTi') is amplified by PCR from *Arabidopsis thaliana* cDNA using the primers FARF2i and RARF2i new which introduce XbaI and AscI sites at the 5' end of the MNT1 PCR fragment, and BamHI and SwaI sites at the 3' end of the PCR fragment.

```
                                    SEQ ID NO. 15
5' GATCTAGAGGCGCGCCGGATCTGAGAACTGGATG 3' FARF2i
      XbaI  AscI

SEQ ID NO. 16
5' GAGGATCCATTTAAATCCGCAGCATCATTCAAGT 3' RARF2inew
      BamHI SwaI
```

The MNTi PCR fragment is A-tailed and ligated into pGEMT, and then excised with AscI and SwaI and ligated into the AscI and SwaI sites of the pFGC5941 RNAi vector 3' to the 35S promoter and 5' to the CHSA intron, which places the fragment in forward orientation. This forms the vector 35S-MNTi-pFGC5941. The MNTi PCR fragment is then excised from pGEMT with BamHI and XbaI and ligated into the BamHI and XbaI sites of the 35S-MNTi-pFGC5941 vector, 3' to the CHSA intron and 5' to the ocs terminator signal, which places the fragment in inverse orientation. This forms the vector 35S-MNTi-inv MNTi-pFGC5941.

4b Transformation into *Arabidopsis thaliana*

Vector 35S-MNTi-inv MNTi-pFGC5941 is transformed into *Agrobacterium tumefaciens* and then into *Arabidopsis thaliana*.

4c Analysis of Seed Weights in Plants Transformed with the 35S::MNT RNAi Vector

Figure 13B:
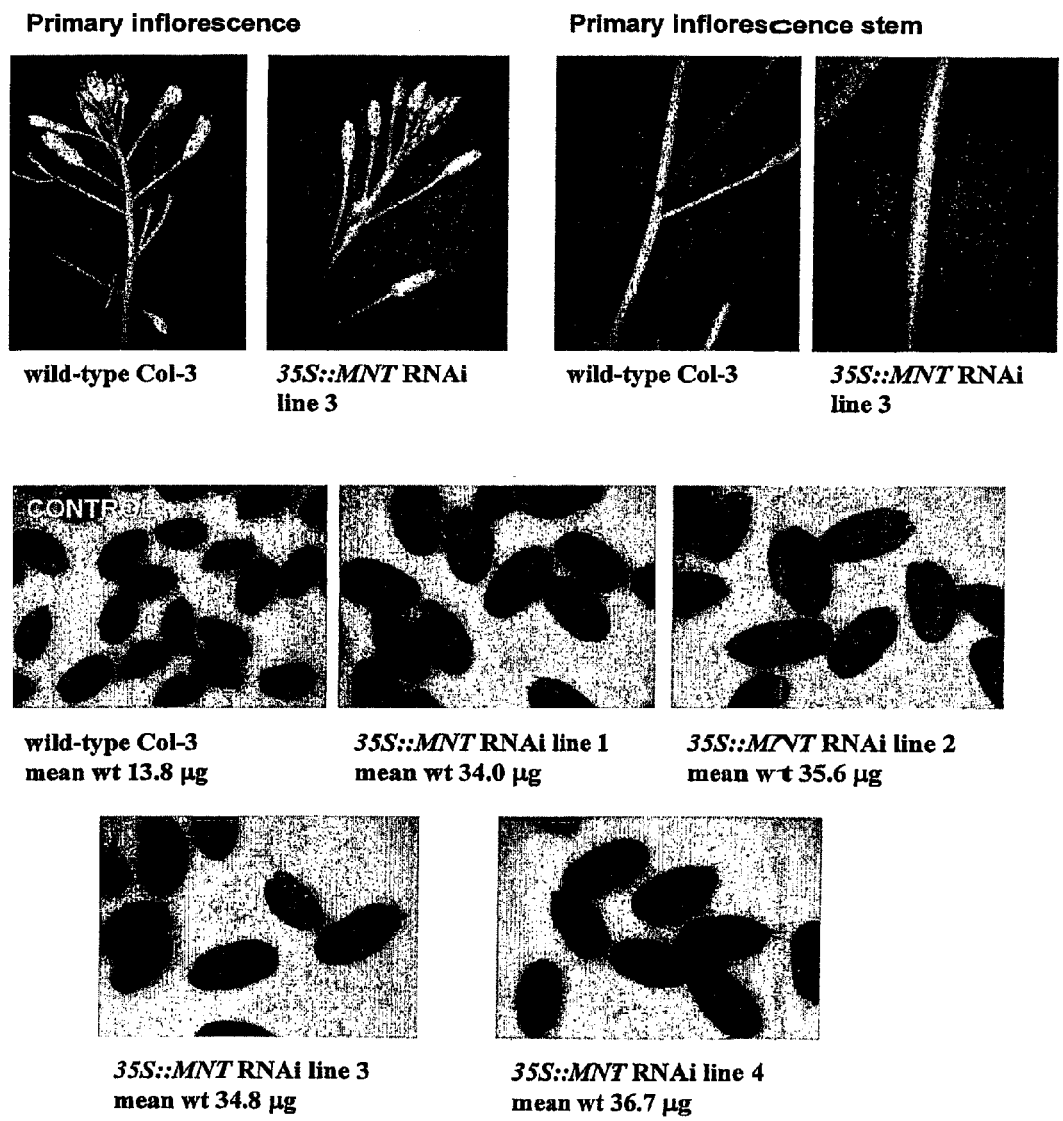
FIG. 13B is a series of photographs illustrating inflorescence and stem phenotypes (top) and seed sizes and weights (bottom) from independently transformed lines containing the 35S::MNT RNAi expression cassette compared with a wild-type control. Inflorescences and stems were photographed at the same scale, and seeds were photographed at the same scale.

Wild-type plants transformed with the 35S::MNT RNAi vector described in Example 4a, b have the mnt mutant phenotype, including closed flowers for most of the plant's life cycle (FIG. 13B top left), inflorescence stems with increased diameter (FIG. 13B top right), and large seeds (FIG. 13B, bottom). Seeds from four independently transformed lines, along with wild-type plants grown under the same conditions, are shown in FIG. 13B (bottom). The mean weight for these four lines was 35.3 μg, compared with 13.8 μg for the wild-type control.

Example 5

Figure 14:
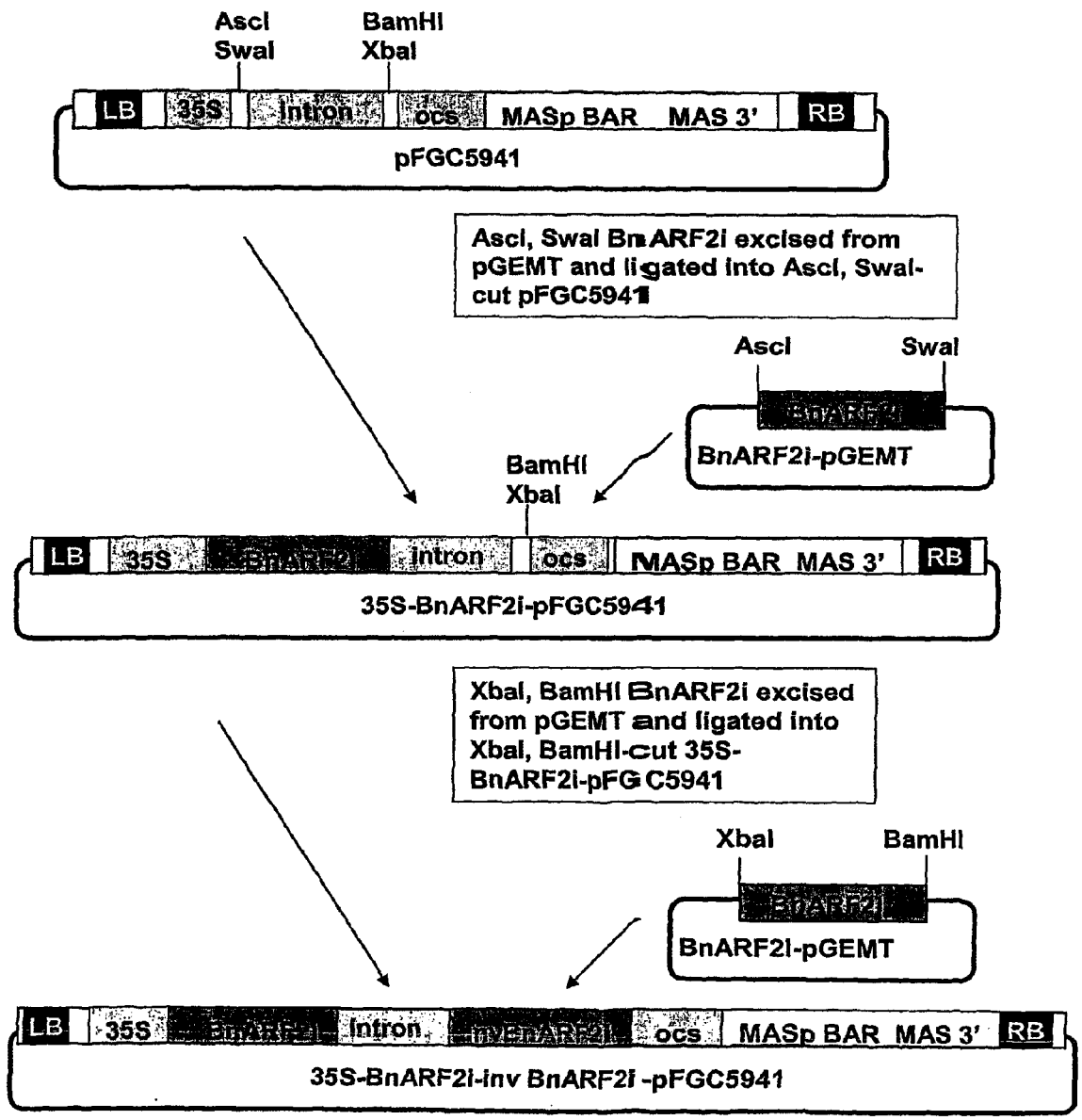
FIG. 14 illustrates a cloning strategy for constructing an RNAi vector to constitutively decrease BnARF2 expression (Example 5)

Construction and Transformation of an RNAi Cassette that Decreases BnARF2 Expression in *Brassica napus*, Including Decreased Expression in the Integuments/Seed Coat The cloning strategy is shown in FIG. 14.

5a Construction of RNAi Cassette

An RNAi vector based on the BnARF2 gene (Example 2, above) is constructed as described below. A 0.56 kb fragment of the BnARF2 cDNA (BnARF2i) is amplified by PCR from *Brassica napus* cDNA using the primers FBnARF21 and RBnARF21 which introduce XbaI and AscI sites at the 5' end of the BnARF21 PCR fragment, and BamHI and SwaI sites at the 3' end of the PCR fragment.

```
                                          SEQ ID NO. 17
5'GATCTAGAGGCGCGCCGCGATATGAGAACTGGATA 3' FBnARF2i
    XbaI  AscI

SEQ ID NO. 18
5'GAGGATCCATTTAAATGTAGGCCCCGCAGGGTCA 3' RBnARF2i
    BamHI SwaI
```

The BnARF2i PCR fragment is A-tailed and ligated into pGEMT and then excised with AscI and SwaI and ligated into the AscI and SwaI sites of the pFGC5941 RNAi vector 3' to the 35S promoter and 5' to the CHSA intron using the enzymes AscI and SwaI, which places the fragment in forward orientation. This forms the vector 35S-BnARF2i-pFGC5941. The BnARF21 PCR fragment is then excised from pGEMT with BamHI and XbaI and ligated into the BamHI and XbaI sites of the 35S-BnARF2i-pFGC5941 vector 3' to the CHSA intron and 5' to the ocs terminator, which places the fragment in inverse orientation. This forms the vector 35S-BnARF2i-inv BnARF2i-pFGC5941.

5b Transformation

Vector 35S-BnARF2i-inv BnARF2i-pFGC5941 is transformed into *Agrobacterium tumefaciens* and then into *Brassica napus*.

Example 6

Construction and Transformation of RNAi Cassettes that Decrease MNT Expression Primarily in the Integuments/Seed Coat of *Arabidopsis thaliana*

This is specifically to phenocopy the big seed effect of mnt mutations without other effects on plant growth, development, or fertility.

The cloning strategy is shown in FIG. 15.

6a Construction of RNAi Vectors Containing an Integument/Seed Coat Promoter

6a(i) TT8

An RNAi vector in which the TT8 promoter (Nesi et al., 2000; At4g09820, accession no. AJ277509) drives an inverted repeat of an MNT nucleic acid fragment (see Example 4, above) is constructed as described below. A 1.7 kb fragment including the TT8 promoter is amplified by PCR from *Arabidopsis thaliana* genomic DNA 5' to translational start of the TT8 gene using the primers TT8 EcoRI F and TT8 NcoI R which introduce an EcoRI and an NcoI site at the 5' and 3' ends of the TT8 PCR fragment respectively.

```
                                          SEQ ID NO. 19
5' GAATTCCCAACGGGATCATGGGATTAC 3' TT8Fi
   EcoRI

SEQ ID NO. 20
5' CCATGGCGTTCCCGGAGATACGAAAAC 3' TT8Ri
   NcoI
```

The TT8 PCR fragment is A-tailed and ligated into pGEMT, and then excised with EcoRI and NcoI and exchanged for the 35S promoter in the vector 35S-MNT-inv MNTi-pFGC5941 (Example 4, above), forming the vector TT8-MNT-inv MNTi-pFGC5941.

6a(ii) INO

An RNAi vector in which the INO promoter (Villanueva et al., 1999; At1g23420, accession no. AF195047) drives an inverted repeat of an MNT nucleic acid fragment (see Example 4, above) is constructed as described below. A 1.5 kb fragment including the INO promoter is amplified by PCR from *Arabidopsis thaliana* genomic DNA 5' to translational start of the INO gene using the primers FINOi and RINOi_which introduce an EcoRI and an NcoI site at the 5' and 3' ends of the INO PCR fragment respectively.

```
                                          SEQ ID NO. 21
5' GAATTCCCTGGATTAGTGCAAGCC 3' FINOi
   EcoRI

SEQ ID NO. 22
5' CCATGGGAGAGTGTGTGTGTACGATG 3' RINOi
   NcoI
```

The INO PCR fragment is A-tailed and ligated into pGEMT, and then excised with EcoRI and NcoI and exchanged for the 35S promoter in the vector 35S-MNT-inv MNTi-pFGC5941 (Example 4, above), forming the vector INO-MNT-inv MNTi-pFGC5941.

6b Transformation into *Arabidopsis thaliana*

The TT8-MNT-inv MNTi-pFGC5941 and INO-MNT-inv MNTi-pFGC5941 vectors are transformed into *Agrobacterium tumefaciens* and then into *Arabidopsis thaliana*.

Example 7

Construction and Transformation of RNAi Cassettes that Decrease BnARF2 Expression Primarily in the Integuments/Seed Coat of *Brassica napus*

The cloning strategy is shown in FIG. 16.

7a Construction of RNAi Vectors Containing an Integument/Seed Coat Promoter

7a(i) TT8

An RNAi vector in which the TT8 promoter (Nesi et al., 2000; At4g09820, accession no. AJ277509) drives an inverted repeat of a BnARF2 nucleic acid fragment (see Example 5, above) is constructed as described below. A 1.7 kb fragment including the TT8 promoter with EcoRI and NcoI linkers is amplified by PCR from *Arabidopsis thaliana* genomic DNA as described in Example 6a(i) above.

The TT8 PCR fragment is A-tailed and ligated into pGEMT, and then excised with EcoRI and NcoI and exchanged for the 35S promoter in the vector 35S-BnARF2-inv BnARF2i-pFGC5941 (Example 5, above), forming the vector TT8-BnARF2-inv BnARF21-pFGC5941.

7a(ii) INO

An RNAi vector in which the INO promoter (Villanueva et al., 1999; At1g23420, accession no. AF195047) drives an inverted repeat of a BnARF2 nucleic acid fragment (see Example 5, above) is constructed as described below. A 1.5 kb fragment including the INO promoter with EcoRI and NcoI linkers is amplified by PCR from *Arabidopsis thaliana* genomic DNA as described in Example 6a(ii) above.

The INO PCR fragment is A-tailed and ligated into pGEMT, and then excised with EcoRI and NcoI and exchanged for the 35S promoter in the vector 35S-BnARF2-inv BnARF2i-pFGC5941 (Example 5, above), forming the vector INO-BnARF2-inv BnARF21-pFGC5941.

7b Transformation into *Brassica napus*

The TT8-BnARF2-inv BnARF2i-pFGC5941 and INO-BnARF2-inv BnARF2i-pFGC5941 vectors are transformed into *Agrobacterium tumefaciens* and then into *Brassica napus*.

Example 8

Construction and Transformation of an Expression Vector that Increases MNT Expression in *Arabidopsis thaliana*, Including Increased Expression in the Integuments/Seed Coat This is to produce a plant with altered seed size.
The cloning strategy is shown in FIG. 17.
8a Construction of a Vector for Constitutive Expression of MNT Construction of an expression vector with the CaMV 35S promoter driving the MNT gene is described below. The MNT cDNA including the translational start and stop is amplified by PCR from *Arabidopsis thaliana* cDNA using the primers 35S Xho new and 35S Bam new which introduce a XhoI and a BamHI site at the 5' and 3' ends of the MNT PCR fragment respectively.

```
                                    SEQ ID NO. 23
5' CTCGAGGAAGGTATGGCGAGT 3'  35S Xho new
   XhoI SEQ ID NO. 24
5' GGATCCTCCAGTCTCCACCAA 3'  35S Bam new
   BamHI
```

The MNT PCR fragment is A-tailed and ligated into pGEMT, and then excised with XhoI and BamHI and ligated into the XhoI and BamHI sites of pART7, 3' to the 35S promoter and 5' to the ocs terminator, forming the vector 35S-MNT-pART7.

8b Construction of Binary Vectors and Transformation into *Arabidopsis thaliana*

The 35S::MNT expression cassette (including the ocs terminator signal) is excised from 35S-MNT-pART7 with NotI and ligated into the NotI sites of the binary vector BJ40, forming the vector 35S-MNT-BJ40. The binary vector is transformed into *Agrobacterium tumefaciens* and then into *Arabidopsis thaliana*.

8c Analysis of Seed Weights in Plants Transformed with the 35S::MNT Cassette

Wild-type plants transformed with the 35S::MNT cassette described in Example 8a, b have the mnt mutant phenotype, including closed flowers for most of the plant's life cycle (FIG. 17B, top), and large seeds. Seeds from three independently transformed lines, along with wild-type plants grown under the same conditions, are shown in FIG. 17B, middle. The overall mean weight for these three lines was 25.5.mu.g, compared with 15.0.mu.g for the wild-type control. Expression of MNT/ARF2 was assayed in transformed and wild-type plants by semiquantitative RT-PCR (FIG. 17B, bottom) using multiplex RT-PCR with primers RTARF2-F (5'-GAGTGGGTGGAGTGTGTTTG-3') (SEQ ID NO:63) and RTARF2-R (5% AGTTGGTTTTCGTTTGAGCAT-3') (SEQ ID NO:64), and control primers to the GAPC gene, GAPC--F (5'-CACTTGAAGGGTGGTGCCAAG-3') (SEQ ID NO:65) and GAPC--R (5'-CCTGTTGTCGCCAAC-GAAGTC-3') (SEQ ID NO:66). PCR was initiated with RTARF2 primers and run for 4 cycles at an annealing temperature of 55.degree. C., extension time 2 min. GAPC primers were added to each reaction mix and the reaction was run for an additional 22 cycles. This showed that plants transformed with the 35S::MNT cassette did not have lower levels of MNT expression than wild-type plants; therefore the mutant phenotype was not due to cosuppression. Therefore constitutive expression of the MNT gene (such as achieved under control of the 35S promoter) provides a further method for producing large seeds.

Example 9

Construction and Transformation of an Expression Cassette that Increases BnARF2 Expression in *Brassica napus*, Including Increased Expression in the Integuments/Seed Coat This is also to produce a plant with altered seed size.
The cloning strategy is shown in FIG. 17.
9a Construction of a Vector for Constitutive Expression of BnARF2

Construction of an expression vector with the CaMV 35S promoter driving the BnARF2 gene is described below. The BnARF2 cDNA from translational start to stop is amplified by PCR from *Brassica napus* cDNA using the primers BnARF2 XhoI F and BnARF2 BamHI R which introduce a XhoI and a BamHI site at the 5' and 3' ends of the BnARF2 PCR fragment respectively.

```
                                       SEQ ID NO. 25
5' CTCGAGATGGCGAGTTCGGAGGTTTC 3'  BnARF2 XhoI F
   XhoI

SEQ ID NO. 26
5' GGATCCTTAAGAGTTTCCGGCGCTGG 3'  BnARF2 BamHI R
   BamHI
```

The BnARF2 PCR fragment is A-tailed and ligated into pGEMT, and then excised with XhoI and BamHI and ligated into the XhoI and BamHI sites of pART7, 3' to the 35S promoter and 5' to the ocs terminator, forming the vector 35S-BnARF2-pART7.

9b Construction of Binary Vectors and Transformation into *Brassica napus*

The 35S::BnARF2 expression cassette (including the ocs terminator signal) is excised from 35S-BnARF2-pART7 with NotI and cloned into the NotI sites of the binary vector BJ40, forming the vector 35S-BnARF2-BJ40.

The binary vector is transformed into *Agrobacterium tumefaciens* and then into *Brassica napus*. Constitutive expression of the BnARF2 gene (such as achieved under control of the 35S promoter) provides a further method for producing large seeds.

Example 10

Construction and Transformation of Expression Cassettes that Increase MNT Expression Primarily in the Integuments/Seed Coat of *Arabidopsis thaliana*

The cloning strategy is shown in FIG. 18.

10a Construction of Expression Vectors Containing an Integument/Seed Coat Promoter 10a(i) TT8

An expression vector based on the TT8 promoter (Nesi et al., 2000; At4g09820, accession no. AJ277509) is constructed as described below. A 1.7 kb fragment including the TT8 promoter with NdeI and PstI linkers is amplified by PCR from *Arabidopsis thaliana* genomic DNA as described in Example 3a(i), above. The 278 PCR fragment is A-tailed and ligated into pGEMT, and then excised with NdeI and PstI and ligated into the NdeI and PstI sites of BJ36, 5' to the ocs terminator signal, forming the vector TT8-BJ36.

10a(ii) INO

An expression vector based on the promoter of the INO gene (Villanueva et al., 1999; At1g23420, accession no. AF195047) is constructed as described below. A 1.5 kb fragment including the INO promoter is amplified by PCR from *Arabidopsis thaliana* genomic DNA 5' to translational start of the INO gene using the primers INOF and INOR which introduce an NdeI and a PstI site at the 5' and 3' ends of the INO PCR fragment respectively.

```
                                            SEQ ID NO. 27
5'  CATATGCCTGGATTAGTGCAAGGCAA 3' INOF
    NdeI

SEQ ID NO. 28
5'  CTGCAGGAGAGTGTGTGTGTACGATG 3' INOR
    PstI
```

The INO PCR fragment is A-tailed and ligated into pGEMT, and then excised with NdeI and PstI and ligated into the NdeI and PstI sites of BJ36, 5' to the ocs terminator signal, forming the vector INO-BJ36.

10b Construction of Expression Vectors Containing a Promoter::MNT Expression Cassette The MNT cDNA with XhoI and BamHI linkers is amplified by PCR from *Arabidopsis thaliana* cDNA and ligated into pGEMT as described in Example 8a, above.

10b(i) TT8-MNT

The MNT PCR fragment is excised from pGEMT with XhoI and BamHI and ligated into the XhoI and BamHI sites of the TT8-BJ36 vector, 3' to the TT8 promoter, forming the vector TT8-MNT-BJ36.

10b(ii) INO-MNT

The MNT PCR fragment is excised from pGEMT with XhoI and BamHI and ligated into the XhoI and BamHI sites of the INO-BJ36 vector, 3' to the INO promoter, forming the vector INO-MNT-BJ36.

10c Construction of Binary Vectors and Transformation

10c(i) TT8-MNT

The TT8::MNT expression cassette (including the ocs terminator signal) is excised from TT8-MNT-BJ36 with NotI and cloned into the NoI sites of the binary vector BJ40, forming the vector TT8-MNT-BJ40.

10c(ii) INO-MNT

The INO::MNT expression cassette (including the ocs terminator signal) is excised from INO-MNT-BJ36 with NotI and cloned into the NotI sites of the binary vector BJ40, forming the vector INO-MNT-BJ40.

The TT8-MNT-BJ40 and INO-MNT-BJ40 binary vectors are transformed into *Agrobacterium tumefaciens* and then into *Arabidopsis thaliana*.

Example 11

Construction and Transformation of Expression Vectors that Increase BnARF2 Expression Primarily in the Integuments/Seed Coat of *Brassica napus*

The cloning strategy is shown in FIG. 19.

11a Construction of Expression Vectors Containing an Integument/Seed Coat Promoter 11a(i) TT8

An expression vector based on the promoter of the TT8 gene (Nesi et al., 2000; At4g09820, accession no. AJ277509) is constructed as described below. A 1.7 kb fragment including the TT8 promoter is amplified by PCR from *Arabidopsis thaliana* genomic DNA 5' to translational start of the TT8 gene using the primers TT8F and TT8 MluI R which introduce an NdeI and an MluI site at the 5' and 3' ends of the 778 PCR fragment respectively.

```
                                            SEQ ID NO. 11
5'  AAACATATGCCAACGGGATCATGGGATTAC 3' TT8F
       NdeI

SEQ ID NO. 29
5'  AAAACGCGTCGTTCCCGGAGATACGAAAAC 3' TT8 MluI R
       MluI
```

The TT8 PCR fragment is A-tailed and ligated into pGEMT, and then excised with NdeI and MluI and ligated into the NdeI and MluI sites of BJ36, 5' to the ocs terminator signal, forming the vector TT8 (NdeI MluI)-BJ36.

11a(ii) INO

An expression vector based on the promoter of the INO gene (Villanueva et al., 1999; At1g23420, accession no. AF195047) is constructed as described below. A 1.5 kb fragment including the INO promoter is amplified by PCR from *Arabidopsis thaliana* genomic DNA 5' to translational start of the INO gene using the primers INOF and INO MluI R which introduce an NdeI and an MluI site at the 5' and 3' ends of the INO PCR fragment respectively.

```
                                            SEQ ID NO. 27
5'  CATATGCCTGGATTAGTGCAAGGCAA 3' INOF
    NdeI

SEQ ID NO. 30
5'  ACGCGTGAGAGTGTGTGTCTACGATG 3' INO MluI R
    MluI
```

The INO PCR fragment is A-tailed and ligated into pGEMT, and then excised with NdeI and MluI and ligated into the NdeI and MluI sites of BJ36, 5' to the ocs terminator signal, forming the vector INO (NdeI MluI)-BJ36.

11b Construction of Expression Vectors Containing a Promoter::BnARF2 Expression Cassette The BnARF2 cDNA with XhoI and BamHI linkers is amplified by PCR from *Brassica napus* cDNA and ligated into pGEMT as described in Example 9a, above.

11b(i) TT8

The BnARF2 PCR fragment is excised from pGEMT with XhoI and BamHI and ligated into the XhoI and BamHI sites of the TT8 (NdeI MluI)-BJ36 vector, 3' to the TT8 promoter, forming the vector TT8-BnARF2-BJ36.

11b(ii) INO

The BnARF2 PCR fragment is excised from pGEMT with XhoI and BamHI and ligated into the XhoI and BamHI sites of the INO (NdeI MluI)-BJ36 vector, 3' to the INO promoter, forming the vector INO-BnARF2-BJ36.

11c Construction of Binary Vectors and Transformation

11c(i) TT8

The TT8-BnARF2 expression cassette (including the ocs terminator signal) is excised from TT8-BnARF2-BJ36 with NotI and ligated into the NotI sites of the binary vector BJ40, forming the vector TT8-BnARF2-BJ40.

11c(ii) INO

The INO-BnARF2 expression cassette (including the ocs terminator signal) is excised from INO-BnARF2-BJ36 with NotI and ligated into the NotI sites of the binary vector BJ40, forming the vector INO-BnARF2-BJ40.

The binary vectors TT8-BnARF2-BJ40 and INO-BnARF2-BJ40 are transformed into *Agrobacterium tumefaciens* and then into *Brassica napus*.

Example 12

Construction, Transformation, and Analysis of Expression Vectors that Increase Expression of a Gene Promoting Cell Division in the Integuments/Seed Coat of *Arabidopsis thaliana*

Figure 20:
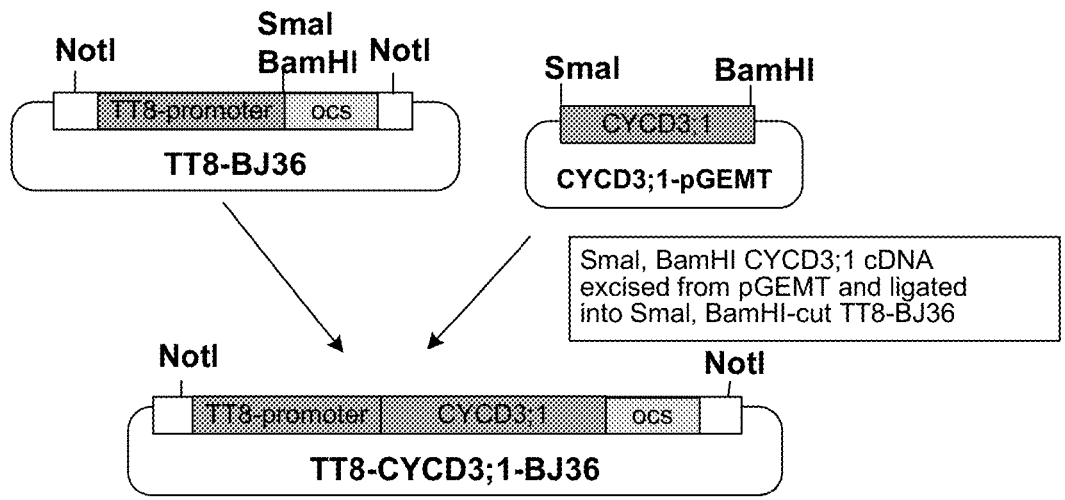
FIG. 20 illustrates a cloning strategy for constructing vectors for expression of genes promoting cell division in the integuments/seed coat (Examples 12, 13)
Figure 20:
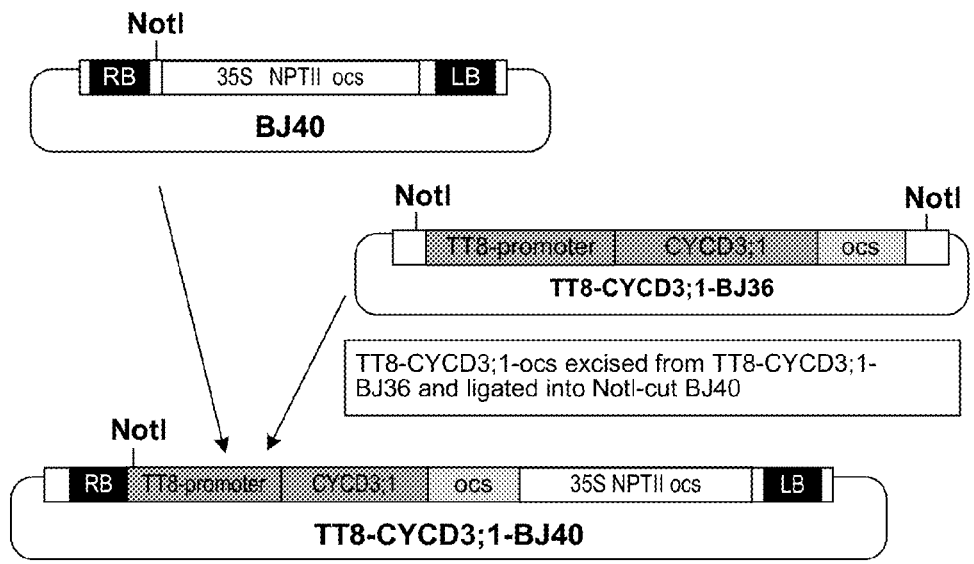

The cloning strategy is shown in FIG. 20.

12a Construction of Expression Vectors Containing an Integument/Seed Coat Promoter 12a(i) TT8

An expression vector based on the TT8 promoter (Nesi et al., 2000; At4g09820, accession no. AJ277509) is constructed as described below. A 1.7 kb fragment including the TT8 promoter with NdeI and PstI linkers is amplified by PCR from *Arabidopsis thaliana* genomic DNA as described in Example 3a(i), above. The TT8 PCR fragment is A-tailed and ligated into pGEMT, and then excised with NdeI and PstI and ligated into the NdeI and PstI sites of BJ36, 5' to the ocs terminator signal, forming the vector TT8-BJ36.

12a(ii) TT12

An expression vector based on the TT12 promoter (Debeaujon et al., 2000; At3g59030, accession no. AJ294464) is constructed as described below. A 1.7 kb fragment including the TT12 promoter with NdeI and PstI linkers is amplified by PCR from *Arabidopsis thaliana* genomic DNA as described in Example 3a(ii), above. The TT12 PCR fragment is A-tailed and ligated into pGEMT, and then excised with NdeI and PstI and ligated into the NdeI and PstI sites of BJ36, 5' to the ocs terminator signal, forming the vector TT12-BJ36.

12a(iii) INO

An expression vector based on the INO promoter (Villanueva et al., 1999; At1g23420, accession no. AF195047) is constructed as described below. A 1.5 kb fragment including the INO promoter with NdeI and PstI linkers is amplified by PCR from *Arabidopsis thaliana* genomic DNA as described in Example 10a(ii), above. The INO PCR fragment is A-tailed and ligated into pGEMT, and then excised with NdeI and PstI and ligated into the NdeI and PstI sites of BJ36, 5' to the ocs terminator signal, forming the vector INO-BJ36.

12a(iv) BAN

An expression vector based on the promoter of the BAN gene (Devic et al., 1999; At1g61720, accession no. AF092912) is constructed as described below. A 0.4 kb fragment including the BAN promoter is amplified by PCR from *Arabidopsis thaliana* genomic DNA 5' to translational start of the BAN gene using the primers BANF and BANR which introduce an NdeI and a PstI site at the 5' and 3' ends of the BAN PCR fragment respectively.

```
                                      SEQ ID NO. 31
5' CATATGGAGAATTTGACAGATTGGTG 3' BANF
   NdeI

SEQ ID NO. 32
5' CTGCAGGTTTATCGTCTTGAGACTTC 3' BANR
   PstI
```

The BAN PCR fragment is A-tailed and ligated into pG-EMT, and then excised with NdeI and PstI and ligated into the NdeI and PstI sites of BJ36, 5' to the ocs terminator signal, forming the vector BAN-BJ36.

12b Construction of Expression Cassettes Containing are Integument/Seed Coat Promoter Driving a Gene Promoting Cell Division 12b(i) Promoter::CYCD3; 1

Construction of expression vectors with an integument seed coat promoter driving the CYCD3; 1 gene is described below. The CYCD3; 1 cDNA (formerly Cycδ3; Soni et al., 1995; Vandepoele et al., 2002; At4g34160, accession no. X83371) is amplified by PCR from *Arabidopsis thaliana* cDNA using the primers CYCD3F and CYCD3R which introduce a SmaI and a BamHI site at the 5' and 3' ends of the CYCD3; 1 PCR fragment respectively.

```
                                      SEQ ID NO. 33
5' AAACCCGGGATGGCGATTCGGAAGGAGGAA 3' CYCD3F
      SmaI

SEQ ID NO. 34
5' AAAGGATCCTTATGGAGTGGCTACGATTGC 3' CYCD3R
      BamHI
```

The CYCD3; 1 PCR fragment is A-tailed and ligated into pGEMT, and then excised with SmaI and BamHI and ligated into the SmaI and BamHI sites of the following vectors:
TT8-BJ36 vector, 3' to the TT8 promoter and 5' to the ocs terminator signal, forming the vector TT8-CYCD3;1-BJ36
TT12-BJ36 vector, 3' to the TT12 promoter and 5' to the ocs terminator signal, forming the vector TT12-CYCD3;1-BJ36
INO-BJ36 vector, 3' to the INO promoter and 5' to the ocs terminator signal, forming the vector INO-CYCD3;1-BJ36
BAN-BJ36 vector, 3' to the BAN promoter and 5' to the ocs terminator signal, forming the vector BAN-CYCD3;1-BJ36

12b(ii) Promoter::IPT1

Construction of expression vectors with an integument/seed coat promoter driving the IPT1 gene is described below. The IPT1 gene (Takei et al., 2001; At1g68460, accession no. AB062607) is amplified by PCR from *Arabidopsis thaliana* genomic DNA (the IPT1 gene contains no introns) using the primers IPT1F and IPT1R which introduce a SmaI and a BamHI site at the 5' and 3' ends of the IPT1 PCR fragment respectively.

```
                                      SEQ ID NO. 35
5' AAACCCGGGATGACAGAACTCAACTTCCAC 3' IPT1F
      SmaI

SEQ ID NO. 36
5' AAAGGATCCCTAATTTTGCACCAAATGCCG 3' IPT1R
      BamHI
```

The IPT1 PCR fragment is A-tailed and ligated into pGEMT, and then excised with SmaI and BamHI and ligated into the SmaI and BamHI sites of the following vectors:
TT8-BJ36 vector, 3' to the TT8 promoter and 5' to the ocs terminator signal, forming the vector TT8-IPT1-BJ36
TT12-BJ36 vector, 3' to the TT12 promoter and 5' to the ocs terminator signal, forming the vector TT12-IPT1-BJ36
INO-BJ36 vector, 3' to the INO promoter and 5' to the ocs terminator signal, forming the vector INO-IPT1-BJ36
BAN-BJ36 vector, 3' to the BAN promoter and 5' to the ocs terminator signal, forming the vector BAN-IPT1-BJ36

12b(iii) Promoter::ANT

Construction of expression vectors with an integument/seed coat promoter driving the ANT gene is described below. The ANT gene (Klucher et al., 1996; At4g37750, accession no. NM_119937) is amplified by PCR from *Arabidopsis thaliana* cDNA using the primers ANTF and ANTR which introduce a SmaI and a BamHI site at the 5' and 3' ends of the ANT PCR fragment respectively.

```
                                         SEQ ID NO. 37
5' CCCGGGGGTGTGTTCGTTGTGTAACC 3'  ANTF
   SmaI

SEQ ID NO. 38
5' GGATCCGATCAAGAATCAGCCCAAGC 3'  ANTR
   BamHI
```

The ANT PCR fragment is A-tailed and ligated into pGEMT, and then excised with SmaI and BamHI and ligated into the SmaI and BamHI sites of the following vectors:
TT8-BJ36 vector, 3' to the T7'8 promoter and 5' to the ocs terminator signal, forming the vector TT8-ANT-BJ36
TT12-BJ36 vector, 3' to the TT12 promoter and 5' to the ocs terminator signal, forming the vector TT12-ANT-BJ36
INO-BJ36 vector, 3' to the JNO promoter and 5' to the ocs terminator signal, forming the vector INO-ANT-BJ36
BAN-BJ36 vector, 3' to the BAN promoter and 5' to the ocs terminator signal, forming the vector BAN-ANT-BJ36

12b(iv) Promoter::CYCB1;1

Construction of expression vectors with an integument/seed coat promoter driving the CYCB1;1 gene is described below. The CYCB1;1 gene (formerly CyclaAt; Ferreira et al., 1994; Vandepoele et al., 2002; At4g37490, accession no. NM_119913) is amplified by PCR from *Arabidopsis thaliana* cDNA using the primers CYCB1F and CYCB1R which introduce a SmaI and a BamHI site at the 5' and 3' ends of the CYCB1;1 PCR fragment respectively.

```
                                         SEQ ID NO. 39
5' CCCGGGCACTAAGATGATGACTTCTC 3'  CB1F
   SmaI

SEQ ID NO. 40
5' GGATCCAAGCGACTCATTAGACTTGT 3'  CB1R
   BamHI
```

The CYCB1;1 PCR fragment is A-tailed and ligated into pGEMT, and then excised with SmaI and BamHI and ligated into the SmaI and BamHI sites of the following vectors:
TT8-BJ36 vector, 3' to the TT8 promoter and 5' to the ocs terminator signal, forming the vector TT8-CYCB1;1-BJ36
TT12-BJ36 vector, 3' to the TT12 promoter and 5' to the ocs terminator signal, forming the vector TT12-CYCB1;1-BJ36
INO-BJ36 vector, 3' to the INO promoter and 5' to the ocs terminator signal, forming the vector INO-CYCB1;1-BJ36
BAN-BJ36 vector, 3' to the BAN promoter and 5' to the ocs terminator signal, forming the vector BAN-CYCB1;1-BJ36

12c Construction of Binary Vectors and Transformation into *Arabidopsis thaliana*

Expression cassettes (including the ocs terminator) are excised with NotI from the following vectors
TT8-CYCD3;1-BJ36
TT8-IPT1-BJ36
TT8-ANT-BJ36
TT8-CYCB1;1-BJ36
TT12-CYCD3;1-BJ36
TT12-IPT1-BJ36
TT12-ANT-BJ36
TT12-CYCB1;1-BJ36
INO-CYCD3;1-BJ36
INO-IPT1-BJ36
INO-ANT-BJ36
INO-CYCB1;1-BJ36
BAN-CYCD3;1-BJ36
BAN-IPT1-BJ36
BAN-ANT-BJ36
BAN-CYCB1;1-BJ36
and ligated into the NotI sites of the binary vector BJ40, forming the following vectors for transformation:
TT8-CYCD3;1-BJ40
TT8-IPT1-BJ40
TT8-ANT-BJ40
TT8-CYCB1;1-BJ40
TT12-CYCD3;1-BJ40
TT12-IPT1-BJ40
TT12-ANT-BJ40
TT12-CYCB1;1-BJ40
INO-CYCD3;1-BJ40
INO-IPT1-BJ40
INO-ANT-BJ40
INO-CYCB1;1-BJ40
BAN-CYCD3;1-BJ40
BAN-IPT1-BJ40
BAN-ANT-BJ40
BAN-CYCB1;1-BJ40

The binary vectors are transformed into *Agrobacterium tumefaciens* and then into *Arabidopsis thaliana*.

12d Analysis of Seed Weights in Transformants

Results from some primary transformants using the TT8 promoter are shown in Table 2A and FIG. 21A. The histogram shows that seeds from TT8::CYCD3;1 and TT8::IPT1 plants have a broader distribution and higher peak of weights than the controls. TT8::uidA lines were used as controls, as expression of the uidA gene is not found to affect plant growth and development. Individual TT8::CYCD3;1 plants produced seeds up to 97% heavier than controls, with a mean increase over 27 lines of 37%. TT8::IPT1 plants produced seeds up to 107% heavier, with a mean increase over 24 lines of 28%. The mean weights of TT8::CYCD3;1 and TT8::IPT1 seeds were compared with the controls using t-tests and found to be significantly different from the controls with P<0.000. It should be noted that some of the TT8::IPT1 lines, including the highest weighing line, also had a vegetative phenotype including dwarfing, serrated leaves, and extremely low fertility, most likely due to the TT8 promoter driving vegetative expression of IPT1 in some lines. However limes with normal vegetative development also produced large seeds. It is likely that vegetative expression of TT8 could be prevented if required by the technique of promoter dissection (e.g. Chandrasekharan et al., 2003).

TABLE 2A

Seed weights in individual primary transformants from TT8::GUS (control), TT8::CYCD3;1, and TT8::IPT1 families

| | TT8::GUS (controls) | TT8::CYCD3;1 | TT8::IPT1 |
|---|---|---|---|
| | 17.0 µg (n = 52) | 19.0 µg (n = 77) | 21.8 µg (n = 45) |
| | 14.2 (79) | 21.6 (61) | 15.6 (62) |
| | 14.7 (51) | 22.5 (52) | 23.4 (68) |
| | 13.9 (47) | 17.9 (52) | 20.9 (95) |
| | 14.7 (66) | 17.5 (63) | 11.2 (58) |
| | 15.1 (43) | 16.9 (89) | 19.3 (89) |
| | 14.2 (50) | 16.6 (54) | *19.9 (119) |
| | 14.8 (61) | 18.6 (57) | 17.9 (64) |
| | | 13.9 (54) | 17.7 (56) |
| | | 24.3 (64) | 18.6 (54) |
| | | 21.9 (57) | 13.2 (48) |
| | | 29.2 (49) | 17.6 (72) |
| | | 18.2 (49) | 20.8 (66) |
| | | 17.0 (72) | *30.6 (43) |
| | | 23.0 (45) | 14.0 (61) |
| | | 18.6 (56) | 19.5 (64) |
| | | 28.1 (56) | 20.5 (47) |
| | | 20.1 (47) | 18.8 (68) |
| | | 17.8 (47) | 15.8 (65) |
| | | 18.8 (58) | 22.1 (47) |
| | | 26.1 (55) | 14.2 (47) |
| | | 16.4 (55) | 19.6 (49) |
| | | 24.6 (56) | 17.3 (50) |
| | | 19.5 (49) | *26.7 (51) |
| | | 16.1 (51) | |
| | | 25.8 (58) | |
| | | 18.0 (62) | |
| | | | *plants with very low fertility |
| Mean | 14.8 | 20.3 | 19.0 |
| Range | 13.9 to 17.0 | 13.9 to 29.2 | 11.2 to 30.6 |
| Standard error | 0.3 | 0.8 | 0.9 | ttest for control vs TT8::CYCD3;1 and TT8:IPT1, P < 0.000, significant

Further results from plants transformed with expression vectors to increase seed size are shown in Table 2B and FIG. 21B. For these experiments, we selected kanamycin resistant lines with heavy seeds and confirmed the presence of the expression vector using PCR. For two of the lines below we weighed seeds produced by T3 plants, confirming the heritability of the large seed trait. In Table 2B, weights of controls (in this case the controls were wild-type Col-0 are shown alongside transformants where the controls and transformants were grown together. BAN::CYCD3;1 seeds were 35% heavier than controls grown under the same conditions, and INO::ANT seeds were 53% heavier. INO::ANT seeds were also misshapen (FIG. 21B), suggesting that the expression cassette indeed affects seed coat development.

TABLE 2B

Seed weights from plants transformed with expression cassettes to increase seed size

| | transformant | w.t. Col-3 (controls) |
|---|---|---|
| BAN::CYCD3;1 (seeds from T2 plants) | 23.9 µg | 17.7 µg |
| INO::ANT (T2) | 23.1 | 15.1 |
| INO::IPT1 (T3) | 26.4 | |
| TT8::CYCD3;1 (T3) | 23.2 | |

Example 13

Construction, Transformation, and Analysis of Expression Vectors that Increase Expression of a Gene Promoting Cell Division in the Integuments/Seed Coat of *Brassica napus*

The binary vectors described in Example 12c (above) are transformed into *Brassica napus*.

Example 14

Figure 22:
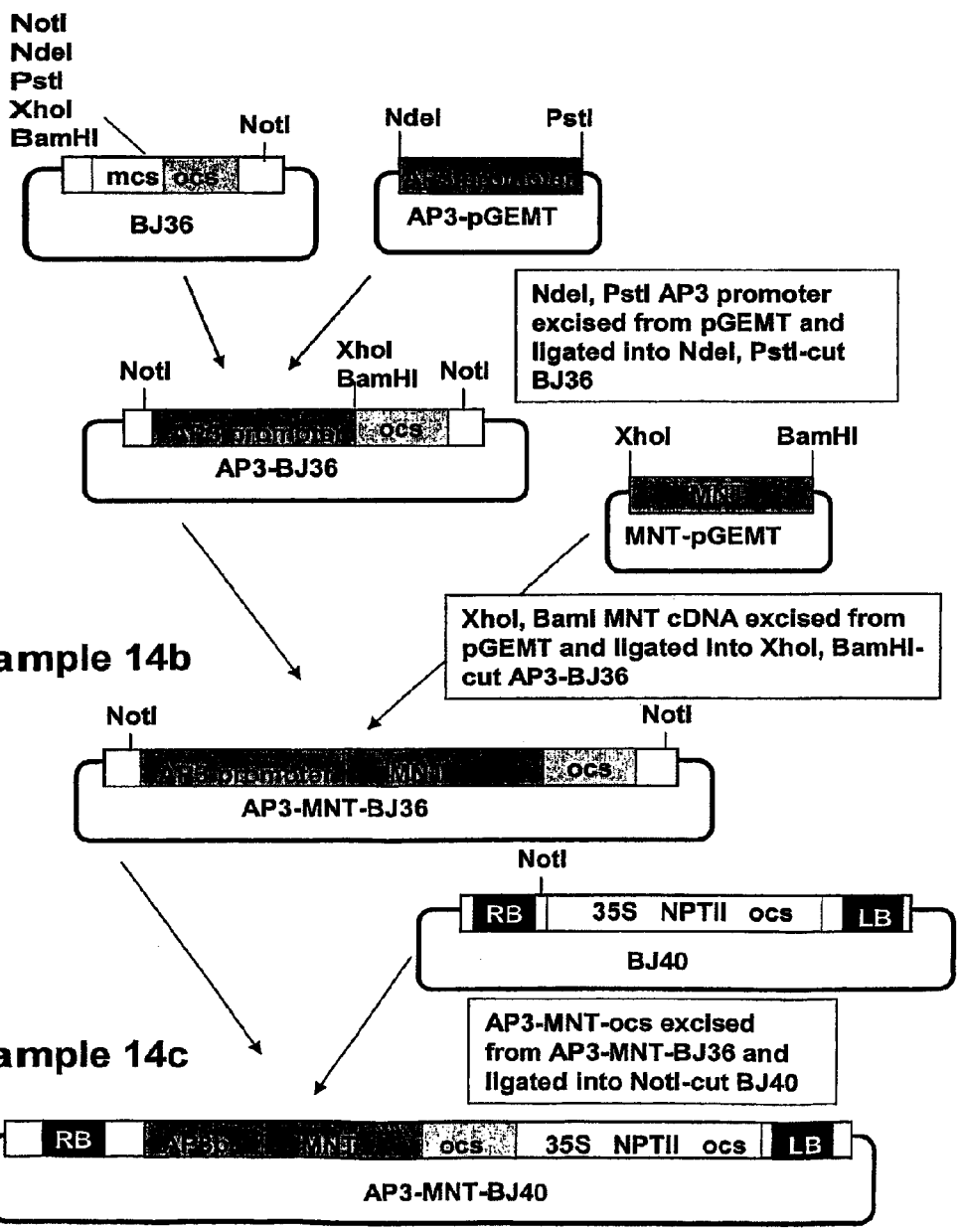
FIG. 22 illustrates a cloning strategy for constructing a vector for expression of MNT in petals and stamens (Example 14)

Construction of an Expression Vector Containing a Petal- and Stamen-Specific Promoter Driving MNT and Transformation into MNT Mutants The cloning strategy is shown in FIG. 22.

14a Construction of an Expression Vector Based on the AP3 Promoter

An expression vector based on the promoter of the AP3 gene (Jack et al., 1992; At3g54340, accession no. AY142590) is constructed as described below. A 1 kb fragment including the AP3 promoter is amplified by PCR from *Arabidopsis thaliana* genomic DNA 5' to translational start of the AP3 gene using the primers AP3F and AP3R which introduce an NdeI and a PstI site at the 5' and 3' ends of the AP3 PCR fragment respectively.

```
                                    SEQ ID NO. 41
5' AAACATATGGATACACAAGTTCTTTGG 3' AP3F
      NdeI

SEQ ID NO. 42
5' AAACTGCAGATTCTTCTCTCTTTGTTTAA 3' AP3R
      PstI
```

The AP3 PCR fragment is A-tailed and ligated into pGEMT, and then excised with NdeI and PstI and ligated into the NdeI and PstI sites of the BJ36 vector, 5' to the ocs terminator signal, forming the vector AP3-BJ36.

14b Construction of an Expression Vector Containing an AP3::MNT Expression Cassette The MNT cDNA with XhoI and BamHI linkers is amplified by PCR from *Arabidopsis thaliana* cDNA and ligated into pGEMT as described in Example 8a, above. The MNT PCR fragment is excised with XhoI and BamHI and ligated into the XhoI and BamHI sites of the AP3-BJ36 vector, 3' to the AP3 promoter and 5' to the ocs terminator, forming the vector AP3-MNT-BJ36.

14c Construction of Binary Vector and Transformation into *Arabidopsis thaliana*

The AP3::MNT expression cassette (including the ocs terminator signal) is excised from AP3-MNT-BJ36 with NotI and cloned into the NoI sites of the binary vector BJ40, forming the vector AP3-MNT-BJ40.

The binary vector is transformed into *Agrobacterium tumefaciens* and then into *Arabidopsis thaliana*.

Example 15

Construction of an Expression Vector Containing a Sepal- and Petal-Specific Promoter Driving MNT and Transformation into MNT Mutants The cloning strategy is shown in FIG. 23.

15a Construction of an Expression Vector Based on the AP1 Promoter

An expression vector based on the promoter of the AP1 gene (Mandel et al., 1992; At1g69120, accession no. NM_105581) is constructed as described below. A 1.7 kb fragment including the AP1 promoter is amplified by PCR from *Arabidopsis thaliana* genomic DNA 5' to translational start of the AP1 gene using the primers AP1F and AP1R which introduce an NdeI and a PstI site at the 5' and 3' ends of the AP3 PCR fragment respectively.

```
                                        SEQ ID NO. 43
5' CATATG GTGACATCTTTTTAGCATAGGTTC 3' AP1F
   NdeI

SEQ ID NO. 44
5' CTGCAG TTTTGATCCTTTTTTAAGAAACTT 3' AP1R
   PstI
```

The AP1 PCR fragment is A-tailed and ligated into pGEMT, and then excised with NdeI and PstI and ligated into the NdeI and PstI sites of the BJ36 vector, 5' to the ocs terminator signal, forming the vector AP1-BJ36.

15b Construction of an Expression Vector Containing an AP1::MNT Expression Cassette The MNT cDNA with XhoI and BamHI linkers is amplified by PCR from *Arabidopsis thaliana* cDNA and ligated into pGEMT as described in Example 8a, above. The MNT PCR fragment is excised with XhoI and BamHI and ligated into the XhoI and BamHI sites of the AP1-BJ36 vector, 3' to the AP1 promoter and 5' to the ocs terminator, forming the vector AP1-MNT-BJ36.

15c Construction of Binary Vector and Transformation into *Arabidopsis thaliana*

The AP1::MNT expression cassette (including the ocs terminator signal) is excised from AP1-MNT-BJ36 with NotI and cloned into the NotI sites of the binary vector BJ40, forming the vector AP1-MNT-BJ40.

The binary vector is transformed into *Agrobacterium tumefaciens* and then into *Arabidopsis thaliana*.

Example 16

Value of mnt Mutants in Understanding and Modifying Growth of the Inflorescence Stem mnt-1 mutants have thick inflorescence stems compared with wild-type plants. The increased diameter of mnt-1 stems is caused by extra cell divisions (FIG. 24B). Therefore it is expected that stem thickness may be increased in other species by altering expression of an MNT orthologue and thereby increasing the number of cells in the stem.

Example 17

Construction and Transformation of an RNAi Cassette that Decreases MNT Expression In *Arabidopsis thaliana*, Including Decreased Expression in the Stem The cloning and transformation strategy is described in Example 4. The cloning strategy is shown in FIG. 13A. Transformed plants have an increased stem diameter with respect to wild type (mean inflorescence stem diameter between nodes 2 and 3: w.t., 1.293±s.e.m. 0.4 mm, n=13; 35S::MNT RNAi, 1.419 b 0.4, n=14; two-tailed t-test shows that diameters of w.t. and 35S::MNT RNAi stems are significantly different at $P<0.05$). The stem phenotype of transformed plants compared with wild-type plants is shown in FIG. 13B.

Example 18

Figure 25:
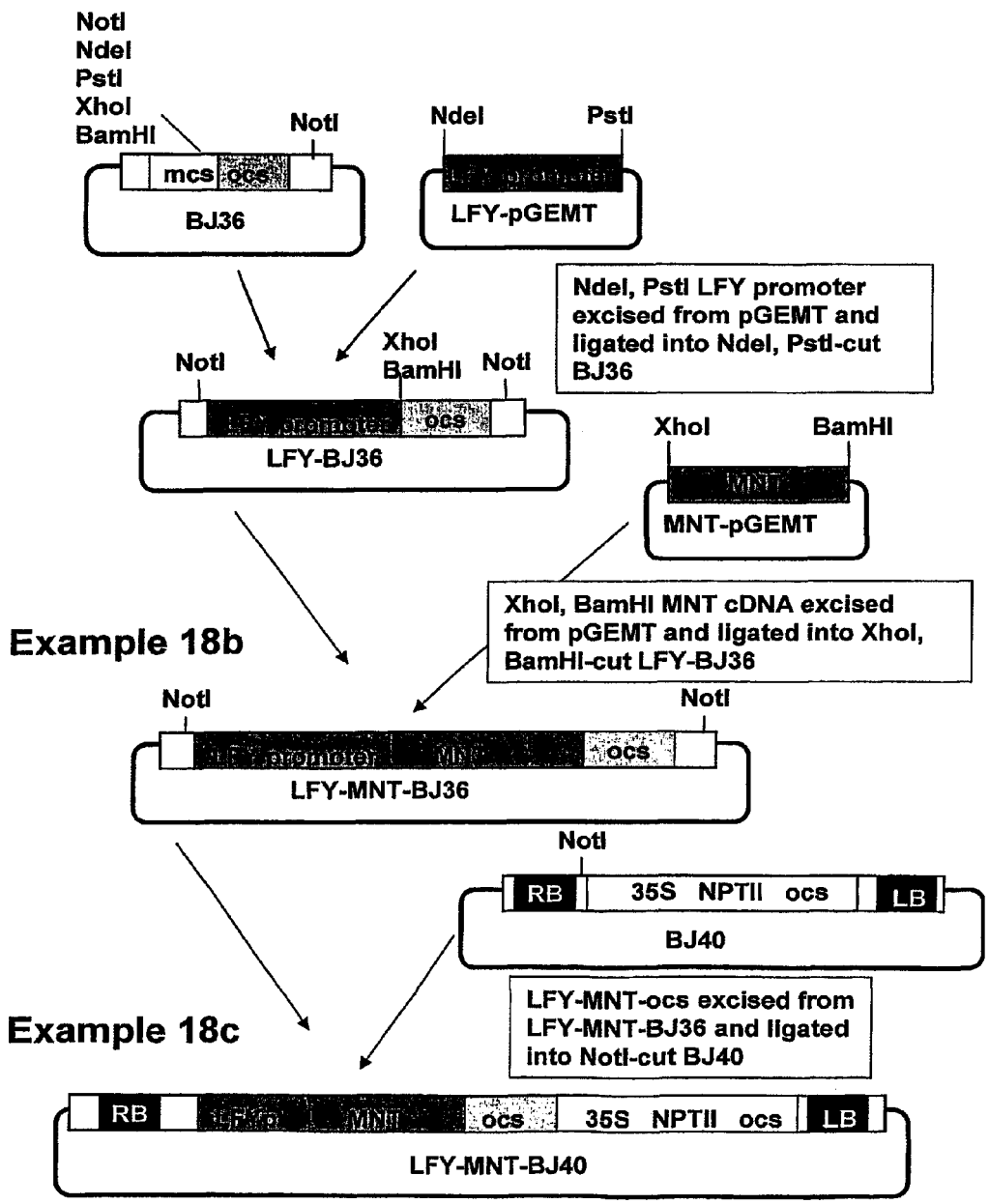
FIG. 25 illustrates a cloning strategy for constructing a vector for expression of MNT in flowers (Example 18).

Construction of an Expression Vector Containing a Flower-Preferred Promoter Driving MNT and Transformation into mnt Mutants The cloning strategy is shown in FIG. 25.

18a Construction of an Expression Vector Based on the LFY Promoter

An expression vector based on the promoter of the LFY gene (Weigel et al., 1992; At5g61850, accession no. NM_125579) is constructed as described below. A 2.1 kb fragment including the LFY promoter is amplified by PCR from *Arabidopsis thaliana* genomic DNA 5' to translational start of the LFY gene using the primers LFYF and LFYR which introduce an NdeI and a PstI site at the 5' and 3' ends of the AP3 PCR fragment respectively.

```
                                      SEQ ID NO. 45
5' CATATG TGTAACTGCAAAGTGTAGTTCGG 3' LFYF
   NdeI

SEQ ID NO. 46
5' CTGCAG AATCTATTTTTCTCTCTCTCTC 3' LFYR
   PstI
```

The LFY PCR fragment is A-tailed and ligated into pGEMT, and then excised with NdeI and PstI and ligated into the NdeI and PstI sites of the BJ36 vector, 5' to the ocs terminator signal, forming the vector LFY-BJ36.

18b Construction of an Expression Vector Containing an LFY::MNT Expression Cassette The MNT cDNA with XhoI and BamHI linkers is amplified by PCR from *Arabidopsis thaliana* cDNA and ligated into pGEMT as described in Example 8a, above. The MNT PCR fragment is excised with XhoI and BamHI and ligated into the XhoI and BamHI sites of the LFY-BJ36 vector, 3' to the LFY promoter and 5' to the ocs terminator, forming the vector AP1-LFY-BJ36.

18c Construction of Binary Vector and Transformation into *Arabidopsis thaliana*

The LFY::MNT expression cassette (including the ocs terminator signal) is excised from AP1-LFY-BJ36 with NotI and cloned into the NotI sites of the binary vector BJ40, forming the vector AP1-LFY-BJ40.

The binary vector is transformed into *Agrobacterium tumefaciens* and then into *Arabidopsis thaliana*.

SEQ ID NOS
1 MNT genomic DNA w.t Col-0
2 MNT cDNA w.t. Col-0
3 MNT predicted protein w.t. Col-0
4 mnt-1 genomic DNA Col-3
5 mnt-1 cDNA Col-3, translational start to stop
6 mnt-1 predicted protein Col-3
7 F primer for amplifying *Brassica napus* ARF2 cDNA
8 R primer for amplifying *Brassica napus* ARF2 cDNA
9 BnARF2 cDNA, translational start to stop
10 BnARF2 predicted protein
11 F primer for TT8 promoter with NdeI linker
12 R primer for TT8 promoter with PstI linker
13 F primer for TT12 promoter with NdeI linker
14 R primer for TT12 promoter with PstI linker
15 F primer for MNT RNAi fragment with XbaI and AscI linkers
16 R primer for MNT RNAi fragment with BamHI and SawI linkers 17 F primer for BnARF2 RNAi fragment with XbaI and AscI linkers
18 R primer for BnARF2 RNAi fragment with BamHI and SwaI linkers
19 F primer for TT8 promoter with EcoRI linker
20 R primer for TT8 promoter with NcoI linker
21 F primer for INO promoter with EcoRI linker
22 R primer for INO promoter with NcoI linker
23 F primer for MNT cDNA with XhoI linker
24 R primer for MNT cDNA with BamHI linker
25 F primer for BnARF2 cDNA with XhoI linker
26 R primer for BnARF2 cDNA with BamHI linker
27 F primer for INO promoter with NdeI linker
28 R primer for INO promoter with PstI linker
29 R primer for 778 promoter with MluI linker
30 R primer for INO promoter with MluI linker
31 F primer for BAN promoter with NdeI linker
32 R primer for BAN promoter with PstI linker
33 F primer for CYCD3;1 cDNA with SmaI linker
34 R primer for CYCD3;1 cDNA with BamHI linker
35 F primer for IPT1 cDNA with SmaI linker
36 R primer for IPT1 cDNA with BamHI linker
37 F primer for ANT cDNA with SmaI linker
38 R primer for ANT cDNA with BamHI linker
39 F primer for CYCB1;1 cDNA with SmaI linker
40 R primer for CYCB1;1 cDNA with BamHI linker
41 F primer for AP3 promoter with NdeI linker
42 R primer for AP3 promoter with PstI linker
43 F primer for AP1 promoter with NdeI linker
44 R primer for AP1 promoter with PstI linker
45 F primer for LFY promoter with NdeI linker
46 R primer for LFY promoter with PstI linker SEQ ID NO. 1
MNT wild-type genomic DNA, Col-0
agccattttgtaactgaccaccgagtaatctgtaatctgagctcttttat
taatcggattgaataaaattcgcttggagtccgtcagtcgtgtccgtgagc
gcgtgtctcactcgcttgagctgatgaagtgcgataatgacgtggcatgt
tgggatggagaccaaagaccagcatttttattttatttttatagtaactaat
tttaaaaaccaaacaacctgagattaaaattttaattttttactgtactgt
agtaaatttgggtcctgattaagattaggcatatttatctcatagtttat
aacaagtagcagctgaaatttgtattactagcttatagtaattaaactaa
aaactacgttccaggttttaaattattgtttaaagaagatataataatat
attaagaaaatagttaattaaggtaaggaggaaagtagggtttggtctgt
aggttagggttcaaagagggaagagattaggagaaaggaagcatgaaggc
atgacccatttcttcaattagtgctccttaatctggtgacacgtgtaggt
cccacgtgtaatcacttcacattgttattttcaaaaaatcaattagtaa
aaacaaaactttgtccatcatcaaatagtagtagttttttatgtgtggtt
acaatattgtaagaagctctccccctttactatgtaattcaaccccact
ctaattttttaaaatatttatgtaaagctttacccgaaaacaatctatcat
gggttggtaatgacacatttcattaacagtgttagagaatgattcctta
atttttctacagtaaaatgttaggtgatctcattgtactacatcggaaaa
tactcaaaattatgtcgtgtaaatttagataatggacgaatatggttttga
aatatttatggatacccaacaagatttataactagaaagacaaaaaata
gagcacattttgctcgttttccatcaaccctatttctccaatttgttcac
atcatgatcaaaaatacagtagcaattaaaaaataaaataacaaatataa
atggctatatagatcaaccctatctagctattagtattactagaaattga
caataaaggaaacattcacgtgtgtgagcatgtactactctacacacatg
tccacagttattatatactgagtactagtatacgttgatgttatcaataa
taaaaactcgaaattaagtattattttcttataataatctatttaaccat
atttgctactgtactatttagtctatttttcttttgccaacctttgtatta
aatatttgtactattagttttcaattataggtctatcactatgtatatgtc
cgaataatggtctaaaattgttaatataaaatacagattttatttcagct
aaagatagttgaaattacacaagaaaatagaagagataaaaatgatcaat
cagctatgtaagacgtcgtatggatagttcaataattgtggtaatactta
aagacatatatcaaaattatcaacaagcctcgaacacaaacttttacaaaa
agcctgtgtctactttatgagtgtttgattattaaattgcaaggtcgtag
tataaaaatttcgtaggctttcaggacacaagattaaattcatttatcta
aatggtgatggagtacttttattttatatatcaaaatggtgatgatata
cgaagaccatatatttagattattaaagaaaaaacgagaaaagaagaaag
aaaatataaaaaaatggttttctttttaacggacaaagattcctacaat
ggttgcttttagaccacacacaaatgctacacagtactcttgggtcccac
acctcttagcaagtgcgttaccaacacgtgaatttcctctccccattttc
tcgtcctttcctctcaatattgtatcgtctcgttttccttgtcatatcg
cgtgtgacgtgttattggcttattgctgaacagtcttcttttttatttc
catcgttatcctgatttttttttttttccaaatttgattttcatggtttg
taattttgcaatagattttgtgtttcacagagagatagtttacgtgttgt
taaaaataatttgtgcaaaatagtgtgcgtgtgttaaatattaaacgata
tataataattagaagaaaataaaaagtttttgtcgcgattagttatttgat
atttaccttgttcttttgtttatcgctgcgacaagcaccgacggtataaa
atataaagaaaaaagaaagagagatgaaggtgagatgaatgaaagagtc
gcagcgacagatctgaagagataggagaaagggaatttgagacgctgaaa
attccagcgtctacggaatggccgaattacagtcgatgcggcagagatga
aaaaaatgagaaatgaaagtgaaaaagagatgagaactttttttgggtcg
caggtagctgacgcagcaatcaacaaaagaacatggccaacgttttagta
gatactactataaaagaaaaaggttgatttaattcattcgtaatttggac
ttaattttttttaggaacactaattaatcttatttgccagctgtatgag
tggactacaataaactcttgtctataaaccagattttcttccttttttaac
gcttccacttacaacaatatatgtaaatatgtaattatgacggggcatac
ggaaatttaattttttgaagcagattcatcccattagccagctgtattaag
tggtaatccaagagttaatttagttgttcagcaaatgatttttagataaaa
tcaactactagtttaaaataactatcgaatgactgttaaggcttcgtatt
ttttgttctgccatcaggatatcataaatatggttgaggttcgtataata
ttcgacgatctttttatatatctgagttgtaattgaattagagaaaataaa -continued aaacagataatgaaacgtctttgtttttccataaaaagaaaaacagggta
aattaaagtacgagagattcacgagacgaaaattcctagaggcgcacgat
agccaaaagaccatagaaaatgacatccgaaatatctttaaaatgctaaa
atgcacatattttctggtgccacgtagcattttctccctctctcgttc
tctctacgtccacccagacctgcctgttcacagcacgacaaagccacttc
ccaataaaaacacaacacctttcccattgacgctctcttttcccaaacacc
gttatcctcttacccaatcaaaagttgacgcttgctcacgacttgttga
cgccgttagtcccatctaaaaagtaaagcagcctttcttacttgctaat
cccctctacacatttaattattttctccctaatggatttttttggca
acttgagtatttattttcaactcacagtaactgtaaataaataaaagta
ttcaactcacagtcaccagtaaataaatactaccagaccatagtttttc
aagaattgttttggtcaacaattttaggatgacttaaattgctatatttc
tggggaaatacgacttggaaatgtctgcaatttgggtcttttcttcaatt
tatcttctccaatttgtttttaaaaaattaaattttagaaaaggatatg
tcaattttttctattgaaaaggctttattaaaaaataagaaaaagtggag
gaaagaaaataaaatcgtcacttgtctttggttttgtgaggtcgcagacc
ctggtcccccggaaatggttacaaccggtaatagccggtatgaaagaggg
aatggtaaccggtgaatgccggttatccatatggggttagaagtttaccgc
ggttgaaatgattgaagctgagttttgactacctctggttaagcccattg
gtcgcctcatacccagaaaaacaaaggtaggaaagacgaagaaataaa
aagagagagaatgttagagagacaaactctgagagacaaaacaagagaaa
atcgctcgtcgtcggtattcaagcgtctgtgactccgataaagcctagac
tagcgaggacggcgagagagagagagagagagctttggagttgtcgtatc
tctaaatcggaggcaatttgaggtgaaattggtggttttatcgtttgatt
ctagggtttatcttctctgatagttttatcgagtaatgtcaaggagctaa
actagtggtgattgtgtttgttagtgagataaagacaaaggaaggaatca
agtggactaccgaagcgagttttgagcttttcagagacggatttggaga
tttcttgttgatatcgtctgcttcagaggcttatttggtaccagatgaaac
agatctgagcttcggaaggtATGGCGAGTTCGGAGGTTTCAATGAAAGGT
AATCGTGGAGGAGATAACTTCTCCTCCTCTGGTTTTAGTGACCCTAAGGA
GACTAGAAATGTCTCCGTCGCCGGCGAGGGGCAAAAAAGTAATTCTACCC
GATCCGCTGCGGCTGAGCGTGCTTgtaagtctccgttttcttagggtttct
taagcttggttttggttacagactgacttgatctaatttatcttcttcttcttcttctt
cttcgtcttcatagTGGACCCTGAGGCTGCTCTTTACAGAGAGCTATGGC
ACGCTTGTGCTGGTCCGCTTGTGACGGTTCCTAGACAAGACGACCGAGTC
TTCTATTTTCCTCAAGGACACATCGAGCAGgtgagatatttcatctatga
gttcttgctattttttggctaaatctttgagttaacccctctgtgattcgt
acctgttgagatattttctaatgaactttgtcggtttccattgttttatg
attagGTGGAGGCTTCGACGAACCAGGCGGCAGAACAACAGATGCCTCTC
TATGATCTTCCGTCAAAGCTTCTCTGTCGAGTTATTAATGTAGATTTAAA Ggtaggttctcttaacttcttggaaaattttggtttctgtgtcttggatt
gtcagctaacaagagttttgtttatgattttacagGCAGAGGCAGATACA
GATGAAGTTTATGCGCAGATTACTCTTCTTCCTGAGGCTAATgtaagttt
tgttttctgatttattggtttgagtgttgtagaggtgatcttattcttca
agatgctgaattctatatatttttgttccatacagCAAGACGAGAATGC
AATTGAGAAAGAAGCGCCTCTTCCTCCACCTCCGAGGTTCCAGGTGCATT
CGTTCTGCAAAACCTTGACTGCATCCGACACAAGTACACATGGTGGATTT
TCTGTTCTTAGGCGACATGCGGATGAATGTCTCCCACCTCTGgttggtgt
ttcatttgcgcttctaactatctattcattggcttattttttcctgaattt
tgttctaagattgccttcaattcattttttgtttcttccctcagGATATG
TCTCGACAGCCTCCCACTCAAGAGTTAGTTGCAAAGGATTTGCATGCAAA
TGAGTGGCGATTCAGACATATATTCCGGGtataggaatctgtaacttt
ttattttctgtttttctcgagtctgtgtgtcatcaaacttatctggttgt
tgatgtttgtgataatggaccagGTCAACCACGGAGGCATTTGCTACAGA
GTGGGTGGAGTGTGTTTGTTAGCTCCAAAAGGCTAGTTGCAGGCGATGCG
TTTATATTTCTAAGgtttgtggattttagttcattgtttttctttagctgt
atctgttagtttctataatgtggaatatataatcttctacagGGGCGAGA
ATGGAGAATTAAGAGTTGGTGTAAGGCGTGCGATGCGACAACAAGGAAAC
GTGCCGTCTTCTGTTATATCTAGCCATAGCATGCATCTTGGAGTACTGGC
CACCGCATGGCATGCCATTTCAACAGGGACTATGTTTACAGTCTACTACA
AACCCAGgtttgtatttgtattagctcacaaaacagctttcagtttttg
agctctttgctttgtatgtctctatatgtctgatgcttggtagtgaatca
ctctactaaattttcatgcggtgttgttttgtttaatacagGACGAGCCC
ATCTGAGTTTATTGTTCCGTTCGATCAGTATATGGAGTCTGTTAAGAATA
ACTACTCTATTGGCATGAGATTCAAAATGAGATTTGAAGGCGAAGAGGCT
CCTGAGCAGAGgtaaaacctgtcttctgcttttgaaatatgttagctctt
gagccttttctcttggaataacgaacctaacaagttgtattgatttata
ttagGTTTACTGGCACAATCGTTGGGATTGAAGAGTCTGATCCTACTAGG
TGGCCAAAATCAAAGTGGAGATCCCTCAAGgtatgacctagtttctagag
aggatcaagactattgtttgaatataatgaatgctgattgttcaattgtc
tttcagGTGAGATGGGATGAGACTTCTAGTATTCCTCGACCTGATAGAGT
ATCTCCGTGGAAAGTAGAGCCAGCTCTTGCTCCTCCTGCTTTGAGTCCTG
TTCCAATGCCTAGGCCTAAGAGGCCCAGATCAAATATAGCACCTTCATCT
CCTGACTCTTCGATGCTTACCAGAGAAGgtaatgtcttcccccttccactg
tagtacacatagtagtgcgtctgaaacttaattgaacttgtcagtgggag
tctaattcattgtacacaaaacagGTACAACTAAGGCAAACATGGACCCT
TTACCAGCAAGCGGACTTTCAAGGGTCTTGCAAGGTCAAGAATACTCGAC
CTTGAGGACGAAACATACTGAGAGTGTAGAGTGTGATGCTCCTGAGAATT
CTGTTGTCTGGCAATCTTCAGCGGATGATGATAAGGTTGACGTGGTTTCG
GGTTCTAGAAGATATGGATCTGAGAACTGGATGTCCTCAGCCAGGCATGA

```
ACCTACTTACACAGATTTGCTCTCCGGCTTTGGGACTAACATAGATCCAT
CCCATGGTCAGCGGATACCTTTTTATGACCATTCATCATCACCTTCTATG
CCTGCAAAGAGAATCTTGAGTGATTCAGAAGGCAAGTTCGATTATCTTGC
TAACCAGTGGCAGATGATACACTCTGGTCTCTCCCTGAAGTTACATGAAT
CTCCTAAGGTACCTGCAGCAACTGATGCGTCTCTCCAAGGGCGATGCAAT
GTTAAATACAGCGAATATCCTGTTCTTAATGGTCTATCGACTGAGAATGC
TGGTGGTAACTGGCCAATACGTCCACGTGCTTTGAATTATTATGAGGAAG
TGGTCAATGCTCAAGCGCAAGCTCAGGCTAGGGAGCAAGTAACAAAACAA
CCCTTCACGATACAAGAGGAGACAGCAAAGTCAAGAGAAGGGAACTGCAG
GCTCTTTGGCATTCCTCTGACCAACAACATGAATGGGACAGACTCAACCA
TGTCTCAGAGAAACAACTTGAATGATGCTGCGGGCTTACACAGATAGCA
TCACCAAAGGTTCAGGACCTTTCAGATCAGTCAAAAGGGTCAAAATCAAC
AAACGATCATCGTGAACAGGGAAGACCATTCCAGACTAATAATCCTCATC
CGAAGGATGCTCAAACGAAAACCAACTCAAGTAGGAGTTGCACAAAGgta
atttttgcaatatgtagcacaaagtgtatgaggttgtgataacccttga
atcacttttcaactaacacatgacacattgatgtaaagGTTCACAAGCAG
GGAATTGCACTTGGCCGTTCAGTGGATCTTTCAAAGTTCCAAAACTATGA
GGAGTTAGTCGCTGAGCTGGACAGGCTGTTTGAGTTCAATGGAGAGTTGA
TGGCTCCTAAGAAAGATTGGTTGATAGTTTACACAGATGAAGAGAATGAT
ATGATGCTTGTTGGTGACGATCCTTGGCAgtaagattttgcaaatttttcc
atcttagtttatatcgatgttagtgttttttcttataacactgacacaatg
atctctcttgcagGGAGTTTTGTTGCATGGTTCGCAAAATCTTCATATAC
ACGAAAGAGGAAGTGAGGAAGATGAACCCGGGGACTTTAAGCTGTAGGAG
CGAGGAAGAAGCAGTTGTTGGGGAAGGATCAGATGCAAAGGACGCCAAGT
CTGCATCAAATCCTTCATTGTCCAGCGCTGGGAACTCTTAAacaaacaaa
ataaccaacaacccttttgctgcaagccgaggtatgtaaaagcttttgag
atattagtagactagagacacagccaaaagtttatgtcattacattcgac
tgatgtttgttctgttaatgacagcaggatgggggtcgattggtggagac
tggagagcaaaatggatgatgggtttaagataagatattaaaaatgcaa
ttttgaagtattttgttggccacttagataattagcatcttccatcacc
cttattatctatctaataataattaatagatattataaagtaaaacataa
aaaggttacaggtattatatagtagaatatgaaaagctcttttataagta
gaatatgatggtgtggagttgtagtcggaggctggtatcggttcttttta
tggatgtatttttttccttcttccaaagatctcttgaagtcttttttattg
tttatattaatcccaatgtacataagttttcaagctcttgcccttttta
attatcttgtcgattc
                                SEQ ID NO. 2
MNT complete cDNA wild-type Col-0
cccattggtcgcctcatacccagaaaaacaaaaggataggaaagacgaag
aaataaaaagagagagaatgttagagagacaaactctgagagacaaaaca
agagaaaatcgctcgtcgtcggtattcaagcgtctgtgactccgataaag
cctagactagcgaggacggcgagagagagagagagagagctttggagttg
tcgtatctctaaatcggaggcaatttgagtgagataaagacaaaggaagg
aatcaagtggactaccgaagcgagttttgagcttttcagagacggattt
ggagatttcttgttgatatcgtctgcttagaggcttatttggtaccagat
gaaacagatctgagcttcggaaggtatggcgagttcggaggtttcaatga
aaggtaatcgtggaggagataacttctcctcctctggttttagtgaccct
aaggagactagaaatgtctccgtcgccggcgaggggcaaaaaagtaattc
tacccgatccgctgcggctgagcgtgctttggaccctgaggctgctcttt
acagagagctatggcacgcttgtgctggtccgcttgtgacggttcctaga
caagacgaccgagtcttctatttcctcaaggacacatcgagcaggtgga
ggcttcgacgaaccaggcggcagaacaacagatgcctctctatgatcttc
cgtcaaagcttctctgtcgagttattaatgtagatttaaaggcagaggca
gatacagatgaagtttatgcgcagattactcttcttcctgaggctaatca
agacgagaatgcaattgagaaagaagcgcctcttcctccacctccgaggt
tccaggtgcattcgttctgcaaaaccttgactgcatccgacacaagtaca
catggtggattttctgttcttaggcgacatgcggatgaatgtctcccacc
tctggatatgtctcgacagcctcccactcaagagttagttgcaaaggatt
tgcatgcaaatgagtggcgattcagacatatattccggggtcaaccacgg
aggcatttgctacagagtgggtggagtgtgtttgttagctccaaaaggct
agttgcaggcgatgcgtttatatttctaaggggcgagaatggagaattaa
gagttggtgtaaggcgtgcgatgcgacaacaaggaaacgtgccgtcttct
gttatatctagccatagcatgcatcttggagtactggccaccgcatggca
tgccatttcaacagggactatgtttacagtctactacaaacccaggacga
gcccatctgagtttattgttccgttcgatcagtatatggagtctgttaag
aataactactctattggcatgagattcaaaatgagatttgaaggcgaaga
ggctcctgagcagaggtttactggcacaatcgttgggattgaagagtctg
atcctactaggtggccaaaatcaaagtggagatccctcaaggtgagatgg
gatgagacttctagtattcctcgacctgatagagtatctccgtggaaagt
agagccagctcttgctcctcctgctttgagtcctgttccaatgcctaggc
ctaagaggcccagatcaaatatagcaccttcatctcctgactcttcgatg
cttaccagagaaggtacaactaaggcaaacatggacccttttaccagcaag
cggactttcaagggtcttgcaaggtcaagaatactcgaccttgaggacga
aacatactgagagtgtagagtgtgatgctcctgagaattctgttgtctgg
caatcttcagcggatgatgataaggttgacgtggtttcgggttctagaag
atatggatctgagaactggatgtcctcagccaggcatgaacctacttaca
cagatttgctctccggctttgggactaacatagatccatcccatggtcag
cggatacctttttatgaccattcatcatcaccttctatgcctgcaaagag
aatcttgagtgattcagaaggcaagttcgattatcttgctaaccagtggc
agatgatacactctggtactccctgaagttacatgaatctcctaaggtac
ctgcagcaactgatgcgtctctccaagggcgatgcaatgttaaatacagc
```

-continued

```
gaatatcctgttcttaatggtctatcgactgagaatgctggtggtaactg
gccaatacgtccacgtgctttgaattattatgaggaagtggtcaatgctc
aagcgcaagctcaggctagggagcaagtaacaaaacaacccttcacgata
caagaggagacagcaaagtcaagagaagggaactgcaggctcttttggcat
tcctctgaccaacaacatgaatgggacagactcaaccatgtctcagagaa
acaacttgaatgatgctgcggggcttacacagatagcatcaccaaaggtt
caggacctttcagatcagtcaaaagggtcaaaatcaacaaacgatcatcg
tgaacagggaagaccattccagactaataatcctcatccgaaggatgctc
aaacgaaaaccaactcaagtaggagttgcacaaaggttcacaagcaggga
attgcacttggccgttcagtggatctttcaaagttccaaaactatgagga
gttagtcgctgagctggacaggctgtttgagttcaatggagagttgatgg
ctcctaagaaagattggttgatagtttacacagatgaagagaatgatatg
atgcttgttggtgacgatccttggcaggagttttgttgcatggttcgcaa
aatcttcatatacacgaaagaggaagtgaggaagatgaacccggggactt
taagctgtaggagcgaggaagaagcagttgttgggaaggatcagatgca
aaggacgccaagtctgcatcaaatccttcattgtccagcgctgggaactc
ttaaacaaacaaaataaccaacaacctttttgctgcaagccgaggatggg
ggtcgattggtggagactgagagcaaaatgggatgatgggtttaagata
agatattaaaaatgcaattttttgaagtattttgttggccacttagataat
tagcatcttccatcaccctttattatctatctaataataattaatagatat
tataaagtaaaacataaaaaggttacaggtattatatagtagaatatgaa
aagctcttttataagtagaatatgatggtgtggagttgtagtcggaggct
ggtatcggttcttttatggatgtatttttttccttcttccaaagatctc
ttgaagtcttttattgtttatattaatcccaatgtacataagttttcaa
gctcttgcccttttttaattatcttgtcgattc
```

SEQ ID NO. 3
MNT predicted protein wild-type Col-0
MASSEVSMKGNRGGDNFSSSGFSDPKETRNVSVAGEGQKSNSTRSAAAER
ALDPEAALYRELWHACAGPLVTVPRQDDRVFYFPQGHIEQVEASTNQAAE
QQMPLYDLPSKLLCRVINVDLKAEADTDEVYAQITLLPEANQDENAIEKE
APLPPPPRFQVHSFCKTLTASDTSTHGGFSVLRRHADECLPPLDMSRQPP
TQELVAKDLHANEWRFRHIFRGQPRRHLLQSGWSVFVSSKRLVAGDAFIF
LRGENGELRVGVRRAMRQQGNVPSSVISSHSMHLGVLATAWHAISTGTMF
TVYYKPRTSPSEFIVPFDQYMESVKNNYSIGMRFKMRFEGEEAPEQRFTG
TIVGIEESDPTRWPKSKWRSLKVRWDETSSIPRPDRVSPWKVEPALAPPA
LSPVPMPRPKRPRSNIAPSSPDSSMLTREGTTKANMDPLPASGLSRVLQG
QEYSTLRTKHTESVECDAPENSVVWQSSADDDKVDVVSGSRRYGSENWMS
SARHEPTYTDLLSGFGTNIDPSHGQRIPFYDHSSSPSMPAKRILSDSEGK
FDYLANQWQMIHSGLSLKLHESPKVPAATDASLQGRCNVKYSEYPVLNGL
STENAGGNWPIRPRALNYYEEVVNAQAQAQAREQVTKQPFTIQEETAKSR
EGNCRLFGIPLTNNMNGTDSTMSQRNNLNDAAGLTQIASPKVQDLSDQSK GSKSTNDHREQGRPFQTNNPHPKDAQTKTNSSRSCTKVHKQGIALGRSVD
LSKFQNYEELVAELDRLFEFNGELMAPKKDWLIVYTDEENDMMLVGDDPW
QEFCCMVRKIFIYTKEEVRKMNPGTLSCRSEEEAVVGEGSDAKDAKSASN
PSLSSAGNS SEQ ID NO. 4
mnt-1 genomic DNA Col-3
```
AGCCATTTTGTAACTGACCACCGAGTAATCTGTAATCTGAGCTCTTTTAT
TAATCGGATTGAATAAATTCGCTTGGAGTCCGTCAGTCGTGTCCGTGAG
CGCGTGTCTCACTCGCTTGAGCTGATGAAGTGCGATAATGACGTGGCAT
GTTGGGATGGAGACCAAAGACCAGCATTTTATTTTATTTTATAGTAACTA
ATTTTAAAAACCAAACAACCTGAGATTAAAATTTTAATTTTTACTGTACT
GTAGTAAATTTGGGTCCTGATTAAGATTAGGCATATTTATCTCATAGTTT
ATAACAAGTAGCAGCTGAAATTTGTATTACTAGCTTATAGTAATTAAAC
TAAAAACTACGTTCCAGGTTTTAAATTATTGTTTAAAGAAGATATAATA
ATATATTAAGAAAATAGTTAATTAAGGTAAGGAGGAAAGTAGGGTTTG
GTCTGTAGGTTAGGGTTCAAAGAGGGAAGAGATTAGGAGAAAGGAAGC
ATGAAGGCATGACCCATTTCTTCAATTAGTGCTCCTTAATCTGGTGACAC
GTGTAGGTCCCACGTGTAATCACTTCACATTGTTATTTTTCAAAAAATCA
ATTAGTAAAACAAAACTTTGTCCATCATCAAATAGTAGTAGTTTTTTAT
GTGTGGTTACAATATTGTAAGAAGCTCTCCCCCTTTTACTATGTAATTCA
ACCCCACTCTAATTTTTAAAATATTTATGTAAAGCTTTACCCGAAAACAA
TCTATCATGGGTTGGTAATGACACATTTCATTAACAGTGTTAGAGAATG
ATTCCTTTAATTTTTCTACAGTAAAATGTTAGGTGATCTCATTGTACTAC
ATCGGAAAATACTCAAAATTATGTCGTGTAATTTAGATAATGGACGAAT
ATGGTTTTGAAATATTTATGGATACCCAACAAGATTTCTTAACTAGAAA
GACAAAAAATAGAGCACATTTTGCTCGTTTTCCATCAACCCTATTTCTC
CAATTTGTTCACATCATGATCAAAAATACAGTAGCAATTAAAAAATAAA
ATAACAAATATAAATGGCTATATAGATCAACCCTATCTAGCTATTAGTA
TTACTAGAAATTGACAATAAAGGAAACATTCACGTGTGTGAGCATGTAC
TACTCTACACACATGTCCACAGTTATTATATACTGAGTACTAGTATACGT
TGATGTTATCAATAATAAAAACTCGAAATTAAGTATTATTTTCTTATAAT
AATCTATTTAACCATATTTGCTACTGTACTATTTAGTCTATTTTCTTTTG
CCAACCTTTGTATTAAATATTTGTACTATTAGTTTCAATTATAGGTCTAT
CACTATGTATATGTCCGAATAATGGTCTAAAATTGTTAATATAAAATACA
GATTTTATTTCAGCTAAAGATAGTTGAAATTACACAAGAAAATAGAAGA
GATAAAATGATCAATCAGCTATGTAAGACGTCGTATGGATAGTTCAAT
AATTGTGGTAATACTTAAAGACATATATCAAAATTATCAACAAGCCTCG
AACACAAACTTTACAAAAAGCCTGTGTCTACTTTATGAGTGTTTGATTAT
TAAATTGCAAGGTCGTAGTATAAAAATTTCGTAGGCTTTCAGGACACAA
GATTAAATTCATTTATCTAAATGGTGATGGAGTACTTTTATTTTTATATA
TCAAAATGGTGATGATATACGAAGACCATATATTTAGATTATTAAAGAA -continued

```
AAAACGAGAAAAGAAGAAAGAAAAATATAAAAAAATGGTTTTTCTTTTT

AACGGACAAAGATTCCTACAATGGTTGCTTTTAGACCACACACAAATGC

TACACAGTACTCTTGGGTCCCACACCTCTTAGCAAGTGCGTTACCAACA

CGTGAATTTCCTCTCCCCATTTTCTCGTCCTTTTCCTCTCAATATTGTAT

CGTCTCGTTTTCCTTGTCATATCGCGTGTGACGTGTTATTGGCTTATTGC

TGAACAGTCTTCTTTTTTATTTTCCATCGTTATCCTGATTTTTTTTTTT

TCCAAATTTGATTTTCATGGTTTGTAATTTTGCAATAGATTTTGTGTTTC

ACAGAGAGATAGTTTACGTGTTGTTAAAAATAATTTGTGCAAAATAGTGT

GCGTGTGTTAAATATTAAACGATATATAATAATTAGAAGAAAATAAAAAG

TTTTGTCGCGATTAGTTATTTGATATTTACCTTGTTCTTTTGTTTATCGC

TGCGACAAGCACCGACGGTATAAAATATAAAGAAAAAAAGAAAGAGAGAT

GAAGGTGAGATGAATGAAAGAGTCGCAGCGACAGATCTGAAGAGATAG

GAGAAAGGGAATTTGAGACGCTGAAAATTCCAGCGTCTACGGAATGGC

CGAATTACAGTCGATGCGGCAGAGATGAAAAAAATGAGAAATGAAAGT

GAAAAAGAGATGAGAACTTTTTTTGGGTCGCAGGTAGCTGACGCAGCAA

TCAACAAAAGAACATGGCCAACGTTTTAGTAGATACTACTATAAAAGAA

AAAGGTTGATTTAATTCATTCGTAATTTGGACTTAATTTTTTTTAGGAA

CACTAATTAATCTTATTTGCCAGCTGTATGAGTGGACTACAATAAAACTCT

TGTCTATAAACCAGATTTTCTTCCTTTTTAACGCTTCCACTTACAACAAT

ATATGTAAATATGTAATTATGACGGGGCATACGGAAATTTAATTTTTGA

AGCAGATTCATCCCATTAGCCAGCTGTATTAAGTGGTAATCCAAGAGTT

AATTTAGTTGTTCAGCAAATGATTTTAGATAAAATCAACTACTAGTTTAA

AATAACTATCGAATGACTGTTAAGGCTTCGTATTTTTGTTCTGCCATCA

GGATATCATAAATATGGTTGAGGTTCGTATAATATTCGACGATCTTTTAT

ATATCTGAGTTGTAATTGAATTAGAGAAAATAAAAAACAGATAATGAA

ACGTCTTTGTTTTTCCATAAAAAGAAAAACAGGGTAAATTAAAGTACGA

GAGATTCACGAGACGAAAATTCCTAGAGGCGCACGATAGCCAAAAGAC

CATAGAAAATGACATCCGAAATATCTTTAAAATGCTAAAATGCACATAT

TTTTCTGGTGCCACGTAGCATTTTTCTCCCTCTCTCGTTCTCTCTACGTC

CACCCAGACCTGCCTGTTCACAGCACGACAAAGCCACTTCCCAATAAAAA

CACAACACCTTTCCCATTGACGCTCTCTTTCCCAAACACCGTTATCCTCT

TTACCCAATCAAAAGTTGACGCTTGCTCACGACTTGTTGACGCCGTTAGT

CCCATCTAAAAAAGTAAAGCAGCCTTTCTTACTTGCTAATCCCCTCTACA

CATTTAATTTATTTTCTCCCCTAATGGATTTTTTTTGGCAACTTGAGTAT

TTATTTTTCAACTCACAGTAACTGTAAATAAATAAAAGTATTCAACTCAC

AGTCACCAGTAAATAAATACTACCAGACCATAGTTTTTTCAAGAATTGT

TTTGGTCAACAATTTTAGGATGACTTAAATTGCTATATTTCTGGGGAAAT

ACGACTTGGAAATGTCTGCAATTTGGGTCTTTTCTTCAATTTATCTTCTC

CAATTTGTTTTTAAAAAATTAAATTTTAGAAAAGGATATGTCAATTTTT

TCTATTGAAAGGCTTTATTAAAAAATAAGAAAAAGTGGAGGAAAGAAA
```

```
ATAAAATCGTCACTTGTCTTTGGTTTTGTGAGGTCGCAGACCCTGGTCCC

CCGGAAATGGTTACAACCGGTAATAGCCGGTATGAAAGAGGGAATGGT

AACCGGTAATGCCGGTTATCCATATGGGTTAGAAGTTTACCGCGGTTG

AAATGATTGAAGCTGAGTTTTGACTACCTCTGGTTAAGCCCATTGGTCGC

CTCATACCCAGAAAAACAAAAGGATAGGAAAGACGAAGAAATAAAAA

GAGAGAGAATGTTAGAGAGACAAACTCTGAGAGACAAAACAAGAGAA

AATCGCTCGTCGTCGGTATTCAAGCGTCTGTGACTCCGATAAAGCCTAG

ACTAGCGAGGACGGCGAGAGAGAGAGAGAGAGCTTTGGAGTTGTCG

TATCTCTAAATCGGAGGCAATTTGAGGTGAAATTGGTGGTTTTATCGTTT

GATTCTAGGGTTTATCTTCTCTGATAGTTTTATCGAGTAATGTCAAGGAG

CTAAACTAGTGGTGATTGTGTTTGTTAGTGAGATAAAGACAAAGGAAGG

AATCAAGTGGACTACCGAAGCGAGTTTTGAGCTTTTTCAGAGACGGATT

TGGAGATTCTTGTTGATATCGTCTGCTTAGAGGCTTATTTGGTACCAGA

TGAAACAGATCTGAGCTTCGGAAGGTATGGCGAGTTCGGAGGTTTCAAT

GAAAGGTAATCGTGGAGGAGATAACTTCTCCTCCTCTGGTTTTAGTGAC

CCTAAGGAGACTAGAAATGTCTCCGTCGCCGGCGAGGGGCAAAAAGT

AATTCTACCCGATCCGCTGCGGCTGAGCGTGCTTGTAAGTCTCCGTTTCT

TAGGGTTTCTTAAGCTTGGTTTTGGTTACAGACTGACTTGATCTAATTTA

TCTTCTTCTTCTTCGTCTTCATAGTGGACCCTGAGGCTGCTCTTTACAGA

GAGCTATGGCACGCTTGTGCTGGTCCGCTTGTGACGGTTCCTAGACAAG

ACGACCGAGTCTTCTATTTTCCTCAAGGACACATCGAGCAGGTGAGATA

TTTCATCTATGAGTTCTTGCTATTTTTGGCTAAATCTTTGAGTTAACCCC

TCTGTGATTCGTACCTGTTGAGATATTTTCTAATGAACTTTGTCGGTTTC

CATTGTTTTATGATTAGGTGGAGGCTTCGACGAACCAGGCGGCAGAACAA

CAGATGCCTCTCTATGATCTTCCGTCAAAGCTTCTCTGTCGAGTTATTAA

TGTAGATTTAAAGGTAGGTTTCTTTAACTTCTTGGAAAATTTTGGTTTCT

GTGTCTTGGATTGTCAGCTAACAAGAGTTTTGTTTATGATTTTACAAGCA

GAGGCAGATACAGATGAAGTTTATGCGCAGATTACTCTTCTTCCTGAGG

CTAATGTAAGTTTTGTTTTCTGATTTATTGGTTTGAGTGTTGTAGAGGTG

ATCTTATTCTTCAAGATGCTGAATTCTATATATTTTTTGTTCCATACAGC

AAGACGAGAATGCAATTGAGAAAGAAGCGCCTCTTCCTCCACCTCCGAGG

TTCCAGGTGCATTCGTTCTGCAAAACCTTGACTGCATCCGACACAAGTA

CACATGGTGGATTTTCTGTTCTTAGGCGACATGCGGATGAATGTCTCCCA

CCTCTGGTTGGTGTTTCATTTGCGCTTCTAACTATCTATTCATTGGCTTA

TTTTTCCTGAATTTTGTTCTAAGATTGCCTTCAATTCATTTTTTGTTTCT

TCCCTCAGGATATGTCTCGACAGCCTCCCACTCAAGAGTTAGTTGCAAAG

GATTTGCATGCAAATGAGTGGCGATTCAGACATATATTCCGGGGTATAGG

AATCTGTAACTTTTTTATTTTCTGTTTTTCTCGAGTCTGTGTGTCATCAA

ACTTATCTGGTTGTTGATGTTTGTGATAATGGACCAGGTCAACCACGGAG

GCATTTGCTACAGAGTGGGTGGAGTGTGTTTGTTAGCTCCAAAAGGCTAG
```

TTGCAGGCGATGCGTTTATATTTCTAAGGTTTGTGGATTTTAGTTCATTG
TTTTCTTTAGCTGTATCTGTTAGTTTCTATAATGTGGAATATCTTAATCT
TCTACAGGGGCGAGAATGGAGAATTAAGAGTTGGTGTAAGGCGTGCGAT
GCGACAACAAGGAAACGTGCCGTCTTCTGTTATATCTAGCCATAGCATG
CATCTTGGAGTACTGGCCACCGCATGGCATGCCATTTCAACAGGGACTA
TGTTTACAGTCTACTACAAACCCAGGTTTGTATTTGTATTAGCTCACAAA
ACAGCTTTCAGTTTTTTGAGCTCTTTGCTTTGTATGTCTCTATATGTCTG
ATGCTTGGTAGTGAATCACTCTACTAAATTTTCATGCGGTGTTGTTTTGT
TTAATACAGGACGAGCCCATCTGAGTTTATTGTTCCGTTCGATCAGTATA
TGGAGTCTGTTAAGAATAACTACTCTATTGGCATGAGATTCAAAATGAGA
TTTGAAGGCGAAGAGGCTCCTGAGCAGAGGTAAAACCTGTCTTCTGCTTT
TGAAATATGTTAGCTCTTGAGCCTTTTTCTCTTGGAATAACGAACCTAAC
AAGTTGTATTGATTTATATTAGGTTTACTGGCACAATCGTTGGGATTGAA
GAGTCTGATCCTACTAGGTGGCCAAAATCAAAGTGGAGATCCCTCAAGG
TATGACCTAGTTTCTAGAGAGGATCAAGACTATTGTTTGAATATAATGA
ATGCTGATTGTTCAATTGTCTTTCAGGTGAGATGGGATGAGACTTCTAGT
ATTCCTCGACCTGATAGAGTATCTCCGTGGAAAGTAGAGCCAGCTCTTG
CTCCTCCTGCTTTGAGTCCTGTTCCAATGCCTAGGCCTAAGAGGCCCAGA
TCAAATATAGCACCTTCATCTCCTGACTCTTCGATGCTTACCAGAGAAGG
TAATGTCTTCCCCTTCCACTGTAGTACACATAGTAGTGCGTCTGAAACTT
AATTGAACTTGTCAGTGGGAGTCTAATTCATTGTACACAAAACAGGTAC
AACTAAGGCAAACATGGACCCTTTACCAGCAAGCGGACTTTCAAGGGTC
TTGCAAGGTCAAGAATACTCGACCTTGAGGACGAAACATACTGAGAGTG
TAGAGTGTGATGCTCCTGAGAATTCTGTTGTCTGGCAATCTTCAGCGGAT
GATGATAAGGTTGACGTGGTTTCGGGTTCTAGAAGATATGGATCTGAGA
ACTGGATGTCCTCAGCCAGGCATGAACCTACTTACACAGATTTGCTCTCC
GGCTTTGGGACTAACATAGATCCATCCCATGGTCAGCGGATACCTTTTTA
TGACCATTCATCATCACCTTCTATGCCTGCAAAGAGAATCTTGAGTGATT
CAGAAGGCAAGTTCGATTATCTTGCTAACCAGTGGCAGATGATACACTC
TGGTCTCTCCCTGAAGTTACATGAATCTCCTAAGGTACCTGCAGCAACTG
ATGCGTCTCTCCAAGGGCGATGCAATGTTAAATACAGCGAATATCCTGT
TCTTAATGGTCTATCGACTGAGAATGCTGGTGGTAACTGGCCAATACGT
CCACGTGCTTTGAATTATTATGAGGAAGTGGTCAATGCTCAAGCGCAAG
CTCAGGCTAGGGAGCAAGTAACAAAACAACCCTTCACGATACAAGAGG
AGACAGCAAAGTCAAGAGAAGGGAACTGCAGGCTCTTTGGCATTCCTCT
GACCAACAACATGAATGGGACAGACTCAACCATGTCTCAGAGAAACAA
CTTGAATGATGCTGCGGGGCTTACACAGATAGCATCACCAAAGGTTCAG
GACCTTTCAGATCAGTCAAAAGGGTCAAAATCAACAAACGATCATCGTG
AACAGGGAAGACCATTCCAGACTAATAATCCTCATCCGAAGGATGCTCA
AACGAAAACCAACTCAAGTAGGAGTTGCACAAAGGTAAATTTTTGCAAT

ATGTAGCACAAAGTGTATGAGGTTGTGATAACCCTTGAATCACTTTTCA
ACTAACACATGACACATTGATGTAAAGGTTCACAAGCAGGGAATTGCAC
TTGGCCGTTCAGTGGATCTTTCAAAGTTCCAAAACTATGAGGAGTTAGT
CGCTGAGCTGGACAGGCTGTTTGAGTTCAATGGAGAGTTGATGGCTCCT
AAGAAAGATTGGTTGATAGTTTACACAGATGAAGAGAATGATATGATGC
TTGTTGGTGACGATCCTTGGCAGTAAGATTTTGCAAATTTTCCATCTTAG
TTTATATCGATGTTAGTGTTTTTCTTATAACACTGACACAATGATCTCTC
TTGCAGGGAGTTTTGTTGCATGGTTCGCAAAATCTTCATATACACGAAAG
AGGAAGTGAGGAAGATGAACCCGGGGACTTTAAGCTGTAGGAGCGAGG
AAGAAGCAGTTGTTGGGGAAGGATCAGATGCAAAGGACGCCAAGTCTG
CATCAAATCCTTCATTGTCCAGCGCTGGGAACTCTTAAACAAACAAAAT
AACCAACAACCCTTTTGCTGCAAGCCGAGGTATGTAAAAGCTTTTGAGA
TATTAGTAGACTAGAGACACAGCCAAAAGTTTATGTCATTACATTCGAC
TGATGTTTGTTCTGTTAATGACAGCAGGATGGGGGTCGATTGGTGGAGA
CTGGAGAGCAAAATGGGATGATGGGTTTAAGATAAGATATTAAAAATG
CAATTTTTGAAGTATTTTGTTGGCCACTTAGATAATTAGCATCTTCCATC
ACCCTTATTATCTATCTAATAATAATTAATAGATATTATAAAGTAAAACA
TAAAAAGGTTACAGGTATTATATAGTAGAATATGAAAAGCTCTTTTATA
AGTAGAATATGATGGTGTGGAGTTGTAGTCGGAGGCTGGTATCGGTTCT
TTTTATGGATGTATTTTTTTCCTTCTTCCAAAGATCTCTTGAAGTCTTTT
TATTGTTTATATTAATCCCAATGTACATAAGTTTTCAAGCTCTTGCCCTT
TTTTAATTATCTTGTCGATTC

SEQ ID NO. 5
mnt-1 cDNA translational start to stop
ATGGCGAGTTCGGAGGTTTCAATGAAAGGTAATCGTGGAGGAGATAACT
TCTCCTCCTCTGGTTTTAGTGACCCTAAGGACTAGAAATGTCTCCGTC
GCCGGCGAGGGGCAAAAAAGTAATTCTACCCGATCCGCTGCGGCTGAG
CGTGCTTTGGACCCTGAGGCTGCTCTTTACAGAGAGCTATGGCACGCTT
GTGCTGGTCCGCTTGTGACGGTTCCTAGACAAGACGACCGAGTCTTCTA
TTTTCCTCAAGGACACATCGAGCAGGTGGAGGCTTCGACGAACCAGGCG
GCAGAACAACAGATGCCTCTCTATGATCTTCCGTCAAAGCTTCTCTGTCG
AGTTATTAATGTAGATTTAAAGAGGCAGATACAGATGAAGTTTATGCGC
AGATTACTCTTCTTCCTGAGGCTAATCAAGACGAGAATGCAATTGAGAA
AGAAGCGCCTCTTCCTCCACCTCCGAGGTTCCAGGTGCATTCGTTCTGCA
AAACCTTGACTGCATCCGACACAAGTACACATGGTGGATTTTCTGTTCTT
AGGCGACATGCGGATGAATGTCTCCCACCTCTGGATATGTCTCGACAGC
CTCCCACTCAAGAGTTAGTTGCAAAGGATTTGCATGCAAATGAGTGGCG
ATTCAGACATATATTCCGGGGTCAACCACGGAGGCATTTGCTACAGAGT
GGGTGGAGTGTGTTTGTTAGCTCCAAAAGGCTAGTTGCAGGCGATGCGT
TTATATTTCTAAGGGGCGAGAATGGAGAATTAAGAGTTGGTGTAAGGCG
TGCGATGCGACAACAAGGAAACGTGCCGTCTTCTGTTATATCTAGCCAT AGCATGCATCTTGGAGTACTGGCCACCGCATGGCATGCCATTTCAACAG
GGACTATGTTTACAGTCTACTACAAACCCAGGACGAGCCCATCTGAGTT
TATTGTTCCGTTCGATCAGTATATGGAGTCTGTTAAGAATAACTACTCTA
TTGGCATGAGATTCAAAATGAGATTTGAAGGCGAAGAGGCTCCTGAGCA
GAGGTTTACTGGCACAATCGTTGGGATTGAAGAGTCTGATCCTACTAGG
TGGCCAAAATCAAAGTGGAGATCCCTCAAGGTGAGATGGGATGAGACT
TCTAGTATTCCTCGACCTGATAGAGTATCTCCGTGGAAAGTAGAGCCAG
CTCTTGCTCCTCCTGCTTTGAGTCCTGTTCCAATGCCTAGGCCTAAGAGG
CCCAGATCAAATATAGCACCTTCATCTCCTGACTCTTCGATGCTTACCAG
AGAAGGTACAACTAAGGCAAACATGGACCCTTTACCAGCAAGCGGACT
TTCAAGGGTCTTGCAAGGTCAAGAATACTCGACCTTGAGGACGAAACAT
ACTGAGAGTGTAGAGTGTGATGCTCCTGAGAATTCTGTTGTCTGGCAAT
CTTCAGCGGATGATGATAAGGTTGACGTGGTTTCGGGTTCTAGAAGATA
TGGATCTGAGAACTGGATGTCCTCAGCCAGGCATGAACCTACTTACACA
GATTTGCTCTCCGGCTTTGGGACTAACATAGATCCATCCCATGGTCAGCG
GATACCTTTTTATGACCATTCATCATCACCTTCTATGCCTGCAAAGAGAA
TCTTGAGTGATTCAGAAGGCAAGTTCGATTATCTTQCTAACCAGTGGCA
GATGATACACTCTGGTCTCTCCCTGAAGTTACATGAATCTCCTAAGGTAC
CTGCAGCAACTGATGCGTCTCTCCAAGGGCGATGCAATGTTAAATACAG
CGAATATCCTGTTCTTAATGGTCTATCGACTGAGAATGCTGGTGGTAACT
GGCCAATACGTCCACGTGCTTTGAATTATTATGAGGAAGTGGTCAATGC
TCAAGCGCAAGCTCAGGCTAGGGAGCAAGTAACAAAACAACCCTTCAC
GATACAAGAGGAGACAGCAAAGTCAAGAGAAGGGAACTGCAGGCTCTT
TGGCATTCCTCTGACCAACAACATGAATGGGACAGACTCAACCATGTCT
CAGAGAAACAACTTGAATGATGCTGCGGGCTTACACAGATAGCATCAC
CAAAGGTTCAGGACCTTTCAGATCAGTCAAAAGGGTCAAAATCAACAA
ACGATCATCGTGAACAGGGAAGACCATTCCAGACTAATAATCCTCATCC
GAAGGATGCTCAAACGAAAACCAACTCAAGTAGGAGTTGCACAAAGGT
TCACAAGCAGGGAATTGCACTTGGCCGTTCAGTGGATCTTTCAAAGTTC
CAAAACTATGAGGAGTTAGTCGCTGAGCTGGACAGGCTGTTTGAGTTCA
ATGGAGAGTTGATGGCTCCTAAGAAAGATTGGTTGATAGTTTACACAGA
TGAAGAGAATGATATGATGCTTGTTGGTGACGATCCTTGGCAGGAGTTT
TGTTGCATGGTTCGCAAAATCTTCATATACACGAAAGAGGAAGTGAGGA
AGATGAACCCGGGGACTTTAAGCTGTAGGAGCGAGGAAGAAGCAGTTG
TTGGGGAAGGATCAGATGCAAAGGACGCCAAGTCTGCATCAAATCCTTC
ATTGTCCAGCGCTGGGAACTCTTAA SEQ ID NO. 6
mnt-1 predicted protein Col-3
MASSEVSMKGNRGGDNFSSSGFSDPKETRNVSVAGEGQKSNSTRSAAAER
ALDPEAALYRELWHACAGPLVTVPRQDDRVFYFPQGHIEQVEASTNQAAE
QQMPLYDLPSKLLCRVINVDLKRQIQMKFMRRLLFFLRLIKTRMQLRKKR
LFLHLRGSRCIRSAKP SEQ ID NO. 7
Forward primer for amplifying Brassica napus ARF2
5' ATGGCGAGTTCGGAGGTTT 3'

SEQ ID NO. 8
Reverse primer for amplifying Brassica napus ARF2
5' TGGACAATGAAGGATTTGATG 3'

SEQ ID NO. 9
BnARF2 cDNA, translational start to stop
ATGGCGAGTTCGGAGGTTTCTATGAAAGGAAATCGTGGACGAGGAGAA
AACTTCTCCTCCGCTGGTTACAGTGACCCGACGGTCGCCGGCGAGGCGC
AGAAAACTCAGTCTAACCGATCTGTGGCTGCAGAGCGCGTTGTCGACCC
GGAAGCTGCTCTCTACCGTGAGCTGTGGCACGCTTGTGCTGGTCCTCTCG
TGACAGTCCCTCGACAAGATGACCGAGTCTTCTACTTCCCTCAGGGGCA
CATCGAGCAGGTGGAAGCATCGACAAATCAAGCTGCAGAACAGCAGAT
GCCTCTCTATGATCTTCCTTCGAAGATCCTTTGTCGTGTCATTAATGTTG
ATTTAAAGGCAGAGGCAGACACCGACGAAGTTTATGCGCAGATTACTCT
TCTTCCGGAGCCTGTTCAAGACGAGAATTCAATAGAGAAAGAGGCGCCT
CCTCCTCCGCCCCAAGGTTCCAAGTGCACTCCTTCTGCAAAACCTTGAC
TGCATCGGACACAAGTACACATGGTGGATTTTCTGTGCTTAGGCGGCAT
GCGGATGAATGTCTCCCACCTCTGGATATGTCACGTCAACCTCCTACTCA
GGAGTTAGTTGCAAAAGATCTGCATGCAAGCGAGTGGCGTTTCCGACAT
ATTTTCCGAGGTCAACCACGAAGGCATTTGCTTCAGAGTGGATGGAGCG
TGTTTGTTAGCTCCAAGAGGCTGGTCGCAGGCGATGCTTTTATATTTCTA
AGGGGCGAGAATGGAGAATTACGTGTGGGTGTAAGGCGTGCAATGCGG
CAGCAAGGAAATGTGCCATCCTCTGTTATATCAAGCCACAGCATGCATC
TCGGAGTATTGGCCACTGCCTGGCACGCTATTTCAACTGGAACCATGTTT
ACAGTCTACTATAAACCGAGGACTAGTCCTTCAGAGTTTATTGTTCCGTT
TGATCAGTATACGGAGTCCGTGAAGATTAACTACTCCATAGGCATGAGA
TTTAAAATGAGATTTGAAGGCGAAGAGGCTCCCGAGCAGAGGTTTACTG
GCACAATCGTTGGGATTGAAGACTCTGACCCCACGAGGTGGGCAAAATC
AAAATGGAGATCCCTCAAGGTACGGTGGGATGAGACCACTAGTATTCCT
CGCCCTGATAGAGTATCCCGTGGAAGATAGAGCCAGCTCTTTCTCCTC
CTGCTTTGAGCCCTGTACCAATGCCTAGGCCTAAGAGGCCCAGATCTAA
TCTAGCTTCTTCAACTCCGGACTCTTCCATGCGCATAAGGGAAGGCTCAT
CTAAGGCAAACATGGACCCTTTACCGGCAAGTGGACTATCAAGGGTCTT
GCAAGGTCAAGAATACCCGACCTTGAGAACGAAACATGTTGAGAGTGT
AGAATGCGATGCTCCTGAAAATTCGGTTGTGTGGCAATCGTCAACTGAT
GATGACAAGGTTGATGTGATTTCAGCTTCTAGGAGATATGAGAACTGGA
TATCCTCAGGTAGGCATGGACCTACTTGCACGGATTTGCTTTCTGGCTTT
GGGACAAACATAGAACCACCTCACGGTCATCAGATACCTTTTTATGACC
GTTTATCATCACCACCTTCTGTGGCTGCAAGGAAAATCCTCAGCGACCA -continued

```
GGATGGCAAGTTTGAATATCTTGCTAACCAGTGGATGATGCACTCAGGC

CTTTCCCTGAAGTTACATGAATCTCCTAAAGTCCCTGCCGCATCTGATGC

CTCTTTCCAAGGGATAGGCAATCCCAATTACGGCGAATATGCTTTGCCTC

GTGCAGTGACGACTGAGAATGCTGCTGGCAACTGGCCAATACGTCCACG

TGCTCTAAATTATTTTGAAGAAGCGGTTCATGCTCAGGCTAGAGAGCAT

GTGACAAAACGTCCTGCGGTCGTACAAGAGGAGGCAGCAAAGCCAAGA

GACGGGAACTGCAGGCTTTTTGGCATTCCTCTGGTGAACAACGTGAATG

GGACAGATACAACTTTGTCTCAGAGAAACAATTTGAATGACCCTGCGGG

GCCTACGCAGATGGCATCACCAAAGGTTCAGGATCTTTCTGACCAGTCC

AAAGGGTCAAAATCGACAAATGATCATCGTGAGCAAGGACGACCATTC

CCGGTTAGTAAACCCCATCCGAAAGACGTTCAAACCAAAACAAACTCAT

GTAGGAGCTGCACGAAGGTTCAGAAGCAGGGGATTGCACTTGGCCGGT

CAGTGGATCTCTCAAAGTTCCAGAACTATGAGGAGTTGGTTACTGAATT

GGATAGGCTGTTTGAGTTCAATGGAGAGTTGATGGCTCCTAAGAAAGAT

TGGCTGATAGTTTACACAGATGATGAGAATGATATGATGCTTGTTGGAG

ACGATCCTTGGCAGGAGTTTTGTTGCATGGTTCGTAAAATCTTCATATAC

ACGAAAGAGGAGGTCAGGAAGATGAACCCGGGAACTCTATGCTGTAGG

AACGAGGAAGAACCAGTTGTTGGGGAAGGATCAGATGCAAAGGACGCG

AAGTCTGCATCAAATCCTTCATTGTCCAGCGCCGGAAACTCTTAA
```

SEQ ID NO. 10
BnARF2 predicted protein
```
MASSEVSMKGNRGRGENFSSAGYSDPTVAGEAQKTQSNRSVAAERVVDPE

AALYRELWHACAGPLVTVPRQDDRVFYFPQGHIEQVEASTNQAAEQQMPL

YDLPSKILCRVINVDLKAEADTDEVYAQITLLPEPVQDENSIEKEAPPPP

PPRFQVHSFCKTLTASDTSTHGGFSVLRRHADECLPPLDMSRQPPTQELV

AKDLHASEWRFRHIFRGQPRRHLLQSGWSVFVSSKRLVAGDAFIFLRGEN

GELRVGVRRAMRQQGNVPSSVISSHSMHLGVLATAWHAISTGTMFTVYYK

PRTSPSEFIVPFDQYTESVKINYSIGMRFKMRFEGEEAPEQRFTGTIVGI

EDSDPTRWAKSKWRSLKVRWDETTSIPRPDRVSPWKIEPALSPPALSPVP

MPRPKRPRSNLASSTPDSSMRIREGSSKANMDPLPASGLSRVLQGQEYPT

LRTKHVESVECDAPENSVVWQSSTDDDKVDVISASRRYENWISSGRHGPT

CTDLLSGFGTNIEPPHGHQIPFYDRLSSPPSVAARKILSDQDGKFEYLAN

QWMMHSGLSLKLHESPKVPAASDASFQGIGNPNYGEYALPRAVTTENAAG

NWPIRPRALNYFEEAVHAQAREHVTKRPAVVQEEAAKPRDGNCRLFGIPL

VNNVNGTDTTLSQRNNLNDPAGPTQMASPKVQDLSDQSKGSKSTNDHREQ

GRPFPVSKPHPKDVQTKTNSCRSCTKVQKQGIALGRSVDLSKFQNYEELV

TELDRLFEFNGELMAPKKDWLIVYTDDENDMMLVGDDPWQEFCCMVRKIF

IYTKEEVRKMNPGTLCCRNEEEPVVGEGSDAKDAKSASNPSLSSAGNS
```

REFERENCES

Adams, S., Vinkenoog, R., Spielman, M., Dickinson, H. G., and Scott, R. J. (2000). Parental imprinting in *Arabidopsis thaliana* requires DNA methylation. *Development* 127, 2493-2502.

Alexander, H. M. and Wulff, R. D. (1985). Experimental ecological genetics in *Plantago* X. The effects of maternal temperature on seed and seedling characters in *P. lanceolata*. *Journal of Ecology* 73, 271-282.

Austin, R. B. (1980). Physiological limitations to cereal yields and ways of rescuing them by breeding. In *Opportunities for increasing crop yields* (eds R. G. Hurd, P. V. Biscoe, and C. Dennis), pp. 3-20. Pitman, London.

Alonso, J. M. et al. (2003). Genome-wide insertional mutagenesis of *Arabidopsis thaliana*. *Science* 301, 653-657.

Alonso-Blanco, C., Blankestijn-De Vries, H., Hanhart, C. J., and Koornneef, M. (1999). Natural allelic variation at seed size loci in relation to other life history traits of *Arabidopsis thaliana*. *PNAS USA* 96, 4710-4717.

Baker, S. C., Robinson-Beers, K., Villanueva, J. M., Gaiser, J. C., and Gasser, C. S. (1997). Interactions among genes regulating ovule developing in *Arabidopsis thaliana*. *Genetics* 145, 1109-24.

Board, J. (2001). Reduced lodging for soybean in low plant population is related to light quality. *Crop Science* 41, 379-384.

Beeckman, T., De Rycke, R., Viane, R., and Inzé, D. (2000). Histological study of seed coat development in *Arabidopsis thaliana*. *Journal of Plant Research* 113, 139-148.

Bouman, F. (1975). Integument initiation and testa development in some Cruciferae. *Botanical Journal of the Linnean Society* 70, 213-229.

Bouman, F. (1984). The ovule. In *Embryology of angiosperms* (ed. B. M. Johri), pp. 123-157. Springer, Berlin.

Branen, J. K., Shintani, D. K., and Engeseth, N. J. (2003). Expression of antisense acyl carier protein-4 reduces lipid content in *Arabidopsis* leaf tissue. *Plant Physiology* 132, 748-756.

Brown, J. W. S, and Simpson, C. G. (1998). Splice site selection in plant pre-mRNA splicing. *Annual Review of Plant Physiology and Plant Molecular Biology* 49, 77-95.

Chandrasekharan, M. B., Bishop, K. J., and Hall, T. C. (2003). Module-specific regulation of the β-phaseolin promoter during embryogenesis. *Plant Journal* 33, 853-866.

Cheng, W.-H., Taliercio, E. W., and Chourey, P. S. (1996). The Miniature 1 seed locus of maize encodes a cell wall invertase required for normal development of endosperm and maternal cells in the pedicel. *Plant Cell* 8, 971-983.

Choi, D. S., Lee, Y., Cho, H. T., and Kende, H. (2003). Regulation of expansin gene expression affects growth and development in transgenic rice plants. *Plant Cell* 15, 1386-1398.

Clough, S. J. and Bent, A. F. (1998). Floral dip: a simplified method for *Agrobacterium*-mediated transformation of *Arabidopsis thaliana*. *Plant Journal* 16, 735-743.

Debeaujon, I., Peeters, A. J. M., Léon-Kloosterziel, K. M., and Koornneef, M. (2001). The TRANSPARENT TESTA12 gene of *Arabidopsis* encodes a multidrug secondary transporter-like protein required for flavonoid sequestration in vacuoles of the seed coat endothelium. *Plant Cell* 13, 853-871.

Devic, M., Guilleminot, J., Debeaujon, I., Bechtold, N., Bensaude, E., Koornneef, M., Pelletier, G., and Delseny, M. (1999). The BANYULS gene encodes a DFR-Like protein and is a marker of early seed coat development. *Plant Journal* 19, 387-398.

Doyholos, M. K., and Sieburth, L. E. (2000). Separable whorl-specific expression and negative regulation by enhancer elements within the AGAMOUS second intron. *Plant Cell* 12, 1799-1810.

Duvick, D. N. (1992) Genetic contributions to advances in yield of United States maize. *Maydica* 37, 69-79.

Esau (1965) Plant Anatomy (2$^{nd}$ Edition) Wiyley N.Y.

Ferreira, P. C. G., Hemerly, A. S., de Almeida Engler, J., Van Montagu, M., Engler, G., and Inzé, D. (1994). Developmental expression of the *Arabidopsis* cyclin gene cycl *At. Plant Cell* 6, 1763-1774.

Garcia, D., Saingery, V., Chambrier, P., Mayer, U., Jürgens, G., and Berger, F. (2003). *Arabidopsis* haiku mutants reveal new controls of seed size by endosperm. *Plant Physiology* 131, 1661-1670.

Garcia, D., Fitz Gerald, J. N., and Berger, F. (2005). Maternal control of integument cell elongation and zygotic control of endosperm growth are coordinated to determine seed size in *Arabidopsis*. *Plant Cell* 17, 52-60.

Gleave, A. P. (1992). A versatile binary vector system with a T-DNA organisational structure conducive to efficient integration of cloned DNA into the plant genome. *Plant Molecular Biology* 20, 1203-1207.

Goto, K. and Meyerowitz, E. M. (1994). Function and regulation of the *Arabidopsis* floral homeotic gene PISTILLATA. *Genes and Development* 8, 1548-1560.

Guberac, V., Martinic, J. and Maric, S. (1998). Influence of seed size on germinability, germ length, root length and grain yield in spring oat. *Bodenkultur* 49, 13-18.

Hagen, G. and Guilfoyle, T. (2002). Auxin-responsive gene expression: genes, promoters and regulatory factors. *Plant Molecular Biology* 49, 373-385.

Harper, J. L., Lovell, P. H., and Moore, K. G. (1970). The shapes and sizes of seeds. *Annual Review of Ecology and Systematics* 1, 327-356.

Hemerly, A., de Almeida Engler, J., Bergounioux, C., Van Montagu, M., Engler, G., Inzé, D., and Ferreira, P. (1995). Dominant negative mutants of the CDC2 kinase uncouple cell division from interative plant development. *EMBO Journal* 14, 3925-3936.

Hu, Y., Xie, Q., and Chua, N.-H. (2003). The *Arabidopsis* auxin-inducible gene ARGOS controls lateral organ size. *Plant Cell* 15, 1951-1961.

Jack, T., Brockman, L. L., and Meyerowitz, E. M. (1992). The homeotic gene APETALA3 of *Arabidopsis thaliana* encodes a MADS box and is expressed in petals and stamens. *Cell* 68, 683-697.

Jefferson, R. A. (1987). Assaying chimeric genes in plants: the GUS gene fusion system. *Plant Molecular Biology Reporter* 5, 387-405.

Jofuku, K. D., Omidyar, P. K., Gee, Z., and Okamuro, J. K. (2005). Control of seed mass and seed yield by the floral homeotic gene APETALA2. *PNAS* 102, 3117-3122.

Jones, R. J., Schreiber, B. M. N., and Roessler, J. A. (1996). Kernel sink capacity in maize: genotypic and maternal regulation. *Crop Science* 36, 301-306.

Klucher, K. M., Chow, H., Reiser, L., and Fischer, R. L. (1996). The AINTEGUMENTA gene of *Arabidopsis* required for ovule and female gametophyte development is related to the floral homeotic gene APETALA2. *Plant Cell* 8, 137-53.

Krannitz, P. G., Aarssen, L. W., and Dow, J. M. (1991). The effect of genetically based differences in seed size on seedling survival in *Arabidopsis thaliana* (Brassicacea). *American Journal of Botany* 78, 446-450.

Leyser, O. (2002). Molecular genetics of auxin signaling. *Annual Review of Plant Biology* 53, 377-398.

Liscum, E. and Reed, J. W. (2002). Genetics of Aux/IAA and ARF action in plant growth and development. *Plant Molecular Biology* 49, 387-400.

Lopez-Dee, Z. P., Wittich, P., Pé, M. E., Rigola, D., del Buono, I., Sari Gorla, M., Kater, M. M., and Colombo, L. (1999). OsMADS13, a novel rice MADS-box gene expressed during ovule development. *Developmental Genetics* 25, 237-244.

Mandel, A. M., Gustafson-Brown, C., Savidge, B., and Yanofsky, M. F. (1992). Molecular characterization of the *Arabidopsis* floral homeotic gene APETALA1. *Nature* 360, 273-277.

Manga and Yadav (1995). Effect of seed size on developmental traits and ability to tolerate drought in pearl-millet. *Journal of Arid Environments* 29, 169-172.

Marshall, D. L. (1986). Effect of seed size on seedling success in three species of Sesbania (Fabaceae). *American Journal of Botany* 73, 457-464.

Miliuviene, L., Novickiene, L., Gaveliene, V., Brazauskiene, I., and Pakalniskyte, L. (2004). Possibilities to use growth regulators in winter oilseed rape growing technology. 1. The effect of retardant analogues on oilseed rape growth. *Agronomy Research* 2, 207-215.

Moloney, M. M., Walker, J. M., and Sharma, K. K. (1989) *Plant Cell Reports* 8, 238-242.

Nahm, M. Y., Kim, S. W., Yun, D. J., Lee, S. Y., Cho, M. J., and Bahk, J. D. (2003). Molecular and biochemical analysis of OsRAB7, a rice Rab$^7$ homolog. *Plant and Cell Physiology* 44, 1341-1349.

Nesi, N., Debeaujon, I., Jond, C., Pelletier, G., Caboche, M., and Lepiniec, L. (2000). The TT8 gene encodes a basic helix-loop-helix domain protein required for expression of DFR and BAN genes in *Arabidopsis* siliques. *Plant Cell* 12, 1863-1878.

Nesi, N., Jond, C., Debeaujon, I., Caboche, M., and Lepiniec, L. (2001). The *Arabidopsis* TT2 gene encodes an R2R3 MYB domain protein that acts as a key determinant for proanthocyanidin accumulation in developing seed. *Plant Cell* 13, 2099-2114.

Nesi, N., Debeaujon, I., Jond, C., Stewart, A. J., Jenkins, G. I., Caboche, M., and Lepiniec. L. (2002). The TRANSPARENT TESTA16 locus encodes the *ARABIDOPSIS* BSISTER MADS domain protein and is required for proper development and pigmentation of the seed coat. *Plant Cell* 14, 2463-2479.

Nicholas, K. B. and Nicholas, H. B., Jr. (1997). GeneDoc: a tool for editing and annotating multiple sequence alignments. http://www.psc.edu/biomed/genedoc Ohto, M., Fischer, R. L., Goldberg, R. B., Nakamura, K., and Harada, J. J. (2005). Control of seed mass by APETALA2. *PNAS* 102, 3123-3128.

Patrick, J. W. and Offler, C. E. (1995). Poist-sieve element transport of sucrose in developing seeds. *Australian Journal of Plant Physiology* 22, 681-702.

Paul, M. J. and Foyer, C. H. (2001). Sink regulation of photosynthesis. *Journal of Experimental Botany* 52, 1383-1400.

Resier, L., Modrusan, Z., Margossian, L., Samach, A., Ohad, N., Haughn, G. W., and Fischer, R. L. (1995). The BELL1 gene encodes a homeodomain protein involved in pattern formation in the *Arabidopsis* ovule primordium. *Cell* 83, 735-742.

Reynolds, M. P., Skovmand, B., Trethowan, R. M., Singh, R. P., and van Ginkel, M. (2001). Applying physiological strategies to wheat breeding. *Research highlights of the CIMMYT wheat program* 1999-2000, http://www.cimmyt.cgiar.org Robinson-Beers, K., Pruitt, R. E., and Gasser, C. S. (1992). Ovule development in wild-type *Arabidopsis* and two female-sterile mutants. *Plant Cell* 4, 1237-1249.

Sagasser, M., Lu, G.-H., Hahlbrock, K., and Weisshaar, B. (2002). *A. thaliana* TRANSPARENT TESTA 1 is involved in seed coat development and defines the WIP subfamily of plant zinc finger proteins. *Genes and Development* 16, 138-149.

Sato, Y., Nishimura, A., Ito, M., Ashikari, M., Hirano, H.-Y., and Matsuoka, M. (2001). Auxin response factor family in rice. *Genes Genet. Syst.* 76, 373-380.

Schaal, B A. (1980). Reproductive capacity and seed size in Lupinus texensis. *American Journal of Botany* 67, 703-709.

Schneitz, K., Hülskamp, M., and Pruitt, R. E. (1995). Wild-type ovule development in *Arabidopsis thaliana*: a light microscope study of cleared whole-mount tissue. *Plant Journal* 7, 731-749.

Scott, R. J, Spielman, M., Bailey, J., and Dickinson, H. G. (1998) Parent-of-origin effects on seed development in *Arabidopsis thaliana. Development* 125, 3329-3341.

Soni, R., Carmichael, J. P., Shah, Z. H., and Murray, J. A. H. (1995). A family of cyclin D homologs from plants differentially controlled by growth regulators and containing the conserved retinoblastoma protein interaction motif. *Plant Cell* 7, 85-103.

Stals, H. and Inzé, D. (2001). When plant cells decide to divide. *Trends in Plant Science* 6, 359-364.

Swank, J. C., Egli, D. B., and Pfeiffer, T. W. (1987). Seed growth characteristics of soybean genotypes differing in duration of seed fill. *Crop Science* 1, 85-89.

Takei, K., Sakakibara, H., and Sugiyama, T. (2001). Identification of genes encoding adenylate isopentenyltransferase, a cytokinin biosynthesis enzyme, in *Arabidopsis thaliana. Journal of Biological Chemistry* 276, 26405-26410.

Till, B. J. et al. (2003). Large-scale discovery of induced point mutations with high-throughput TILLING. *Genome Research* 13, 524-530.

Tiwari, S. B., Hagen, G., and Guilfoyle, T. J. (2003). The roles of auxin response factor domains in auxin-responsive transcription. *Plant Cell* 15, 533-543.

Ulmasov, T., Hagen, G., and Guilfoyle, T. J. (1999a). Dimerization and DNA binding of auxin response factors. *Plant Journal* 19, 309-319.

Ulmasov, T., Hagen, G., and Guilfoyle, T. J. (1999b). Activation and repression of transcription by auxin-response factors. *PNAS USA* 96, 5844-5849.

Vandepoele, K., Raes, J., De Veylder, L., Rouzé, P., Rombauts, S., and Inzé, D. (2002). Genome-wide analysis of core cell cycle genes in *Arabidopsis. Plant Cell* 14, 1-16.

Villanueva, J. M., Broadhvest, J., Hauser, B. A., Meister, R. J., Schnitz, K., and Gasser, C. S. (1999). INNER NO OUTER regulates abaxial-adaxial patterning in *Arabidopsis* ovules. *Genes and Development* 13, 3160-3169.

Vinkenoog, R., Spielman, M., Adams, S., Fischer, R. L., and Dickinson, H. G. (2000). Hypomethylation promotes autonomous endosperm development and rescues post-fertilization lethality in fie mutants. *Plant Cell* 12, 2271-2282.

Wan, L., Xia, Q., Qui, X., and Selvaraj, G. (2002). Early stages of seed development in *Brassica napus*: a seed coat-specific cysteine proteinase associated with programmed cell death of the inner integument. *Plant Journal* 30, 1-10.

Wang, M.-B. and Waterhouse, P. M. (2001). Application of gene silencing in plants. *Current Opinion in Plant Biology* 5, 146-150.

Weber, H., Borisjuk, L., and Wobus, U. (1996). Controlling seed development and seed size in *Vicia faba*: a role for seed coat-associated invertases and carbohydrate state. *Plant Journal* 10, 823-824.

Weber, H., Borisjuk, Ljudmilla, and Wobus, U. (1997). Sugar import and metabolism during seed development. *Trends in Plant Science* 2, 169-174.

Weigel, D., Alvarez, J., Smyth, D. R., Yanofksy, M. F., and Meyerowitz, E. M. (1992). LEAFY controls floral meristem identity in *Arabidopsis. Cell* 69, 843-859.

Weschke, W., Panitz, R., Gubatz, S., Wang, Q., Radchuk, R., Weber, H., and Wobus, U. (2003). The role of invertases and hexose transporters in controlling sugar ratios in maternal and filial tissues of barley caryopses during early development. *Plant Journal* 33, 395-411.

Winn, A. A. (1985). Effects of seed size and microsite on seedling emergence of Prunella vulgaris in four habitats. *Journal of Ecology* 73, 831-840.

Wulff, R. D. (1986). Seed size variation in Desmondium paniculatum II. Effects on seedling growth and physiological performance. *Journal of Ecology* 74, 99-114.

Yamada, T., Ito, M., and Kato, M. (2003). Expression pattern of INNER NO OUTER homologue in *Nymphaea* (water lily family, Nymphaeaceae). *Development Genes and Evolution* 213, 510-513.

Zuber, U. Winzeler, H., Messmer, M. M., Keller, M., Keller, B., Schmid, J. E., and Stamp, P. (1999). Morphological traits associated with lodging resistance of spring wheat (*Triticum aestivum* L.). *Journal of Agronomy and Crop Science* 182, 17-24.

SEQUENCE LISTING

<160> NUMBER OF SEQ ID NOS: 66

<210> SEQ ID NO 1
<211> LENGTH: 8718
<212> TYPE: DNA
<213> ORGANISM: Arabidopsis thaliana

<400> SEQUENCE: 1

```
agccattttg taactgacca ccgagtaatc tgtaatctga gctcttttat taatcggatt      60
gaataaattc gcttggagtc cgtcagtcgt gtccgtgagc gcgtgtctca ctcgcttgag     120
```

```
ctgatgaagt gcgataatga cgtggcatgt tgggatggag accaaagacc agcattttat    180
tttattttat agtaactaat tttaaaaacc aaacaacctg agattaaaat tttaattttt    240
actgtactgt agtaaatttg ggtcctgatt aagattaggc atatttatct catagtttat    300
aacaagtagc agctgaaatt tgtattacta gcttatagta attaaactaa aaactacgtt    360
ccaggtttta aattattgtt taaagaagat ataataatat attaagaaaa tagttaatta    420
aggtaaggag gaaagtaggg tttggtctgt aggttagggt tcaaagaggg aagagattag    480
gagaaaggaa gcatgaaggc atgacccatt tcttcaatta gtgctcctta atctggtgac    540
acgtgtaggc cccacgtgta atcacttcac attgttattt ttcaaaaaat caattagtaa    600
aaacaaaact ttgtccatca tcaaatagta gtagtttttt atgtgtggtt acaatattgt    660
aagaagctct ccccctttta ctatgtaatt caaccccact ctaatttttg aaatatttat    720
gtaaagcttt acccgaaaac aatctatcat gggttggtaa tgacacattt cattaacagt    780
gttagagaat gattccttta atttttctac agtaaaatgt taggtgatct cattgtacta    840
catcggaaaa tactcaaaat tatgtcgtgt aattagata atggacgaat atggttttga    900
aatatttatg gataccacac aagatttctt aactagaaag acaaaaaaat agagcacatt    960
ttgctcgttt tccatcaacc ctattctcc aatttgttca catcatgatc aaaaatacag   1020
tagcaattaa aaaataaaat aacaaatata aatggctata tagatcaacc ctatctagct   1080
attagtatta ctagaaattg acaataaagg aaacattcac gtgtgtgagc atgtactact   1140
ctacacacat gtccacagtt attatatact gagtactagt atacgttgat gttatcaata   1200
ataaaaactc gaaattaagt attattttct tataataatc tatttaaca tatttgctac   1260 tgtactattt agtctatttt cttttgccaa cctttgtatt aaatatttgt actattagtt   1320
tcaattatag gtctatcact atgtatatgt ccgaataatg gtctaaaatt gttaatataa   1380
aatacagatt ttatttcagc taaagatagt tgaaattaca caagaaaata gaagagataa   1440
aaatgatcaa tcagctatgt aagacgtcgt atggatagtt caataattgt ggtaatactt   1500
aaagacatat atcaaaatta tcaacaagcc tcgaacacaa actttacaaa aagcctgtgt   1560
ctactttatg agtgtttgat tattaaattg caaggtcgta gtataaaaat ttcgtaggct   1620
ttcaggacac aagattaaat tcatttatct aaatggtgat ggagtacttt tatttttata   1680
tatcaaaatg gtgatgatat acgaagacca tatatttaga ttattaaaga aaaacgaga   1740 aaagaagaaa gaaaatataa aaaaatggtt tttcttttta acggacaaag attcctacaa   1800
tggttgcttt tagaccacac acaaatgcta cacagtactc ttgggtccca cacctcttag   1860
caagtgcgtt accaacacgt gaatttcctc tccccatttt ctcgtccttt tcctctcaat   1920
attgtatcgt ctcgttttcc ttgtcatatc gcgtgtgacg tgttattggc ttattgctga   1980
acagtcttct ttttttatttt ccatcgttat cctgattttt ttttttttcc aaatttgatt   2040
ttcatggttt gtaattttgc aatagatttt gtgtttcaca gagagatagt ttacgtgttg   2100
ttaaaaataa tttgtgcaaa atagtgtgcg tgtgttaaat attaaacgat atataataat   2160
tagaagaaaa taaaagtttt tgtcgcgatt agttatttga tatttacctt gttctttgt   2220 ttatcgctgc gacaagcacc gacggtataa aatataaaga aaaaagaaa gagagatgaa   2280 ggtgagatga atgaaagagt cgcagcgaca gatctgaaga gataggagaa agggaatttg   2340
agacgctgaa aattccagcg tctacggaat ggccgaatta cagtcgatgc ggcagagatg   2400
aaaaaaatga gaaatgaaag tgaaaagag atgagaactt ttttgggtc gcaggtagct   2460 gacgcagcaa tcaacaaaag aacatggcca acgttttagt agatactact ataaaagaaa   2520
```

```
aaggttgatt taattcattc gtaatttgga cttaattttt ttttaggaac actaattaat    2580
cttatttgcc agctgtatga gtggactaca ataaactctt gtctataaac cagattttct    2640 tccttttaa cgcttccact tacaacaata tatgtaaata tgtaattatg acggggcata    2700
cggaaattta attttgaag cagattcatc ccattagcca gctgtattaa gtggtaatcc    2760
aagagttaat ttagttgttc agcaaatgat tttagataaa atcaactact agtttaaaat    2820
aactatcgaa tgactgttaa ggcttcgtat ttttgttct gccatcagga tatcataaat    2880
atggttgagg ttcgtataat attcgacgat cttttatata tctgagttgt aattgaatta    2940
gagaaaataa aaacagata atgaaacgtc tttgtttttc cataaaaaga aaaacagggt    3000
aaattaaagt acgagagatt cacgagacga aaattcctag aggcgcacga tagccaaaag    3060
accatagaaa atgacatccg aaatatcttt aaaatgctaa aatgcacata ttttctggt    3120 gccacgtagc attttctcc ctctctcgtt ctctctacgt ccacccagac ctgcctgttc    3180
acagcacgac aaagccactt cccaataaaa acacaacacc tttcccattg acgctctctt    3240
tcccaaacac cgttatcctc tttacccaat caaaagttga cgcttgctca cgacttgttg    3300
acgccgttag tcccatctaa aaaagtaaag cagcctttct tacttgctaa tcccctctac    3360
acatttaatt tattttctcc cctaatggat ttttttggc aacttgagta tttattttc    3420 aactcacagt aactgtaaat aaataaaagt attcaactca cagtcaccag taaataaata    3480
ctaccagacc atagtttttt caagaattgt tttggtcaac aattttagga tgacttaaat    3540
tgctatattt ctggggaaat acgacttgga aatgtctgca atttgggtct tttcttcaat    3600
ttatcttctc caatttgttt tttaaaaaat taaatttag aaaaggatat gtcaattttt    3660
tctattgaaa aggctttatt aaaaaataag aaaaagtgga ggaaagaaaa taaaatcgtc    3720
acttgtcttt ggttttgtga ggtcgcagac cctggtcccc cggaaatggt tacaaccggt    3780
aatagccggt atgaaagagg gaatggtaac cggtgaatgc cggttatcca tatgggttag    3840
aagtttaccg cggttgaaat gattgaagct gagttttgac tacctctggt taagcccatt    3900
ggtcgcctca tacccagaaa acaaaagga taggaaagac gaagaaataa aaagagagag    3960
aatgttagag agacaaactc tgagagacaa aacaagagaa aatcgctcgt cgtcggtatt    4020
caagcgtctg tgactccgat aaagcctaga ctagcgagga cggcgagaga gagagagaga    4080
gagctttgga gttgtcgtat ctctaaatcg gaggcaattt gaggtgaaat tggtggtttt    4140
atcgtttgat tctagggttt atcttctctg atagttttat cgagtaatgt caaggagcta    4200
aactagtggt gattgtgttt gttagtgaga taaagacaaa ggaaggaatc aagtggacta    4260
ccgaagcgag ttttgagctt tttcagagac ggatttggag atttcttgtt gatatcgtct    4320
gcttagaggc ttatttggta ccagatgaaa cagatcgag cttcggaagg tatggcgagt    4380
tcggaggttt caatgaaagg taatcgtgga ggagataact tctcctcctc tggttttagt    4440
gaccctaagg agactagaaa tgtctccgtc gccggcgagg ggcaaaaaag taattctacc    4500
cgatccgctg cggctgagcg tgcttgtaag tctccgtttc ttagggtttc ttaagcttgg    4560
ttttggttac agactgactt gatctaattt atcttcttct tcttcgtctt catagtggac    4620
cctgaggctc tcctttacag agagctatgg cacgcttgtg ctggtccgct tgtgacggtt    4680
cctagacaag acgaccgagt cttctatttt cctcaaggac acatcgagca ggtgagatat    4740
ttcatctatg agttccttgct attttttggct aaatctttga gttaacccct ctgtgattcg    4800
tacctgttga gatatttct aatgaacttt gtcggtttcc attgttttat gattaggtgg    4860
```

```
aggcttcgac gaaccaggcg gcagaacaac agatgcctct ctatgatctt ccgtcaaagc    4920
ttctctgtcg agttattaat gtagatttaa aggtaggttt ctttaacttc ttggaaaatt    4980
ttggtttctg tgtcttggat tgtcagctaa caagagtttt gtttatgatt ttacaggcag    5040
aggcagatac agatgaagtt tatgcgcaga ttactcttct tcctgaggct aatgtaagtt    5100
ttgttttctg atttattggt ttgagtgttg tagaggtgat cttattcttc aagatgctga    5160
attctatata ttttttgttc catacagcaa gacgagaatg caattgagaa agaagcgcct    5220
cttcctccac ctccgaggtt ccaggtgcat tcgttctgca aaaccttgac tgcatccgac    5280
acaagtacac atggtggatt ttctgttctt aggcgacatg cggatgaatg tctcccacct    5340
ctggttggtg tttcatttgc gcttctaact atctattcat tggcttattt ttcctgaatt    5400
ttgttctaag attgccttca attcattttt tgtttcttcc ctcaggatat gtctcgacag    5460
cctcccactc aagagttagt tgcaaaggat ttgcatgcaa atgagtggcg attcagacat    5520
atattccggg gtataggaat ctgtaacttt tttatttttct gttttttctcg agtctgtgtg    5580 tcatcaaact tatctggttg ttgatgtttg tgataatgga ccaggtcaac cacggaggca    5640
tttgctacag agtgggtgga gtgtgtttgt tagctccaaa aggctagttg caggcgatgc    5700
gtttatattt ctaaggtttg tggattttag ttcattgttt tctttagctg tatctgttag    5760
tttctataat gtggaatatc ttaatcttct acagggcga gaatggagaa ttaagagttg    5820
gtgtaaggcg tgcgatgcga caacaaggaa acgtgccgtc ttctgttata tctagccata    5880
gcatgcatct tggagtactg gccaccgcat ggcatgccat ttcaacaggg actatgttta    5940
cagtctacta caaacccagg tttgtatttg tattagctca caaacagct ttcagttttt    6000 tgagctcttt gctttgtatg tctctatatg tctgatgctt ggtagtgaat cactctacta    6060
aattttcatg cggtgttgtt ttgtttaata caggacgagc ccatctgagt ttattgttcc    6120
gttcgatcag tatatggagt ctgttaagaa taactactct attggcatga gattcaaaat    6180
gagatttgaa ggcgaagagg ctcctgagca gaggtaaaac ctgtcttctg cttttgaaat    6240
atgttagctc ttgagccttt ttctcttgga ataacgaacc taacaagttg tattgattta    6300
tattaggttt actggcacaa tcgttgggat tgaagagtct gatcctacta ggtggccaaa    6360
atcaaagtgg agatccctca aggtatgacc tagtttctag agaggatcaa gactattgtt    6420 tgaatatat gaatgctgat tgttcaattg tctttcaggt gagatgggat gagacttcta    6480
gtattcctcg acctgataga gtatctccgt ggaaagtaga gccagctctt gctcctcctg    6540 cttttgagtcc tgttccaatg cctaggccta agaggcccag atcaaatata gcaccttcat    6600
ctcctgactc ttcgatgctt accagagaag gtaatgtctt cccccttccac tgtagtacac    6660 atagtagtgc gtctgaaact taattgaact tgtcagtggg agtctaattc attgtacaca    6720
aaacaggtac aactaaggca aacatggacc ctttaccagc aagcggactt tcaagggtct    6780
tgcaaggtca agaatactcg accttgagga cgaaacatac tgagagtgta gagtgtgatg    6840
ctcctgagaa ttctgttgtc tggcaatctt cagcggatga tgataaggtt gacgtggttt    6900
cgggttctag aagatatgga tctgagaact ggatgtcctc agccaggcat gaacctactt    6960
acacagattt gctctccggc tttgggacta acatagatcc atcccatggt cagcggatac    7020 cttttttatga ccattcatca tcaccttcta tgcctgcaaa gagaatcttg agtgattcag    7080
aaggcaagtt cgattatctt gctaaccagt ggcagatgat acactctggt ctctcccctga    7140 agttacatga atctcctaag gtacctgcag caactgatgc gtctctccaa gggcgatgca    7200
atgttaaata cagcgaatat cctgttctta atggtctatc gactgagaat gctggtggta    7260
```

```
actggccaat acgtccacgt gctttgaatt attatgagga agtggtcaat gctcaagcgc    7320
aagctcaggc tagggagcaa gtaacaaaac aacccttcac gatacaagag gagacagcaa    7380
agtcaagaga agggaactgc aggctctttg gcattcctct gaccaacaac atgaatggga    7440
cagactcaac catgtctcag agaaacaact tgaatgatgc tgcggggctt acacagatag    7500
catcaccaaa ggttcaggac ctttcagatc agtcaaaagg gtcaaaatca acaaacgatc    7560
atcgtgaaca gggaagacca ttccagacta ataatcctca tccgaaggat gctcaaacga    7620
aaaccaactc aagtaggagt tgcacaaagg taaattttg caatatgtag cacaaagtgt    7680
atgaggttgt gataaccctt gaatcacttt tcaactaaca catgacacat tgatgtaaag    7740
gttcacaagc agggaattgc acttggccgt tcagtggatc tttcaaagtt ccaaaactat    7800
gaggagttag tcgctgagct ggacaggctg tttgagttca atggagagtt gatggctcct    7860
aagaaagatt ggttgatagt ttacacagat gaagagaatg atatgatgct tgttggtgac    7920
gatccttggc agtaagattt tgcaaatttt ccatcttagt ttatatcgat gttagtgttt    7980
ttcttataac actgacacaa tgatctctct tgcagggagt tttgttgcat ggttcgcaaa    8040
atcttcatat acacgaaaga ggaagtgagg aagatgaacc cggggacttt aagctgtagg    8100
agcgaggaag aagcagttgt tggggaagga tcagatgcaa aggacgccaa gtctgcatca    8160
aatccttcat tgtccagcgc tgggaactct taaacaaaca aaataaccaa caacccttt    8220 gctgcaagcc gaggtatgta aagcttttg agatattagt agactagaga cacagccaaa    8280
agtttatgtc attacattcg actgatgttt gttctgttaa tgcagcagg atgggggtcg    8340 attggtggag actggagagc aaaatgggat gatgggttta agataagata ttaaaaatgc    8400 aattttttgaa gtattttgtt ggccacttag ataattagca tcttccatca cccttattat    8460
ctatctaata ataattaata gatattataa agtaaaacat aaaaaggtta caggtattat    8520
atagtagaat atgaaaagct ctttttataag tagaatatga tggtgtggag ttgtagtcgg    8580
aggctggtat cggttctttt tatggatgta tttttttcct tcttccaaag atctcttgaa    8640 gtcttttttat tgttatatt aatcccaatg tacataagtt ttcaagctct tgcccttttt    8700
taattatctt gtcgattc                                                   8718
```

<210> SEQ ID NO 2
<211> LENGTH: 3384
<212> TYPE: DNA
<213> ORGANISM: Arabidopsis thaliana

<400> SEQUENCE: 2

```
cccattggtc gcctcatacc cagaaaaaca aaggatagg aaagacgaag aaataaaaag      60
agagagaatg ttagagagac aaactctgag agacaaaaca agagaaaatc gctcgtcgtc    120
ggtattcaag cgtctgtgac tccgataaag cctagactag cgaggacggc gagagagaga    180
gagagagagc tttggagttg tcgtatctct aaatcggagg caatttgagt gagataaaga    240
caaaggaagg aatcaagtgg actaccgaag cgagttttga gcttttttcag agacggattt    300 ggagatttct tgttgatatc gtctgcttag aggcttattt ggtaccagat gaaacagatc    360
tgagcttcgg aaggtatggc gagttcggag gtttcaatga aaggtaatcg tggaggagat    420
aacttctcct cctctggttt tagtgaccct aaggagacta gaaatgtctc cgtcgccggc    480 gagggggcaaa aaagtaattc tacccgatcc gctgcggctg agcgtgcttt ggaccctgag    540
gctgctcttt acagagagct atggcacgct tgtgctggtc cgcttgtgac ggttcctaga    600
```

```
caagacgacc gagtcttcta ttttcctcaa ggacacatcg agcaggtgga ggcttcgacg    660
aaccaggcgg cagaacaaca gatgcctctc tatgatcttc cgtcaaagct tctctgtcga    720
gttattaatg tagatttaaa ggcagaggca gatacagatg aagtttatgc gcagattact    780
cttcttcctg aggctaatca agacgagaat gcaattgaga agaagcgcc tcttcctcca     840 cctccgaggt tccaggtgca ttcgttctgc aaaaccttga ctgcatccga cacaagtaca    900
catggtggat tttctgttct taggcgacat gcggatgaat gtctcccacc tctggatatg    960
tctcgacagc ctcccactca agagttagtt gcaaaggatt tgcatgcaaa tgagtggcga   1020
ttcagacata tattccgggg tcaaccacgg aggcatttgc tacagagtgg gtggagtgtg   1080
tttgttagct ccaaaaggct agttgcaggc gatgcgttta tatttctaag gggcgagaat   1140
ggagaattaa gagttggtgt aaggcgtgcg atgcgacaac aaggaaacgt gccgtcttct   1200
gttatatcta gccatagcat gcatcttgga gtactggcca ccgcatggca tgccatttca   1260
acagggacta tgtttacagt ctactacaaa cccaggacga gcccatctga gtttattgtt   1320
ccgttcgatc agtatatgga gtctgttaag aataactact ctattggcat gagattcaaa   1380
atgagatttg aaggcgaaga ggctcctgag cagaggttta ctggcacaat cgttgggatt   1440
gaagagtctg atcctactag gtggccaaaa tcaaagtgga gatccctcaa ggtgagatgg   1500
gatgagactt ctagtattcc tcgacctgat agagtatctc cgtggaaagt agagccagct   1560
cttgctcctc ctgctttgag tcctgttcca atgcctaggc ctaagaggcc cagatcaaat   1620
atagcacctt catctcctga ctcttcgatg cttaccagag aaggtacaac taaggcaaac   1680
atggacccct taccagcaag cggactttca agggtcttgc aaggtcaaga atactcgacc   1740
ttgaggacga aacatactga gagtgtagag tgtgatgctc ctgagaattc tgttgtctgg   1800
caatcttcag cggatgatga taaggttgac gtggtttcgg gttctagaag atatggatct   1860
gagaactgga tgtcctcagc caggcatgaa cctacttaca cagatttgct ctccggcttt   1920
gggactaaca tagatccatc ccatggtcag cggatacctt tttatgacca ttcatcatca   1980
ccttctatgc ctgcaaagag aatcttgagt gattcagaag gcaagttcga ttatcttgct   2040
aaccagtggc agatgataca ctctggtctc tccctgaagt tacatgaatc tcctaaggta   2100
cctgcagcaa ctgatgcgtc tctccaaggg cgatgcaatg ttaaatacag cgaatatcct   2160
gttcttaatg gtctatcgac tgagaatgct ggtggtaact ggccaatacg tccacgtgct   2220
ttgaattatt atgaggaagt ggtcaatgct caagcgcaag ctcaggctag ggagcaagta   2280
acaaaacaac ccttcacgat acaagaggag acagcaaagt caagagaagg gaactgcagg   2340
ctctttggca ttcctctgac caacaacatg aatgggacag actcaaccat gtctcagaga   2400
aacaacttga atgatgctgc ggggcttaca cagatagcat caccaaaggt tcaggacctt   2460
tcagatcagt caaaagggtc aaaatcaaca aacgatcatc gtgaacaggg aagaccattc   2520
cagactaata atcctcatcc gaaggatgct caaacgaaaa ccaactcaag taggagttgc   2580
acaaaggttc acaagcaggg aattgcactt ggccgttcag tggatctttc aaagttccaa   2640
aactatgagg agttagtcgc tgagctggac aggctgtttg agttcaatgg agagttgatg   2700
gctcctaaga aagattggtt gatagtttac acagatgaag agaatgatat gatgcttgtt   2760
ggtgacgatc cttggcagga gttttgttgc atggttcgca aaatcttcat atacacgaaa   2820
gaggaagtga ggaagatgaa cccgggggact ttaagctgta ggagcgagga agaagcagtt   2880
gttggggaag gatcagatgc aaaggacgcc aagtctgcat caaatccttc attgtccagc   2940
gctgggaact cttaaacaaa caaaataacc aacaacccct tgctgcaag ccgaggatgg    3000
```

```
gggtcgattg gtggagactg gagagcaaaa tgggatgatg ggtttaagat aagatattaa   3060
aaatgcaatt tttgaagtat tttgttggcc acttagataa ttagcatctt ccatcaccct   3120
tattatctat ctaataataa ttaatagata ttataaagta aaacataaaa aggttacagg   3180
tattatatag tagaatatga aaagctcttt tataagtaga atatgatggt gtggagttgt   3240
agtcggaggc tggtatcggt tcttttatg gatgtatttt tttccttctt ccaaagatct   3300
cttgaagtct ttttattgtt tatattaatc ccaatgtaca taagttttca agctcttgcc   3360
cttttttaat tatcttgtcg attc                                         3384
```

<210> SEQ ID NO 3
<211> LENGTH: 859
<212> TYPE: PRT
<213> ORGANISM: Arabidopsis thaliana

<400> SEQUENCE: 3

```
Met Ala Ser Ser Glu Val Ser Met Lys Gly Asn Arg Gly Gly Asp Asn
1               5                   10                  15

Phe Ser Ser Ser Gly Phe Ser Asp Pro Lys Glu Thr Arg Asn Val Ser
            20                  25                  30

Val Ala Gly Glu Gly Gln Lys Ser Asn Ser Thr Arg Ser Ala Ala Ala
        35                  40                  45

Glu Arg Ala Leu Asp Pro Glu Ala Ala Leu Tyr Arg Glu Leu Trp His
    50                  55                  60

Ala Cys Ala Gly Pro Leu Val Thr Val Pro Arg Gln Asp Asp Arg Val
65                  70                  75                  80

Phe Tyr Phe Pro Gln Gly His Ile Glu Gln Val Glu Ala Ser Thr Asn
                85                  90                  95

Gln Ala Ala Glu Gln Gln Met Pro Leu Tyr Asp Leu Pro Ser Lys Leu
            100                 105                 110

Leu Cys Arg Val Ile Asn Val Asp Leu Lys Ala Glu Ala Asp Thr Asp
        115                 120                 125

Glu Val Tyr Ala Gln Ile Thr Leu Leu Pro Glu Ala Asn Gln Asp Glu
    130                 135                 140

Asn Ala Ile Glu Lys Glu Ala Pro Leu Pro Pro Pro Arg Phe Gln
145                 150                 155                 160

Val His Ser Phe Cys Lys Thr Leu Thr Ala Ser Asp Thr Ser Thr His
                165                 170                 175

Gly Gly Phe Ser Val Leu Arg Arg His Ala Asp Glu Cys Leu Pro Pro
            180                 185                 190

Leu Asp Met Ser Arg Gln Pro Pro Thr Gln Glu Leu Val Ala Lys Asp
        195                 200                 205

Leu His Ala Asn Glu Trp Arg Phe Arg His Ile Phe Arg Gly Gln Pro
    210                 215                 220

Arg Arg His Leu Leu Gln Ser Gly Trp Ser Val Phe Val Ser Ser Lys
225                 230                 235                 240

Arg Leu Val Ala Gly Asp Ala Phe Ile Phe Leu Arg Gly Glu Asn Gly
                245                 250                 255

Glu Leu Arg Val Gly Val Arg Arg Ala Met Arg Gln Gln Gly Asn Val
            260                 265                 270

Pro Ser Ser Val Ile Ser Ser His Ser Met His Leu Gly Val Leu Ala
        275                 280                 285

Thr Ala Trp His Ala Ile Ser Thr Gly Thr Met Phe Thr Val Tyr Tyr
    290                 295                 300
```

```
Lys Pro Arg Thr Ser Pro Ser Glu Phe Ile Val Pro Phe Asp Gln Tyr
305                 310                 315                 320

Met Glu Ser Val Lys Asn Asn Tyr Ser Ile Gly Met Arg Phe Lys Met
            325                 330                 335

Arg Phe Glu Gly Glu Glu Ala Pro Glu Gln Arg Phe Thr Gly Thr Ile
                340                 345                 350

Val Gly Ile Glu Glu Ser Asp Pro Thr Arg Trp Pro Lys Ser Lys Trp
            355                 360                 365

Arg Ser Leu Lys Val Arg Trp Asp Glu Thr Ser Ser Ile Pro Arg Pro
370                 375                 380

Asp Arg Val Ser Pro Trp Lys Val Glu Pro Ala Leu Ala Pro Pro Ala
385                 390                 395                 400

Leu Ser Pro Val Pro Met Pro Arg Pro Lys Arg Pro Arg Ser Asn Ile
                405                 410                 415

Ala Pro Ser Ser Pro Asp Ser Ser Met Leu Thr Arg Glu Gly Thr Thr
                420                 425                 430

Lys Ala Asn Met Asp Pro Leu Pro Ala Ser Gly Leu Ser Arg Val Leu
            435                 440                 445

Gln Gly Gln Glu Tyr Ser Thr Leu Arg Thr Lys His Thr Glu Ser Val
450                 455                 460

Glu Cys Asp Ala Pro Glu Asn Ser Val Val Trp Gln Ser Ser Ala Asp
465                 470                 475                 480

Asp Asp Lys Val Asp Val Ser Gly Ser Arg Arg Tyr Gly Ser Glu
                485                 490                 495

Asn Trp Met Ser Ser Ala Arg His Glu Pro Thr Tyr Thr Asp Leu Leu
            500                 505                 510

Ser Gly Phe Gly Thr Asn Ile Asp Pro Ser His Gly Gln Arg Ile Pro
            515                 520                 525

Phe Tyr Asp His Ser Ser Pro Ser Met Pro Ala Lys Arg Ile Leu
530                 535                 540

Ser Asp Ser Glu Gly Lys Phe Asp Tyr Leu Ala Asn Gln Trp Gln Met
545                 550                 555                 560

Ile His Ser Gly Leu Ser Leu Lys Leu His Glu Ser Pro Lys Val Pro
                565                 570                 575

Ala Ala Thr Asp Ala Ser Leu Gln Gly Arg Cys Asn Val Lys Tyr Ser
                580                 585                 590

Glu Tyr Pro Val Leu Asn Gly Leu Ser Thr Glu Asn Ala Gly Gly Asn
            595                 600                 605

Trp Pro Ile Arg Pro Arg Ala Leu Asn Tyr Tyr Glu Val Val Asn
            610                 615                 620

Ala Gln Ala Gln Ala Gln Ala Arg Glu Gln Val Thr Lys Gln Pro Phe
625                 630                 635                 640

Thr Ile Gln Glu Glu Thr Ala Lys Ser Arg Glu Gly Asn Cys Arg Leu
                645                 650                 655

Phe Gly Ile Pro Leu Thr Asn Asn Met Asn Gly Thr Asp Ser Thr Met
                660                 665                 670

Ser Gln Arg Asn Asn Leu Asn Asp Ala Ala Gly Leu Thr Gln Ile Ala
            675                 680                 685

Ser Pro Lys Val Gln Asp Leu Ser Asp Gln Ser Lys Gly Ser Lys Ser
            690                 695                 700

Thr Asn Asp His Arg Glu Gln Gly Arg Pro Phe Gln Thr Asn Asn Pro
705                 710                 715                 720
```

His Pro Lys Asp Ala Gln Thr Lys Thr Asn Ser Ser Arg Ser Cys Thr
               725                 730                 735

Lys Val His Lys Gln Gly Ile Ala Leu Gly Arg Ser Val Asp Leu Ser
           740                 745                 750

Lys Phe Gln Asn Tyr Glu Glu Leu Val Ala Glu Leu Asp Arg Leu Phe
       755                 760                 765

Glu Phe Asn Gly Glu Leu Met Ala Pro Lys Lys Asp Trp Leu Ile Val
   770                 775                 780

Tyr Thr Asp Glu Glu Asn Asp Met Met Leu Val Gly Asp Pro Trp
785                 790                 795                 800

Gln Glu Phe Cys Cys Met Val Arg Lys Ile Phe Ile Tyr Thr Lys Glu
               805                 810                 815

Glu Val Arg Lys Met Asn Pro Gly Thr Leu Ser Cys Arg Ser Glu Glu
           820                 825                 830

Glu Ala Val Val Gly Glu Gly Ser Asp Ala Lys Asp Ala Lys Ser Ala
       835                 840                 845

Ser Asn Pro Ser Leu Ser Ser Ala Gly Asn Ser
   850                 855

<210> SEQ ID NO 4
<211> LENGTH: 8718
<212> TYPE: DNA
<213> ORGANISM: Arabidopsis thaliana

<400> SEQUENCE: 4
agccattttg taactgacca ccgagtaatc tgtaatctga gctctttat taatcggatt         60 gaataaattc gcttggagtc cgtcagtcgt gtccgtgagc gcgtgtctca ctcgcttgag       120
ctgatgaagt gcgataatga cgtggcatgt tgggatggag accaaagacc agcatttat        180 tttattttat agtaactaat tttaaaaacc aaacaacctg agattaaaat tttaattttt       240
actgtactgt agtaaatttg ggtcctgatt aagattaggc atatttatct catagtttat       300
aacaagtagc agctgaaatt tgtattacta gcttatagta attaaactaa aaactacgtt       360
ccaggtttta aattattgtt taagaagat ataataatat attaagaaaa tagttaatta       420
aggtaaggag gaaagtaggg tttggtctgt aggttagggt tcaaagaggg aagagattag       480
gagaaaggaa gcatgaaggc atgacccatt tcttcaatta gtgctcctta atctggtgac       540
acgtgtaggt cccacgtgta atcacttcac attgttattt ttcaaaaaat caattagtaa       600
aaacaaaact tgtccatca tcaaatagta gtagtttttt atgtgtggtt acaatattgt        660
aagaagctct ccccctttta ctatgtaatt caacccccact ctaattttta aaatatttat     720
gtaaagcttt acccgaaaac aatctatcat gggttggtaa tgacacattt cattaacagt      780
gttagagaat gattccttta attttctac agtaaaatgt taggtgatct cattgtacta       840
catcggaaaa tactcaaaat tatgtcgtgt aatttagata atggacgaat atggttttga      900
aatatttatg gataccccaac aagatttctt aactagaaag acaaaaaaat agagcacatt     960
ttgctcgttt tccatcaacc ctatttctcc aatttgttca catcatgatc aaaaatacag     1020
tagcaattaa aaataaaat aacaaatata aatggctata tagatcaacc ctatctagct      1080
attagtatta ctagaaattg acaataaagg aaacattcac gtgtgtgagc atgtactact     1140
ctacacacat gtccacagtt attatatact gagtactagt atacgttgat gttatcaata     1200
ataaaaactc gaaattaagt attatttct tataataatc tatttaacca tatttgctac      1260
tgtactattt agtctatttt cttttgccaa cctttgtatt aaatatttgt actattagtt     1320

```
tcaattatag gtctatcact atgtatatgt ccgaataatg gtctaaaatt gttaatataa    1380
aatacagatt ttatttcagc taaagatagt tgaaattaca caagaaaata gaagagataa    1440
aaatgatcaa tcagctatgt aagacgtcgt atggatagtt caataattgt ggtaatactt    1500
aaagacatat atcaaaatta tcaacaagcc tcgaacacaa actttacaaa aagcctgtgt    1560
ctactttatg agtgtttgat tattaaattg caaggtcgta gtataaaaat ttcgtaggct    1620
ttcaggacac aagattaaat tcatttatct aaatggtgat ggagtacttt tattttata    1680 tatcaaaatg gtgatgatat acgaagacca tatatttaga ttattaaaga aaaaacgaga    1740
aaagaagaaa gaaatataaa aaaaatggtt tttcttttta acggacaaag attcctacaa    1800
tggttgcttt tagaccacac acaaatgcta cacagtactc ttgggtccca cacctcttag    1860
caagtgcgtt accaacacgt gaatttcctc tccccatttt ctcgtccttt tcctctcaat    1920
attgtatcgt ctcgttttcc ttgtcatatc gcgtgtgacg tgttattggc ttattgctga    1980
acagtcttct ttttatttt ccatcgttat cctgattttt tttttttcc aaatttgatt    2040 ttcatggttt gtaattttgc aatagatttt gtgtttcaca gagagatagt ttacgtgttg    2100
ttaaaaataa tttgtgcaaa atagtgtgcg tgtgttaaat attaaacgat atataataat    2160
tagaagaaaa taaaaagttt tgtcgcgatt agttatttga tatttacctt gttcttttgt    2220
ttatcgctgc gacaagcacc gacggtataa aatataaaga aaaaagaaa gagagatgaa    2280 ggtgagatga atgaaagagt cgcagcgaca gatctgaaga gataggagaa agggaatttg    2340
agacgctgaa aattccagcg tctacggaat ggccgaatta cagtcgatgc ggcagagatg    2400
aaaaaaatga gaaatgaaag tgaaaagag atgagaactt ttttgggtc gcaggtagct    2460 gacgcagcaa tcaacaaaag aacatggcca acgttttagt agatactact ataaagaaa    2520 aaggttgatt taattcattc gtaatttgga cttaattttt ttttaggaac actaattaat    2580
cttatttgcc agctgtatga gtggactaca ataaactctt gtctataaac cagattttct    2640 tccttttttaa cgcttccact tacaacaata tatgtaaata tgtaattatg acggggcata    2700
cggaaattta attttgaag cagattcatc ccattagcca gctgtattaa gtggtaatcc    2760
aagagttaat ttagttgttc agcaaatgat tttagataaa atcaactact agtttaaaat    2820
aactatcgaa tgactgttaa ggcttcgtat tttttgttct gccatcagga tatcataaat    2880
atggttgagg ttcgtataat attcgacgat ctttttatata tctgagttgt aattgaatta    2940
gagaaaataa aaacagata atgaaacgtc tttgtttttc cataaaaaga aaaacagggt    3000
aaattaaagt acgagagatt cacgagacga aaattcctag aggcgcacga tagccaaaag    3060
accatagaaa atgacatccg aaatatcttt aaaatgctaa aatgcacata tttttctggt    3120
gccacgtagc attttctcc ctctctcgtt ctctctacgt ccacccagac ctgcctgttc    3180
acagcacgac aaagccactt cccaataaaa acacaacacc tttcccattg acgctctctt    3240
tcccaaacac cgttatcctc tttacccaat caaaagttga cgcttgctca cgacttgttg    3300
acgccgttag tcccatctaa aaaagtaaag cagcctttct tacttgctaa tcccctctac    3360
acatttaatt tattttctcc cctaatggat ttttttggc aacttgagta tttattttc    3420 aactcacagt aactgtaaat aaataaaagt attcaactca cagtcaccag taaataaata    3480
ctaccagacc atagttttt caagaattgt tttggtcaac aattttagga tgacttaaat    3540
tgctatattt ctggggaaat acgacttgga aatgtctgca atttgggtct tttcttcaat    3600
ttatcttctc caatttgttt tttaaaaaat taaattttag aaaaggatat gtcaattttt    3660
tctattgaaa aggctttatt aaaaaataag aaaaagtgga ggaaagaaaa taaaatcgtc    3720
```

```
acttgtcttt ggttttgtga ggtcgcagac cctggtcccc cggaaatggt tacaaccggt    3780
aatagccggt atgaaagagg gaatggtaac cggtgaatgc cggttatcca tatgggttag    3840
aagtttaccg cggttgaaat gattgaagct gagttttgac tacctctggt taagcccatt    3900
ggtcgcctca tacccagaaa aacaaaagga taggaaagac gaagaaataa aaagagagag    3960
aatgttagag agacaaactc tgagagacaa aacaagagaa aatcgctcgt cgtcggtatt    4020
caagcgtctg tgactccgat aaagcctaga ctagcgagga cggcgagaga gagagagaga    4080
gagctttgga gttgtcgtat ctctaaatcg gaggcaattt gaggtgaaat tggtggtttt    4140
atcgtttgat tctagggttt atcttctctg atagttttat cgagtaatgt caaggagcta    4200
aactagtggt gattgtgttt gttagtgaga taaagacaaa ggaaggaatc aagtggacta    4260
ccgaagcgag ttttgagctt tttcagagac ggatttggag atttcttgtt gatatcgtct    4320
gcttagaggc ttatttggta ccagatgaaa cagatctgag cttcggaagg tatggcgagt    4380
tcggaggttt caatgaaagg taatcgtgga ggagataact tctcctcctc tggttttagt    4440
gaccctaagg agactagaaa tgtctccgtc gccggcgagg ggcaaaaaag taattctacc    4500
cgatccgctg cggctgagcg tgcttgtaag tctccgtttc ttagggtttc ttaagcttgg    4560
ttttggttac agactgactt gatctaattt atcttcttct tcttcgtctt catagtggac    4620
cctgaggctc tctttacag agagctatgg cacgcttgtg ctggtccgct tgtgacggtt    4680
cctagacaag acgaccgagt cttctatttt cctcaaggac acatcgagca ggtgagatat    4740
ttcatctatg agttcttgct attttttggct aaatctttga gttaacccct ctgtgattcg    4800
tacctgttga gatattttct aatgaacttt gtcggtttcc attgttttat gattaggtgg    4860
aggcttcgac gaaccaggcg gcagaacaac agatgcctct ctatgatctt ccgtcaaagc    4920
ttctctgtcg agttattaat gtagatttaa aggtaggttt ctttaacttc ttggaaaatt    4980
ttggtttctg tgtcttggat tgtcagctaa caagagtttt gtttatgatt ttacaagcag    5040
aggcagatac agatgaagtt tatgcgcaga ttactcttct tcctgaggct aatgtaagtt    5100
ttgttttctg atttattggt ttgagtgttg tagaggtgat cttattcttc aagatgctga    5160
attctatata ttttttgttc catacagcaa gacgagaatg caattgagaa agaagcgcct    5220
cttcctccac ctccgaggtt ccaggtgcat tcgttctgca aaaccttgac tgcatccgac    5280
acaagtacac atggtggatt ttctgttctt aggcgacatg cggatgaatg tctcccacct    5340
ctggttggtg tttcatttgc gcttctaact atctattcat tggcttattt ttcctgaatt    5400
ttgttctaag attgccttca attcattttt tgtttcttcc ctcaggatat gtctcgacag    5460
cctcccactc aagagttagt tgcaaaggat ttgcatgcaa atgagtggcg attcagacat    5520
atattccggg gtataggaat ctgtaacttt tttattttct gttttttctcg agtctgtgtg    5580 tcatcaaact tatctggttg ttgatgtttg tgataatgga ccaggtcaac cacggaggca    5640
tttgctacag agtgggtgga gtgtgttgt tagctccaaa aggctagttg caggcgatgc    5700
gtttatattt ctaaggtttg tggattttag ttcattgttt tctttagctg tatctgttag    5760
tttctataat gtggaatatc ttaatcttct acaggggcga gaatggagaa ttaagagttg    5820
gtgtaaggcg tgcgatgcga caacaaggaa acgtgccgtc ttctgttata tctagccata    5880
gcatgcatct tggagtactg gccaccgcat ggcatgccat ttcaacaggg actatgttta    5940
cagtctacta caaacccagg tttgtatttg tattagctca caaaacagct ttcagttttt    6000
tgagctcttt gctttgtatg tctctatatg tctgatgctt ggtagtgaat cactctacta    6060
```

```
aattttcatg cggtgttgtt ttgtttaata caggacgagc ccatctgagt ttattgttcc    6120
gttcgatcag tatatggagt ctgttaagaa taactactct attggcatga gattcaaaat    6180
gagatttgaa ggcgaagagg ctcctgagca gaggtaaaac ctgtcttctg cttttgaaat    6240
atgttagctc ttgagccttt ttctcttgga ataacgaacc taacaagttg tattgattta    6300
tattaggttt actggcacaa tcgttgggat tgaagagtct gatcctacta ggtggccaaa    6360
atcaaagtgg agatccctca aggtatgacc tagtttctag agaggatcaa gactattgtt    6420
tgaatataat gaatgctgat tgttcaattg tctttcaggt gagatgggat gagacttcta    6480
gtattcctcg acctgataga gtatctccgt ggaaagtaga gccagctctt gctcctcctg    6540
ctttgagtcc tgttccaatg cctaggccta agaggcccag atcaaatata gcaccttcat    6600
ctcctgactc ttcgatgctt accagagaag gtaatgtctt cccttccac tgtagtacac     6660 atagtagtgc gtctgaaact taattgaact tgtcagtggg agtctaattc attgtacaca    6720
aaacaggtac aactaaggca acatggaccc ctttaccagc aagcggactt tcaagggtct    6780
tgcaaggtca agaatactcg accttgagga cgaaacatac tgagagtgta gagtgtgatg    6840
ctcctgagaa ttctgttgtc tggcaatctt cagcggatga tgataaggtt gacgtggttt    6900
cgggttctag aagatatgga tctgagaact ggatgtcctc agccaggcat gaacctactt    6960
acacagattt gctctccggc tttgggacta acatagatcc atcccatggt cagcggatac    7020 cttttatga ccattcatca tcaccttcta tgcctgcaaa gagaatcttg agtgattcag     7080
aaggcaagtt cgattatctt gctaaccagt ggcagatgat acactctggt ctctccctga    7140
agttacatga atctcctaag gtacctgcag caactgatgc gtctctccaa gggcgatgca    7200
atgttaaata cagcgaatat cctgttctta atggtctatc gactgagaat gctggtggta    7260
actggccaat acgtccacgt gctttgaatt attatgagga agtggtcaat gctcaagcgc    7320
aagctcaggc tagggagcaa gtaacaaaac aacccttcac gatacaagag gagacagcaa    7380
agtcaagaga agggaactgc aggctctttg gcattcctct gaccaacaac atgaatggga    7440
cagactcaac catgtctcag agaaacaact tgaatgatgc tgcggggctt acacagatag    7500
catcaccaaa ggttcaggac ctttcagatc agtcaaaagg gtcaaaatca acaaacgatc    7560
atcgtgaaca gggaagacca ttccagacta ataatcctca tccgaaggat gctcaaacga    7620
aaaccaactc aagtaggagt tgcacaaagg taaattttg caatatgtag cacaaagtgt     7680
atgaggttgt gataacccctt gaatcacttt tcaactaaca catgacacat tgatgtaaag   7740
gttcacaagc agggaattgc acttggccgt tcagtggatc tttcaaagtt ccaaaactat    7800
gaggagttag tcgctgagct ggacaggctg tttgagttca atggagagtt gatggctcct    7860
aagaaagatt ggttgatagt ttacacagat gaagagaatg atatgatgct tgttggtgac    7920
gatccttggc agtaagattt tgcaaatttt ccatcttagt ttatatcgat gttagtgttt    7980
ttcttataac actgacacaa tgatctctct tgcagggagt tttgttgcat ggttcgcaaa    8040
atcttcatat acacgaaaga ggaagtgagg aagatgaacc cggggacttt aagctgtagg    8100
agcgaggaag aagcagttgt tggggaagga tcagatgcaa aggacgccaa gtctgcatca    8160
aatccttcat tgtccagcgc tgggaactct taaacaaaca aataaccaa caacccttt      8220 gctgcaagcc gaggtatgta aaagcttttg agatattagt agactagaga cacagccaaa    8280
agtttatgtc attacattcg actgatgttt gttctgttaa tgacagcagg atggggggtcg   8340 attggtggag actggagagc aaaatgggat gatgggttta agataagata ttaaaaatgc    8400 aattttttgaa gtattttgtt ggccacttag ataattagca tcttccatca cccttattat   8460
```

```
ctatctaata ataattaata gatattataa agtaaaacat aaaaaggtta caggtattat    8520
atagtagaat atgaaaagct cttttataag tagaatatga tggtgtggag ttgtagtcgg    8580
aggctggtat cggttctttt tatggatgta ttttttttcct tcttccaaag atctcttgaa   8640 gtcttttttat tgtttatatt aatcccaatg tacataagtt ttcaagctct tgcccttttt   8700
taattatctt gtcgattc                                                  8718

<210> SEQ ID NO 5
<211> LENGTH: 2576
<212> TYPE: DNA
<213> ORGANISM: Arabidopsis thaliana

<400> SEQUENCE: 5
atggcgagtt cggaggtttc aatgaaaggt aatcgtggag gagataactt ctcctcctct      60
ggttttagtg accctaagga gactagaaat gtctccgtcg ccggcgaggg gcaaaaaagt     120
aattctaccc gatccgctgc ggctgagcgt gctttggacc ctgaggctgc tctttacaga     180
gagctatggc acgcttgtgc tggtccgctt gtgacggttc ctagacaaga cgaccgagtc     240
ttctattttc ctcaaggaca catcgagcag gtggaggctt cgacgaacca ggcggcagaa     300
caacagatgc ctctctatga tcttccgtca aagcttctct gtcgagttat taatgtagat     360
ttaaagaggc agatacagat gaagtttatg cgcagattac tcttcttcct gaggctaatc     420
aagacgagaa tgcaattgag aaagaagcgc ctcttcctcc acctccgagg ttccaggtgc     480
attcgttctg caaaaccttg actgcatccg acacaagtac acatggtgga ttttctgttc     540
ttaggcgaca tgcggatgaa tgtctcccac ctctggatat gtctcgacag cctcccactc     600
aagagttagt tgcaaaggat ttgcatgcaa atgagtggcg attcagacat atattccggg     660
gtcaaccacg gaggcatttg ctacagagtg ggtggagtgt gtttgttagc tccaaaaggc     720
tagttgcagg cgatgcgttt atatttctaa ggggcgagaa tggagaatta agagttggtg     780
taaggcgtgc gatgcgacaa caaggaaacg tgccgtcttc tgttatatct agccatagca     840
tgcatcttgg agtactggcc accgcatggc atgccatttc aacagggact atgtttacag     900
tctactacaa acccaggacg agcccatctg agtttattgt tccgttcgat cagtatatgg     960
agtctgttaa gaataactac tctattggca tgagattcaa aatgagattt gaaggcgaag    1020
aggctcctga gcagaggttt actggcacaa tcgttgggat tgaagagtct gatcctacta    1080
ggtggccaaa atcaaagtgg agatccctca aggtgagatg ggatgagact tctagtattc    1140
ctcgacctga tagagtatct ccgtggaaag tagagccagc tcttgctcct cctgctttga    1200
gtcctgttcc aatgcctagg cctaagaggc ccagatcaaa tatagcacct tcatctcctg    1260
actcttcgat gcttaccaga gaaggtacaa ctaaggcaaa catggaccct ttaccagcaa    1320
gcggactttc aagggtcttg caaggtcaag aatactcgac cttgaggacg aaacatactg    1380
agagtgtaga gtgtgatgct cctgagaatt ctgttgtctg caatcttca gcggatgatg    1440 ataaggttga cgtggtttcg ggttctagaa gatatggatc tgagaactgg atgtcctcag    1500
ccaggcatga acctacttac acagatttgc tctccggctt tgggactaac atagatccat    1560
cccatggtca gcggatacct ttttatgacc attcatcatc accttctatg cctgcaaaga    1620
gaatcttgag tgattcagaa ggcaagttcg attatcttgc taaccagtgg cagatgatac    1680
actctggtct ctcccctgaag ttacatgaat ctcctaaggt acctgcagca actgatgcgt    1740
ctctccaagg gcgatgcaat gttaaataca gcgaatatcc tgttcttaat ggtctatcga    1800
```

| | | |
|---|---|---|
| ctgagaatgc tggtggtaac tggccaatac gtccacgtgc tttgaattat tatgaggaag | 1860 |
| tggtcaatgc tcaagcgcaa gctcaggcta gggagcaagt aacaaaacaa cccttcacga | 1920 |
| tacaagagga gacagcaaag tcaagagaag ggaactgcag gctctttggc attcctctga | 1980 |
| ccaacaacat gaatgggaca gactcaacca tgtctcagag aaacaacttg aatgatgctg | 2040 |
| cggggcttac acagatagca tcaccaaagg ttcaggacct ttcagatcag tcaaaagggt | 2100 |
| caaaatcaac aaacgatcat cgtgaacagg gaagaccatt ccagactaat aatcctcatc | 2160 |
| cgaaggatgc tcaaacgaaa accaactcaa gtaggagttg cacaaaggtt cacaagcagg | 2220 |
| gaattgcact tggccgttca gtggatcttt caaagttcca aaactatgag gagttagtcg | 2280 |
| ctgagctgga caggctgttt gagttcaatg gagagttgat ggctcctaag aaagattggt | 2340 |
| tgatagttta cacagatgaa gagaatgata tgatgcttgt tggtgacgat ccttggcagg | 2400 |
| agttttgttg catggttcgc aaaatcttca tatacacgaa agaggaagtg aggaagatga | 2460 |
| acccggggac tttaagctgt aggagcgagg aagaagcagt tgttggggaa ggatcagatg | 2520 |
| caaaggacgc caagtctgca tcaaatcctt cattgtccag cgctgggaac tcttaa | 2576 |

<210> SEQ ID NO 6
<211> LENGTH: 166
<212> TYPE: PRT
<213> ORGANISM: Arabidopsis thaliana

<400> SEQUENCE: 6

```
Met Ala Ser Ser Glu Val Ser Met Lys Gly Asn Arg Gly Gly Asp Asn
1               5                   10                  15

Phe Ser Ser Ser Gly Phe Ser Asp Pro Lys Glu Thr Arg Asn Val Ser
            20                  25                  30

Val Ala Gly Glu Gly Gln Lys Ser Asn Ser Thr Arg Ser Ala Ala Ala
        35                  40                  45

Glu Arg Ala Leu Asp Pro Glu Ala Ala Leu Tyr Arg Glu Leu Trp His
    50                  55                  60

Ala Cys Ala Gly Pro Leu Val Thr Val Pro Arg Gln Asp Asp Arg Val
65                  70                  75                  80

Phe Tyr Phe Pro Gln Gly His Ile Glu Gln Val Glu Ala Ser Thr Asn
                85                  90                  95

Gln Ala Ala Glu Gln Gln Met Pro Leu Tyr Asp Leu Pro Ser Lys Leu
            100                 105                 110

Leu Cys Arg Val Ile Asn Val Asp Leu Lys Arg Gln Ile Gln Met Lys
        115                 120                 125

Phe Met Arg Arg Leu Leu Phe Leu Arg Leu Ile Lys Thr Arg Met
    130                 135                 140

Gln Leu Arg Lys Lys Arg Leu Phe Leu His Leu Arg Gly Ser Arg Cys
145                 150                 155                 160

Ile Arg Ser Ala Lys Pro
                165
```

<210> SEQ ID NO 7
<211> LENGTH: 19
<212> TYPE: DNA
<213> ORGANISM: Artificial Sequence
<220> FEATURE:
<223> OTHER INFORMATION: engineered primer sequence

<400> SEQUENCE: 7
atggcgagtt cggaggttt                                            19

<210> SEQ ID NO 8
<211> LENGTH: 21
<212> TYPE: DNA
<213> ORGANISM: Artificial Sequence
<220> FEATURE:
<223> OTHER INFORMATION: engineered primer sequence

<400> SEQUENCE: 8
tggacaatga aggatttgat g                                              21

<210> SEQ ID NO 9
<211> LENGTH: 2547
<212> TYPE: DNA
<213> ORGANISM: Brassica napus

<400> SEQUENCE: 9

| | | |
|---|---|---|
| atggcgagtt cggaggtttc tatgaaagga aatcgtggac gaggagaaaa cttctcctcc | 60 |
| gctggttaca gtgacccgac ggtcgccggc gaggcgcaga aaactcagtc taaccgatct | 120 |
| gtggctgcag agcgcgttgt cgacccggaa gctgctctct accgtgagct gtggcacgct | 180 |
| tgtgctggtc ctctcgtgac agtccctcga caagatgacc gagtcttcta cttccctcag | 240 |
| gggcacatcg agcaggtgga agcatcgaca aatcaagctg cagaacagca gatgcctctc | 300 |
| tatgatcttc cttcgaagat cctttgtcgt gtcattaatg ttgatttaaa ggcagaggca | 360 |
| gacaccgacg aagtttatgc gcagattact cttcttccgg agcctgttca agacgagaat | 420 |
| tcaatagaga aagaggcgcc tcctcctccg cccccaaggt tccaagtgca ctccttctgc | 480 |
| aaaaccttga ctgcatcgga cacaagtaca catggtggat tttctgtgct taggcggcat | 540 |
| gcggatgaat gtctcccacc tctggatatg tcacgtcaac ctcctactca ggagttagtt | 600 |
| gcaaaagatc tgcatgcaag cgagtggcgt ttccgacata ttttccgagg tcaaccacga | 660 |
| aggcatttgc ttcagagtgg atggagcgtg tttgttagct ccaagaggct ggtcgcaggc | 720 |
| gatgctttta tatttctaag gggcgagaat ggagaattac gtgtgggtgt aaggcgtgca | 780 |
| atgcggcagc aaggaaatgt gccatcctct gttatatcaa gccacagcat gcatctcgga | 840 |
| gtattggcca ctgcctggca cgctatttca actggaacca tgtttacagt ctactataaa | 900 |
| ccgaggacta gtccttcaga gtttattgtt ccgtttgatc agtatacgga gtccgtgaag | 960 |
| attaactact ccataggcat gagatttaaa atgagatttg aaggcgaaga ggctcccgag | 1020 |
| cagaggttta ctggcacaat cgttgggatt gaagactctg accccacgag gtgggcaaaa | 1080 |
| tcaaaatgga gatccctcaa ggtacggtgg gatgagacca ctagtattcc tcgccctgat | 1140 |
| agagtatccc cgtggaagat agagccagct ctttctcctc ctgctttgag ccctgtacca | 1200 |
| atgcctaggc ctaagaggcc cagatctaat ctagcttctt caactccgga ctcttccatg | 1260 |
| cgcataaggg aaggctcatc taaggcaaac atggacccctt accggcaag tggactatca | 1320 |
| agggtcttgc aaggtcaaga atacccgacc ttgagaacga acatgttga gagtgtagaa | 1380 |
| tgcgatgctc ctgaaaattc ggttgtgtgg caatcgtcaa ctgatgatga caaggttgat | 1440 |
| gtgatttcag cttctaggag atatgagaac tggatatcct caggtaggca tggacctact | 1500 |
| tgcacggatt tgctttctgg ctttgggaca aacatagaac cacctcacgg tcatcagata | 1560 |
| ccttttatg accgtttatc atcaccacct tctgtggctg caaggaaaat cctcagcgac | 1620 |
| caggatggca gtttgaata tcttgctaac cagtggatga tgcactcagg cctttccctg | 1680 |
| aagttacatg aatctcctaa agtccctgcc gcatctgatg cctctttcca agggataggc | 1740 |
| aatcccaatt acggcgaata tgctttgcct cgtgcagtga cgactgagaa tgctgctggc | 1800 |

```
aactggccaa tacgtccacg tgctctaaat tattttgaag aagcggttca tgctcaggct    1860
agagagcatg tgacaaaacg tcctgcggtc gtacaagagg aggcagcaaa gccaagagac    1920
gggaactgca ggcttttgg cattcctctg gtgaacaacg tgaatgggac agatacaact    1980
ttgtctcaga gaaacaattt gaatgaccct gcggggccta cgcagatggc atcaccaaag    2040
gttcaggatc tttctgacca gtccaaaggg tcaaaatcga caaatgatca tcgtgagcaa    2100
ggacgaccat tcccggttag taaacccat ccgaaagacg ttcaaaccaa acaaactca    2160 tgtaggagct gcacgaaggt tcagaagcag gggattgcac ttggccggtc agtggatctc    2220
tcaaagttcc agaactatga ggagttggtt actgaattgg ataggctgtt tgagttcaat    2280
ggagagttga tggctcctaa gaaagattgg ctgatagttt acacagatga tgagaatgat    2340
atgatgcttg ttggagacga tccttggcag gagttttgtt gcatggttcg taaaatcttc    2400
atatacacga agaggaggt caggaagatg aacccgggaa ctctatgctg taggaacgag    2460
gaagaaccag ttgttgggga aggatcagat gcaaaggacg cgaagtctgc atcaaatcct    2520
tcattgtcca gcgccggaaa ctcttaa                                        2547
```

<210> SEQ ID NO 10
<211> LENGTH: 848
<212> TYPE: PRT
<213> ORGANISM: Brassica napus

<400> SEQUENCE: 10

```
Met Ala Ser Ser Glu Val Ser Met Lys Gly Asn Arg Gly Arg Gly Glu
1               5                   10                  15

Asn Phe Ser Ser Ala Gly Tyr Ser Asp Pro Thr Val Ala Gly Glu Ala
            20                  25                  30

Gln Lys Thr Gln Ser Asn Arg Ser Val Ala Ala Glu Arg Val Val Asp
        35                  40                  45

Pro Glu Ala Ala Leu Tyr Arg Glu Leu Trp His Ala Cys Ala Gly Pro
    50                  55                  60

Leu Val Thr Val Pro Arg Gln Asp Asp Arg Val Phe Tyr Phe Pro Gln
65                  70                  75                  80

Gly His Ile Glu Gln Val Glu Ala Ser Thr Asn Gln Ala Ala Glu Gln
                85                  90                  95

Gln Met Pro Leu Tyr Asp Leu Pro Ser Lys Ile Leu Cys Arg Val Ile
            100                 105                 110

Asn Val Asp Leu Lys Ala Glu Ala Asp Thr Asp Glu Val Tyr Ala Gln
        115                 120                 125

Ile Thr Leu Leu Pro Glu Pro Val Gln Asp Glu Asn Ser Ile Glu Lys
    130                 135                 140

Glu Ala Pro Pro Pro Pro Pro Arg Phe Gln Val His Ser Phe Cys
145                 150                 155                 160

Lys Thr Leu Thr Ala Ser Asp Thr Ser Thr His Gly Gly Phe Ser Val
                165                 170                 175

Leu Arg Arg His Ala Asp Glu Cys Leu Pro Pro Leu Asp Met Ser Arg
            180                 185                 190

Gln Pro Pro Thr Gln Glu Leu Val Ala Lys Asp Leu His Ala Ser Glu
        195                 200                 205

Trp Arg Phe Arg His Ile Phe Arg Gly Gln Pro Arg Arg His Leu Leu
    210                 215                 220

Gln Ser Gly Trp Ser Val Phe Val Ser Ser Lys Arg Leu Val Ala Gly
225                 230                 235                 240
```

```
Asp Ala Phe Ile Phe Leu Arg Gly Glu Asn Gly Glu Leu Arg Val Gly
                245                 250                 255

Val Arg Arg Ala Met Arg Gln Gln Gly Asn Val Pro Ser Ser Val Ile
            260                 265                 270

Ser Ser His Ser Met His Leu Gly Val Leu Ala Thr Ala Trp His Ala
        275                 280                 285

Ile Ser Thr Gly Thr Met Phe Thr Val Tyr Tyr Lys Pro Arg Thr Ser
    290                 295                 300

Pro Ser Glu Phe Ile Val Pro Phe Asp Gln Tyr Thr Glu Ser Val Lys
305                 310                 315                 320

Ile Asn Tyr Ser Ile Gly Met Arg Phe Lys Met Arg Phe Glu Gly Glu
                325                 330                 335

Glu Ala Pro Glu Gln Arg Phe Thr Gly Thr Ile Val Gly Ile Glu Asp
            340                 345                 350

Ser Asp Pro Thr Arg Trp Ala Lys Ser Lys Trp Arg Ser Leu Lys Val
        355                 360                 365

Arg Trp Asp Glu Thr Thr Ser Ile Pro Arg Pro Asp Arg Val Ser Pro
    370                 375                 380

Trp Lys Ile Glu Pro Ala Leu Ser Pro Pro Ala Leu Ser Pro Val Pro
385                 390                 395                 400

Met Pro Arg Pro Lys Arg Pro Arg Ser Asn Leu Ala Ser Ser Thr Pro
                405                 410                 415

Asp Ser Ser Met Arg Ile Arg Glu Gly Ser Ser Lys Ala Asn Met Asp
            420                 425                 430

Pro Leu Pro Ala Ser Gly Leu Ser Arg Val Leu Gln Gly Gln Glu Tyr
        435                 440                 445

Pro Thr Leu Arg Thr Lys His Val Glu Ser Val Glu Cys Asp Ala Pro
    450                 455                 460

Glu Asn Ser Val Val Trp Gln Ser Ser Thr Asp Asp Lys Val Asp
465                 470                 475                 480

Val Ile Ser Ala Ser Arg Arg Tyr Glu Asn Trp Ile Ser Ser Gly Arg
                485                 490                 495

His Gly Pro Thr Cys Thr Asp Leu Leu Ser Gly Phe Gly Thr Asn Ile
            500                 505                 510

Glu Pro Pro His Gly His Gln Ile Pro Phe Tyr Asp Arg Leu Ser Ser
        515                 520                 525

Pro Pro Ser Val Ala Ala Arg Lys Ile Leu Ser Asp Gln Asp Gly Lys
    530                 535                 540

Phe Glu Tyr Leu Ala Asn Gln Trp Met Met His Ser Gly Leu Ser Leu
545                 550                 555                 560

Lys Leu His Glu Ser Pro Lys Val Pro Ala Ala Ser Asp Ala Ser Phe
                565                 570                 575

Gln Gly Ile Gly Asn Pro Asn Tyr Gly Glu Tyr Ala Leu Pro Arg Ala
            580                 585                 590

Val Thr Thr Glu Asn Ala Ala Gly Asn Trp Pro Ile Arg Pro Arg Ala
        595                 600                 605

Leu Asn Tyr Phe Glu Glu Ala Val His Ala Gln Ala Arg Glu His Val
    610                 615                 620

Thr Lys Arg Pro Ala Val Val Gln Glu Glu Ala Ala Lys Pro Arg Asp
625                 630                 635                 640

Gly Asn Cys Arg Leu Phe Gly Ile Pro Leu Val Asn Asn Val Asn Gly
                645                 650                 655
```

```
Thr Asp Thr Thr Leu Ser Gln Arg Asn Leu Asn Asp Pro Ala Gly
            660                 665                 670

Pro Thr Gln Met Ala Ser Pro Lys Val Gln Asp Leu Ser Asp Gln Ser
        675                 680                 685

Lys Gly Ser Lys Ser Thr Asn Asp His Arg Glu Gln Gly Arg Pro Phe
    690                 695                 700

Pro Val Ser Lys Pro His Pro Lys Asp Val Gln Thr Lys Thr Asn Ser
705                 710                 715                 720

Cys Arg Ser Cys Thr Lys Val Gln Lys Gln Gly Ile Ala Leu Gly Arg
                725                 730                 735

Ser Val Asp Leu Ser Lys Phe Gln Asn Tyr Glu Glu Leu Val Thr Glu
            740                 745                 750

Leu Asp Arg Leu Phe Glu Phe Asn Gly Glu Leu Met Ala Pro Lys Lys
        755                 760                 765

Asp Trp Leu Ile Val Tyr Thr Asp Asp Glu Asn Asp Met Met Leu Val
    770                 775                 780

Gly Asp Asp Pro Trp Gln Glu Phe Cys Cys Met Val Arg Lys Ile Phe
785                 790                 795                 800

Ile Tyr Thr Lys Glu Glu Val Arg Lys Met Asn Pro Gly Thr Leu Cys
                805                 810                 815

Cys Arg Asn Glu Glu Glu Pro Val Val Gly Glu Gly Ser Asp Ala Lys
            820                 825                 830

Asp Ala Lys Ser Ala Ser Asn Pro Ser Leu Ser Ser Ala Gly Asn Ser
        835                 840                 845

<210> SEQ ID NO 11
<211> LENGTH: 30
<212> TYPE: DNA
<213> ORGANISM: Artificial Sequence
<220> FEATURE:
<223> OTHER INFORMATION: engineered primer sequence

<400> SEQUENCE: 11
aaacatatgc caacgggatc atgggattac                                          30

<210> SEQ ID NO 12
<211> LENGTH: 30
<212> TYPE: DNA
<213> ORGANISM: Artificial Sequence
<220> FEATURE:
<223> OTHER INFORMATION: engineered primer sequence

<400> SEQUENCE: 12
aaactgcagc gttcccggag atacgaaaac                                          30

<210> SEQ ID NO 13
<211> LENGTH: 30
<212> TYPE: DNA
<213> ORGANISM: Artificial Sequence
<220> FEATURE:
<223> OTHER INFORMATION: engineered primer sequence

<400> SEQUENCE: 13
aaacatatgg gaattcacaa tcggaaagtc                                          30

<210> SEQ ID NO 14
<211> LENGTH: 29
<212> TYPE: DNA
<213> ORGANISM: Artificial Sequence
<220> FEATURE:
<223> OTHER INFORMATION: engineered primer sequence
```

<400> SEQUENCE: 14
aaactgcagg gtccgtttat tagttcctc                                    29

<210> SEQ ID NO 15
<211> LENGTH: 34
<212> TYPE: DNA
<213> ORGANISM: Artificial Sequence
<220> FEATURE:
<223> OTHER INFORMATION: engineered primer sequence

<400> SEQUENCE: 15
gatctagagg cgcgccggat ctgagaactg gatg                              34

<210> SEQ ID NO 16
<211> LENGTH: 34
<212> TYPE: DNA
<213> ORGANISM: Artificial Sequence
<220> FEATURE:
<223> OTHER INFORMATION: engineered primer sequence

<400> SEQUENCE: 16
gaggatccat ttaaatccgc agcatcattc aagt                              34

<210> SEQ ID NO 17
<211> LENGTH: 35
<212> TYPE: DNA
<213> ORGANISM: Artificial Sequence
<220> FEATURE:
<223> OTHER INFORMATION: engineered primer sequence

<400> SEQUENCE: 17
gatctagagg cgcgccgcga tatgagaact ggata                             35

<210> SEQ ID NO 18
<211> LENGTH: 34
<212> TYPE: DNA
<213> ORGANISM: Artificial Sequence
<220> FEATURE:
<223> OTHER INFORMATION: engineered primer sequence

<400> SEQUENCE: 18
gaggatccat ttaaatgtag gccccgcagg gtca                              34

<210> SEQ ID NO 19
<211> LENGTH: 27
<212> TYPE: DNA
<213> ORGANISM: Artificial Sequence
<220> FEATURE:
<223> OTHER INFORMATION: engineered primer sequence

<400> SEQUENCE: 19
gaattcccaa cgggatcatg ggattac                                      27

<210> SEQ ID NO 20
<211> LENGTH: 27
<212> TYPE: DNA
<213> ORGANISM: Artificial Sequence
<220> FEATURE:
<223> OTHER INFORMATION: engineered primer sequence

<400> SEQUENCE: 20
ccatggcgtt cccggagata cgaaaac                                      27

<210> SEQ ID NO 21

```
<211> LENGTH: 24
<212> TYPE: DNA
<213> ORGANISM: Artificial Sequence
<220> FEATURE:
<223> OTHER INFORMATION: engineered primer sequence

<400> SEQUENCE: 21
gaattccctg gattagtgca agcc                                          24

<210> SEQ ID NO 22
<211> LENGTH: 26
<212> TYPE: DNA
<213> ORGANISM: Artificial Sequence
<220> FEATURE:
<223> OTHER INFORMATION: engineered primer sequence

<400> SEQUENCE: 22
ccatgggaga gtgtgtgtgt acgatg                                        26

<210> SEQ ID NO 23
<211> LENGTH: 21
<212> TYPE: DNA
<213> ORGANISM: Artificial Sequence
<220> FEATURE:
<223> OTHER INFORMATION: engineered primer sequence

<400> SEQUENCE: 23
ctcgaggaag gtatggcgag t                                             21

<210> SEQ ID NO 24
<211> LENGTH: 21
<212> TYPE: DNA
<213> ORGANISM: Artificial Sequence
<220> FEATURE:
<223> OTHER INFORMATION: engineered primer sequence

<400> SEQUENCE: 24
ggatcctcca gtctccacca a                                             21

<210> SEQ ID NO 25
<211> LENGTH: 26
<212> TYPE: DNA
<213> ORGANISM: Artificial Sequence
<220> FEATURE:
<223> OTHER INFORMATION: engineered primer sequence

<400> SEQUENCE: 25
ctcgagatgg cgagttcgga ggtttc                                        26

<210> SEQ ID NO 26
<211> LENGTH: 26
<212> TYPE: DNA
<213> ORGANISM: Artificial Sequence
<220> FEATURE:
<223> OTHER INFORMATION: engineered primer sequence

<400> SEQUENCE: 26
ggatccttaa gagtttccgg cgctgg                                        26

<210> SEQ ID NO 27
<211> LENGTH: 26
<212> TYPE: DNA
<213> ORGANISM: Artificial Sequence
<220> FEATURE:
<223> OTHER INFORMATION: engineered primer sequence

<400> SEQUENCE: 27
```
catatgcctg gattagtgca aggcaa                                            26

<210> SEQ ID NO 28
<211> LENGTH: 26
<212> TYPE: DNA
<213> ORGANISM: Artificial Sequence
<220> FEATURE:
<223> OTHER INFORMATION: engineered primer sequence

<400> SEQUENCE: 28
ctgcaggaga gtgtgtgtgt acgatg                                            26

<210> SEQ ID NO 29
<211> LENGTH: 30
<212> TYPE: DNA
<213> ORGANISM: Artificial Sequence
<220> FEATURE:
<223> OTHER INFORMATION: engineered primer sequence

<400> SEQUENCE: 29
aaaacgcgtc gttcccggag atacgaaaac                                        30

<210> SEQ ID NO 30
<211> LENGTH: 26
<212> TYPE: DNA
<213> ORGANISM: Artificial Sequence
<220> FEATURE:
<223> OTHER INFORMATION: engineered primer sequence

<400> SEQUENCE: 30
acgcgtgaga gtgtgtgtct acgatg                                            26

<210> SEQ ID NO 31
<211> LENGTH: 26
<212> TYPE: DNA
<213> ORGANISM: Artificial Sequence
<220> FEATURE:
<223> OTHER INFORMATION: engineered primer sequence

<400> SEQUENCE: 31
catatggaga atttgacaga ttggtg                                            26

<210> SEQ ID NO 32
<211> LENGTH: 26
<212> TYPE: DNA
<213> ORGANISM: Artificial Sequence
<220> FEATURE:
<223> OTHER INFORMATION: engineered primer sequence

<400> SEQUENCE: 32
ctgcaggttt atcgtcttga gacttc                                            26

<210> SEQ ID NO 33
<211> LENGTH: 30
<212> TYPE: DNA
<213> ORGANISM: Artificial Sequence
<220> FEATURE:
<223> OTHER INFORMATION: engineered primer sequence

<400> SEQUENCE: 33
aaacccggga tggcgattcg gaaggaggaa                                        30

<210> SEQ ID NO 34
<211> LENGTH: 30
<212> TYPE: DNA

```
<213> ORGANISM: Artificial Sequence
<220> FEATURE:
<223> OTHER INFORMATION: engineered primer sequence

<400> SEQUENCE: 34
aaaggatcct tatggagtgg ctacgattgc                                      30

<210> SEQ ID NO 35
<211> LENGTH: 30
<212> TYPE: DNA
<213> ORGANISM: Artificial Sequence
<220> FEATURE:
<223> OTHER INFORMATION: engineered primer sequence

<400> SEQUENCE: 35
aaacccggga tgacagaact caacttccac                                      30

<210> SEQ ID NO 36
<211> LENGTH: 30
<212> TYPE: DNA
<213> ORGANISM: Artificial Sequence
<220> FEATURE:
<223> OTHER INFORMATION: engineered primer sequence

<400> SEQUENCE: 36
aaaggatccc taattttgca ccaaatgccg                                      30

<210> SEQ ID NO 37
<211> LENGTH: 26
<212> TYPE: DNA
<213> ORGANISM: Artificial Sequence
<220> FEATURE:
<223> OTHER INFORMATION: engineered primer sequence

<400> SEQUENCE: 37 cccggggtg tgttcgttgt gtaacc                                           26

<210> SEQ ID NO 38
<211> LENGTH: 26
<212> TYPE: DNA
<213> ORGANISM: Artificial Sequence
<220> FEATURE:
<223> OTHER INFORMATION: engineered primer sequence

<400> SEQUENCE: 38
ggatccgatc aagaatcagc ccaagc                                          26

<210> SEQ ID NO 39
<211> LENGTH: 26
<212> TYPE: DNA
<213> ORGANISM: Artificial Sequence
<220> FEATURE:
<223> OTHER INFORMATION: engineered primer sequence

<400> SEQUENCE: 39
cccgggcact aagatgatga cttctc                                          26

<210> SEQ ID NO 40
<211> LENGTH: 26
<212> TYPE: DNA
<213> ORGANISM: Artificial Sequence
<220> FEATURE:
<223> OTHER INFORMATION: engineered primer sequence

<400> SEQUENCE: 40
ggatccaagc gactcattag acttgt                                          26
```

<210> SEQ ID NO 41
<211> LENGTH: 27
<212> TYPE: DNA
<213> ORGANISM: Artificial Sequence
<220> FEATURE:
<223> OTHER INFORMATION: engineered primer sequence

<400> SEQUENCE: 41
aaacatatgg atacacaagt tctttgg                                27

<210> SEQ ID NO 42
<211> LENGTH: 29
<212> TYPE: DNA
<213> ORGANISM: Artificial Sequence
<220> FEATURE:
<223> OTHER INFORMATION: engineered primer sequence

<400> SEQUENCE: 42
aaactgcaga ttcttctctc tttgtttaa                              29

<210> SEQ ID NO 43
<211> LENGTH: 30
<212> TYPE: DNA
<213> ORGANISM: Artificial Sequence
<220> FEATURE:
<223> OTHER INFORMATION: engineered primer sequence

<400> SEQUENCE: 43
catatggtga catcttttta gcataggttc                             30

<210> SEQ ID NO 44
<211> LENGTH: 30
<212> TYPE: DNA
<213> ORGANISM: Artificial Sequence
<220> FEATURE:
<223> OTHER INFORMATION: engineered primer sequence

<400> SEQUENCE: 44
ctgcagtttt gatccttttt taagaaactt                             30

<210> SEQ ID NO 45
<211> LENGTH: 29
<212> TYPE: DNA
<213> ORGANISM: Artificial Sequence
<220> FEATURE:
<223> OTHER INFORMATION: engineered primer sequence

<400> SEQUENCE: 45
catatgtgta actgcaaagt gtagttcgg                              29

<210> SEQ ID NO 46
<211> LENGTH: 28
<212> TYPE: DNA
<213> ORGANISM: Artificial Sequence
<220> FEATURE:
<223> OTHER INFORMATION: engineered primer sequence

<400> SEQUENCE: 46
ctgcagaatc tattttctc tctctctc                                28

<210> SEQ ID NO 47
<211> LENGTH: 22
<212> TYPE: DNA
<213> ORGANISM: Artificial Sequence
<220> FEATURE:

<223> OTHER INFORMATION: engineered primer sequence

<400> SEQUENCE: 47
tggttcacgt agtgggccat cg								22

<210> SEQ ID NO 48
<211> LENGTH: 20
<212> TYPE: DNA
<213> ORGANISM: Artificial Sequence
<220> FEATURE:
<223> OTHER INFORMATION: engineered primer sequence

<400> SEQUENCE: 48
gagtgggtgg agtgtgtttg								20

<210> SEQ ID NO 49
<211> LENGTH: 20
<212> TYPE: DNA
<213> ORGANISM: Artificial Sequence
<220> FEATURE:
<223> OTHER INFORMATION: engineered primer sequence

<400> SEQUENCE: 49
gagtgggtgg agtgtgtttg								20

<210> SEQ ID NO 50
<211> LENGTH: 21
<212> TYPE: DNA
<213> ORGANISM: Artificial Sequence
<220> FEATURE:
<223> OTHER INFORMATION: engineered primer sequence

<400> SEQUENCE: 50
agttggtttt cgtttgagca t								21

<210> SEQ ID NO 51
<211> LENGTH: 20
<212> TYPE: DNA
<213> ORGANISM: Artificial Sequence
<220> FEATURE:
<223> OTHER INFORMATION: engineered primer sequence

<400> SEQUENCE: 51
gagtgggtgg agtgtgtttg								20

<210> SEQ ID NO 52
<211> LENGTH: 21
<212> TYPE: DNA
<213> ORGANISM: Artificial Sequence
<220> FEATURE:
<223> OTHER INFORMATION: engineered primer sequence

<400> SEQUENCE: 52
agttggtttt cgtttgagca t								21

<210> SEQ ID NO 53
<211> LENGTH: 21
<212> TYPE: DNA
<213> ORGANISM: Artificial Sequence
<220> FEATURE:
<223> OTHER INFORMATION: engineered primer sequence

<400> SEQUENCE: 53
cacttgaagg gtggtgccaa g								21

```
<210> SEQ ID NO 54
<211> LENGTH: 21
<212> TYPE: DNA
<213> ORGANISM: Artificial Sequence
<220> FEATURE:
<223> OTHER INFORMATION: engineered primer sequence

<400> SEQUENCE: 54
cctgttgtcg ccaacgaagt c                                              21

<210> SEQ ID NO 55
<211> LENGTH: 2580
<212> TYPE: DNA
<213> ORGANISM: Arabidopsis thaliana

<400> SEQUENCE: 55
atggcgagtt cggaggtttc aatgaaaggt aatcgtggag gagataactt ctcctcctct    60
ggttttagtg acccctaagga gactagaaat gtctccgtcg ccggcgaggg gcaaaaaagt  120
aattctaccc gatccgctgc ggctgagcgt gctttggacc ctgaggctgc tctttacaga   180
gagctatggc acgcttgtgc tggtccgctt gtgacggttc ctagacaaga cgaccgagtc   240
ttctattttc ctcaaggaca catcgagcag gtggaggctt cgacgaacca ggcggcagaa   300
caacagatgc ctctctatga tcttccgtca aagcttctct gtcgagttat taatgtagat   360
ttaaaggcag aggcagatac agatgaagtt tatgcgcaga ttactcttct tcctgaggct   420
aatcaagacg agaatgcaat tgagaaagaa gcgcctcttc ctccacctcc gaggttccag   480
gtgcattcgt tctgcaaaac cttgactgca tccgacacaa gtacacatgg tggattttct   540
gttcttaggc gacatgcgga tgaatgtctc ccacctctgg atatgtctcg acagcctccc   600
actcaagagt tagttgcaaa ggatttgcat gcaaatgagt ggcgattcag acatatattc   660
cggggtcaac cacggaggca tttgctacag agtgggtgga gtgtgtttgt tagctccaaa   720
aggctagttg caggcgatgc gtttatattt ctaaggggcg agaatggaga attaagagtt   780
ggtgtaaggc gtgcgatgcg acaacaagga aacgtgccgt cttctgttat atctagccat   840
agcatgcatc ttggagtact ggccaccgca tggcatgcca tttcaacagg gactatgttt   900
acagtctact acaaacccag gacgagccca tctgagttta ttgttccgtt cgatcagtat   960
atggagtctg ttaagaataa ctactctatt ggcatgagat tcaaaatgag atttgaaggc  1020
gaagaggctc tgagcagag gtttactggc acaatcgttg ggattgaaga gtctgatcct  1080
actaggtggc caaaatcaaa gtggagatcc ctcaaggtga gatgggatga gacttctagt  1140
attcctcgac ctgatagagt atctccgtgg aaagtagagc cagctcttgc tcctcctgct  1200
ttgagtcctg ttccaatgcc taggcctaag aggcccagat caaatatagc accttcatct  1260
cctgactctt cgatgcttac cagagaaggt acaactaagg caaacatgga ccctttacca  1320
gcaagcggac tttcaagggt cttgcaaggt caagaatact cgaccttgag gacgaaacat  1380
actgagagtg tagagtgtga tgctcctgag aattctgttg tctggcaatc ttcagcggat  1440
gatgataagg ttgacgtggt ttcgggttct agaagatatg gatctgagaa ctggatgtcc  1500
tcagccaggc atgaacctac ttacacagat ttgctctccg gctttgggac taacatagat  1560
ccatcccatg gtcagcggat acctttttat gaccattcat catcaccttc tatgcctgca  1620
aagagaatct tgagtgattc agaaggcaag ttcgattatc ttgctaacca gtggcagatg  1680
atacactctg gtctctccct gaagttacat gaatctccta aggtacctgc agcaactgat  1740
gcgtctctcc aagggcgatg caatgttaaa tacagcgaat atcctgttct taatggtcta  1800
```

```
tcgactgaga atgctggtgg taactggcca atacgtccac gtgctttgaa ttattatgag    1860
gaagtggtca atgctcaagc gcaagctcag gctagggagc aagtaacaaa acaacccttc    1920
acgatacaag aggagacagc aaagtcaaga gaagggaact gcaggctctt tggcattcct    1980
ctgaccaaca acatgaatgg gacagactca accatgtctc agagaaacaa cttgaatgat    2040
gctgcgggc  ttacacagat agcatcacca aaggttcagg acctttcaga tcagtcaaaa    2100
gggtcaaaat caacaaacga tcatcgtgaa cagggaagac cattccagac taataatcct    2160
catccgaagg atgctcaaac gaaaaccaac tcaagtagga gttgcacaaa ggttcacaag    2220
cagggaattg cacttggccg ttcagtggat ctttcaaagt tccaaaacta tgaggagtta    2280
gtcgctgagc tggacaggct gtttgagttc aatggagagt tgatggctcc taagaaagat    2340
tggttgatag tttacacaga tgaagagaat gatatgatgc ttgttggtga cgatccttgg    2400
caggagtttt gttgcatggt tcgcaaaatc ttcatataca cgaaagagga agtgaggaag    2460
atgaacccgg ggactttaag ctgtaggagc gaggaagaag cagttgttgg ggaaggatca    2520
gatgcaaagg acgccaagtc tgcatcaaat ccttcattgt ccagcgctgg gaactcttaa    2580
```

<210> SEQ ID NO 56
<211> LENGTH: 2576
<212> TYPE: DNA
<213> ORGANISM: Arabidopsis thaliana

<400> SEQUENCE: 56

```
atggcgagtt cggaggtttc aatgaaaggt aatcgtggag gagataactt ctcctcctct      60
ggttttagtg accctaagga gactagaaat gtctccgtcg ccggcgaggg gcaaaaaagt     120
aattctaccc gatccgctgc ggctgagcgt gctttggacc ctgaggctgc tctttacaga     180
gagctatggc acgcttgtgc tggtccgctt gtgacggttc ctagacaaga cgaccgagtc     240
ttctattttc ctcaaggaca catcgagcag gtggaggctt cgacgaacca ggcggcagaa     300
caacagatgc ctctctatga tcttccgtca aagcttctct gtcgagttat taatgtagat     360
ttaaagaggc agatacagat gaagtttatg cgcagattac tcttcttcct gaggctaatc     420
aagacgagaa tgcaattgag aaagaagcgc ctcttcctcc acctccgagg ttccaggtgc     480
attcgttctg caaaaccttg actgcatccg acacaagtac acatggtgga ttttctgttc     540
ttaggcgaca tgcggatgaa tgtctcccac ctctggatat gtctcgacag cctcccactc     600
aagagttagt tgcaaaggat ttgcatgcaa atgagtggcg attcagacat atattccggg     660
gtcaaccacg gaggcatttg ctacagagtg ggtggagtgt gtttgttagc tccaaaaggc     720
tagttgcagg cgatgcgttt atatttctaa ggggcgagaa tggagaatta agagttggtg     780
taaggcgtgc gatgcgacaa caaggaaacg tgccgtcttc tgttatatct agccatagca     840
tgcatcttgg agtactggcc accgcatggc atgccatttc aacagggact atgtttacag     900
tctactacaa acccaggacg agcccatctg agtttattgt tccgttcgat cagtatatgg     960
agtctgttaa gaataactac tctattggca tgagattcaa aatgagattt gaaggcgaag    1020
aggctcctga gcagaggttt actggcacaa tcgttgggat tgaagagtct gatcctacta    1080
ggtggccaaa atcaaagtgg agatccctca aggtgagatg ggatgagact tctagtattc    1140
ctcgacctga tagagtatct ccgtggaaag tagagccagc tcttgctcct cctgctttga    1200
gtcctgttcc aatgcctagg cctaagaggc ccagatcaaa tatagcacct tcatctcctg    1260
actcttcgat gcttaccaga gaaggtacaa ctaaggcaaa catggaccct ttaccagcaa    1320
gcggactttc aagggtcttg caaggtcaag aatactcgac cttgaggacg aaacatactg    1380
```

```
agagtgtaga gtgtgatgct cctgagaatt ctgttgtctg gcaatcttca gcggatgatg    1440
ataaggttga cgtggtttcg ggttctagaa gatatggatc tgagaactgg atgtcctcag    1500
ccaggcatga acctacttac acagatttgc tctccggctt tgggactaac atagatccat    1560
cccatggtca gcggatacct ttttatgacc attcatcatc accttctatg cctgcaaaga    1620
gaatcttgag tgattcagaa ggcaagttcg attatcttgc taaccagtgg cagatgatac    1680
actctggtct ctccctgaag ttacatgaat ctcctaaggt acctgcagca actgatgcgt    1740
ctctccaagg gcgatgcaat gttaaataca gcgaatatcc tgttcttaat ggtctatcga    1800
ctgagaatgc tggtggtaac tggccaatac gtccacgtgc tttgaattat tatgaggaag    1860
tggtcaatgc tcaagcgcaa gctcaggcta gggagcaagt aacaaaacaa cccttcacga    1920
tacaagagga gacagcaaag tcaagagaag ggaactgcag gctctttggc attcctctga    1980
ccaacaacat gaatgggaca gactcaacca tgtctcagag aaacaacttg aatgatgctg    2040
cggggcttac acagatagca tcaccaaagg ttcaggacct ttcagatcag tcaaaagggt    2100
caaaatcaac aaacgatcat cgtgaacagg gaagaccatt ccagactaat aatcctcatc    2160
cgaaggatgc tcaaacgaaa accaactcaa gtaggagttg cacaaaggtt cacaagcagg    2220
gaattgcact tggccgttca gtggatcttt caaagttcca aaactatgag gagttagtcg    2280
ctgagctgga caggctgttt gagttcaatg gagagttgat ggctcctaag aaagattggt    2340
tgatagttta cacagatgaa gagaatgata tgatgcttgt tggtgacgat ccttggcagg    2400
agttttgttg catggttcgc aaaatcttca tatacacgaa agaggaagtg aggaagatga    2460
acccggggac tttaagctgt aggagcgagg aagaagcagt tgttggggaa ggatcagatg    2520
caaaggacgc caagtctgca tcaaatcctt cattgtccag cgctgggaac tcttaa       2576
```

<210> SEQ ID NO 57
<211> LENGTH: 859
<212> TYPE: PRT
<213> ORGANISM: Arabidopsis thaliana

<400> SEQUENCE: 57

```
Met Ala Ser Ser Glu Val Ser Met Lys Gly Asn Arg Gly Gly Asp Asn
1               5                   10                  15

Phe Ser Ser Ser Gly Phe Ser Asp Pro Lys Glu Thr Arg Asn Val Ser
            20                  25                  30

Val Ala Gly Glu Gly Gln Lys Ser Asn Ser Thr Arg Ser Ala Ala Ala
        35                  40                  45

Glu Arg Ala Leu Asp Pro Glu Ala Ala Leu Tyr Arg Glu Leu Trp His
    50                  55                  60

Ala Cys Ala Gly Pro Leu Val Thr Val Pro Arg Gln Asp Asp Arg Val
65                  70                  75                  80

Phe Tyr Phe Pro Gln Gly His Ile Glu Gln Val Glu Ala Ser Thr Asn
                85                  90                  95

Gln Ala Ala Glu Gln Gln Met Pro Leu Tyr Asp Leu Pro Ser Lys Leu
            100                 105                 110

Leu Cys Arg Val Ile Asn Val Asp Leu Lys Ala Glu Ala Asp Thr Asp
        115                 120                 125

Glu Val Tyr Ala Gln Ile Thr Leu Leu Pro Glu Ala Asn Gln Asp Glu
    130                 135                 140

Asn Ala Ile Glu Lys Glu Ala Pro Leu Pro Pro Pro Arg Phe Gln
145                 150                 155                 160
```

-continued

```
Val His Ser Phe Cys Lys Thr Leu Thr Ala Ser Asp Thr Ser Thr His
                165                 170                 175
Gly Gly Phe Ser Val Leu Arg Arg His Ala Asp Glu Cys Leu Pro Pro
            180                 185                 190
Leu Asp Met Ser Arg Gln Pro Pro Thr Gln Glu Leu Val Ala Lys Asp
        195                 200                 205
Leu His Ala Asn Glu Trp Arg Phe Arg His Ile Phe Arg Gly Gln Pro
    210                 215                 220
Arg Arg His Leu Leu Gln Ser Gly Trp Ser Val Phe Val Ser Ser Lys
225                 230                 235                 240
Arg Leu Val Ala Gly Asp Ala Phe Ile Phe Leu Arg Gly Glu Asn Gly
                245                 250                 255
Glu Leu Arg Val Gly Val Arg Arg Ala Met Arg Gln Gln Gly Asn Val
            260                 265                 270
Pro Ser Ser Val Ile Ser Ser His Ser Met His Leu Gly Val Leu Ala
        275                 280                 285
Thr Ala Trp His Ala Ile Ser Thr Gly Thr Met Phe Thr Val Tyr Tyr
    290                 295                 300
Lys Pro Arg Thr Ser Pro Ser Glu Phe Ile Val Pro Phe Asp Gln Tyr
305                 310                 315                 320
Met Glu Ser Val Lys Asn Asn Tyr Ser Ile Gly Met Arg Phe Lys Met
                325                 330                 335
Arg Phe Glu Gly Glu Glu Ala Pro Glu Gln Arg Phe Thr Gly Thr Ile
            340                 345                 350
Val Gly Ile Glu Glu Ser Asp Pro Thr Arg Trp Pro Lys Ser Lys Trp
        355                 360                 365
Arg Ser Leu Lys Val Arg Trp Asp Glu Thr Ser Ser Ile Pro Arg Pro
    370                 375                 380
Asp Arg Val Ser Pro Trp Lys Val Glu Pro Ala Leu Ala Pro Pro Ala
385                 390                 395                 400
Leu Ser Pro Val Pro Met Pro Arg Pro Lys Arg Pro Arg Ser Asn Ile
                405                 410                 415
Ala Pro Ser Ser Pro Asp Ser Ser Met Leu Thr Arg Glu Gly Thr Thr
            420                 425                 430
Lys Ala Asn Met Asp Pro Leu Pro Ala Ser Gly Leu Ser Arg Val Leu
        435                 440                 445
Gln Gly Gln Glu Tyr Ser Thr Leu Arg Thr Lys His Thr Glu Ser Val
    450                 455                 460
Glu Cys Asp Ala Pro Glu Asn Ser Val Val Trp Gln Ser Ser Ala Asp
465                 470                 475                 480
Asp Asp Lys Val Asp Val Val Ser Gly Ser Arg Arg Tyr Gly Ser Glu
                485                 490                 495
Asn Trp Met Ser Ser Ala Arg His Glu Pro Thr Tyr Thr Asp Leu Leu
            500                 505                 510
Ser Gly Phe Gly Thr Asn Ile Asp Pro Ser His Gly Gln Arg Ile Pro
        515                 520                 525
Phe Tyr Asp His Ser Ser Ser Pro Ser Met Pro Ala Lys Arg Ile Leu
    530                 535                 540
Ser Asp Ser Glu Gly Lys Phe Asp Tyr Leu Ala Asn Gln Trp Gln Met
545                 550                 555                 560
Ile His Ser Gly Leu Ser Leu Lys Leu His Glu Ser Pro Lys Val Pro
                565                 570                 575
Ala Ala Thr Asp Ala Ser Leu Gln Gly Arg Cys Asn Val Lys Tyr Ser
```

```
            580                 585                 590
Glu Tyr Pro Val Leu Asn Gly Leu Ser Thr Glu Asn Ala Gly Gly Asn
            595                 600                 605

Trp Pro Ile Arg Pro Arg Ala Leu Asn Tyr Tyr Glu Glu Val Val Asn
        610                 615                 620

Ala Gln Ala Gln Ala Gln Arg Glu Gln Val Thr Lys Gln Pro Phe
625                 630                 635                 640

Thr Ile Gln Glu Glu Thr Ala Lys Ser Arg Glu Gly Asn Cys Arg Leu
                645                 650                 655

Phe Gly Ile Pro Leu Thr Asn Asn Met Asn Gly Thr Asp Ser Thr Met
            660                 665                 670

Ser Gln Arg Asn Asn Leu Asn Asp Ala Ala Gly Leu Thr Gln Ile Ala
        675                 680                 685

Ser Pro Lys Val Gln Asp Leu Ser Asp Gln Ser Lys Gly Ser Lys Ser
    690                 695                 700

Thr Asn Asp His Arg Glu Gln Gly Arg Pro Phe Gln Thr Asn Asn Pro
705                 710                 715                 720

His Pro Lys Asp Ala Gln Thr Lys Thr Asn Ser Ser Arg Ser Cys Thr
                725                 730                 735

Lys Val His Lys Gln Gly Ile Ala Leu Gly Arg Ser Val Asp Leu Ser
            740                 745                 750

Lys Phe Gln Asn Tyr Glu Glu Leu Val Ala Glu Leu Asp Arg Leu Phe
        755                 760                 765

Glu Phe Asn Gly Glu Leu Met Ala Pro Lys Lys Asp Trp Leu Ile Val
    770                 775                 780

Tyr Thr Asp Glu Glu Asn Asp Met Met Leu Val Gly Asp Asp Pro Trp
785                 790                 795                 800

Gln Glu Phe Cys Cys Met Val Arg Lys Ile Phe Ile Tyr Thr Lys Glu
                805                 810                 815

Glu Val Arg Lys Met Asn Pro Gly Thr Leu Ser Cys Arg Ser Glu Glu
            820                 825                 830

Glu Ala Val Val Gly Glu Gly Ser Asp Ala Lys Asp Ala Lys Ser Ala
        835                 840                 845

Ser Asn Pro Ser Leu Ser Ser Ala Gly Asn Ser
    850                 855

<210> SEQ ID NO 58
<211> LENGTH: 166
<212> TYPE: PRT
<213> ORGANISM: Arabidopsis thaliana

<400> SEQUENCE: 58

Met Ala Ser Ser Glu Val Ser Met Lys Gly Asn Arg Gly Gly Asp Asn
1               5                   10                  15

Phe Ser Ser Ser Gly Phe Ser Asp Pro Lys Glu Thr Arg Asn Val Ser
            20                  25                  30

Val Ala Gly Glu Gly Gln Lys Ser Asn Ser Thr Arg Ser Ala Ala Ala
        35                  40                  45

Glu Arg Ala Leu Asp Pro Glu Ala Ala Leu Tyr Arg Glu Leu Trp His
    50                  55                  60

Ala Cys Ala Gly Pro Leu Val Thr Val Pro Arg Gln Asp Asp Arg Val
65                  70                  75                  80

Phe Tyr Phe Pro Gln Gly His Ile Glu Gln Val Glu Ala Ser Thr Asn
                85                  90                  95
```

```
Gln Ala Ala Glu Gln Gln Met Pro Leu Tyr Asp Leu Pro Ser Lys Leu
            100                 105                 110

Leu Cys Arg Val Ile Asn Val Asp Leu Lys Arg Gln Ile Gln Met Lys
        115                 120                 125

Phe Met Arg Arg Leu Leu Phe Phe Leu Arg Leu Ile Lys Thr Arg Met
        130                 135                 140

Gln Leu Arg Lys Lys Arg Leu Phe Leu His Leu Arg Gly Ser Arg Cys
145                 150                 155                 160

Ile Arg Ser Ala Lys Pro
                165

<210> SEQ ID NO 59
<211> LENGTH: 2547
<212> TYPE: DNA
<213> ORGANISM: Brassica napus

<400> SEQUENCE: 59
```

| | | | | | |
|---|---|---|---|---|---|
| atggcgagtt | cggaggtttc | tatgaaagga | atcgtggac | gaggagaaaa | cttctcctcc | 60 |
| gctggttaca | gtgacccgac | ggtcgccggc | gaggcgcaga | aaactcagtc | taaccgatct | 120 |
| gtggctgcag | agcgcgttgt | cgacccggaa | gctgctctct | accgtgagct | gtggcacgct | 180 |
| tgtgctggtc | ctctcgtgac | agtccctcga | caagatgacc | gagtcttcta | cttccctcag | 240 |
| gggcacatcg | agcaggtgga | agcatcgaca | aatcaagctg | cagaacagca | gatgcctctc | 300 |
| tatgatcttc | cttcgaagat | cctttgtcgt | gtcattaatg | ttgatttaaa | ggcagaggca | 360 |
| gacaccgacg | aagtttatgc | gcagattact | cttcttccgg | agcctgttca | agacgagaat | 420 |
| tcaatagaga | aagaggcgcc | tcctcctccg | ccccaaggt | tccaagtgca | ctccttctgc | 480 |
| aaaaccttga | ctgcatcgga | cacaagtaca | catggtggat | tttctgtgct | taggcggcat | 540 |
| gcggatgaat | gtctcccacc | tctggatatg | tcacgtcaac | ctcctactca | ggagttagtt | 600 |
| gcaaaagatc | tgcatgcaag | cgagtggcgt | ttccgacata | ttttccgagg | tcaaccacga | 660 |
| aggcatttgc | ttcagagtgg | atggagcgtg | tttgttagct | ccaagaggct | ggtcgcaggc | 720 |
| gatgctttta | tatttctaag | gggcgagaat | ggagaattac | gtgtgggtgt | aaggcgtgca | 780 |
| atgcggcagc | aaggaaatgt | gccatcctct | gttatatcaa | gccacagcat | gcatctcgga | 840 |
| gtattggcca | ctgcctggca | cgctatttca | actggaacca | tgtttacagt | ctactataaa | 900 |
| ccgaggacta | gtccttcaga | gtttattgtt | ccgtttgatc | agtatacgga | gtccgtgaag | 960 |
| attaactact | ccataggcat | gagatttaaa | atgagatttg | aaggcgaaga | ggctcccgag | 1020 |
| cagaggttta | ctggcacaat | cgttgggatt | gaagactctg | accccacgag | gtgggcaaaa | 1080 |
| tcaaaatgga | gatccctcaa | ggtacggtgg | gatgagacca | ctagtattcc | tcgccctgat | 1140 |
| agagtatccc | cgtggaagat | agagccagct | ctttctcctc | ctgctttgag | ccctgtacca | 1200 |
| atgcctaggc | ctaagaggcc | cagatctaat | ctagcttctt | caactccgga | ctcttccatg | 1260 |
| cgcataaggg | aaggctcatc | taaggcaaac | atggacccctt | accggcaag | tggactatca | 1320 |
| agggtcttgc | aaggtcaaga | atacccgacc | ttgagaacga | acatgttga | gagtgtagaa | 1380 |
| tgcgatgctc | ctgaaaattc | ggttgtgtgg | caatcgtcaa | ctgatgatga | caaggttgat | 1440 |
| gtgatttcag | cttctaggag | atatgagaac | tggatatcct | caggtaggca | tggacctact | 1500 |
| tgcacggatt | tgctttctgg | ctttgggaca | aacatagaac | cacctcacgg | tcatcagata | 1560 |
| ccttttttatg | accgtttatc | atcaccacct | tctgtggctg | caaggaaaat | cctcagcgac | 1620 |
| caggatggca | agtttgaata | tcttgctaac | cagtggatga | tgcactcagg | cctttccctg | 1680 |

```
aagttacatg aatctcctaa agtccctgcc gcatctgatg cctctttcca agggataggc    1740
aatcccaatt acggcgaata tgctttgcct cgtgcagtga cgactgagaa tgctgctggc    1800
aactggccaa tacgtccacg tgctctaaat tattttgaag aagcggttca tgctcaggct    1860
agagagcatg tgacaaaacg tcctgcggtc gtacaagagg aggcagcaaa gccaagagac    1920
gggaactgca ggcttttttgg cattcctctg gtgaacaacg tgaatgggac agatacaact    1980
ttgtctcaga gaacaatttt gaatgaccct gcggggccta cgcagatggc atcaccaaag    2040
gttcaggatc tttctgacca gtccaagggg tcaaaatcga caaatgatca tcgtgagcaa    2100
ggacgaccat tcccggttag taaaccccat ccgaaagacg ttcaaaccaa acaaaactca    2160
tgtaggagct gcacgaaggt tcagaagcag gggattgcac ttggccggtc agtggatctc    2220
tcaaagttcc agaactatga ggagttggtt actgaattgg ataggctgtt tgagttcaat    2280
ggagagttga tggctcctaa gaaagattgg ctgatagttt acacagatga tgagaatgat    2340
atgatgcttg ttggagacga tccttggcag gagttttgtt gcatggttcg taaaatcttc    2400
atatacacga aagaggaggt caggaagatg aacccgggaa ctctatgctg taggaacgag    2460
gaagaaccag ttgttgggga aggatcagat gcaaggacg cgaagtctgc atcaaatcct    2520
tcattgtcca gcgccggaaa ctcttaa                                       2547

<210> SEQ ID NO 60
<211> LENGTH: 848
<212> TYPE: PRT
<213> ORGANISM: Brassica napus

<400> SEQUENCE: 60

Met Ala Ser Ser Glu Val Ser Met Lys Gly Asn Arg Gly Arg Gly Glu
1               5                   10                  15

Asn Phe Ser Ser Ala Gly Tyr Ser Asp Pro Thr Val Ala Gly Glu Ala
                20                  25                  30

Gln Lys Thr Gln Ser Asn Arg Ser Val Ala Ala Glu Arg Val Val Asp
            35                  40                  45

Pro Glu Ala Ala Leu Tyr Arg Glu Leu Trp His Ala Cys Ala Gly Pro
        50                  55                  60

Leu Val Thr Val Pro Arg Gln Asp Asp Arg Val Phe Tyr Phe Pro Gln
65                  70                  75                  80

Gly His Ile Glu Gln Val Glu Ala Ser Thr Asn Gln Ala Ala Glu Gln
                85                  90                  95

Gln Met Pro Leu Tyr Asp Leu Pro Ser Lys Ile Leu Cys Arg Val Ile
            100                 105                 110

Asn Val Asp Leu Lys Ala Glu Ala Asp Thr Asp Glu Val Tyr Ala Gln
        115                 120                 125

Ile Thr Leu Leu Pro Glu Pro Val Gln Asp Glu Asn Ser Ile Glu Lys
    130                 135                 140

Glu Ala Pro Pro Pro Pro Pro Arg Phe Gln Val His Ser Phe Cys
145                 150                 155                 160

Lys Thr Leu Thr Ala Ser Asp Thr Ser Thr His Gly Gly Phe Ser Val
                165                 170                 175

Leu Arg Arg His Ala Asp Glu Cys Leu Pro Pro Leu Asp Met Ser Arg
            180                 185                 190

Gln Pro Pro Thr Gln Glu Leu Val Ala Lys Asp Leu His Ala Ser Glu
        195                 200                 205

Trp Arg Phe Arg His Ile Phe Arg Gly Gln Pro Arg Arg His Leu Leu
    210                 215                 220
```

```
Gln Ser Gly Trp Ser Val Phe Val Ser Lys Arg Leu Val Ala Gly
225                 230                 235                 240

Asp Ala Phe Ile Phe Leu Arg Gly Glu Asn Gly Glu Leu Arg Val Gly
            245                 250                 255

Val Arg Arg Ala Met Arg Gln Gln Gly Asn Val Pro Ser Ser Val Ile
            260                 265                 270

Ser Ser His Ser Met His Leu Gly Val Leu Ala Thr Ala Trp His Ala
            275                 280                 285

Ile Ser Thr Gly Thr Met Phe Thr Val Tyr Tyr Lys Pro Arg Thr Ser
290                 295                 300

Pro Ser Glu Phe Ile Val Pro Phe Asp Gln Tyr Thr Glu Ser Val Lys
305                 310                 315                 320

Ile Asn Tyr Ser Ile Gly Met Arg Phe Lys Met Arg Phe Glu Gly Glu
            325                 330                 335

Glu Ala Pro Glu Gln Arg Phe Thr Gly Thr Ile Val Gly Ile Glu Asp
            340                 345                 350

Ser Asp Pro Thr Arg Trp Ala Lys Ser Lys Trp Arg Ser Leu Lys Val
            355                 360                 365

Arg Trp Asp Glu Thr Thr Ser Ile Pro Arg Pro Asp Arg Val Ser Pro
370                 375                 380

Trp Lys Ile Glu Pro Ala Leu Ser Pro Ala Leu Ser Pro Val Pro
385                 390                 395                 400

Met Pro Arg Pro Lys Arg Pro Arg Ser Asn Leu Ala Ser Ser Thr Pro
            405                 410                 415

Asp Ser Ser Met Arg Ile Arg Glu Gly Ser Ser Lys Ala Asn Met Asp
            420                 425                 430

Pro Leu Pro Ala Ser Gly Leu Ser Arg Val Leu Gln Gly Gln Glu Tyr
            435                 440                 445

Pro Thr Leu Arg Thr Lys His Val Glu Ser Val Glu Cys Asp Ala Pro
            450                 455                 460

Glu Asn Ser Val Val Trp Gln Ser Ser Thr Asp Asp Lys Val Asp
465                 470                 475                 480

Val Ile Ser Ala Ser Arg Arg Tyr Glu Asn Trp Ile Ser Ser Gly Arg
            485                 490                 495

His Gly Pro Thr Cys Thr Asp Leu Leu Ser Gly Phe Gly Thr Asn Ile
            500                 505                 510

Glu Pro Pro His Gly His Gln Ile Pro Phe Tyr Asp Arg Leu Ser Ser
            515                 520                 525

Pro Pro Ser Val Ala Ala Arg Lys Ile Leu Ser Asp Gln Asp Gly Lys
            530                 535                 540

Phe Glu Tyr Leu Ala Asn Gln Trp Met Met His Ser Gly Leu Ser Leu
545                 550                 555                 560

Lys Leu His Glu Ser Pro Lys Val Pro Ala Ala Ser Asp Ala Ser Phe
            565                 570                 575

Gln Gly Ile Gly Asn Pro Asn Tyr Gly Glu Tyr Ala Leu Pro Arg Ala
            580                 585                 590

Val Thr Thr Glu Asn Ala Ala Gly Asn Trp Pro Ile Arg Pro Arg Ala
            595                 600                 605

Leu Asn Tyr Phe Glu Glu Ala Val His Ala Gln Ala Arg Glu His Val
            610                 615                 620

Thr Lys Arg Pro Ala Val Val Gln Glu Glu Ala Ala Lys Pro Arg Asp
625                 630                 635                 640
```

Gly Asn Cys Arg Leu Phe Gly Ile Pro Leu Val Asn Val Asn Gly
                645                 650                 655

Thr Asp Thr Thr Leu Ser Gln Arg Asn Asn Leu Asn Asp Pro Ala Gly
        660                 665                 670

Pro Thr Gln Met Ala Ser Pro Lys Val Gln Asp Leu Ser Asp Gln Ser
            675                 680                 685

Lys Gly Ser Lys Ser Thr Asn Asp His Arg Glu Gln Gly Arg Pro Phe
    690                 695                 700

Pro Val Ser Lys Pro His Pro Lys Asp Val Gln Thr Lys Thr Asn Ser
705                 710                 715                 720

Cys Arg Ser Cys Thr Lys Val Gln Lys Gln Gly Ile Ala Leu Gly Arg
                725                 730                 735

Ser Val Asp Leu Ser Lys Phe Gln Asn Tyr Glu Glu Leu Val Thr Glu
            740                 745                 750

Leu Asp Arg Leu Phe Glu Phe Asn Gly Glu Leu Met Ala Pro Lys Lys
        755                 760                 765

Asp Trp Leu Ile Val Tyr Thr Asp Asp Glu Asn Asp Met Met Leu Val
    770                 775                 780

Gly Asp Asp Pro Trp Gln Glu Phe Cys Cys Met Val Arg Lys Ile Phe
785                 790                 795                 800

Ile Tyr Thr Lys Glu Glu Val Arg Lys Met Asn Pro Gly Thr Leu Cys
                805                 810                 815

Cys Arg Asn Glu Glu Pro Val Val Gly Gly Ser Asp Ala Lys
            820                 825                 830

Asp Ala Lys Ser Ala Ser Asn Pro Ser Leu Ser Ser Ala Gly Asn Ser
        835                 840                 845

<210> SEQ ID NO 61
<211> LENGTH: 791
<212> TYPE: PRT
<213> ORGANISM: Oryza sativa

<400> SEQUENCE: 61

Gly Asp Pro Leu Tyr Asp Glu Leu Trp His Ala Cys Ala Gly Pro Leu
1               5                   10                  15

Val Thr Val Pro Arg Val Gly Asp Leu Val Phe Tyr Phe Pro Gln Gly
                20                  25                  30

His Ile Glu Gln Val Glu Ala Ser Met Asn Gln Val Ala Asp Ser Gln
            35                  40                  45

Met Arg Leu Tyr Asp Leu Pro Ser Lys Leu Leu Cys Arg Val Leu Asn
        50                  55                  60

Val Glu Leu Lys Ala Glu Gln Asp Thr Asp Glu Val Tyr Ala Gln Val
65                  70                  75                  80

Met Leu Met Pro Glu Pro Glu Gln Asn Glu Met Ala Val Glu Lys Thr
                85                  90                  95

Thr Pro Thr Ser Gly Pro Val Gln Ala Arg Pro Pro Val Arg Ser Phe
            100                 105                 110

Cys Lys Thr Leu Thr Ala Ser Asp Thr Ser Thr His Gly Gly Phe Ser
        115                 120                 125

Val Leu Arg Arg His Ala Asp Glu Cys Leu Pro Pro Leu Asp Met Thr
    130                 135                 140

Gln Ser Pro Pro Thr Gln Glu Leu Val Ala Lys Asp Leu His Ser Met
145                 150                 155                 160

Asp Trp Arg Phe Arg His Ile Phe Arg Gly Gln Pro Arg Arg His Leu
                165                 170                 175

-continued

Leu Gln Ser Gly Trp Ser Val Phe Val Ser Ser Lys Arg Leu Val Ala
            180                 185                 190

Gly Asp Ala Phe Ile Phe Leu Arg Gly Glu Asn Gly Glu Leu Arg Val
            195                 200                 205

Gly Val Arg Arg Ala Met Arg Gln Leu Ser Asn Val Pro Ser Ser Val
        210                 215                 220

Ile Ser Ser Gln Ser Met His Leu Gly Val Leu Ala Thr Ala Trp His
225                 230                 235                 240

Ala Ile Asn Thr Lys Ser Met Phe Thr Val Tyr Tyr Lys Pro Arg Thr
                245                 250                 255

Ser Pro Ser Glu Phe Ile Ile Pro Tyr Asp Gln Tyr Met Glu Ser Val
            260                 265                 270

Lys Asn Asn Tyr Ser Val Gly Met Arg Phe Arg Met Arg Phe Glu Gly
        275                 280                 285

Glu Glu Ala Pro Glu Gln Arg Phe Thr Gly Thr Ile Ile Gly Ser Glu
        290                 295                 300

Asn Leu Asp Pro Val Trp Pro Glu Ser Ser Trp Arg Ser Leu Lys Val
305                 310                 315                 320

Arg Trp Asp Glu Pro Ser Thr Ile Pro Arg Pro Asp Arg Val Ser Pro
                325                 330                 335

Trp Lys Ile Glu Pro Ala Ser Ser Pro Pro Val Asn Pro Leu Pro Leu
            340                 345                 350

Ser Arg Val Lys Arg Pro Arg Pro Asn Ala Pro Pro Ala Ser Pro Glu
        355                 360                 365

Ser Pro Ile Leu Thr Lys Glu Ala Ala Thr Lys Val Asp Thr Asp Pro
        370                 375                 380

Ala Gln Ala Gln Arg Ser Gln Asn Ser Thr Val Leu Gln Gly Gln Glu
385                 390                 395                 400

Gln Met Thr Leu Arg Ser Asn Leu Thr Glu Ser Asn Asp Ser Asp Val
                405                 410                 415

Thr Ala His Lys Pro Met Met Trp Ser Pro Ser Pro Asn Ala Ala Lys
            420                 425                 430

Ala His Pro Leu Thr Phe Gln Gln Arg Pro Pro Met Asp Asn Trp Met
        435                 440                 445

Gln Leu Gly Arg Arg Glu Thr Asp Phe Lys Asp Val Arg Ser Gly Ser
450                 455                 460

Gln Ser Phe Gly Asp Ser Pro Gly Phe Phe Met Gln Asn Phe Asp Glu
465                 470                 475                 480

Ala Pro Asn Arg Leu Thr Ser Phe Lys Asn Gln Phe Gln Asp Gln Gly
                485                 490                 495

Ser Ala Arg His Phe Ser Asp Pro Tyr Tyr Tyr Val Ser Pro Gln Pro
            500                 505                 510

Ser Leu Thr Val Glu Ser Ser Thr Gln Met His Thr Asp Ser Lys Glu
        515                 520                 525

Leu His Phe Trp Asn Gly Gln Ser Thr Val Tyr Gly Asn Ser Arg Asp
        530                 535                 540

Arg Pro Gln Asn Phe Arg Phe Glu Gln Asn Ser Ser Ser Trp Leu Asn
545                 550                 555                 560

Gln Ser Phe Ala Arg Pro Glu Gln Pro Arg Val Ile Arg Pro His Ala
                565                 570                 575

Ser Ile Ala Pro Val Glu Leu Glu Lys Thr Glu Gly Ser Gly Phe Lys
            580                 585                 590

```
Ile Phe Gly Phe Lys Val Asp Thr Thr Asn Ala Pro Asn Asn His Leu
            595                 600                 605

Ser Ser Pro Met Ala Ala Thr His Glu Pro Met Leu Gln Thr Pro Ser
610                 615                 620

Ser Leu Asn Gln Leu Gln Pro Val Gln Thr Asp Cys Ile Pro Glu Val
625                 630                 635                 640

Ser Val Ser Thr Ala Gly Thr Ala Thr Glu Asn Glu Lys Ser Gly Gln
                645                 650                 655

Gln Ala Gln Gln Ser Ser Lys Asp Val Gln Ser Lys Thr Gln Val Ala
                660                 665                 670

Ser Thr Arg Ser Cys Thr Lys Val His Lys Gln Gly Val Ala Leu Gly
            675                 680                 685

Arg Ser Val Asp Leu Ser Lys Phe Ser Asn Tyr Asp Glu Leu Lys Ala
        690                 695                 700

Glu Leu Asp Lys Met Phe Glu Phe Asp Gly Glu Leu Val Ser Ser Asn
705                 710                 715                 720

Lys Asn Trp Gln Ile Val Tyr Thr Asp Asn Gly Asp Met Met Leu
                725                 730                 735

Val Gly Asp Asp Pro Trp Glu Glu Phe Cys Ser Ile Val Arg Lys Ile
            740                 745                 750

Tyr Ile Tyr Thr Lys Glu Val Gln Lys Met Asn Ser Lys Ser Asn
        755                 760                 765

Ala Pro Arg Lys Asp Asp Ser Ser Glu Asn Glu Lys Gly His Leu Pro
    770                 775                 780

Met Pro Asn Lys Ser Asp Asn
785                 790

<210> SEQ ID NO 62
<211> LENGTH: 22
<212> TYPE: DNA
<213> ORGANISM: Artificial Sequence
<220> FEATURE:
<223> OTHER INFORMATION: Primer

<400> SEQUENCE: 62
tggttcacgt agtgggccat cg                                           22

<210> SEQ ID NO 63
<211> LENGTH: 20
<212> TYPE: DNA
<213> ORGANISM: Artificial Sequence
<220> FEATURE:
<223> OTHER INFORMATION: Primer

<400> SEQUENCE: 63
gagtgggtgg agtgtgtttg                                              20

<210> SEQ ID NO 64
<211> LENGTH: 21
<212> TYPE: DNA
<213> ORGANISM: Artificial Sequence
<220> FEATURE:
<223> OTHER INFORMATION: Primer

<400> SEQUENCE: 64
agttggtttt cgtttgagca t                                            21

<210> SEQ ID NO 65
<211> LENGTH: 21
<212> TYPE: DNA
```

```
<213> ORGANISM: Artificial Sequence
<220> FEATURE:
<223> OTHER INFORMATION: Primer

<400> SEQUENCE: 65
cacttgaagg gtggtgccaa g                                              21

<210> SEQ ID NO 66
<211> LENGTH: 21
<212> TYPE: DNA
<213> ORGANISM: Artificial Sequence
<220> FEATURE:
<223> OTHER INFORMATION: Primer

<400> SEQUENCE: 66
cctgttgtcg ccaacgaagt c                                              21
```

The invention claimed is:

1. A method of controlling cell proliferation in the integuments and/or seed coats of a plant comprising inhibiting expression or function of an endogenous gene encoding Auxin response factor 2 (ARF2/MNT) or an orthologue thereof that is expressed in the integuments and/or seed coats comprising
  treating a plant with ethyl methanesulfonate (EMS) to inhibit the expression or function of an endogenous gene encoding Auxin response factor 2 (ARF2/MNT) or an orthologue thereof or
  transforming a plant with an antisense, RNAi, or T-DNA vector that inhibits the expression or function of an endogenous gene encoding Auxin response factor 2 (ARF2/MNT) or an orthologue thereof;
  and identifying a plant
    wherein the number of cells in the integuments and/or seed coat is increased in the plant or plant propagating material as compared to a wild type plant.

2. The method of claim 1, wherein the overall size of the integuments and/or seed coat in the plant is increased as compared to a wild type plant.

3. The method of claim 1, wherein the expression or function of an endogenous gene encoding ARF2/MNT is inhibited.

4. The method of claim 2, wherein cell division in the integuments and/or seed coat is increased resulting in a larger seed as compared to a wild type plant.

5. The method of claim 2, wherein the seed is at least 5% heavier than a wild type plant seed.

6. The method of claim 2, wherein the diameter of the stem of the plant is at least 10% greater than a wild type plant stem.

7. The method of claim 2, wherein the number of cells in the integuments and/or seed coat is increased compared to a wild type plant.

8. The method of claim 2, wherein the sepal length of the plant is sufficiently greater than a wild type sepal length as to inhibit flower opening.

9. The method of claim 1, wherein the vector comprises a regulatory sequence comprising a promoter.

10. The method of claim 9, wherein the promoter is a 35S promoter, the promoter of the INO or BEL1 gene, or a promoter of the BAN, TT1, TT2, TT8, TT12, or TT16 gene.

11. The method of claim 1, wherein the plant is further modified to maintain its fertility.

12. The method of claim 1, wherein said method further comprises growing said plant.

13. The method of claim 1, wherein said method comprises treating a plant ethyl methanesulfonate (EMS) to inhibit the expression or function of an endogenous gene encoding Auxin response factor 2 (ARF2/MNT) or an orthologue thereof.

14. The method of claim 1, wherein said method comprises or transforming a plant with an antisense vector that inhibits the expression or function of an endogenous gene encoding Auxin response factor 2 (ARF2/MNT) or an orthologue thereof.

15. The method of claim 1, wherein said method comprises or transforming a plant with a RNAi vector that inhibits the expression or function of an endogenous gene encoding Auxin response factor 2 (ARF2/MNT) or an orthologue thereof.

16. The method of claim 1, wherein said method comprises or transforming a plant with a T-DNA vector that inhibits the expression or function of an endogenous gene encoding Auxin response factor 2 (ARF2/MNT) or an orthologue thereof.

* * * * *